(12) United States Patent
Farley et al.

(10) Patent No.: US 12,054,735 B2
(45) Date of Patent: *Aug. 6, 2024

(54) VIRAL VECTOR PRODUCTION SYSTEM

(71) Applicant: Oxford BioMedica (UK) Limited, Oxford (GB)

(72) Inventors: Daniel Farley, Oxford (GB); Kyriacos Mitrophanous, Oxford (GB)

(73) Assignee: Oxford BioMedica (UK) Limited, Oxford (GB)

( * ) Notice: Subject to any disclaimer, the term of this patent is extended or adjusted under 35 U.S.C. 154(b) by 1271 days.

This patent is subject to a terminal disclaimer.

(21) Appl. No.: 16/714,516

(22) Filed: Dec. 13, 2019

(65) Prior Publication Data

US 2020/0102578 A1 Apr. 2, 2020

Related U.S. Application Data

(62) Division of application No. 15/106,555, filed as application No. PCT/GB2014/053813 on Dec. 19, 2014, now Pat. No. 10,544,429.

(30) Foreign Application Priority Data

Dec. 20, 2013 (GB) ...................................... 1322798

(51) Int. Cl.
*C12N 15/86* (2006.01)
*C12N 7/00* (2006.01)

(52) U.S. Cl.
CPC ............... *C12N 15/86* (2013.01); *C12N 7/00* (2013.01); *C12N 2710/10343* (2013.01); *C12N 2710/10351* (2013.01); *C12N 2740/15043* (2013.01); *C12N 2740/15051* (2013.01); *C12N 2740/15052* (2013.01); *C12N 2740/16043* (2013.01); *C12N 2740/16051* (2013.01); *C12N 2750/14143* (2013.01); *C12N 2750/14151* (2013.01); *C12N 2840/102* (2013.01); *C12N 2840/55* (2013.01)

(58) Field of Classification Search
CPC ...................... C12N 15/86; C12N 7/00; C12N 2710/10343; C12N 2710/10351; C12N 2740/15043; C12N 2740/15051; C12N 2740/15052; C12N 2740/16043; C12N 2740/16051; C12N 2750/14143; C12N 2750/14151; C12N 2840/102; C12N 2840/55; A61P 43/00; A61K 48/00
See application file for complete search history.

(56) References Cited

FOREIGN PATENT DOCUMENTS

WO WO-2007072056 A2 * 6/2007 ............. C12N 15/86
WO WO-2010135716 A1 * 11/2010 ............ C12N 15/111

OTHER PUBLICATIONS

Nie et al. (Different modes and potencies of translational repression by sequence-specific RNA-protein interaction at the 5'-UTR; Nucleic Acid Research; vol. 34, No. 19, pp. 5528-5540, Oct. 5, 2006). (Year: 2006).*
Babitzke et al., Interaction of the trp RNA-Binding Attenuation Protein (TRAP) of Bacillus subtilis with RNA: Effects of the Number of . . . , J. Bacteriol. 178:5159-5163 (1996).

* cited by examiner

Primary Examiner — Robert S Cabral
(74) Attorney, Agent, or Firm — Grimes & Yvon LLP

(57) ABSTRACT

The present invention relates to a nucleic acid sequence comprising a binding site operably linked to a nucleotide of interest, wherein the binding site is capable of interacting with an RNA-binding protein such that translation of the nucleotide of interest is repressed in a viral vector production cell.

13 Claims, 55 Drawing Sheets

Specification includes a Sequence Listing.

A

Reducing number of RAGNN repeats of tbs sequence

```
              1   2   3   4   5   6   7   8   9  10  11      Kozak
tbs         GAGTTTAGCGGAGTGGAGAAGAGCGGAGCCGAGCCTAGCAGAGACGAGTGGAGCTACAGCCACCATGG tbs-x11M    GAGTTTAGCGGAGTGGAGAAGAGCGGAGCCGAGCCTAGCAGAGACGAGaaGAGCTACAGCCACCATGG
tbs-X10M    GAGTTTAGCGGAGTGGAGAAGAGCGGAGCCGAGCCTAGCAGAGACGAGaaACAGCCACCATGG
tbs-x9      GAGTTTAGCGGAGTGGAGAAGAGCGGAGCCGAGCCTAGCAGAGACACAGCCACCATGG
tbs-x8      GAGTTTAGCGGAGTGGAGAAGAGCGGAGCCGAGCCTAGCAACAGCCACCATGG
tbs-x7      GAGTTTAGCGGAGTGGAGAAGAGCGGAGCCGAGCCACAGCCACCATGG
tbs-x6      GAGTTTAGCGGAGTGGAGAAGAGCGGAGCCACAGCCACCATGG
tbs-x5      GAGTTTAGCGGAGTGGAGAAGAGCGACAGCCACCATGG
tbs-x4      GAGTTTAGCGGAGTGGAGAAACAGCCACCATGG
```

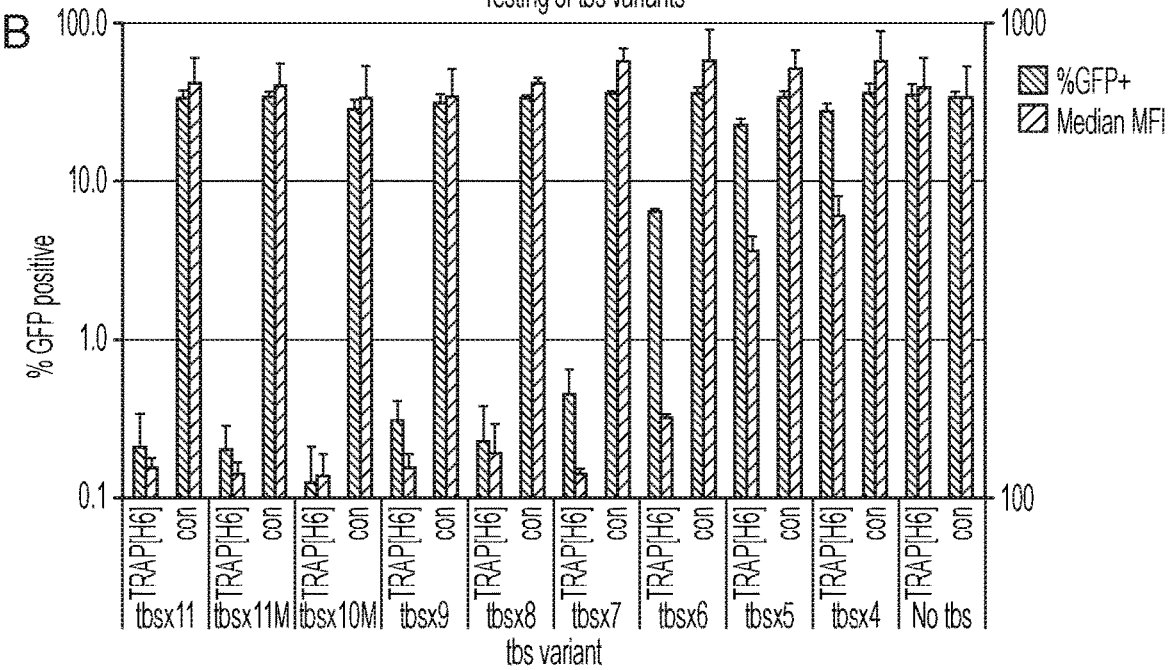

```
Variant name           tbs sequence (N3/N2 spacer variants)
                        1    2    3    4    5    6    7    8    9   10   11
N3x11         (10)  gagatttagacggagttggagaaagagacggagaccgagacctagacagagaacgagaaagagct
N3N2x11       (7)   gag-tttagacggagttggagaaagagacggag-ccgagacctagacagagaacgag-aagagct
N3N2x11       (5)   gag-ttagacggag-tggagaaagagacggag-ccgagacctag-cagagaacgag-aagagct
N3N2x11       (3)   gag-tttag-cggag-tggagaaagagacggag-ccgagacctag-cagag-acgag-aagagct
N3N2x11       (1)   gag-tttag-cggag-tggag-aagagacggag-ccgag-cctag-cagag-acgag-aagagct
N2x11         (0)   gag-tttag-cggag-tggag-aagag-cggag-ccgag-cctag-cagag-acgag-aagagct
(Number of N3]
```

B

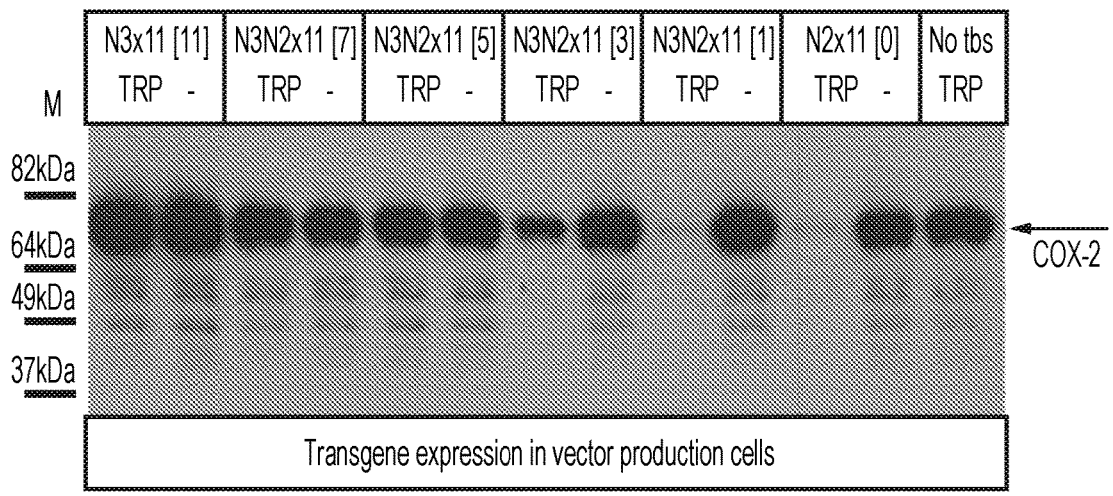

| Variant name | | tbs sequence (N₃/N₂ spacer variants) |
|---|---|---|
| | | 1  2  3  4  5  6  7  8  9  10  11 |
| N2x11 | (0) | gagtttagcggagtggag-aagagcggagccgagcctagcagagacgagaagagct |
| N3N2x8 | (1) | gagtttagcggagtggagaaagagcggagccgagcctagca |
| N3N2x7 | (1) | gagtttagcggagtggagaaagagcggagccgagcc |
| N2x7 | (0) | gagtttagcggagtggag-aagagcggagccgagcc |
| N2x6 | (0) | gagtttagcggagtggag-aagagcggagcc |
| N2x5 | (0) | gagtttagcggagtggag-aagagcg |
| (Number of N₃] | | |

B

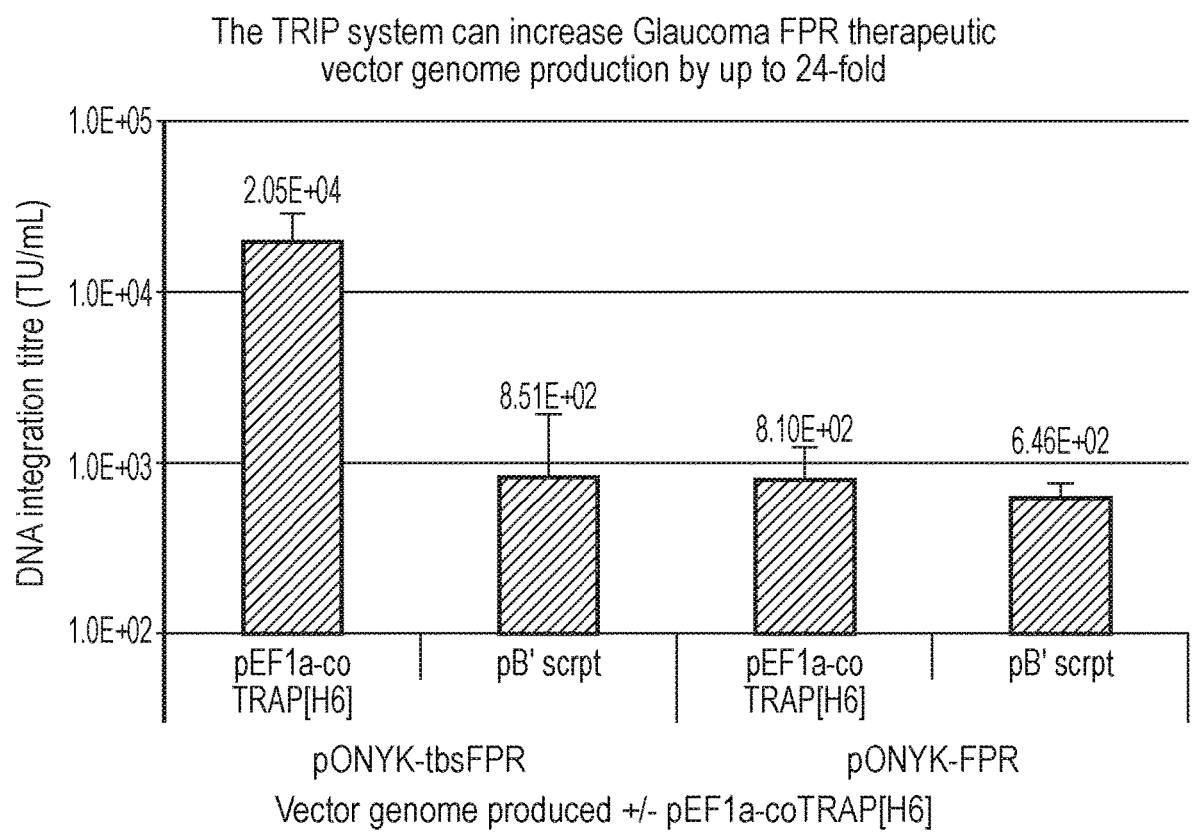
FIG. 18iii

| Organism | Bacteria Lineage | NCBI Ref |
|---|---|---|
| Bacillus subtilis | Firmicutes; Bacilli; Bacillales; Bacillaceae; Bacillus | WP_003230576.1 |
| Geobacillus stearothermophilus | Firmicutes; Bacilli; Bacillales; Bacillaceae; Geobacillus | WP_033013997.1 |
| Bacillus halodurans | Firmicutes; Bacilli; Bacillales; Bacillaceae; Bacillus | WP_010897809.1 |
| Desulfotomaculum hydrothermale | Firmicutes; Clostridia; Clostridiales; Peptococcaceae; Desulfotomaculum | WP_008413223.1 |
| Aminomonas paucivorans | Synergistetes; Synergistia; Synergistiales; Synergistaceae; Aminomonas | WP_006300896.1 |
| Carboxydothermus hydrogenoformans | Firmicutes; Clostridia; Thermoanaerobacterales; Thermoanaerobacteraceae; Carboxydothermus | WP_011344060.1 |

FIG. 21i

TRAP[H6] amino acid sequence alignment

| Bacterial Species | Homology+ | Fold repression# |
|---|---|---|
| B.Subtilis | 100% | ≥100 |
| B.Stearothermophilus | 78% | 20-50 |
| B.Stearothermophilus S72N* | 76% | 50-100 |
| B.Haloduarans** | 70% | 10 |
| D.Hydrothermale | 59% | ≥100 |
| A.Paucivorans | 58% | ≥100 |
| C.Hydrogenoformans | 56% | 10 |

RNA binding residues:
L-trp binding residues:

\* Artificial 12-mer
\*\* Natural 12-mer
† Homology relative to B.Subtilis TRAP[H6]
Fold-repression at pCMV-tbsGFP:pTRAP[H6] ratio of 5:1

FIG. 21iii

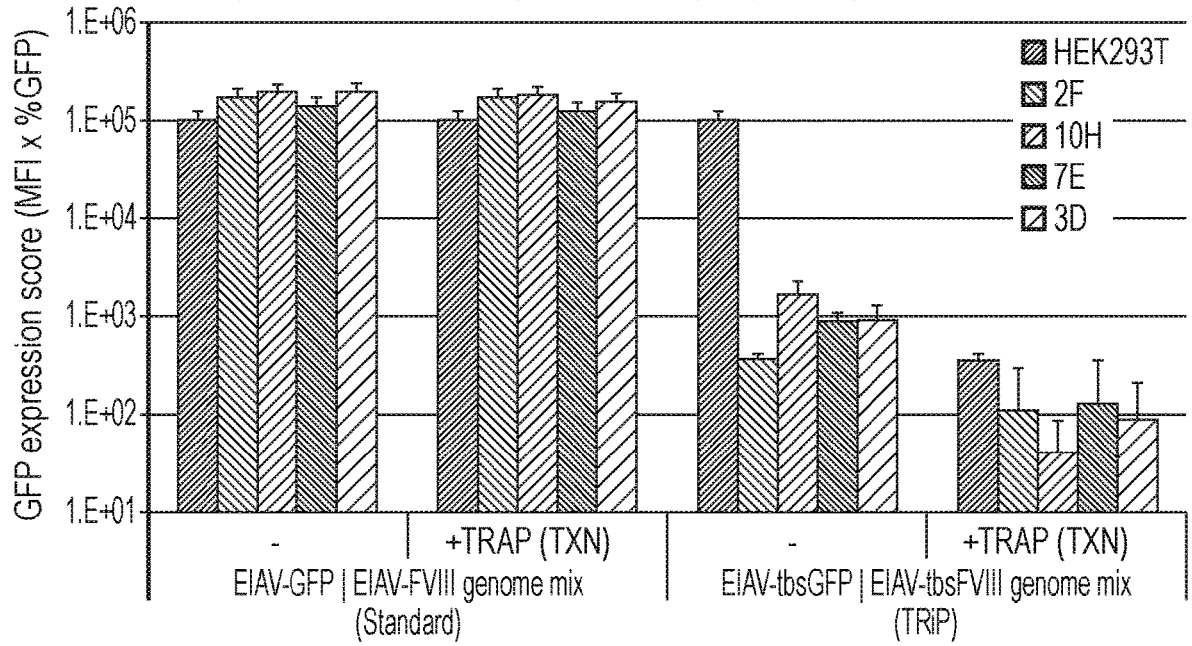
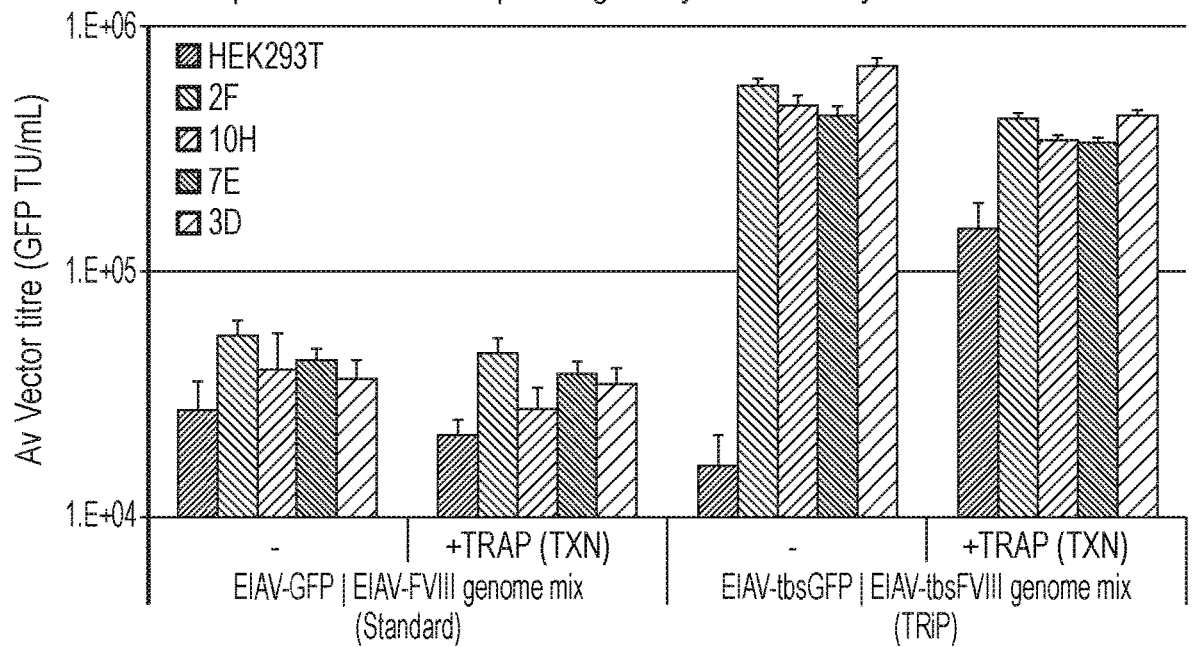
FIG. 22iii

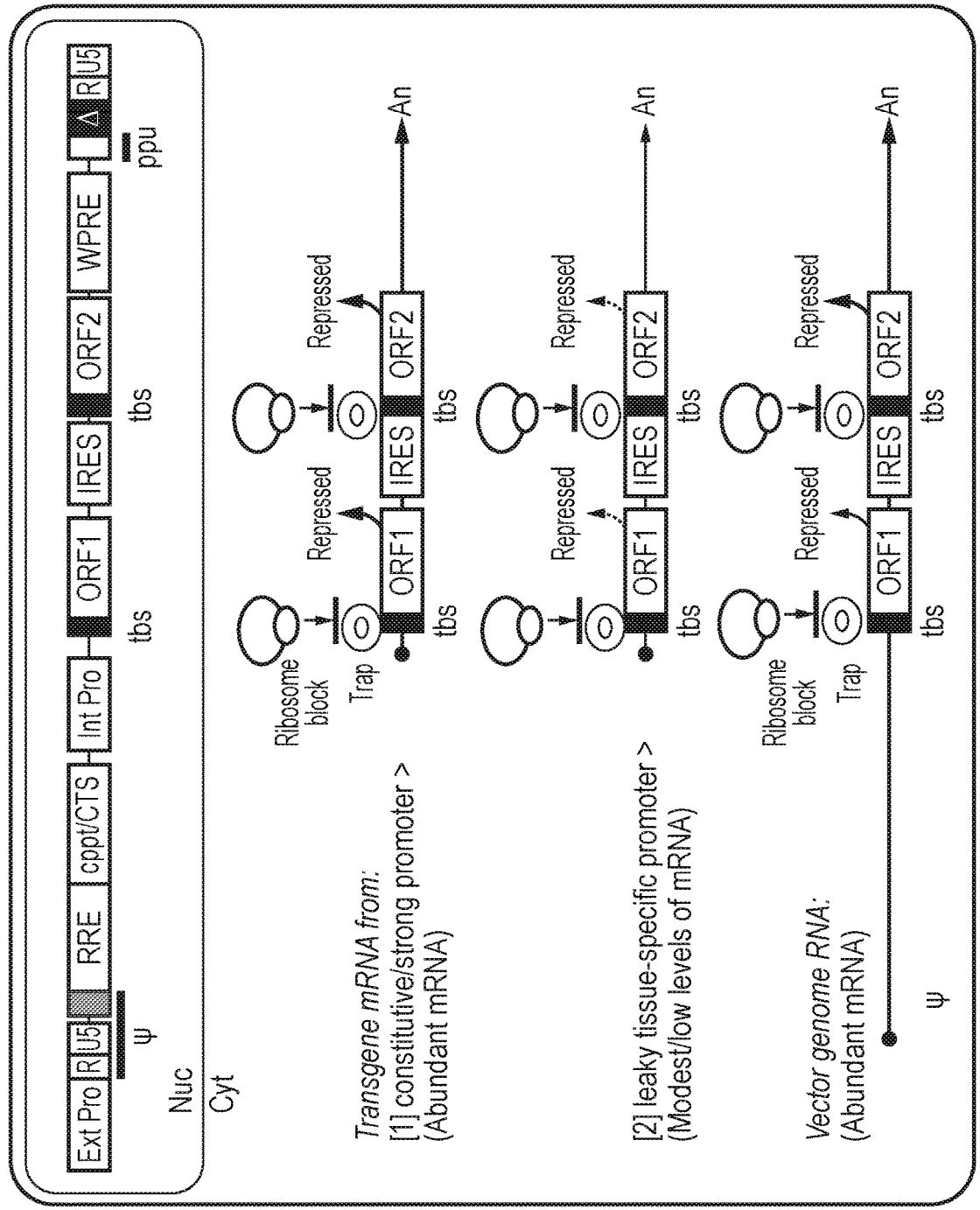
FIG. 27iii

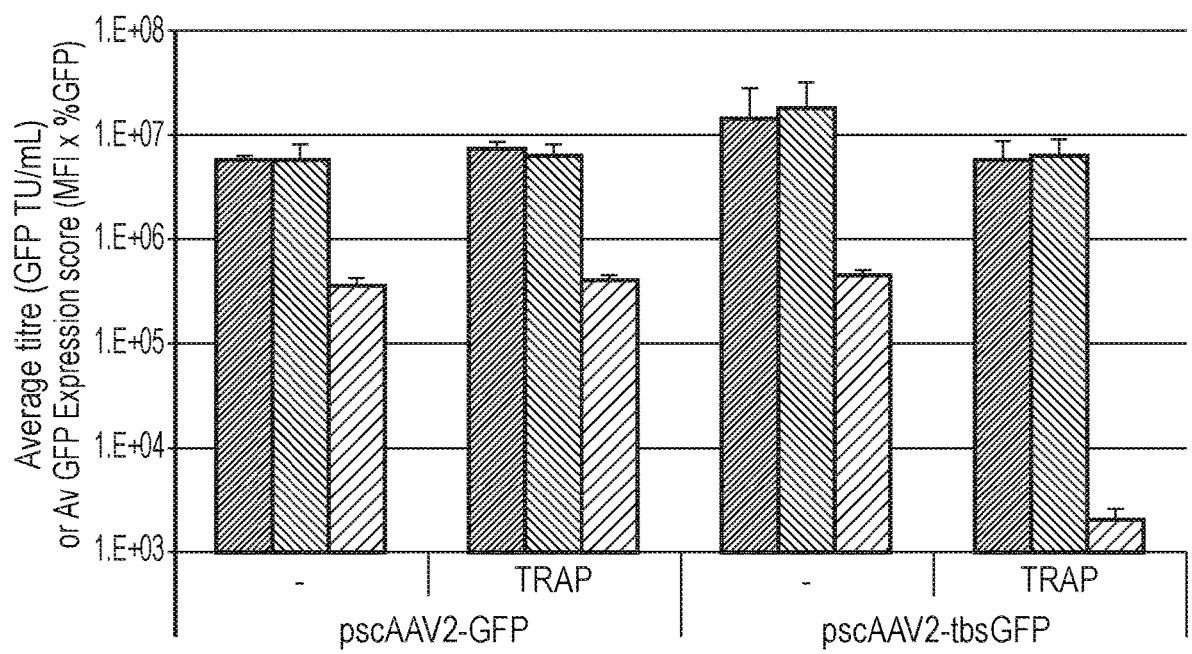
FIG. 28iii

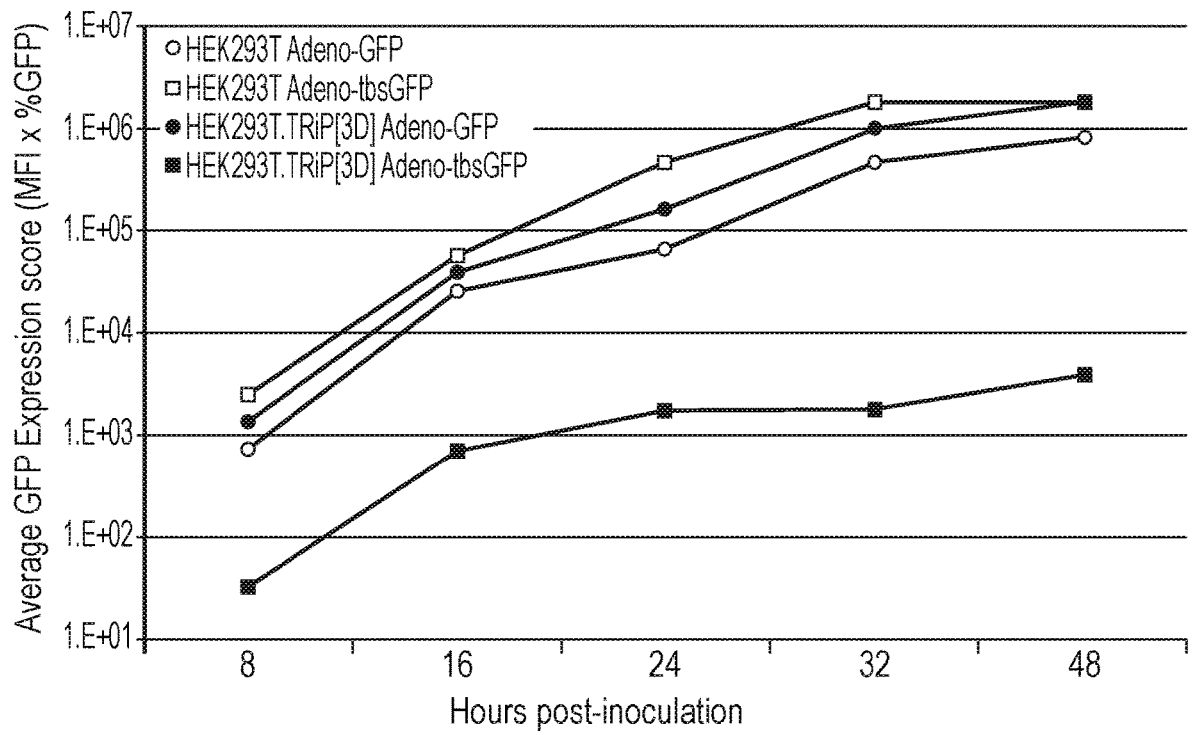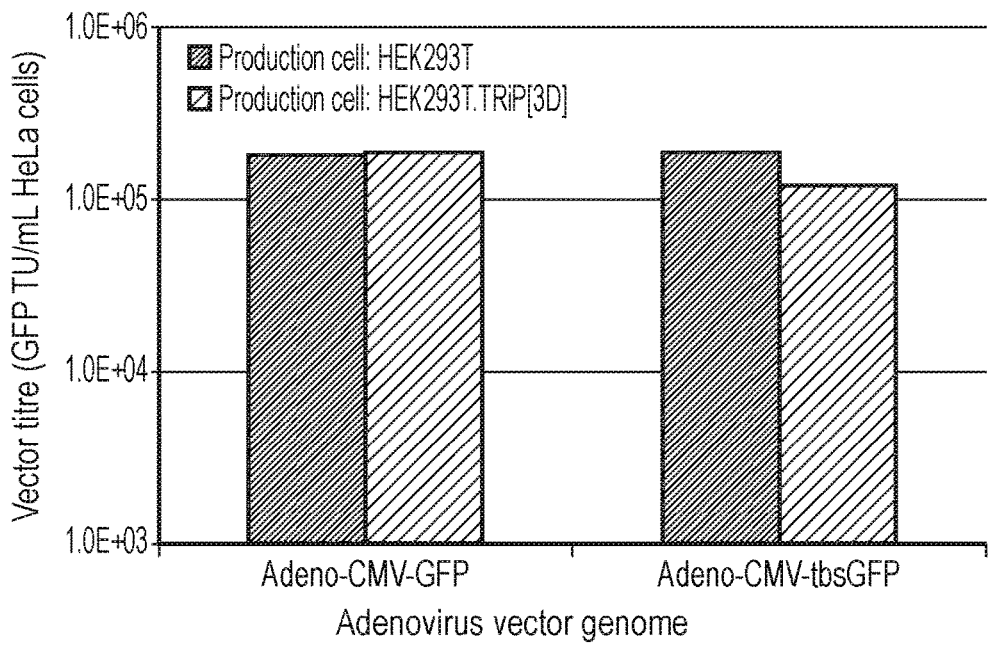
FIG. 29iii

VIRAL VECTOR PRODUCTION SYSTEM

This application is a divisional application of U.S. application Ser. No. 15/106,555, filed on Jun. 20, 2016, which is the national stage under 35 U.S.C. 371 of International Application No. PCT/GB2014/053813, filed on Dec. 19, 2014, and claiming priority to GB Application No. 1322798.8, filed on Dec. 20, 2013, all of which are incorporated herein by reference.

FIELD OF THE INVENTION

The invention relates to the production of viral vectors. More specifically, the present invention relates to modification of the translation of a nucleotide of interest which is encoded by a viral vector, in a viral vector production cell.

BACKGROUND TO THE INVENTION

Gene therapy broadly involves the use of genetic material to treat disease. It includes the supplementation in cells with defective genes (e.g. those harbouring mutations) with functional copies of those genes, the inactivation of improperly functioning genes and the introduction of new therapeutic genes.

Therapeutic genetic material may be incorporated into the target cells of a host using vectors to enable the transfer of nucleic acids. Such vectors can be generally divided into viral and non-viral categories.

Viruses naturally introduce their genetic material into target cells of a host as part of their replication cycle. Engineered viral vectors harness this ability to enable the delivery of a nucleotide of interest (NOI) to a target cell. To date, a number of viruses have been engineered as vectors for gene therapy. These include retroviruses, adenoviruses (AdV), adeno-associated viruses (AAV), herpes simplex viruses (HSV) and vaccinia viruses.

In addition to modification to carry the nucleotide of interest, viral vectors are typically further engineered to be replication defective. As such, the recombinant vectors can directly infect a target cell, but are incapable of producing further generations of infective virions. Other types of viral vectors may be conditionally replication competent within cancer cells only, and may additionally encode a toxic transgene or pro-enzyme.

Retroviral vectors have been developed as therapies for various genetic disorders and are now showing increasing promise in clinical trials (e.g. Galy, A. and A. J. Thrasher (2010) *Curr Opin Allergy Clin Immunol* 11(6): 545-550; Porter, D. L., B. L. Levine, M. Kalos, A. Bagg and C. H. June (2011) *N Engl J Med* 365(8): 725-733; Campochiaro, P. A. (2012) *Gene Ther* 19(2): 121-126; Cartier, N., S. Hacein-Bey-Abina, C. C. Bartholomae, P. Bougneres, M. Schmidt, C. V. Kalle, A. Fischer, M. Cavazzana-Calvo and P. Aubourg (2012) *Methods Enzymol* 507: 187-198; Sadelain, M., I. Riviere, X. Wang, F. Boulad, S. Prockop, P. Giardina, A. Maggio, R. Galanello, F. Locatelli and E. Yannaki (2010) *Ann N Y Acad Sci* 1202: 52-58; DiGiusto, D. L., A. Krishnan, L. Li, H. Li, S. Li, A. Rao, S. Mi, P. Yam, S. Stinson, M. Kalos, J. Alvarnas, S. F. Lacey, J. K. Yee, M. Li, L. Couture, D. Hsu, S. J. Forman, J. J. Rossi and J. A. Zaia (2010) *Sci Transl Med* 2(36): 36ra43 and Segura M M, M. M., Gaillet B, Garnier A. (2013) *Expert opinion in biological therapy*).

Important examples of such vectors include the gamma-retrovirus vector system (based on MMLV), the primate lentivirus vector system (based on HIV-1) and the non-primate lentivirus vector system (based on EIAV).

Reverse genetics has allowed these virus-based vectors to be heavily engineered such that vectors encoding large heterologous sequences (circa 10 kb) can be produced by transfection of mammalian cells with appropriate DNA sequences (reviewed in Bannert, K. (2010) *Caister Academic Press*: 347-370).

Engineering and use of retroviral vectors at the research stage typically involves the production of reporter-gene vectors encoding, for example, GFP or lacZ. The titres of these clinically irrelevant vectors are usually in the region of $1 \times 10^6$ to $1 \times 10^7$ transducing units per mL (TU/mL) of crude harvest material. Further concentration and purification of this material can achieve working stocks in excess of $1 \times 10^{10}$ TU/mL. However, the production of vectors encoding therapeutically relevant NOIs often results in substantially reduced titres compared to these reporter vectors.

There are several factors that are potentially responsible for this effect:
1. The size of the therapeutic genome. Very large genomes can be packaged by retroviruses, but it is thought that reverse transcription and/or integration steps become less efficient as size increases.
2. The stability of vector genome RNA. This may be reduced by the presence of unpredicted instability elements in the NOI.
3. Suboptimal nucleotide usage within the vector genome RNA. Wild-type virus genomes often have a certain nucleotide bias (e.g. HIV-1 is AT rich). Vector genomes tend to be less AT rich, which may affect packaging and/or post-maturation steps.
4. Expression of the NOI in viral vector production cells. (Over-)expressed protein may have an indirect or direct effect on vector virion assembly and/or infectivity.

We have empirically shown that expression of the protein encoded by the NOI within viral vector production cells can adversely affect therapeutic vector titres (see FIGS. 3*i* and 3*ii*).

Incorporation of a protein encoded by the NOI (the protein of interest, POI) into vector virions may also impact downstream processing of vector particles; for example, an NOI encoding a transmembrane POI may lead to high surface expression of the transmembrane protein in the viral vector virion, potentially altering the physical properties of the virions. Furthermore, this incorporation may present the POI to the patient's immune system at the site of delivery, which may negatively impact transduction and/or the long-term expression of the therapeutic gene in vivo. The NOI could also induce the production of undesirable secondary proteins or metabolites which could impact production, purification, recovery and immunogenicity and it is therefore desirable to minimise this.

There is a clear need for the capability to repress the expression of a NOI in viral vector production cells while maintaining effective expression of the NOI in target cells. Whatever mechanism is employed, the 'natural' pathway of assembly and resulting functionality of the viral vector particles must not be impeded. This is not straightforward because the viral vector genome molecule that will be packaged into virions must necessarily encode the NOI expression cassette. In other words, because the vector genome molecule and NOI expression cassettes are operably linked, modification of the NOI expression cassette may have adverse consequences on the ability to produce the vector genome molecule in the cell. For example, if a physical transcription block (e.g. TetR repressor system) is used to repress the NOI expression cassette it is likely that production of the vector genome molecule would also be inhibited through steric hindrance. In addition, control mechanism modifications must also not adversely affect the functionality of the vector genome molecule after virion maturation and release (i.e. with regards to directing transduction of the target cell). For example, a retroviral vector genome RNA molecule must be capable of the processes of reverse transcription and integration—any modification to the NOI expression cassette must not impede these steps in the transduction process.

Repression of NOI expression within viral vector production cells may present further advantages. If NOI expression leads to a reduction in the viability of vector production cells, its repression may benefit manufacturing at large scale which requires large cell numbers. The reduction in cell debris due to cell death would also reduce impurities within the crude vector harvest material. Processing, purification and concentration of the vector platform (i.e. different therapeutic genes encoded within the same vector system) could be standardised; if the only heterologous genes expressed within viral vector production cells are those required for vector production, downstream processing could be more easily optimised for an entire platform of therapeutic vectors, resulting in very similar physical specifications of vector preparations. Variability of immune response to, and toxicity of, resulting vectors in vivo may be minimised, which may lead to more persistent therapeutic NOI expression in the target cells.

Tissue-specific promoters which limit expression of the NOI in production cells are a possible solution to this problem, although leakiness of these promoters might lead to adverse levels of transgene protein. However, greater and more robust expression of the NOI in target cells can be achieved using constitutive promoters. Indeed, such robust expression may be required for efficacy in vivo. In addition, tissue-specific promoters may be less predictable when following a therapeutic vector product through animal models and into humans during pre-clinical and clinical development.

STATEMENTS OF THE INVENTION

As outlined above, the expression of a protein of interest (POI) encoded by the viral vector expression cassette in the viral vector production cell may present a number of problems for the generation of viral vector therapeutics. In particular, such expression may lead to a reduction in titres of the viral vector, and the undesirable incorporation of, or association with, a protein encoded by the NOI into the viral vector particle.

We have shown that this problem can be overcome by using a heterologous translation control system in eukaryotic cell cultures to repress the translation of the NOI and thus repress or prevent expression of the protein encoded by the NOI. We have surprisingly found that use of this system does not impede the production of packageable vector genome molecules nor the activity of vector virions, and does not interfere with the long-term expression of the NOI in the target cell.

In one aspect, the present invention provides a nucleic acid sequence comprising a binding site operably linked to a nucleotide of interest, wherein the binding site is capable of interacting with an RNA-binding protein such that translation of the nucleotide of interest is repressed or prevented in a viral vector production cell.

In a preferred embodiment, the RNA-binding protein is tryptophan RNA-binding attenuation protein (TRAP), for example bacterial tryptophan RNA-binding attenuation protein.

Another aspect of the invention relates to a viral vector comprising the nucleic acid sequence of the invention.

Another aspect of the invention relates to a viral vector production system comprising a set of nucleic acid sequences encoding the components required for production of the viral vector, wherein the vector genome sequence comprises the nucleic acid sequence of the invention.

Another aspect of the invention relates to a DNA construct for use in the viral vector production system of the invention comprising the nucleic acid sequence of the invention.

A further aspect of the invention relates to a DNA construct for use in the viral vector production system of the invention comprising a nucleic acid sequence encoding the RNA-binding protein of the invention.

Another aspect of the invention relates to a set of DNA constructs for use in the viral vector production system of the invention comprising some or all of the DNA constructs of the invention and DNA constructs encoding Gag/Pol proteins and Env protein, or functional substitutes thereof. A DNA construct expressing Rev may also be used in the viral vector production system.

Another aspect of the invention relates to a viral vector production cell comprising the nucleic acid sequence, the viral vector production system, or some or all of the DNA constructs of the invention.

Another aspect of the invention relates to a process for producing viral vectors comprising introducing the nucleic acid sequence, the viral vector production system, or some or all of the DNA constructs of the invention into a viral vector production cell and culturing the production cell under conditions suitable for the production of the viral vectors.

Another aspect of the invention relates to a viral vector produced by the viral vector production system of the invention, using the viral vector production cell of the invention or by the process of the invention.

Another aspect of the invention relates to a cell transduced by the viral vector of the invention.

Another aspect of the invention relates to the nucleic acid sequence, viral vector or a transduced cell of the invention for use in medicine.

Another aspect of the invention relates to the use of the nucleic acid sequence, viral vector or a transduced cell of the invention in medicine.

Another aspect of the invention relates to the use of the nucleic acid sequence, viral vector or the cells of the invention for the preparation of a medicament to deliver a nucleotide of interest to a target site in need of the same.

Another aspect of the invention relates to a method of treatment comprising administering the nucleic acid sequence, viral vector or the transduced cell of the invention to a subject in need of the same.

Another aspect of the invention relates to a pharmaceutical composition comprising the nucleic acid sequence, viral vector or the transduced cell of the invention in combination with a pharmaceutically acceptable carrier, diluent or excipient.

Another aspect of the invention relates to a method of identifying nucleic acid binding sites and/or nucleic acid binding proteins which are capable of interacting such that the translation of a nucleotide of interest is repressed or prevented in a viral vector production cell when operably linked to the nucleic acid binding site, wherein the method comprises analysing the expression of a reporter gene in a cell comprising both the nucleic acid binding site operably linked to the reporter gene, and the nucleic acid binding protein.

SUMMARY OF THE INVENTION

A significant limitation of producing therapeutic retroviral vectors at high or even moderate titres can be the adverse expression of the protein encoded by the transgene/NOI in production cells, particularly when the transgene is driven by a powerful, constitutive promoter. Certain transgene proteins may have variable effects, both direct and indirect, on the cell's ability to produce active, infectious vector particles. Cell metabolism, viral vector particle assembly and/or particle activity may be affected by a particular (known or unknown) action of the transgene product. Tissue-specific promoters to silence transgene expression in production cells have been used as a solution to this problem but a significant drawback with this approach is that often gene expression from tissue specific promoters is not as robust as it is from constitutive ones, and can be less predictable or more variable in the different animal models that are utilised during vector development.

We have surprisingly found that the novel use of an RNA-binding protein (e.g. the bacterial trp operon regulator protein, tryptophan RNA-binding attenuation protein, TRAP), and RNA targets to which it binds, will repress or prevent transgene translation within an RNA or DNA viral vector production cell. In the case of TRAP, this reduction or prevention of transgene translation can result in improved vector titres for vectors encoding certain NOIs by as much as 100-fold. This system is referred to as the Transgene Repression In vector Production cell system or TRIP system.

We demonstrate for the first time the use of a bacterial translation repressor system to increase RNA (retroviral) vector titres in eukaryotic cell production systems by repressing translation of the NOI mRNA. The placement of a binding site for an RNA binding protein (e.g. a TRAP-binding sequence, tbs) upstream of the NOI translation initiation codon allows specific repression of translation of mRNA derived from the internal expression cassette, whilst having no detrimental effect on production or stability of vector RNA. We have also shown that production and function of retroviral vectors appeared to be minimally affected by the presence of the tbs in the vector genome. This implies that either reverse transcriptase (RT) can displace TRAP from the tbs or that TRAP is not efficiently bound to the tbs in the context of the long vector genome RNA packaged within the virion. We have also shown that a similar configuration of tbs placed within the NOI expression cassette of DNA viral vectors, such as AAV, allows NOI translation repression by TRAP whilst maintaining production of active viral vector virions.

The number of nucleotides between the tbs and translation initiation codon of the NOI may preferably be varied from 0 to 12 nucleotides without affecting the degree of repression of mRNA translation. Whilst not wishing to be bound by any theory, the tbs-bound TRAP may be repressing translation initiation by physically blocking the 40S scanning ribosome complex before it can reach the initiation codon, whereupon the more stable and higher-affinity translation machinery would otherwise form.

Also we have found that the tbs may be placed downstream of an internal ribosome entry site (IRES) to repress translation of the NOI in a multicistronic mRNA. Indeed, this supplies further evidence that tbs-bound TRAP might block the passage of the 40S ribosome; IRES elements function to sequester the 40S ribosome subunit to an mRNA in a CAP-independent manner before the full translation complex is formed (see Thompson, S. (2012) *Trends in Microbiology* 20(11): 558-566) for a review on IRES translation initiation). The tbs sequence placed between the IRES and the initiation codon of the NOI slightly impacted non-repressed translation levels but maintained the ability to be functionally acted upon by TRAP. This finding demonstrates that it is possible for the TRIP system to repress multiple open-reading frames from a single mRNA expressed from viral vector genomes. This will be a useful feature of the TRIP system when producing vectors encoding multiple therapeutic genes, especially when all the transgene products might negatively affect vector titres to some degree.

Further characterisation of the tbs sequence revealed that, for TRAP as the RNA-binding protein, preferably the TRIP system works maximally with a tbs sequence containing at least 8 RAGNN repeats, although in one embodiment 7 repeats may be used to still obtain robust transgene repression, and in another embodiment 6 repeats may be used to allow sufficient repression of the transgene to levels that could rescue vector titres. Whilst the RAGNN consensus sequence may be varied to maintain TRAP-mediated repression, preferably the precise sequence chosen may be optimised to ensure high levels of translation in the non-repressed state. For example, the tbs sequences may be optimised by removing splicing sites, unstable sequences or stem-loops that might hamper translation efficiency of the mRNA in the absence of TRAP (i.e. in target cells). Regarding the configuration of the RAGNN repeats of a given tbs, the number of N "spacing" nucleotides between the RAG repeats is preferably two. However, a tbs containing more than two N spacers between at least two RAG repeats may be tolerated (as many as 50% of the repeats containing three Ns may result in a functional tbs as judged by in vitro binding studies; Babitzke P, Y. J., Campanelli D. (1996) *Journal of Bacteriology* 178(17): 5159-5163). Indeed, we have shown that an 11×RAGNN tbs sequence can tolerate up to three replacements with RAGNNN repeats and still retain some potentially useful translation-blocking activity in partnership with TRAP-binding.

The RNA-binding protein (e.g. TRAP) open-reading frame may be codon-optimised for expression in mammalian (e.g. *Homo sapiens*) cells, since the bacterial gene sequence is likely to be non-optimal for expression in mammalian cells. The sequence may also be optimised by removing potential unstable sequences and splicing sites. The use of a HIS-tag C-terminally expressed on the TRAP protein appears to offer a benefit in terms of translation repression and may optionally be used. This C-terminal HIS-tag may improve solubility or stability of the TRAP within eukaryotic cells, although an improved functional benefit cannot be excluded. Nevertheless, both HIS-tagged and untagged TRAP allowed robust repression of transgene expression. Certain cis-acting sequences within the RNA-binding protein (e.g. TRAP) transcription unit may also be optimised; for example, EF1a promoter-driven constructs enable better repression with low inputs of TRAP plasmid compared to CMV promoter-driven constructs in the context of transient transfection.

Robust expression of the RNA-binding protein (e.g. TRAP) within the TRIP system is desirable in order to maximise repression of transgene translation. It had been expected that the requirement to include high levels of the RNA-binding protein plasmid might adversely affect the transfection of the other vector production constructs in a transient vector production system. This is because the amount/ratio of the genome construct is typically optimised in the absence of the additional plasmids; a requirement to co-transfect large amounts of RNA-binding protein-encoding plasmid could adversely affect these optimal ratios, leading to reduced vector titres. However, it was shown that a TRAP-to-retroviral vector genome plasmid ratio of as low as 1-to-10 enabled near-maximum levels of transgene repression when using a transient transfection protocol. Moreover, vector expressing a non-problematic NOI was produced at near maximal titres when a TRAP-to-retroviral vector genome plasmid ratio of as high as 1-to-5 was employed. Therefore, the addition of the TRAP-expressing plasmid at these relatively low inputs during transient transfection of retroviral vector production constructs is not likely to adversely affect previously optimised ratios of such constructs. The ratios of TRAP-expressing plasmid to DNA viral vector component plasmids such as AAV have also been optimised.

These important findings demonstrates that the TRIP system can be used during transient transfection vector production protocols. The TRIP system may also be used for stable production systems and is therefore broadly applicable to viral vector manufacture.

A. A lacZ-encoding vector genome component was mixed at 1:1 or 1:5 ratio with another vector genome during transient vector production, and the impact on vector titre was assayed by X-gal assay on target cells. GFP expression does not impact vector titres and so the level of titre reduction at the different ratios indicates the baseline effect of diluting-out lacZ genome. Therefore, the impact of other vector transgenes on lacZ titres can be measured against the lacZ:GFP mixes B. This experiment indicates that the effect of transgene protein from RetinoStat®, StarGen™, UshStat® and ReQuinate® genomes impact vector titres by 7-to-100 fold. The external and internal promoter elements are both CMV.

Figure 3I:
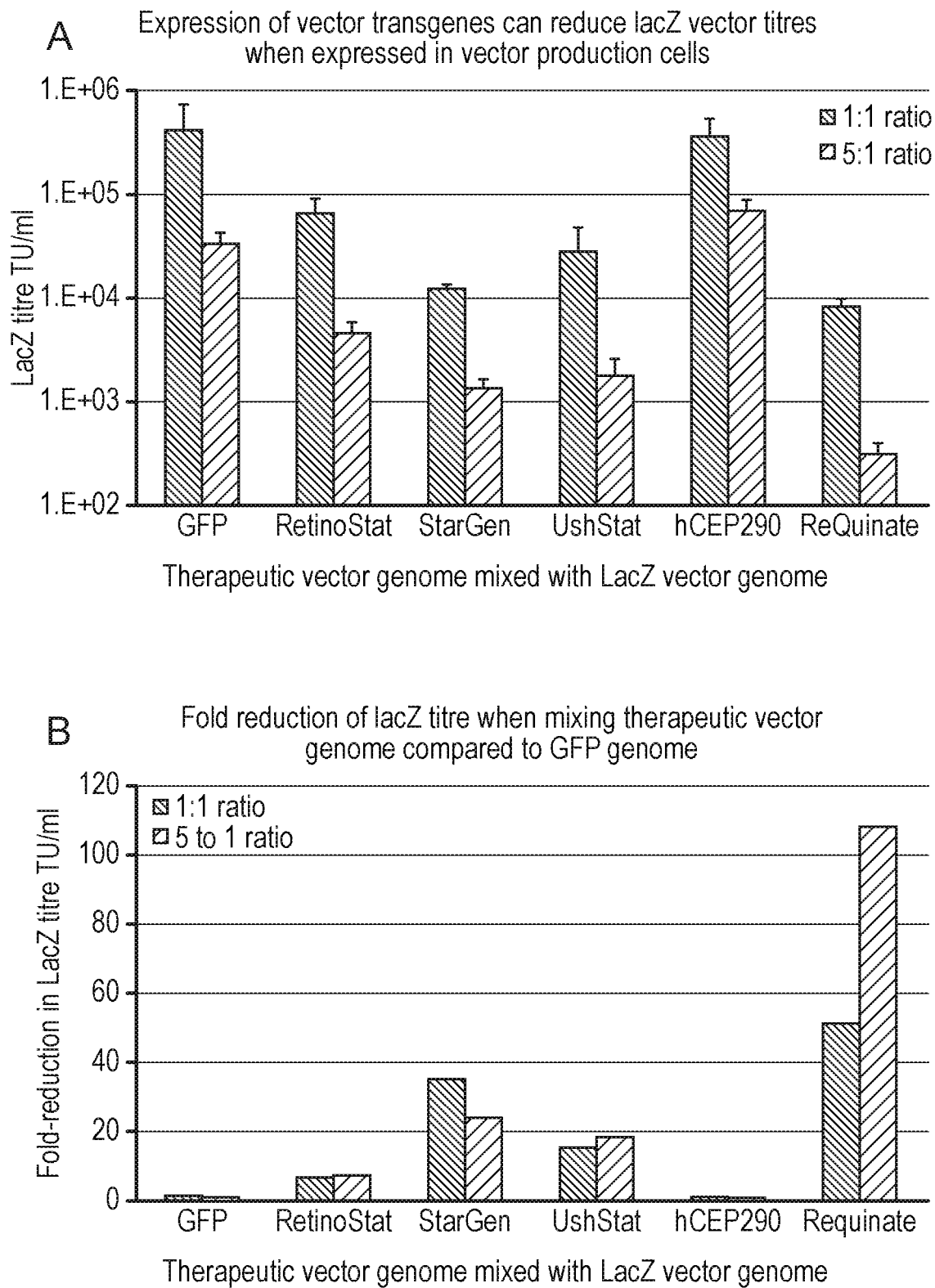
FIG. 3i. Vector genome mixing during production demonstrates impact of transgene protein expression on vector titres.
Figure 3I:
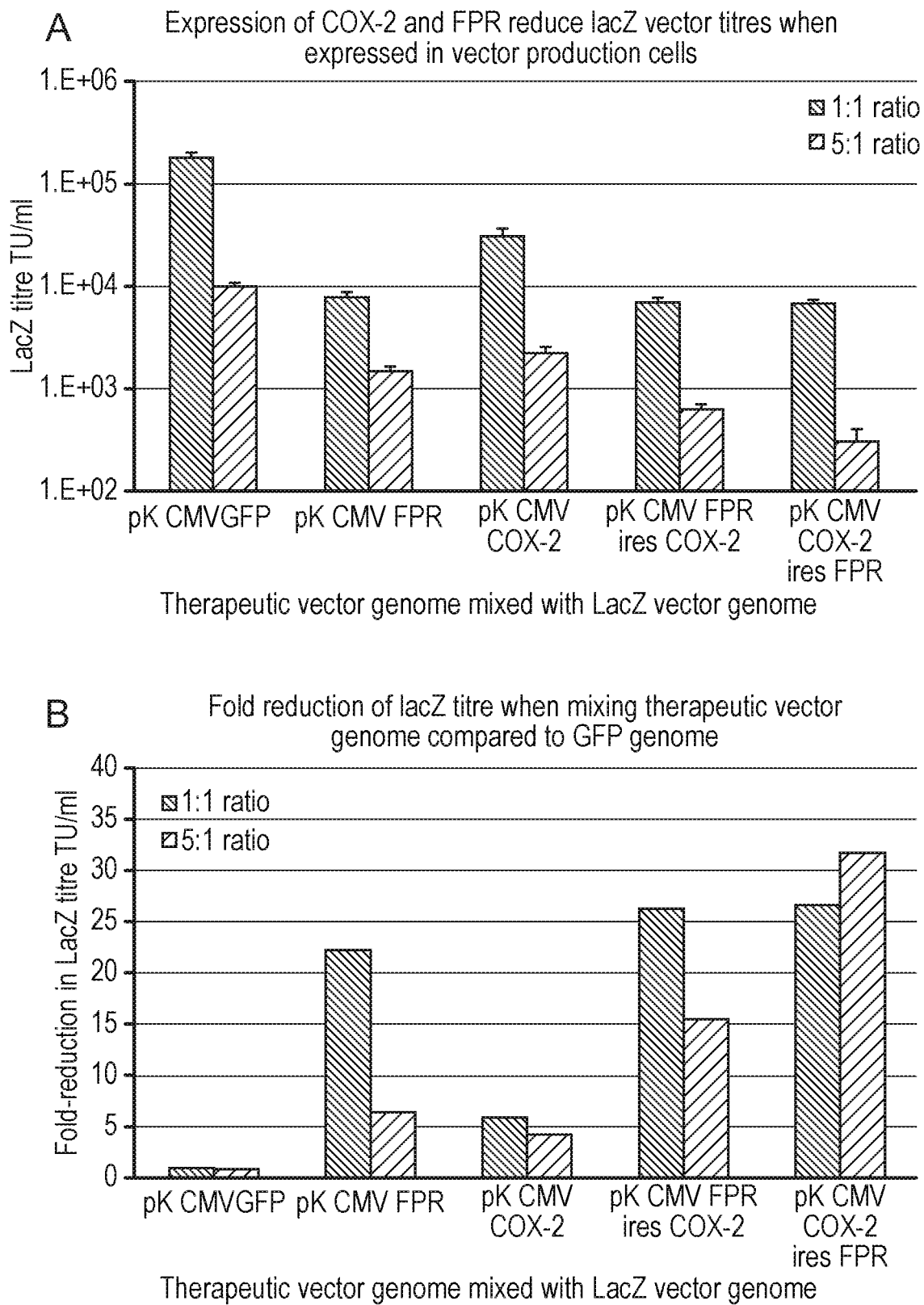

FIG. 3ii. COX-2 and/or FPR genomes and lacZ genome mixing during production demonstrates impact of transgene protein expression on vector titres. A lacZ-encoding vector genome component is mixed at 1:1 or 1:5 ratio with GFP or a therapeutic vector genome during transient transfection vector production, and the impact on lacZ vector titre is assayed by X-gal assay on target cells. GFP expression does not impact vector titres and so the lacZ titre indicates the baseline effect of diluting-out lacZ genome. Therefore, the impact of other vector transgenes on lacZ titres can be measured against the lacZ/GFP mixes at the 1:1 and 1:5 ratios. The therapeutic vectors tested were either single transgene vectors or bicistronic vectors harbouring an IRES element; the impact of COX-2 and FPR on lacZ titres may be additive.

Figure 4:
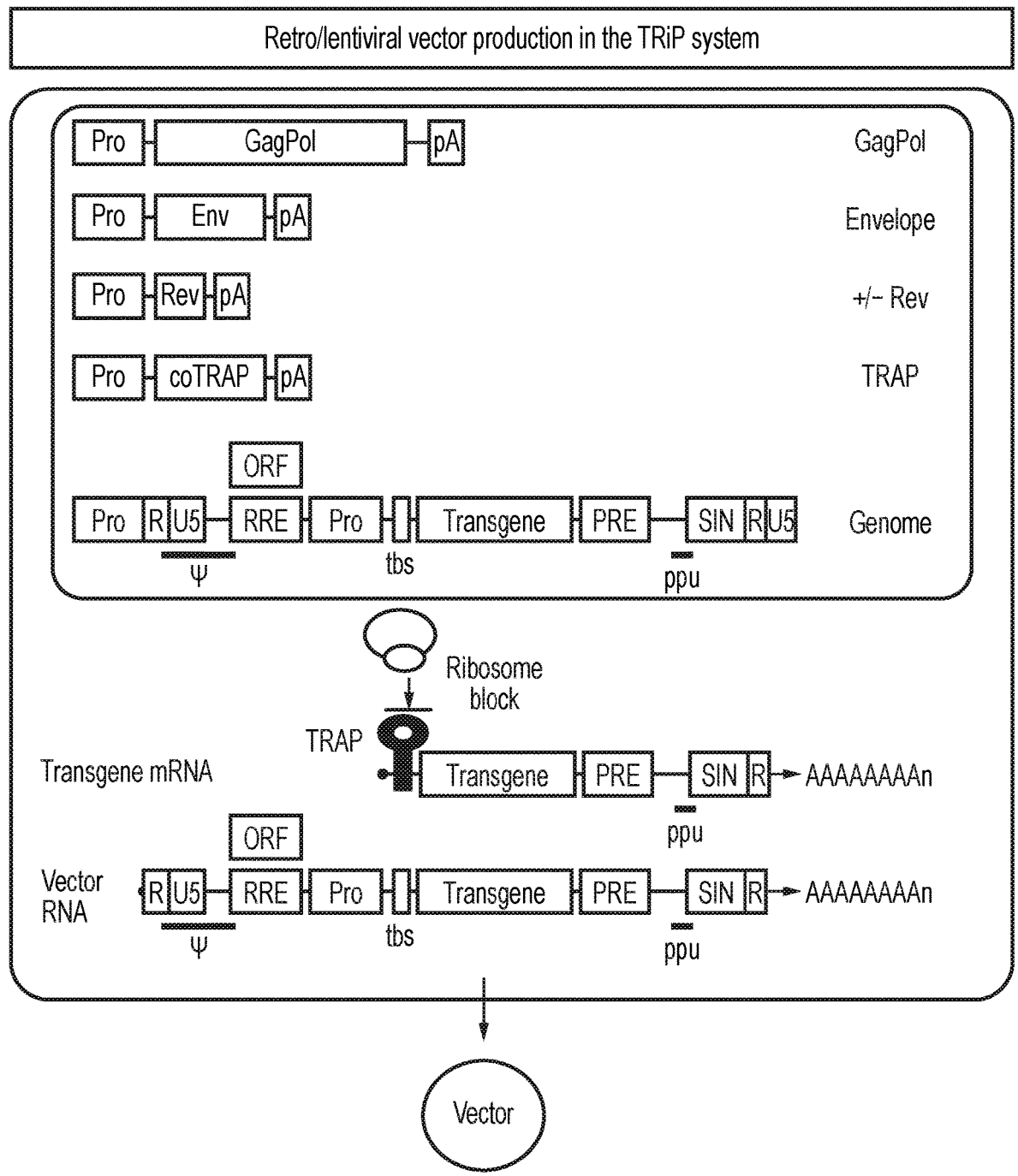

FIG. 4. An example of the TRIP system in repression of transgene expression in retroviral vector production cells. A retroviral vector production cell expressing TRAP or codon-optimised TRAP (coTRAP) where the tbs is inserted in the 5'UTR of the transgene of the vector genome expression cassette. TRAP binds to the tbs and blocks transgene protein translation. Vector RNA molecules are also capable of binding TRAP but surprisingly this does not impede the single-round life cycle of the vector virion i.e. reverse transcription and integration steps are performed normally by the vector particle.

Figure 5:
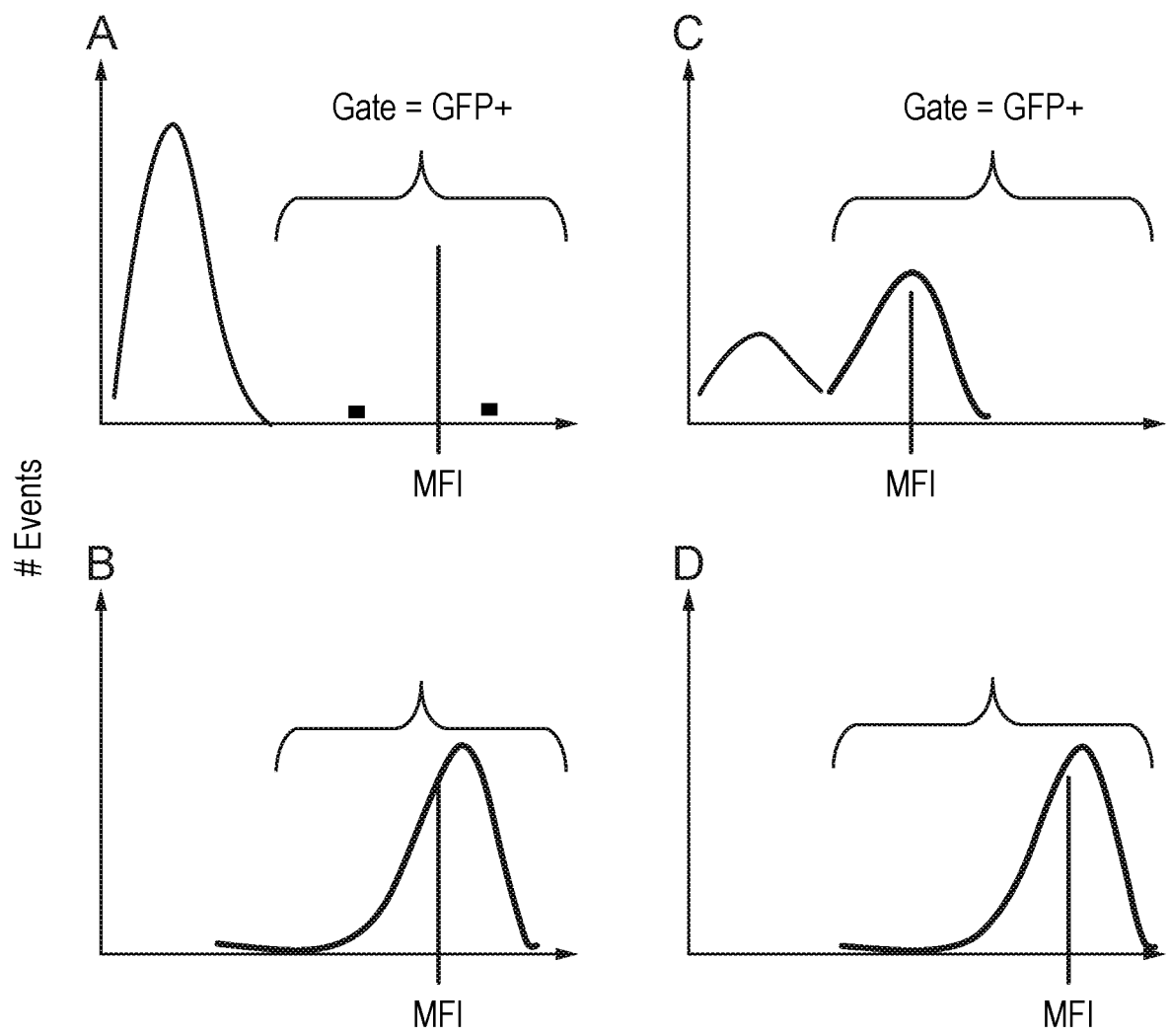

FIG. 5. The limitations of using solely either number of GFP-positive cells or MFI in flow cytometry analysis of GFP-plasmid transfected cell populations. These schematics show potential outcomes in experiments comparing populations with substantially different GFP expression levels. In experiment A/B both GFP-positive populations have the same MFI, and in experiment C/D the GFP-positive populations contain similar numbers of cells but 10-fold different MFIs. Scenario A has been practically demonstrated when using pEF1a-coTRAP[H6]; a very small number (<1%) of very highly expressing GFP-positive HEK293T cells have been consistently observed when co-transfected with pCMV-tbsGFP and pEF1a-coTRAP[H6], suggesting that the EF1a promoter may not be active in this small subpopulation. Therefore, this skews GFP-repression analysis when using solely MFI as a measure of expression in the population. Thus, the Expression score (% GFP-positive×MFI) more effectively describes the global level of GFP protein expression within the gated population.

Figure 6:
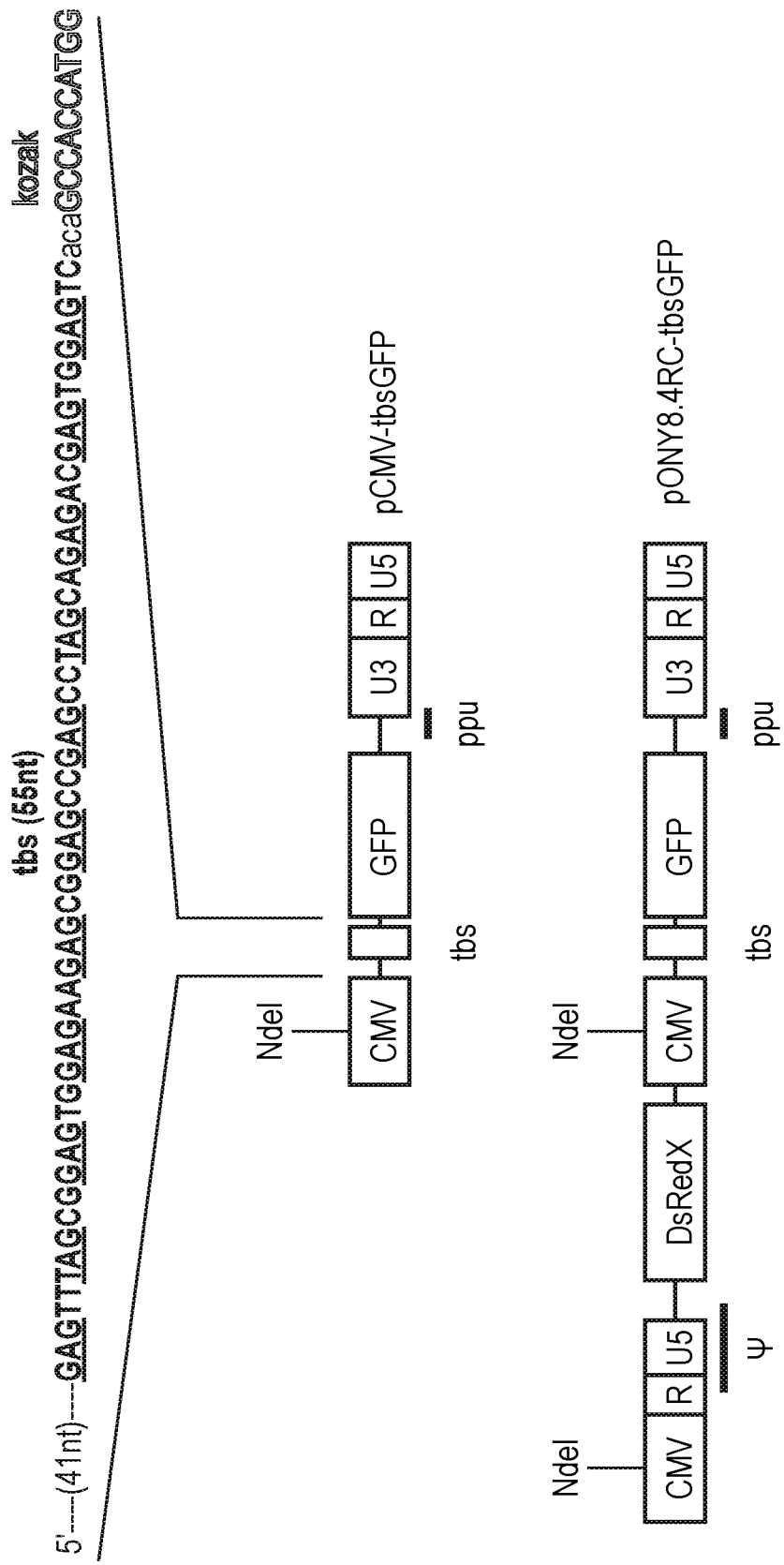

FIG. 6. Fluorescent reporter gene constructs for evaluation of the TRAP/tbs configuration. pCMV-tbsGFP was initially made from pONY8.4RC-GFP for simple evaluation. Subsequent to this, the non-SIN EIAV vector genome pONY8.4RC-tbsGFP was made to evaluate the effect of the TRAP/tbs configuration on vector activity. The tbs sequence [RAGNN]$_{11}$ initially used for evaluation, was flanked by 41 nt proximal and 9 nt distal sequences in front of the translation initiation codon.

Figure 7:
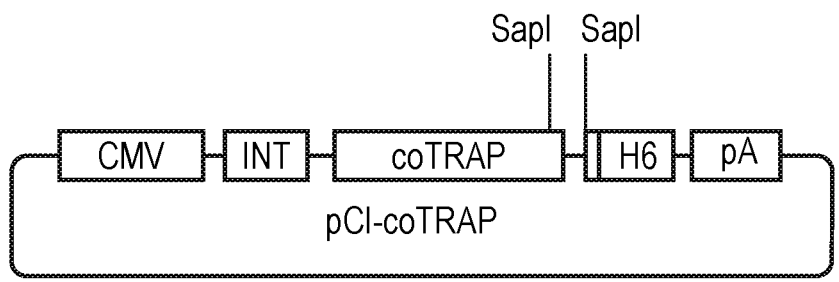
Figure 7:
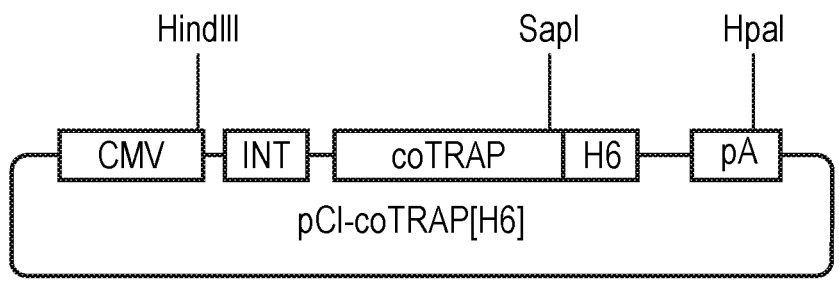
Figure 7:
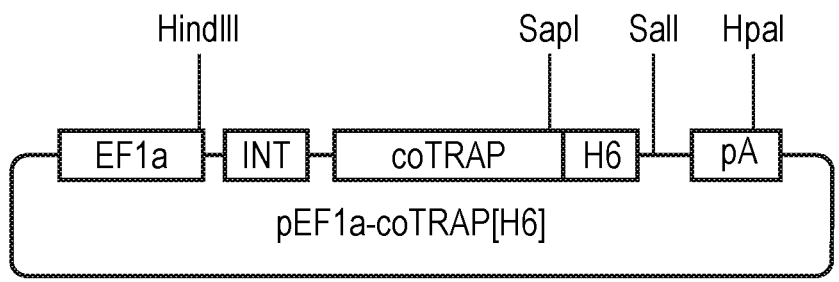
Figure 7:
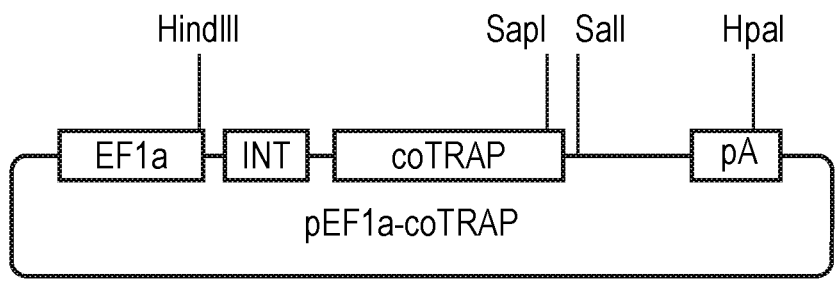
Figure 7:
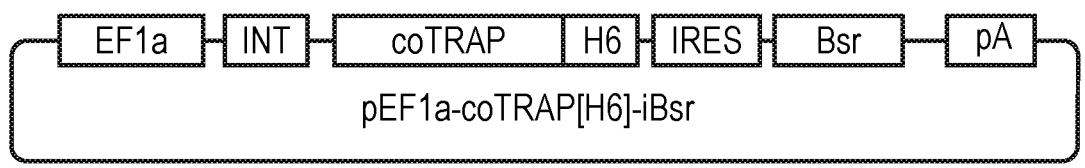

FIG. 7. TRAP-expression plasmids used in transient transfection evaluation studies and to make stable HEK293T-TRAP[H6] cell lines. Initial experiments utilized the pCI-Neo backbone to drive expression of codon/sequence-optimised TRAP of Bacillus subtilis plus/minus a C-terminal HIS$_6$-tag. The EF1a promoter sequence was subsequently used to replace the CMV promoter to yield pEF1a-coTRAP[H6]. The pEF1a-coTRAP plasmid was made by oligo-adaptor replacement of the H6 sequence in pEF1a-coTRAP[H6] such that the 3'UTRs of both EF1a promoter-driven constructs were identical, in contrast to the CMV promoter-driven constructs, wherein the 3'UTRs differ. pEF1a-coTRAP-iBsr was fully re-derived by synthesis and expresses a multicistronic mRNA encoding TRAP[H6] and a Blasticidin-resistance marker; the EMCV IRES was used to drive Bsr translation.

Figure 8:
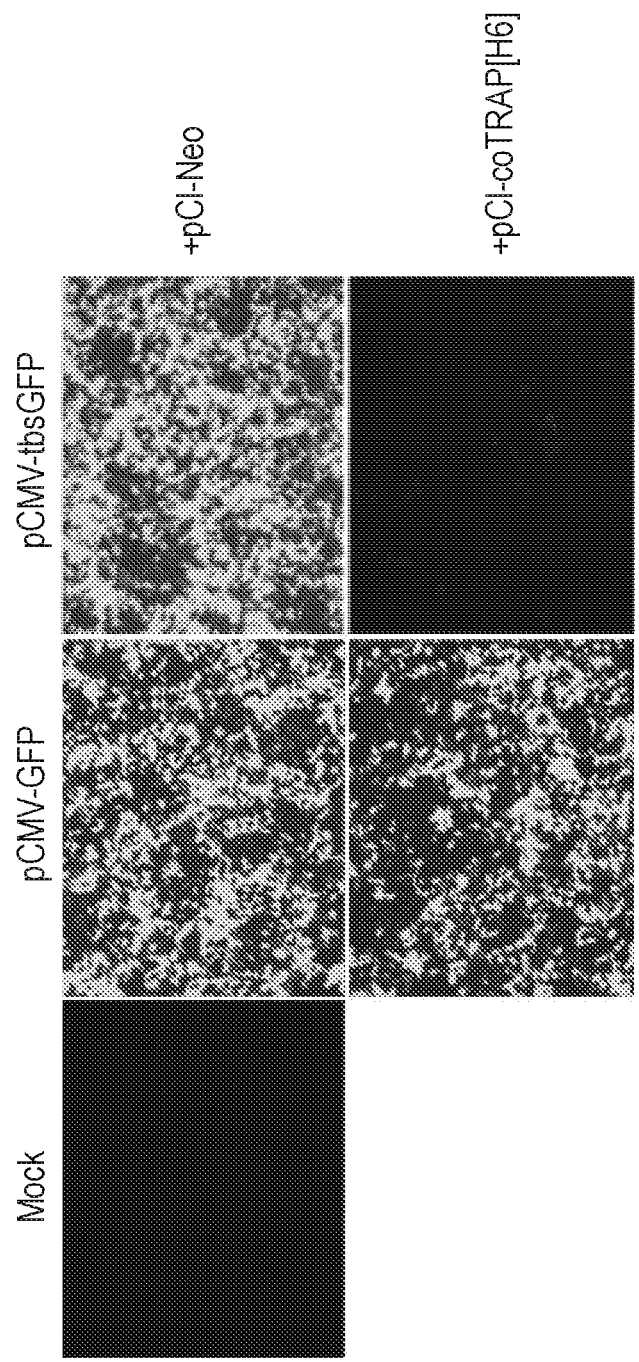

FIG. 8. Select photographs from first transient transfection evaluation study of TRAP-mediated repression of transgene expression in HEK293T cells. Photographic evidence showing the ability of pCI-coTRAP[H6] to repress expression specifically from tbs-containing 5'UTR of pCMV-tbsGFP.

Figure 9:
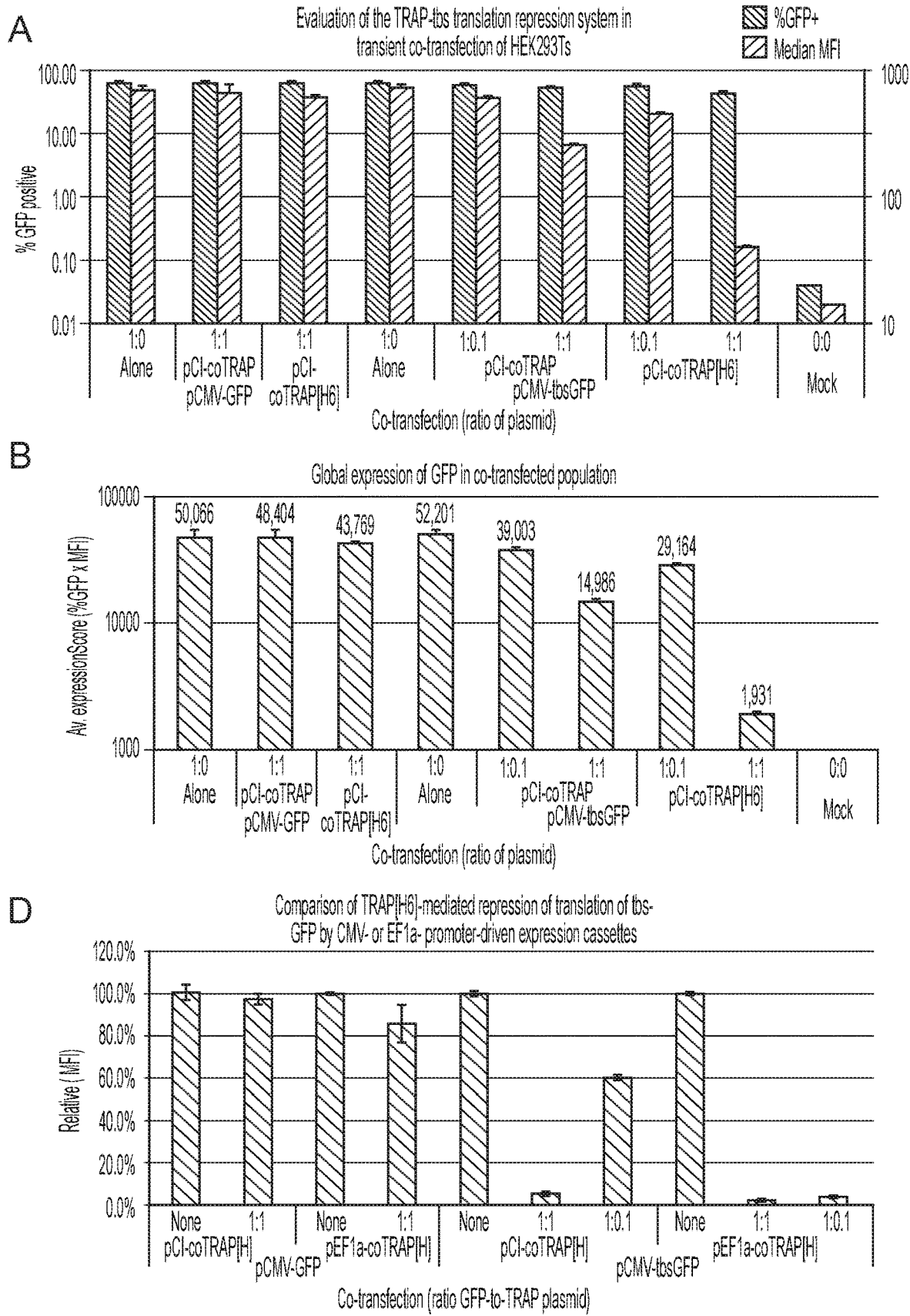
Figure 9:
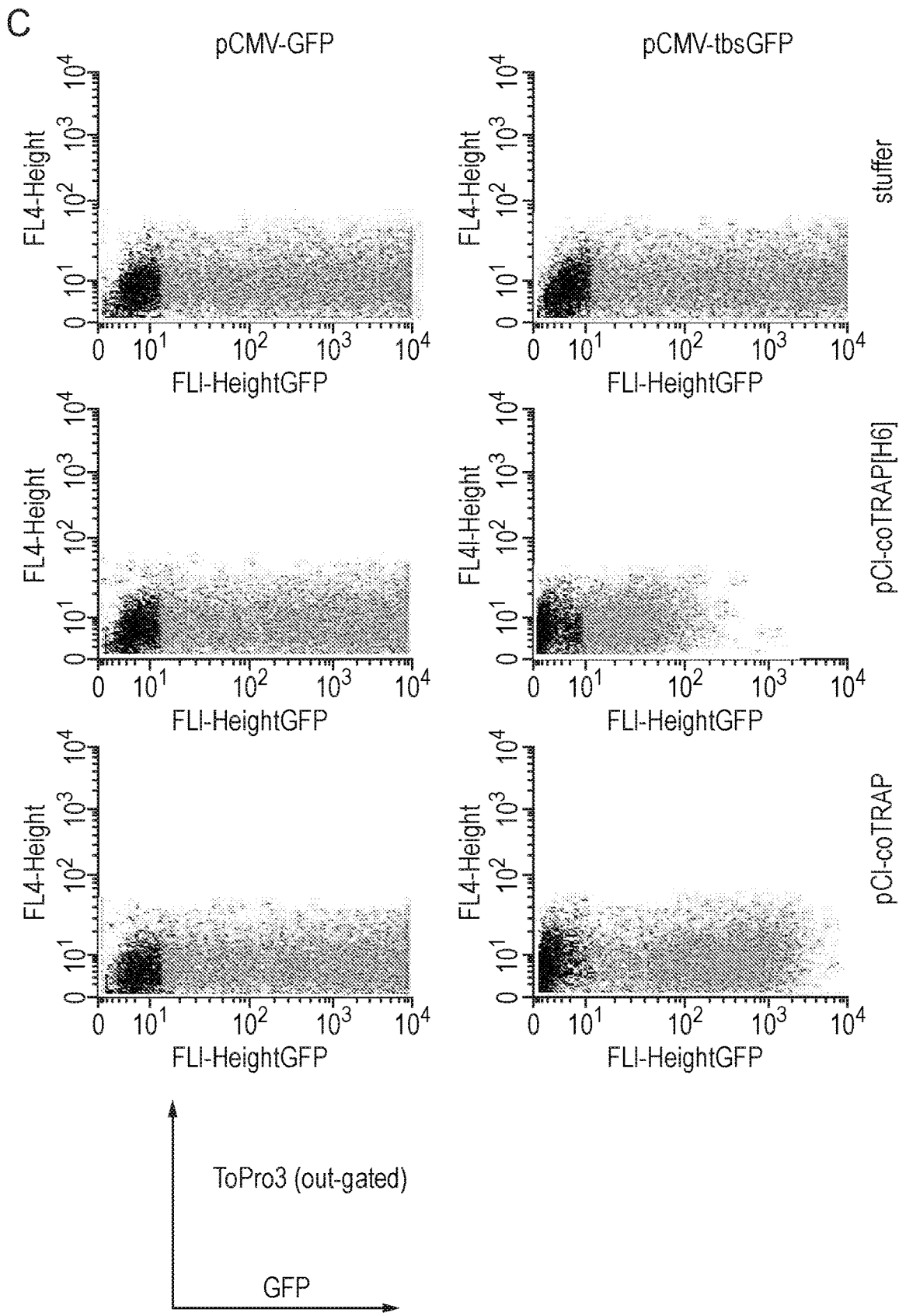

FIG. 9. Summary of flow cytometry data from first transient transfection evaluation study of TRAP-mediated repression of transgene expression in HEK293T cells.

A. Histogram of % positive GFP population and median fluorescence intensity (ArbU) plotted on separate axes. Neither TRAP nor TRAP[H6] had any impact on GFP expression from pCMV-GFP. TRAP[H6] significantly reduced GFP expression from pCMV-tbsGFP at a ratio of 1:1, and in a dose-dependent manner. TRAP appeared less capable of repressing expression from pCMV-tbsGFP.

B. Expression scores were derived for each co-transfected cell culture in order to better asses the magnitude of TRAP-mediated repression. %-positive cell multiplied by the MFI gives an approximation of the total amount of GFP produced per culture. The greatest level of GFP repression by TRAP [H6] as judged by the Expression Scores was ~25-fold in this experiment.

C. Representative flow cytometry dot plots of reporter plasmids co-transfected with pCI-coTRAP or pCI-coTRAP [H6] at 1:1 ratio.

D. GFP Median fluorescence intensityl of cotransfected HEK293T cells with GFP-reporter plasmids and EF1a promoter or CMV promoter driven TRAP[H6] plasmids relative to no TRAP-expression plasmid (stuffer). Near maximal GFP repression from pCMV-tbsGFP was possible using pEF1a-coTRAP[H6] at a 1:0.1 molar ratio of GFP:TRAP plasmid, which was not possible with pCI-coTRAP[H6].

Figure 10:
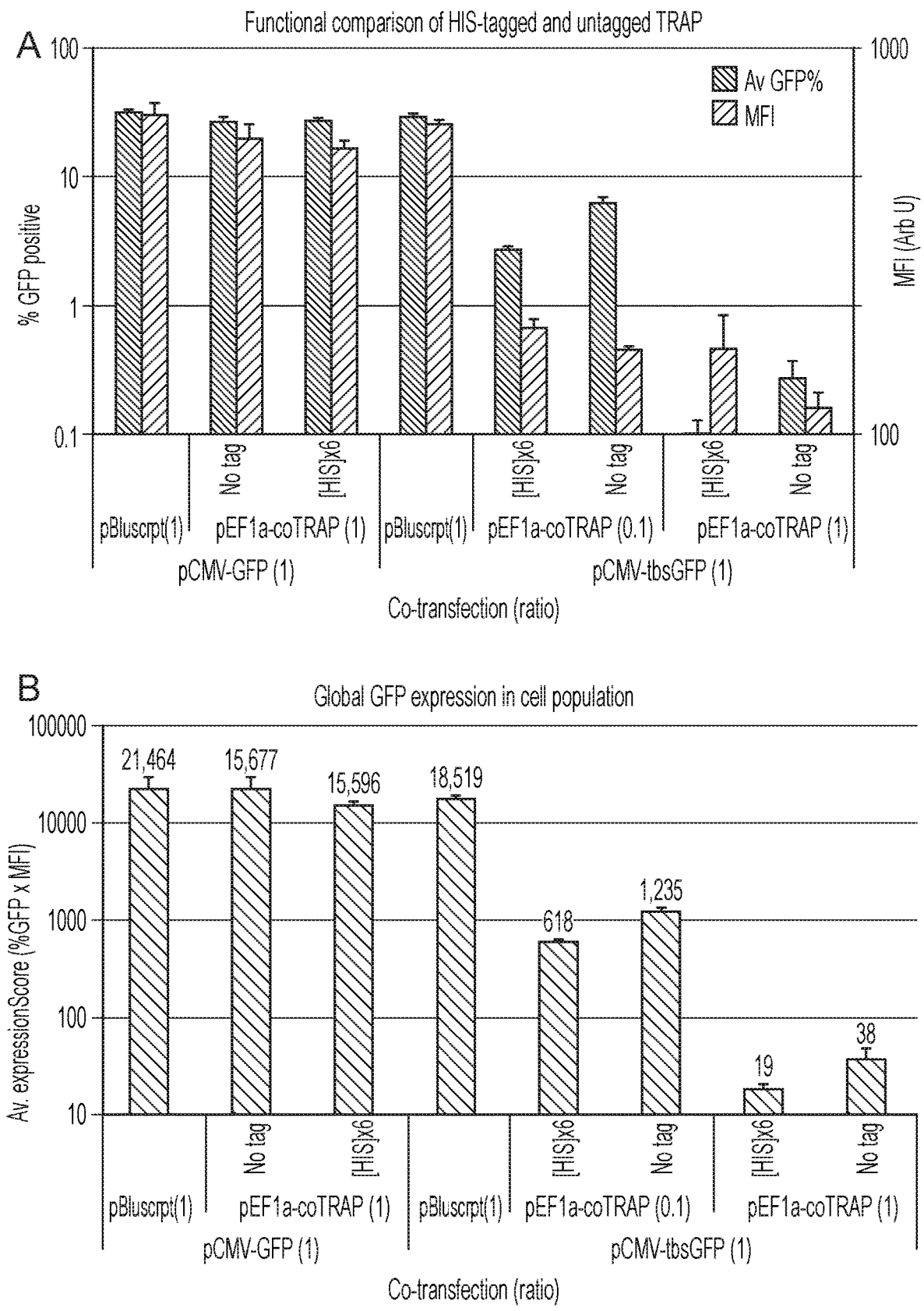

FIG. 10. A functional comparison of HIS$_6$-tagged TRAP and untagged TRAP.

A. Histogram of % positive GFP population and median fluorescence intensity (ArbU) plotted on separate axes. HIS$_6$-tagged or untagged TRAP-expression or stuffer plasmid was co-transfected with either of the GFP reporter plasmids at the indicated ratios (brackets) in triplicate. Transfected cells were analysed by flow cytometry.

B. Expression Scores (MFI×% GFP) give an overall estimate of the effect of TRAP-mediated repression of GFP in the population. The HIS$_6$ C-terminal tag affords a minimal 2-fold increase in TRAP's ability to repress GFP expression by pCMV-tbsGFP.

Figure 11:
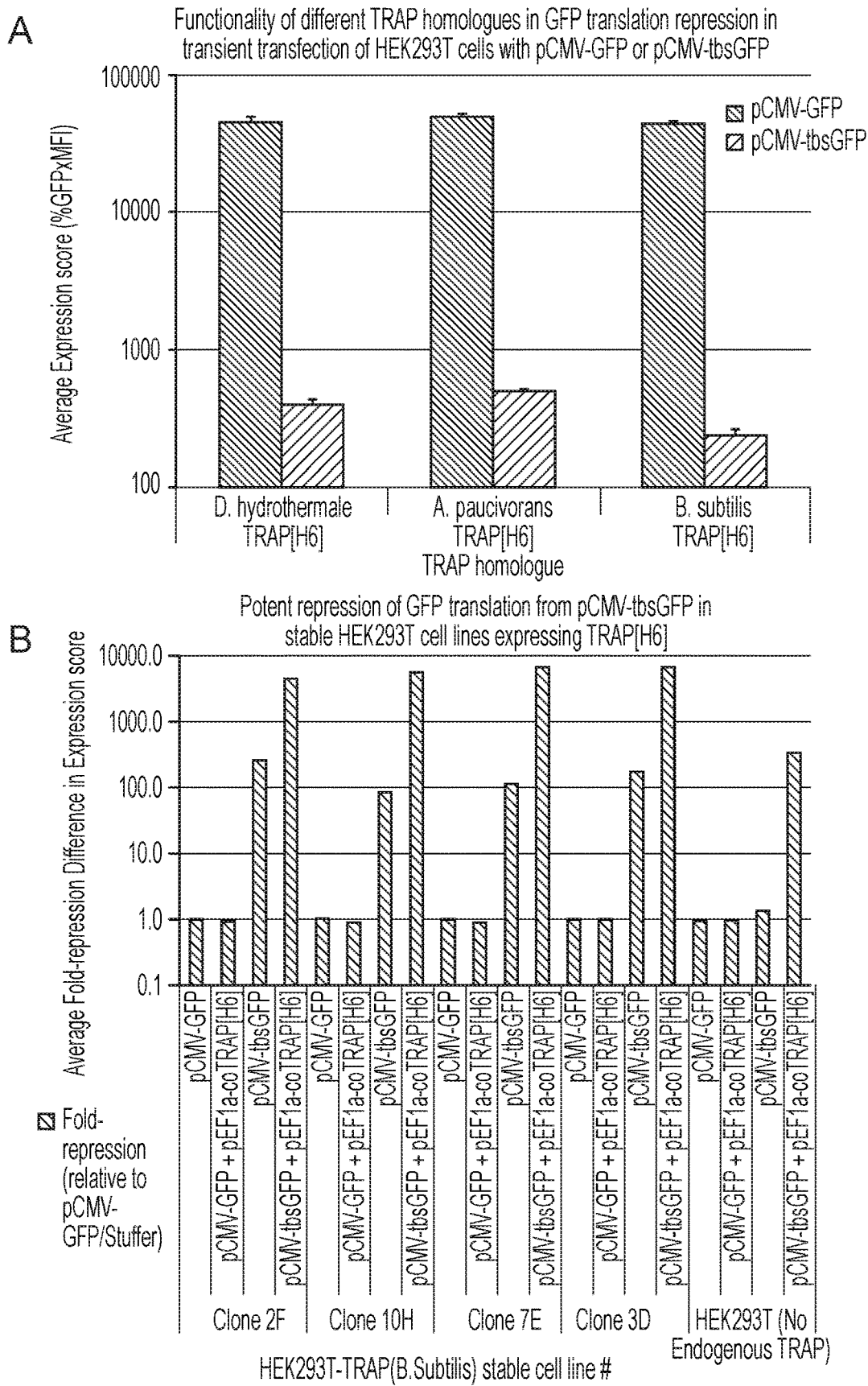

FIG. 11. Ability of different TRAP homologues to repress transgene expression and evaluation of HEK293T-TRAP cell lines.

A. TRAP ORFs from Desulfotomaculum hydrothermale and Aminomonas paucivorans were codon/sequence optimised and cloned into the pEF1a-plasmid backbone. TRAP-expression or stuffer plasmid was co-transfected with either of the GFP reporter plasmids at the indicated ratios (brackets) in triplicate. Transfected cells were analysed by flow cytometry. Average Expression Scores were generated for each transfection condition.

B. Four HEK293T-TRAP[H6] cell lines were compared for their ability to repress transgene expression from pCMV-tbsGFP by transient transfection in triplicate. pCMV-GFP or pCMV-tbsGFP were cotransfected with either stuffer plasmid or pEF1a-coTRAP[H6]. Cells were analysed by flow cytometry and average Expression Scores generated for each condition. Average fold-repression was generated by dividing the Expression Scores of pCMV-GFP/stuffer by the Expression Scores of the other conditions.

Figure 12:
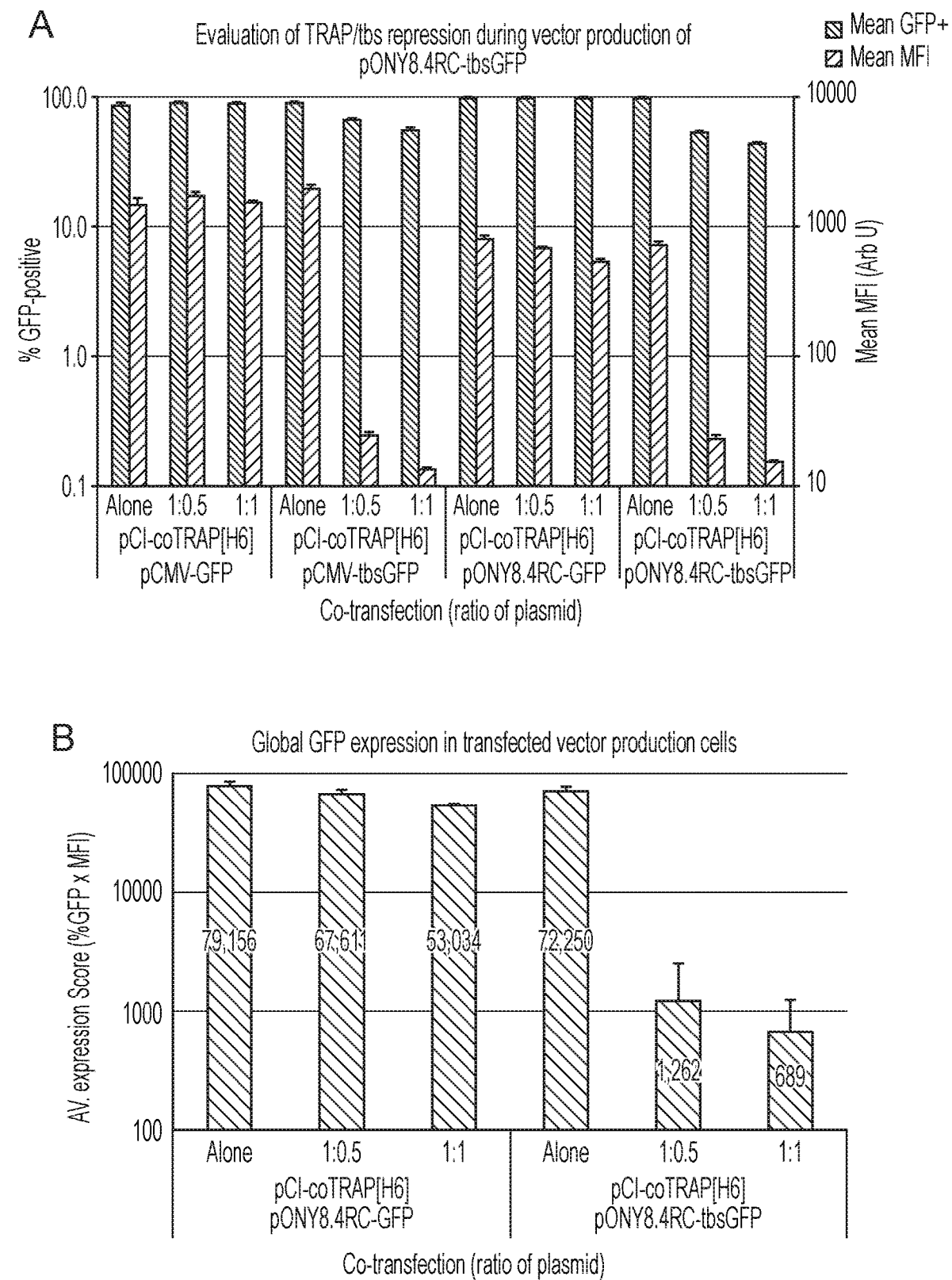
Figure 12:
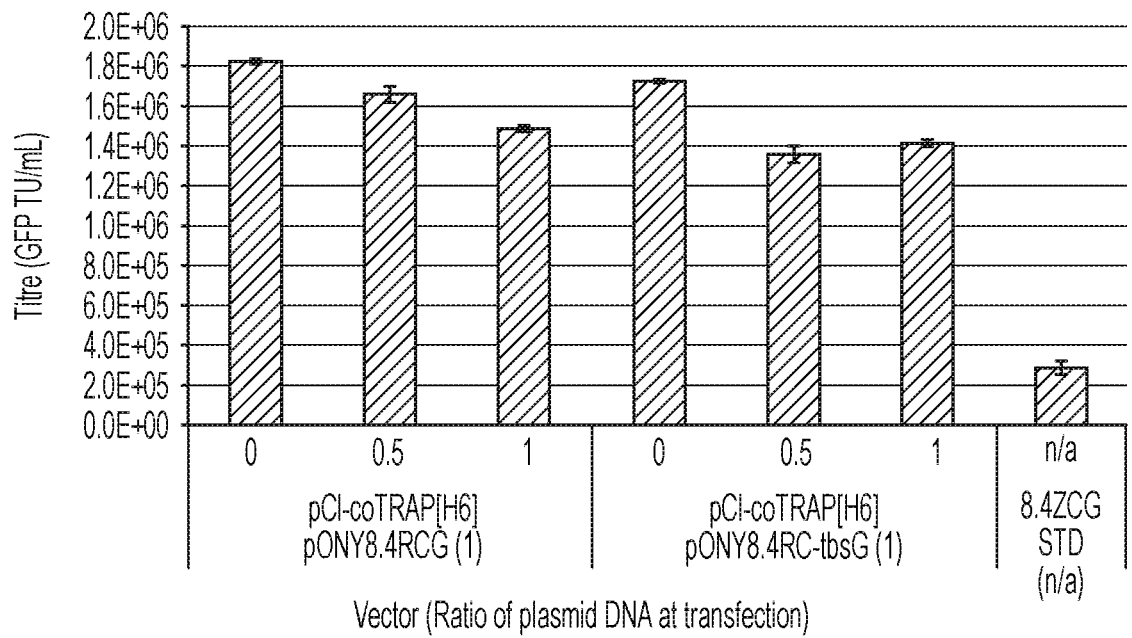

FIG. 12. Summary of flow cytometry data from the evaluation of the TRAP-tbs system in retroviral vector production.

A. Histogram of % positive GFP population and median fluorescence intensity (ArbU) plotted on separate axes. TRAP[H6] expression plasmid was co-transfected into HEK293T cells with either the single GFP reporter plasmids or the non-SIN EIAV vector genome plasmids (see FIG. 6) at the indicated ratios. Vector production was achieved by additional co-transfection of Gag/Pol and VSVG expression plasmids with the non-SIN EIAV vector genome plasmids. GFP repression during the production of vector was very similar to the single GFP reporter context and was dependent on the presence of both TRAP and the tbs sequence.

B. Expression Scores (MFI×% GFP) give an overall estimate of the effect of TRAP-mediated repression of GFP in the population.

C. Vector titres on D17 cells. Vector supernatants generated from the pONY8.4RC-(tbs)GFP vector transfection were used to transduce D17 cells and flow cytometry performed 4 days later. The TRAP/tbs configuration surprisingly had minimal impact on vector titres indicating that the single-round life cycle of the vector particles was not affected by the putative TRAP/tbs interaction on the vector RNA genome.

Figure 13:
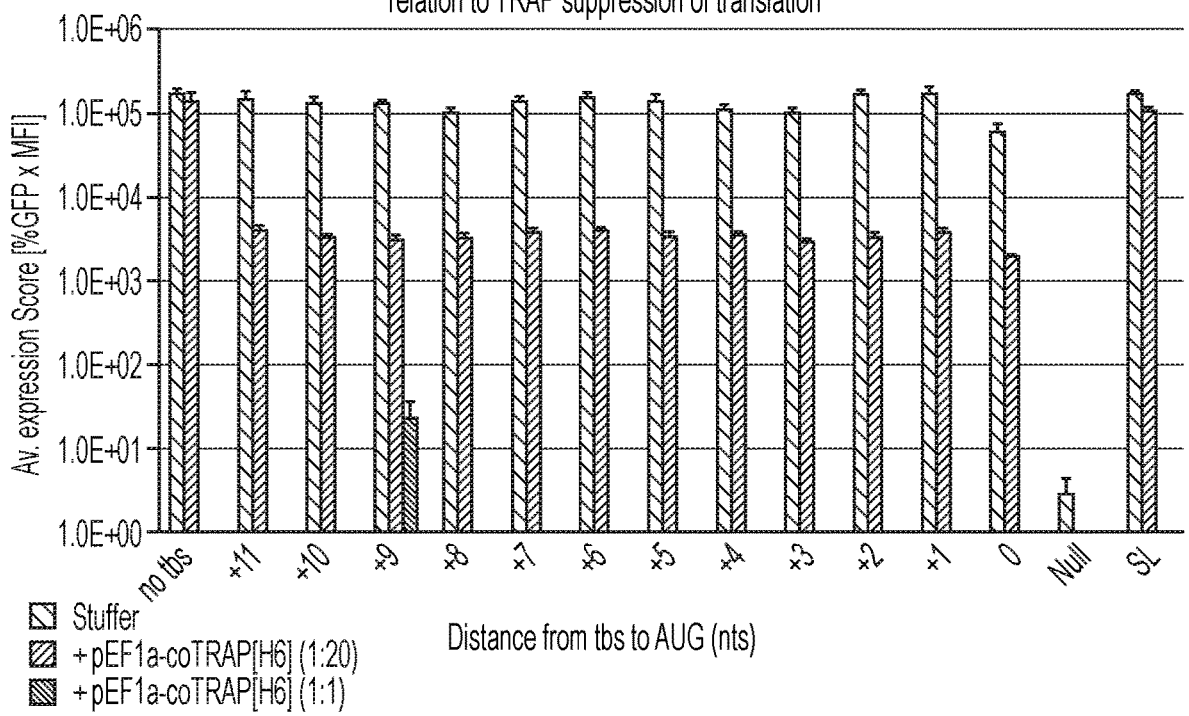

FIG. 13. Summary of flow cytometry data from testing the short spacing requirements between tbs and transgene AUG codon in the TRAP/tbs configuration.

A. A schematic showing the spacing variants tested within the pONY8.4RC-tbsGFP-based vector genome. The 'Null' variant had the AUG changed to a stop codon to control for any GFP expression that might be derived from the full length vector genome RNA i.e. driven from the 'external' CMV promoter (see FIG. 6). The 5'Stem-loop (SL) sequence was derived from the trp operon leader sequence in Bacillus subtilis. Underlined nucleotides denote the kozak sequence.

These spacer variant vector reporter plasmids were cotransfected into HEK293T cells with either stuffer plasmid or pEF1a-coTRAP[H6] at the indicated molar ratio (brackets) in triplicate. Cells were analysed by flow cytometry.

B. Global GFP expression for each condition was assessed by generating average Expression Scores. The efficiency of GFP repression was essentially the same for spacing variants +11 to +1. The '0' variant appeared to be slightly defective for GFP expression in the absence of TRAP[H6]. Unexpectedly, the 5'SL variant was totally unresponsive to TRAP-mediated repression suggesting that the 5'SL perturbs the TRAP-tbs interaction in this system.

Figure 14I:
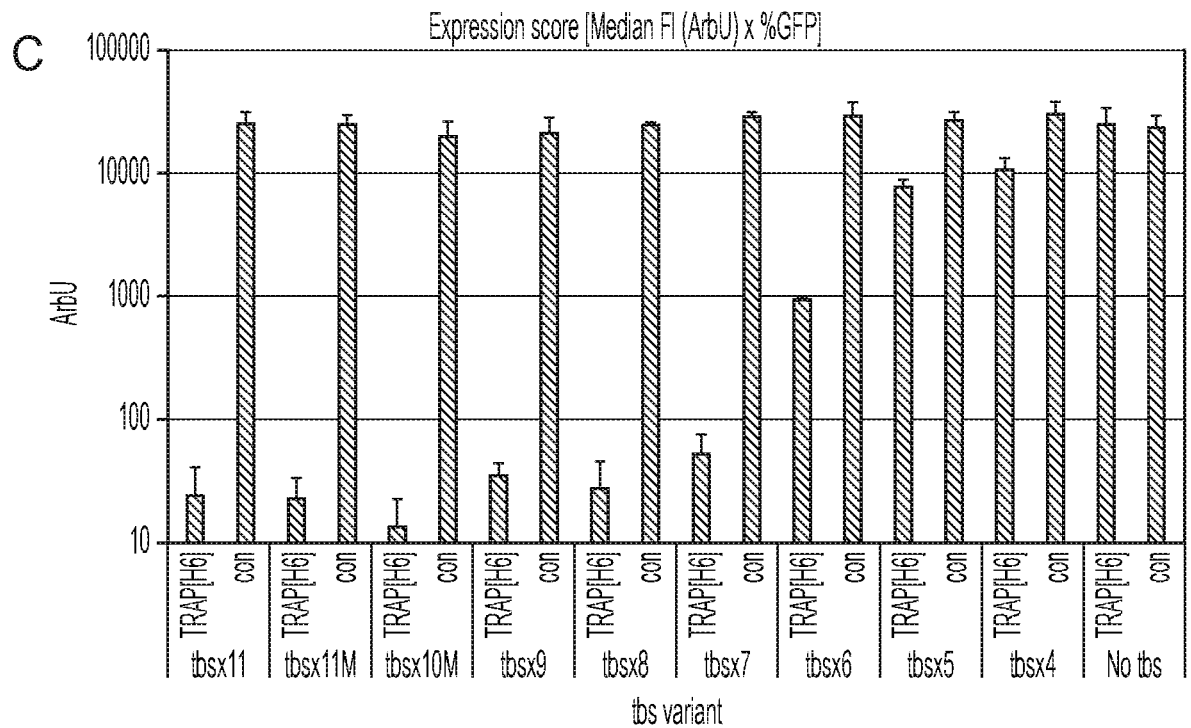
Figure 14I:
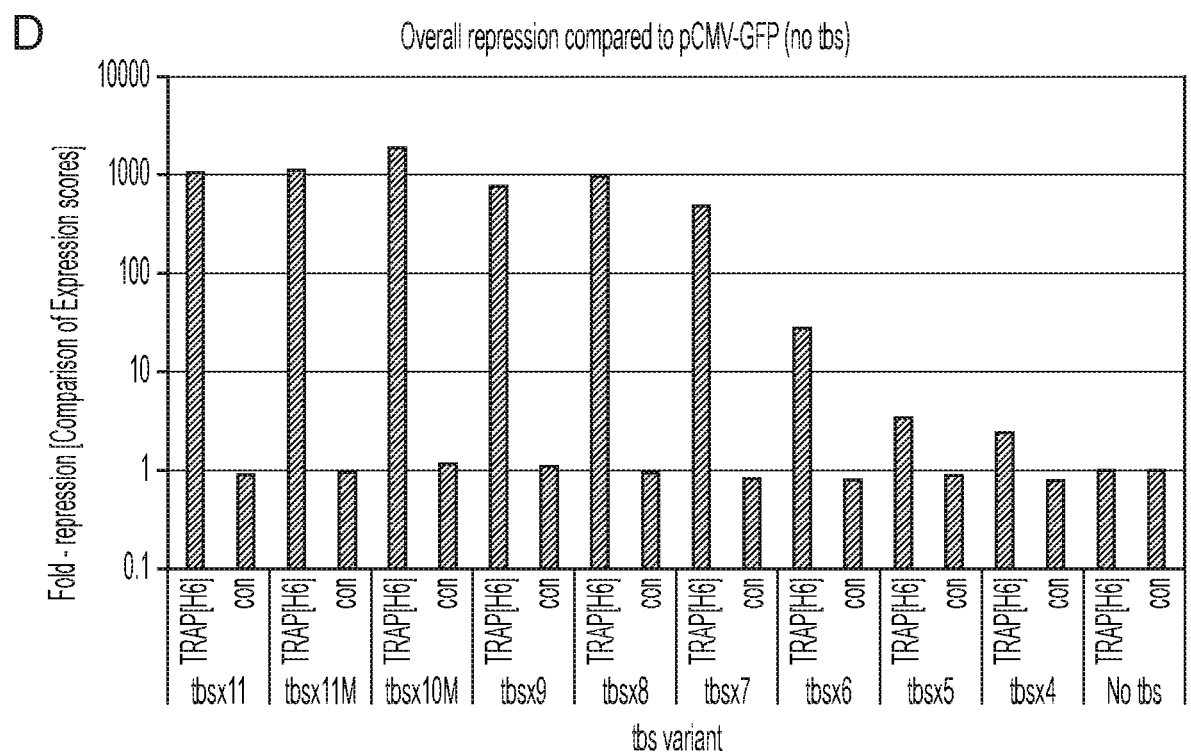
Figure 14I:
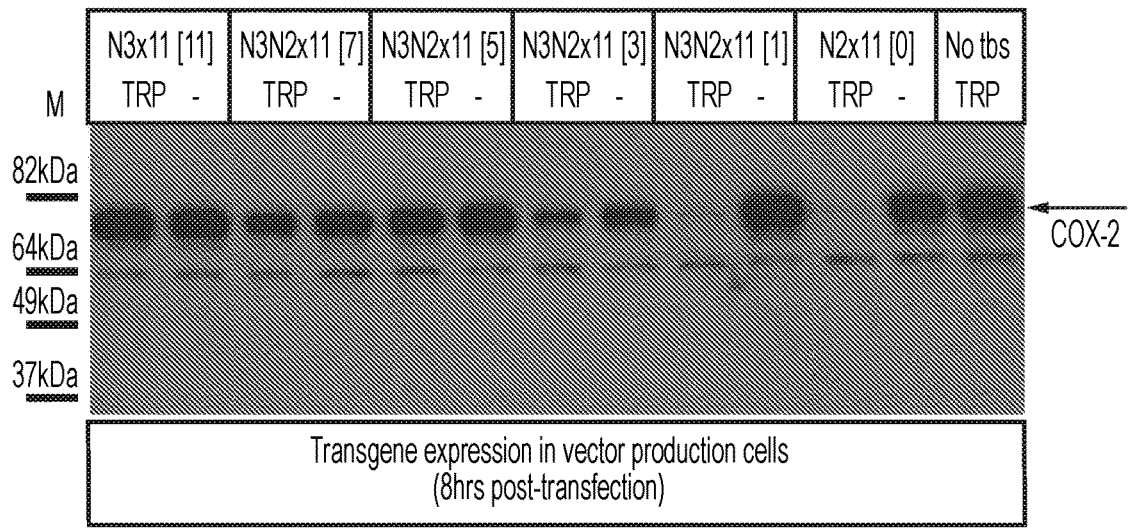
Figure 14I:
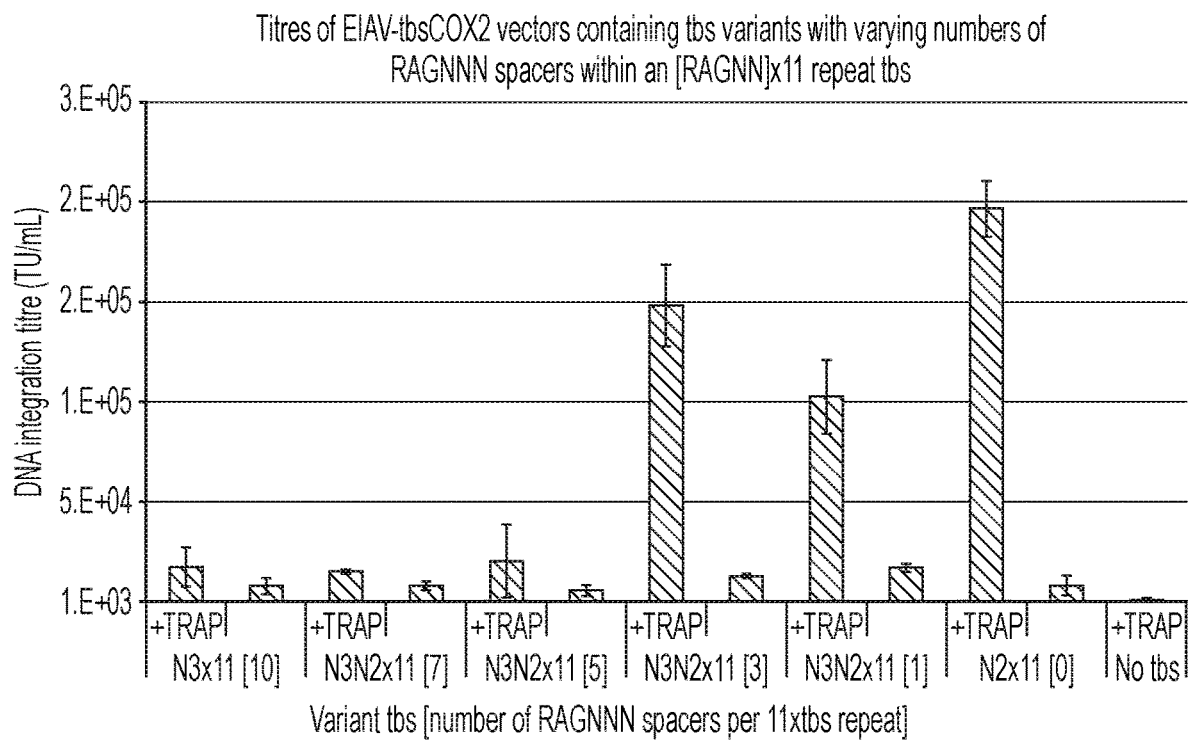

FIG. 14i. Defining the minimal number of RAGNN repeats in the TRAP-binding sequence necessary for the TRAP/tbs configuration to function.

A. The tbs variant sequences cloned into pCMV-tbsGFP for evaluation. The initial tbs sequence evaluated in the study was sequence optimized between the $10^{th}$ and $11^{th}$ RAGNN repeat altering a TG spacer to AA. Therefore variants tbsx11M and tbsx10M were designed such that a potential cryptic SD site is removed. The RAGNN repeats were serially deleted from the 3' end of the tbsx11M variant (11 to 4 repeats only), whilst maintaining the good translation context of the GFP reporter. The repeat-variant tbs-GFP reporter plasmids were cotransfected into HEK293T cells with either stuffer plasmid or pEF1a-coTRAP[H6] at a ratio of 10:1 GFP:TRAP plasmid in triplicate. Cells were analysed by flow cytometry.

B. Histogram of % positive GFP population and median fluorescence intensity (ArbU) plotted on separate axes.

C. Average Expression Scores for each condition were calculated and used as a measure of global GFP expression within the transfected populations.

D. Fold-repression factors were generated by dividing the Expression Scores for each tbs variant transfected with stuffer plasmid by that of the pEF1a-coTRAP[H6] transfection. Maximal repression is possible with 8 RAGNN repeats and the 7 RAGNN repeat tbs allowed near-maximal repression. The 6 RAGNN repeat tbs allowed an intermediate level of transgene repression, whereas 5 and 4 RAGNN repeat tbs sequences were minimally functional.

FIG. 14ii. Assessment of the functionality of tbs sequences with one or more RAGNNN repeats in a background of an 11 RAGNN repeat tbs.

A. The tbsx11M tbs sequence, referred to as $N_2\times11$ in this experiment, was used as the basis for modification with progressively more RAGNNN repeats replacing RAGNN repeats from the centre of the tbs. Thus, the variants progressively contained 1, 3, 5, 7 or 10 RAGNNN repeats (the 3' terminal ct nucleotides do not count as spacers so $N_3\times11$ contains 10 NNN spacing nucleotides). These tbs variants were cloned into the therapeutic vector genome plasmid pONYK-tbsCOX2 (see FIG. 18i), replacing the existing tbs.

B. These tbs variant-containing vector genome plasmids were used to make vector by cotransfection with EIAV vector packaging components and with either stuffer plasmid or pEF1a-coTRAP[H6] at a ratio of 5:1 vector genome: TRAP plasmid. Immunoblotting to COX-2 was carried out on cell lysates from end-of-production cells.

FIG. 14iii. Assessment of the functionality of tbs sequences with one or more RAGNNN repeats in a background of an 11 RAGNN repeat tbs:COX2 protein levels in vector production cells at 8 hours post-transfection. Previously, COX2 levels in end-of-production cells (~48 hours post-transfection) were analysed (see FIG. 14iiB). In order to test if TRAP-tbs mediated repression differed temporally during vector production, production cells were analysed 8 hours post-transfection for COX2 levels by immunoblot. The pattern of expression of COX2 from the different constructs encoding the $N_3N_2$ tbs variants was the same at 8 hours post-transfection as that observed at ~48 hours post-transfection (FIG. 14iiB). This indicates that the degree of repression of TRAP on a given tbs sequence does not change appreciably during vector production.

FIG. 14iv. Assessment of the functionality of tbs sequences with one or more RAGNNN repeats in a background of an 11 RAGNN repeat tbs:vector titres. The crude vector supernatants generated from EIAV-tbsCOX2 producing cells in experiments associated with FIG. 14ii and FIG. 14iii, were titrated by DNA integration assay to determine the impact of COX2 repression during production on vector activity. The data indicate that only modest repression of COX2 during production (see $N_3N_2\times11[3]$ in FIG. 14iiB and FIG. 14iii) is required to substantially enhance EIAV-COX2 vector titre.

Figure 14V:
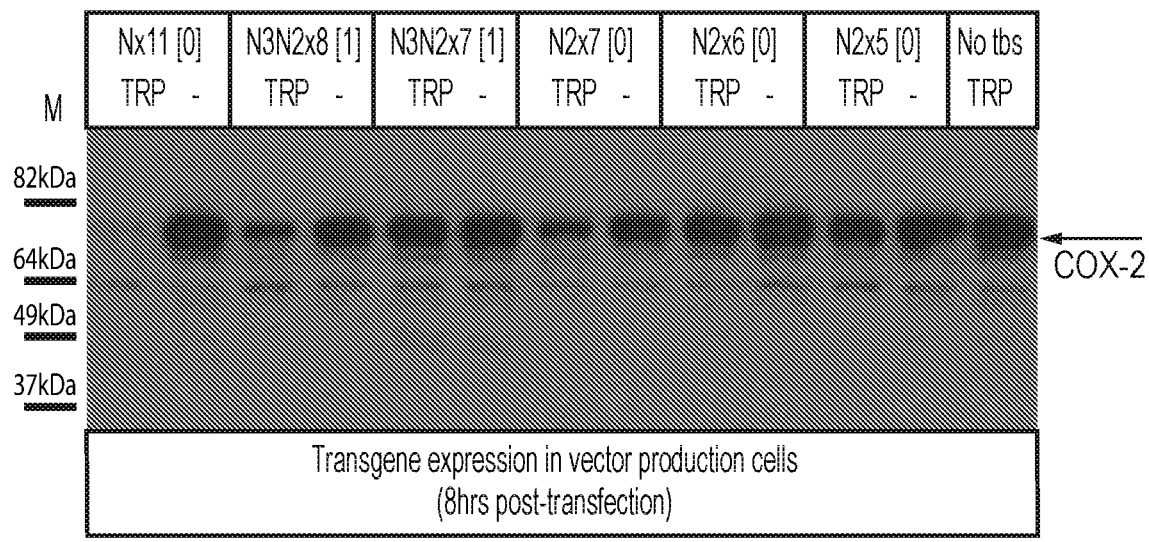

FIG. 14v. Assessment of the functionality of tbs sequences with one or more RAGNNN repeats in a background of x7 and x8 RAGNN repeat tbs.

A. Previous data indicates that maximal or near maximal levels of transgene repression can occur using tbs comprising 8 or 7 RAGNN repeats. A single RAGNNN repeat was inserted into 8×RAGNN and 7×RAGNN tbs to assess the impact on function of these shorter tbs sequences. These were compared alongside RAGNN-containing tbs comprising ×11, ×7, ×6 and ×5 repeats. These tbs variants were cloned into the therapeutic vector genome plasmid pONYK-tbsCOX2 (see FIG. 18i), replacing the existing tbs.

B. These tbs variant-containing vector genome plasmids were used to make vector by co-transfection with EIAV vector packaging components and with either stuffer plasmid or pEF1a-coTRAP[H6] at a ratio of 5:1 vector genome: TRAP plasmid. Immunoblotting to COX-2 was carried out on cell lysates at early times during vector production (i.e. ~8 hours post-transfection). The data show that an RAGNNN repeat can be "tolerated" within an ×8 repeat tbs comprising 7×RAGNN.

Figure 15:
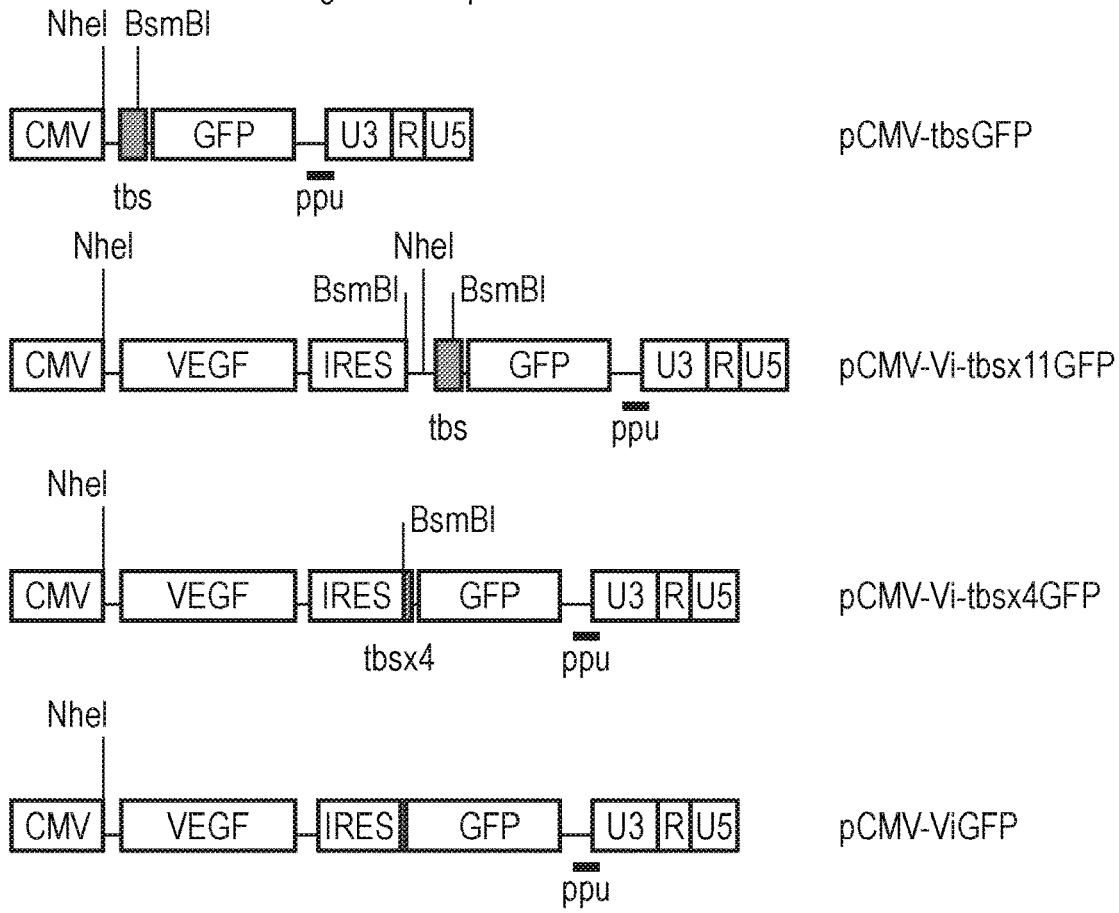
Figure 15:
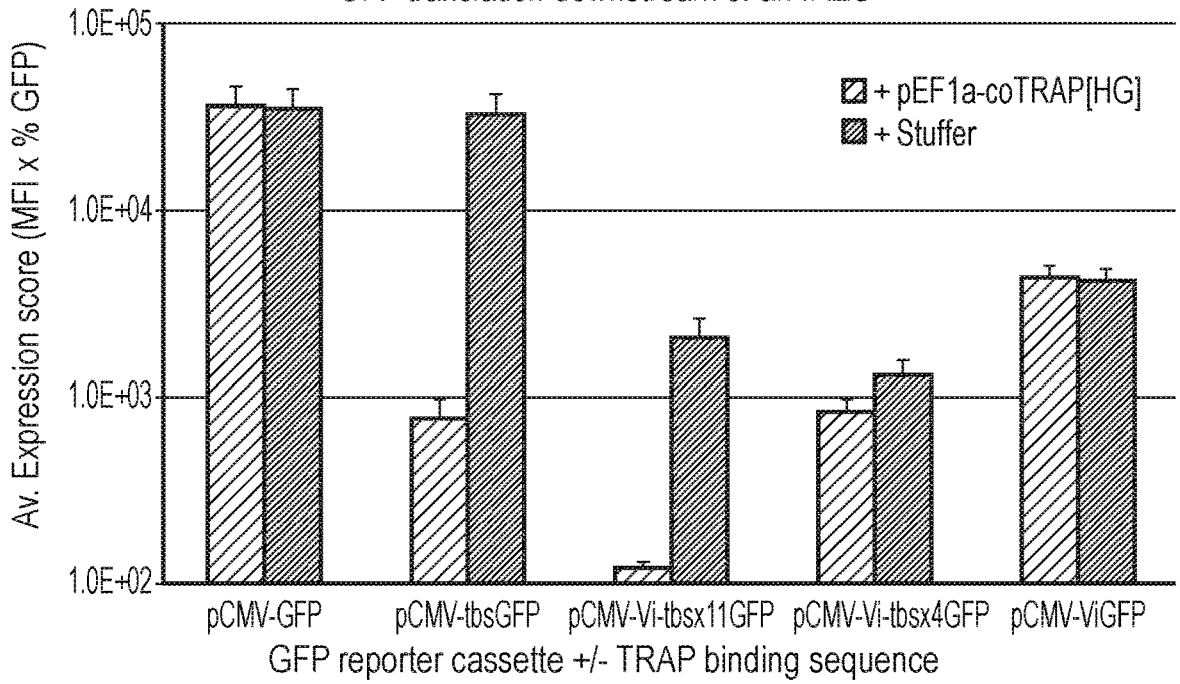

FIG. 15. Construction of IRES-tbs GFP reporter plasmids to test IRES-dependent TRAP/tbs regulation of gene expression.

A. The IRES-tbs GFP reporter constructs were made so that expression from the distal cistron (GFP) would report the degree of repression by TRAP. The distance between the IRES element and the tbs in pCMV-Vi-tbsx11G was 44 nt (encoding spacing nucleotides), whereas this distance was reduced to 4 nt in pCMV-Vi-tbsx4G. pCMV-ViGFP was cloned as a 'no tbs' control.

B. The IRES-tbs GFP reporter plasmids were cotransfected into HEK293T cells with either stuffer plasmid or pEF1a-coTRAP[H6] at a ratio of 10:1 GFP-reporter:TRAP plasmid in triplicate. The single ORF GFP reporter plasmids were included in parallel as a control for TRAP-mediated repression. Cells were analysed by flow cytometry. Average expression scores for each condition were calculated and used as a measure of global GFP expression within the transfected populations. TRAP was capable of repressing GFP expression directed from an IRES at a similar magnitude to 5'CAP-mediated expression.

Figure 16:
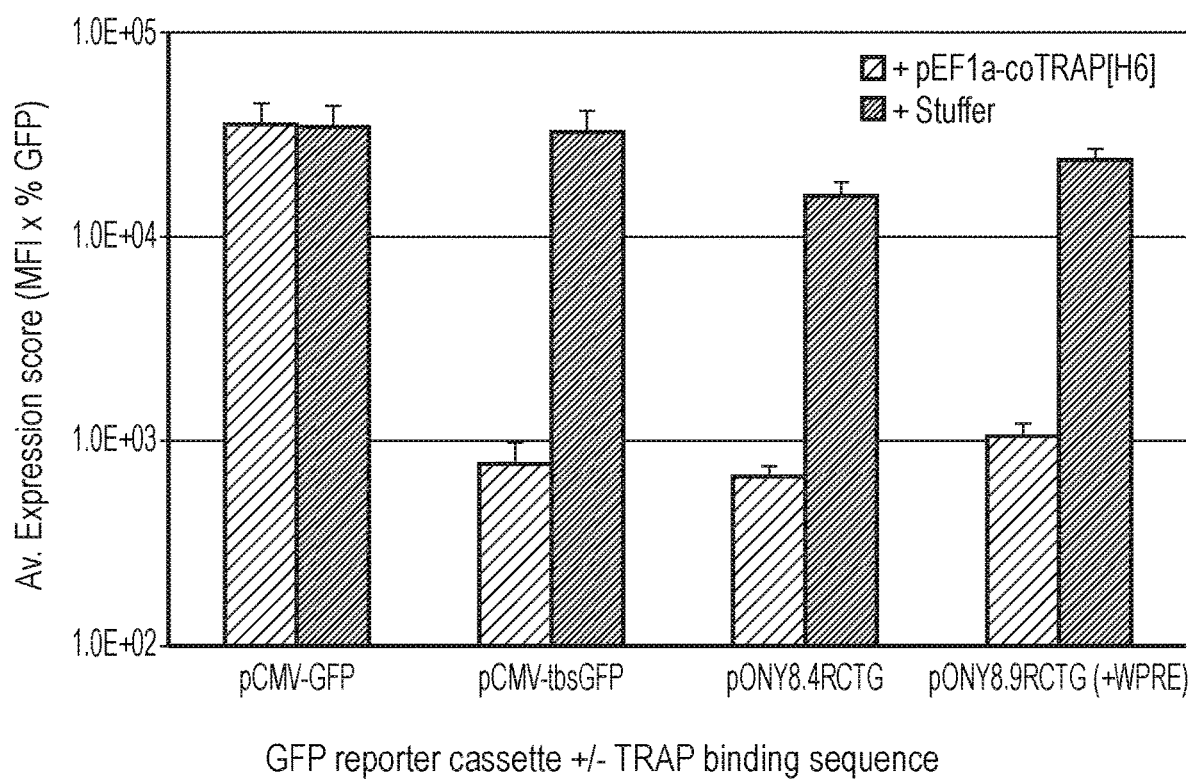

FIG. 16. Production of EIAV SIN-vector containing the WPRE using the TRIP system. The vector genome plasmid pONY8.9RC-tbsGFP(+WPRE) was tested for any impact of the WPRE on the TRAP/tbs configuration. Cells were analysed by flow cytometry. Expression scores were generated for cell populations co-transfected with vector genomes pONY8.4RC-tbsGFP or pONY8.9RC-tbsGFP(+WPRE)

together with pEF1a-coTRAP[H6] or stuffer plasmid. Scores are derived from multiplication of % GFP and median fluorescence intensity values to give a measure of GFP expression in the total population.

Figure 17I:
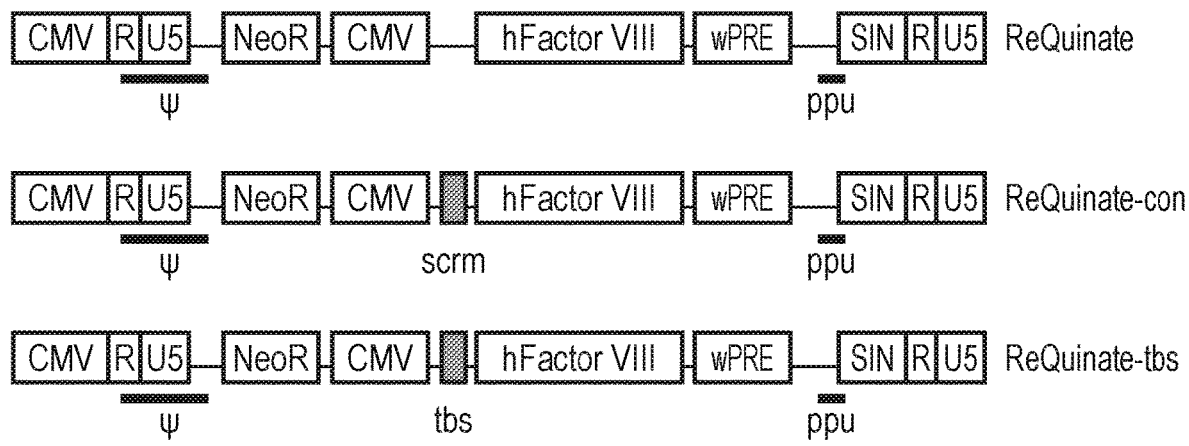
Figure 17I:
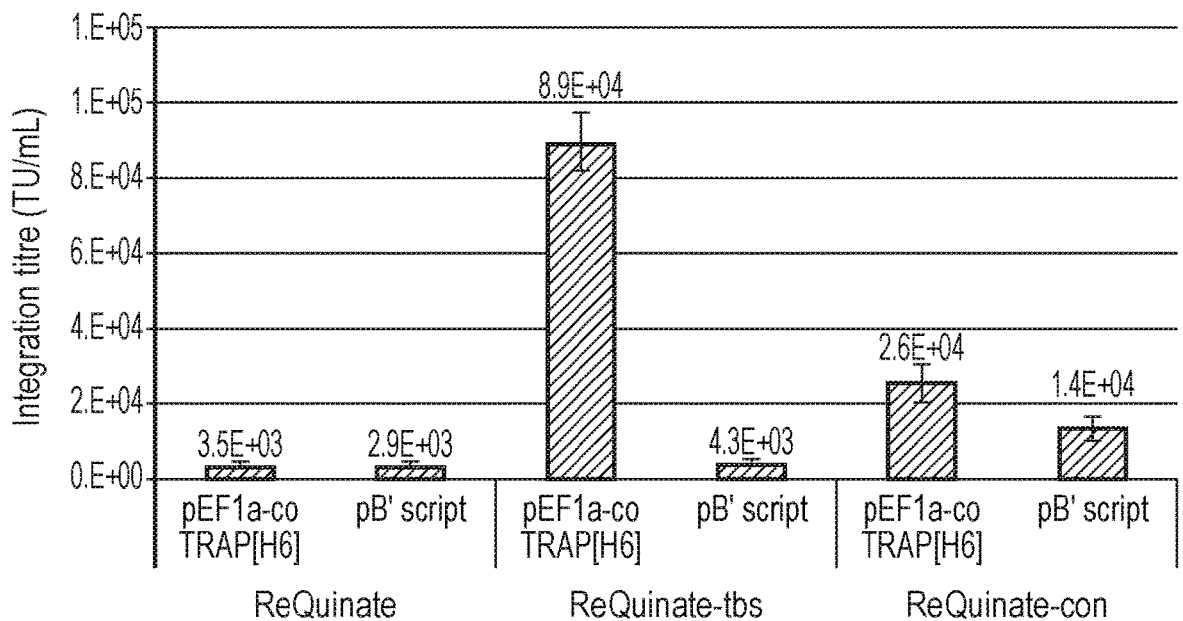
Figure 17I:
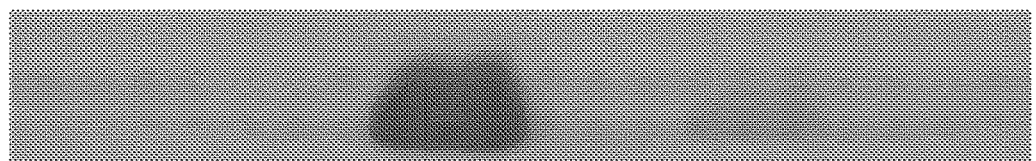
Figure 17I:
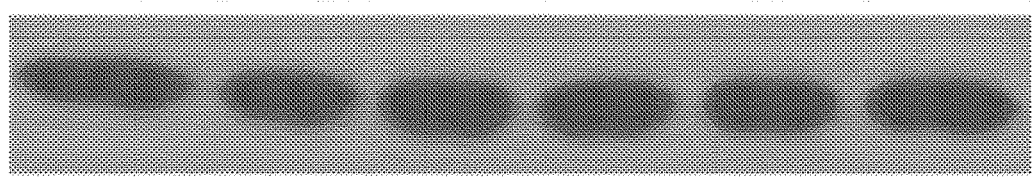

FIG. 17i. A schematic of therapeutic vector genomes based on ReQuinate® modified to contain the tbs. ReQuinate®, a vector for treatment of haemophilia A, encodes the human Factor VIII gene. It is known that Factor VIII impedes VSV-G incorporation into vector virion particle, dramatically reducing vector activity. The tbs or scrambled tbs was cloned into the vector genome to generate ReQuinate-tbs and ReQuinate-con vectors respectively.

FIG. 17ii. Improved ReQuinate® titres using the TRIP system. The ReQuinate-based vectors were produced under standard vector protocol using the TRIP system in HEK293T cells:vector genome plasmids were cotransfected with pEF1a-coTRAP[H6] at a ratio of 5:1, along with EIAV vector packaging components. Vector supernatant was harvested and titrated by integration assay as well as concentrated ~70-fold by centrifugation, followed by PERT assay and then immunoblot to VSV-G and p26 (EIAV capsid).

A. ReQuinate®-tbs vector titres were enhanced 30-fold over ReQuinate® as judged by DNA integration assay, and this was dependent on the presence of TRAP during vector production. The particle to infectivity ratios of vectors were also improved (data not shown).

B. Immunoblot of VSV-G within concentrated vector samples. Vector titres correlated with the degree of VSV-G incorporation into vector virions; hFactor VIII is known to dramatically inhibit the amount of VSV-G incorporated into retroviral vector virions.

C. Immunoblot of vector cores (p26—capsid) demonstrates that equal numbers of vector virions were loaded per well.

Figure 18I:
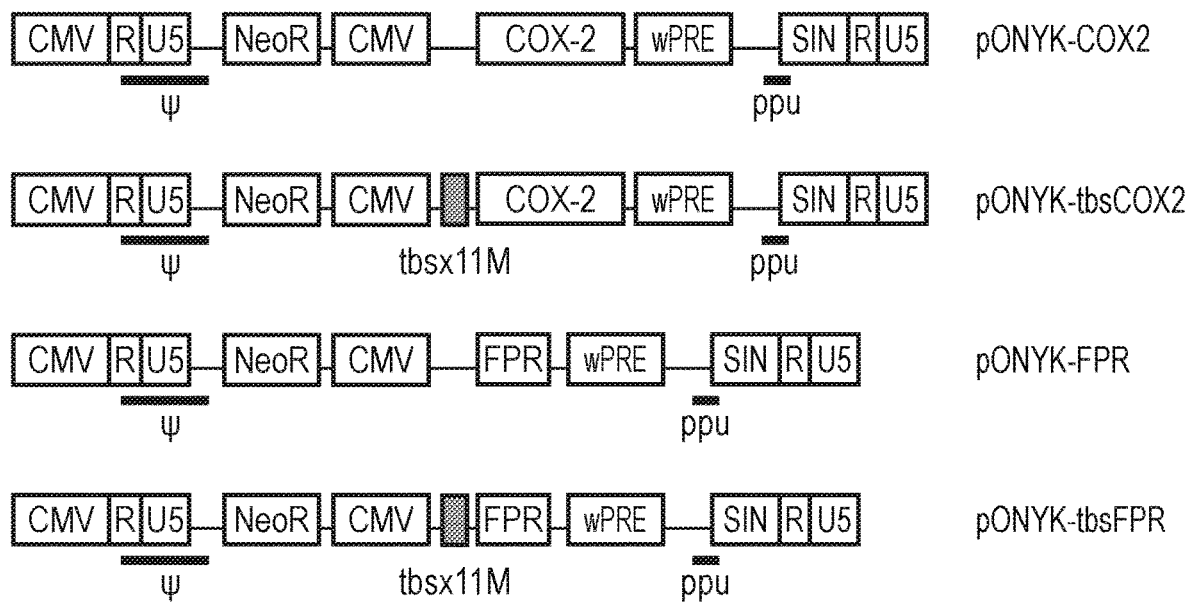

FIG. 18i. A schematic of vector genomes encoding either COX2 or FPR. The tbsx11M variant was cloned into the single gene expression vectors. Note that the 5'UTR sequences +/−tbsx11M are entirely different, in contrast to the control tbs-scrambled-containing 5'UTRs used in the ReQuinate® study.

FIG. 18ii. Improved single gene COX2 vector titres using the TRIP system. The single gene COX-2 based vectors were produced using the TRIP system in HEK293T cells: vector genome plasmids were co-transfected with pEF1a-coTRAP[H6] at a ratio of 5:1, along with EIAV vector packaging components. Vector supernatant was harvested and titrated by Integration assay using equal volumes of crude harvest supernatants, and end-of-production cell lysates probed by anti-COX-2 antibodies on an immunoblot. End-of-Integration assay cells (i.e. those transduced with the COX-2 vector preps) were also analysed for COX-2 expression by immunoblot.

A. COX2 vector titres were enhanced 100-fold as judged by DNA integration assay, and this was dependent on the presence of TRAP and tbs during vector production.

B. Immunoblot of COX-2 within end-of-production cells indicates that vector titre correlated inversely with COX-2 levels.

C. The increase in active vector particles per volume of harvest supernatant resulted in increase transduction and expression of COX-2 in target cells.

FIG. 18iii. Improved single gene FPR vector titres using the TRIP system. The single gene FPR-based vectors were produced using the TRIP system in HEK293T cells:vector genome plasmids were co-transfected with pEF1a-coTRAP[H6] at a ratio of 5:1, along with EIAV vector packaging components. Vector supernatant was harvested and titrated by integration assay using equal volumes of crude harvest supernatants. FPR vector titres were enhanced 24-fold as judged by DNA integration assay, and this was dependent on the presence of TRAP and tbs during vector production.

Figure 19I:
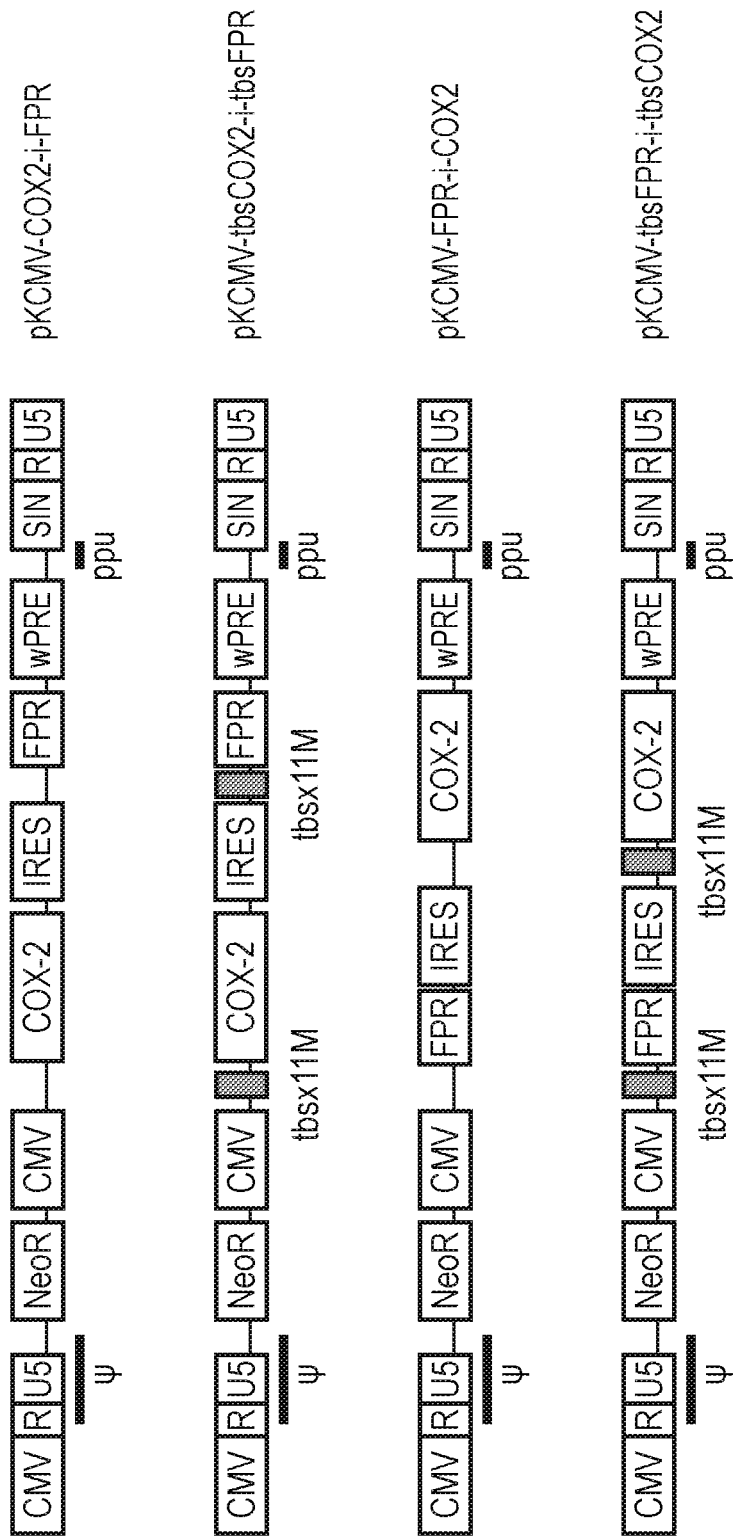
Figure 19I:
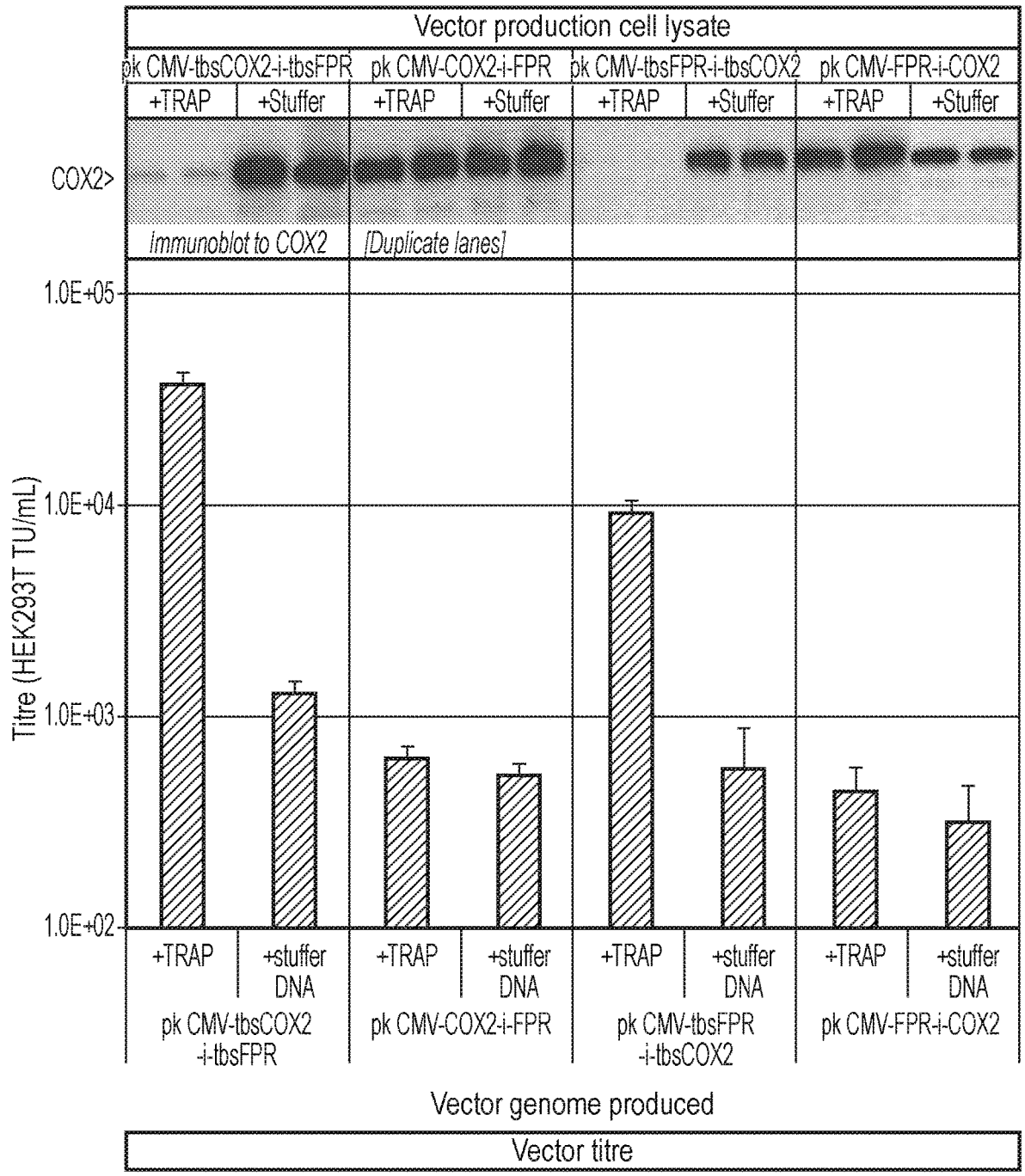

FIG. 19i. A schematic of vector genomes encoding both COX-2 or FPR ORFs. The tbsx11M variant was cloned into the multicistronic vector genome plasmids as indicated. COX-2 and FPR were placed at either upstream or downstream positions and the tbsx111M sequence inserted either at both positions or not any position.

FIG. 19ii. Improved multicistronic COX2/FPR vector titres using the TRIP system. The multicistronic vectors in FIG. 19i were produced using the TRIP system in HEK293T cells:vector genome plasmids were co-transfected with pEF1a-coTRAP[H6] at a ratio of 5:1, along with EIAV vector packaging components. Vector supernatant was harvested and titrated by integration assay using equal volumes of crude harvest supernatants, and end-of-production cell lysates probed by anti-COX-2 antibodies on an immunoblot. COX-2/FPR multicistronic vector titres were enhanced ~100-fold and FPR/COX-2 multicistronic vector titres were enhanced ~50-fold as judged by DNA integration assay, and this was dependent on the presence of TRAP and tbs during vector production. Immunoblot of COX-2 within end-of-production cells indicates that vector titre correlated inversely with COX-2 levels, and the TRAP/tbs configuration was capable of transgene repression at multiple sites on the same mRNA transcript.

Figure 20I:
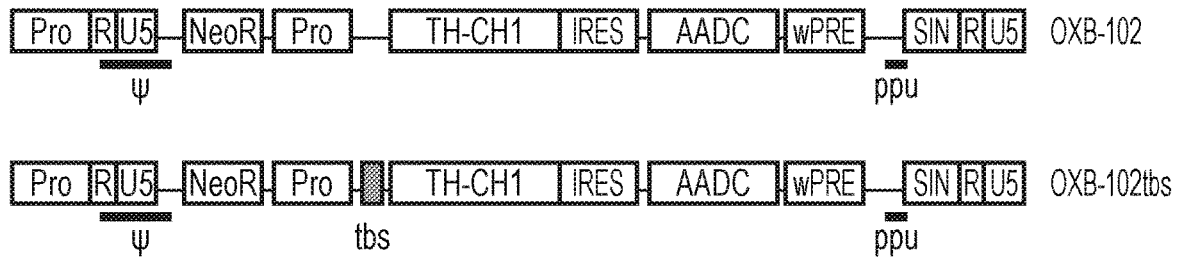
Figure 20I:
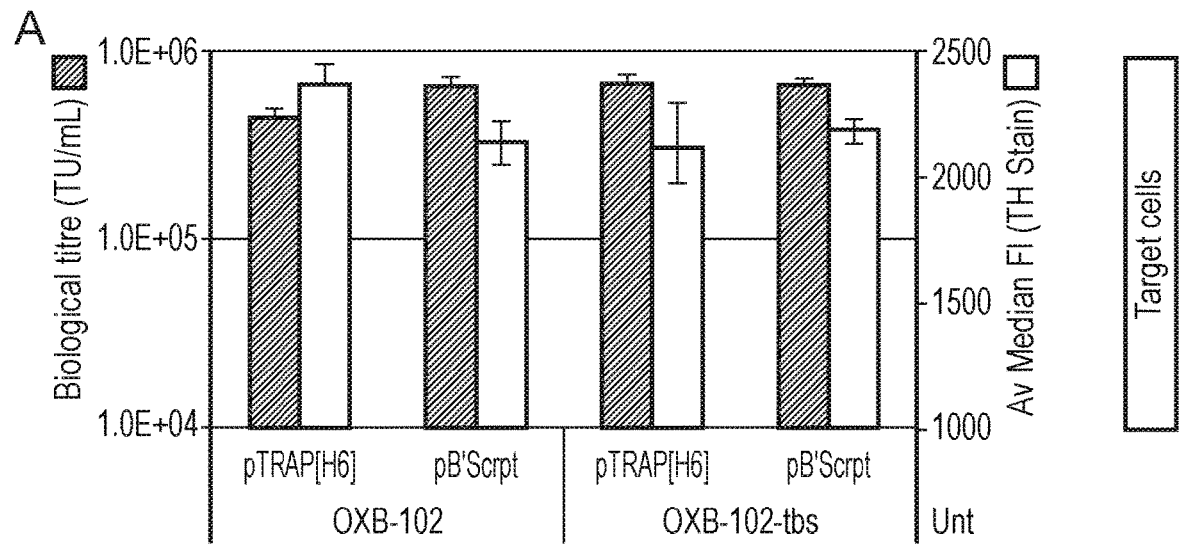
Figure 20I:
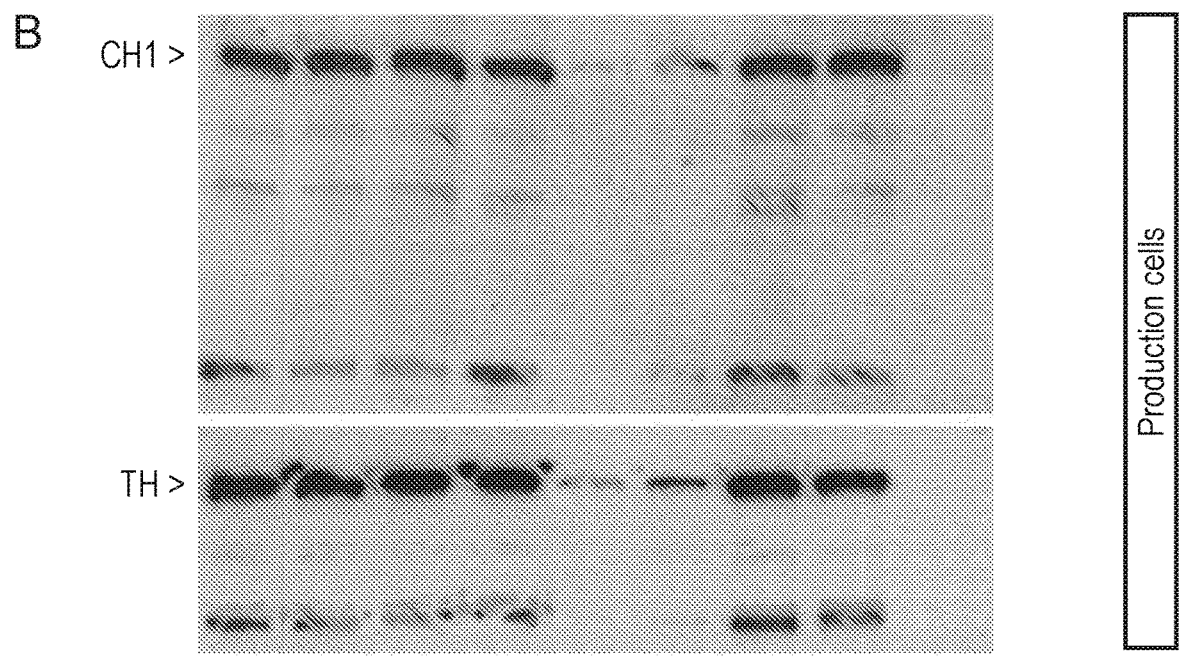

FIG. 20i. A schematic of OXB-102 vector genomes modified for use in the TRIP system. The tbsx11M variant was cloned into the multicistronic vector genome plasmids as indicated. Only the upstream TH-CH1 fusion gene was modified to include the tbsx11M sequence.

FIG. 20ii. Repression of 'non-problematic' transgenes during vector production in the TRIP system. The vectors in FIG. 20i were produced using the TRIP system in HEK293T cells:vector genome plasmids were co-transfected with pEF1a-coTRAP[H6] at a ratio of 5:1, along with EIAV vector packaging components. Vector supernatant was harvested and titrated by immunoflurescence assay using an anti-TH antibody (A), and end-of-production cell lysates probed by anti-TH and anti-CH1 antibodies on an immunoblot (B). The repression of transgenes in production cells by the TRAP/tbs system was evident but had no impact on transgene expression in target cells, indicating that no detectable TRAP-associated activity was transferred to target cells and that the tbs encoded within the 5'UTR of the transgene cassette allowed robust expression of the fusion transgene in cells other than those of the TRIP production cells.

Figure 21I:
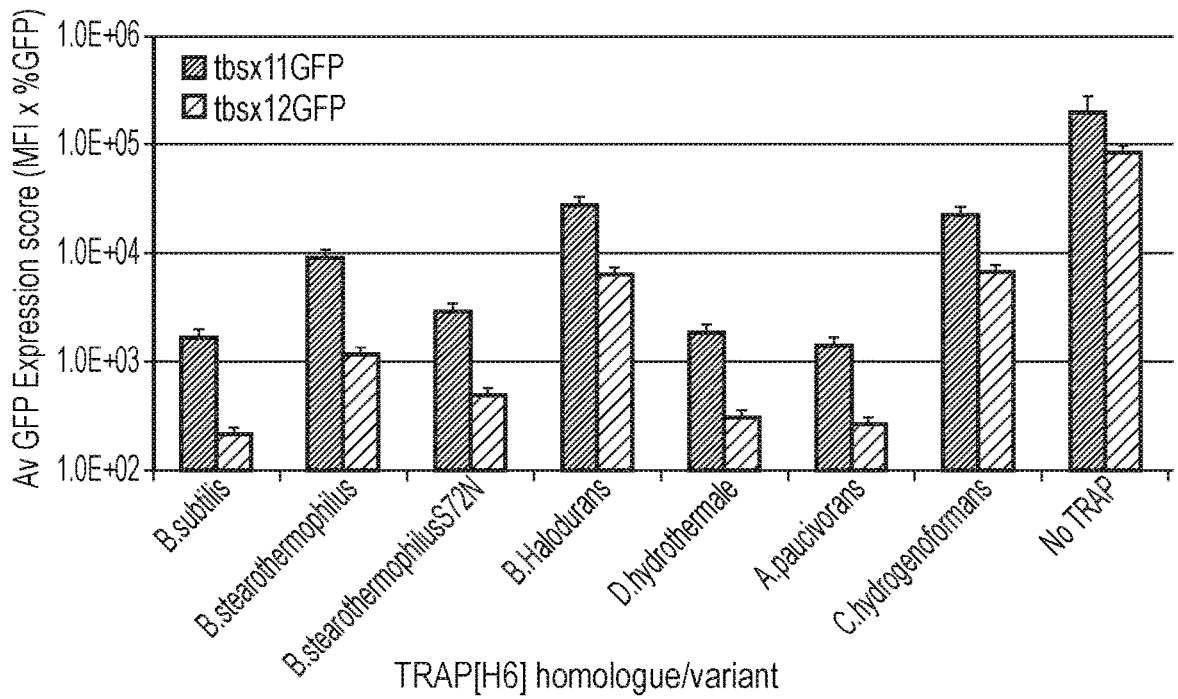
Figure 21I:
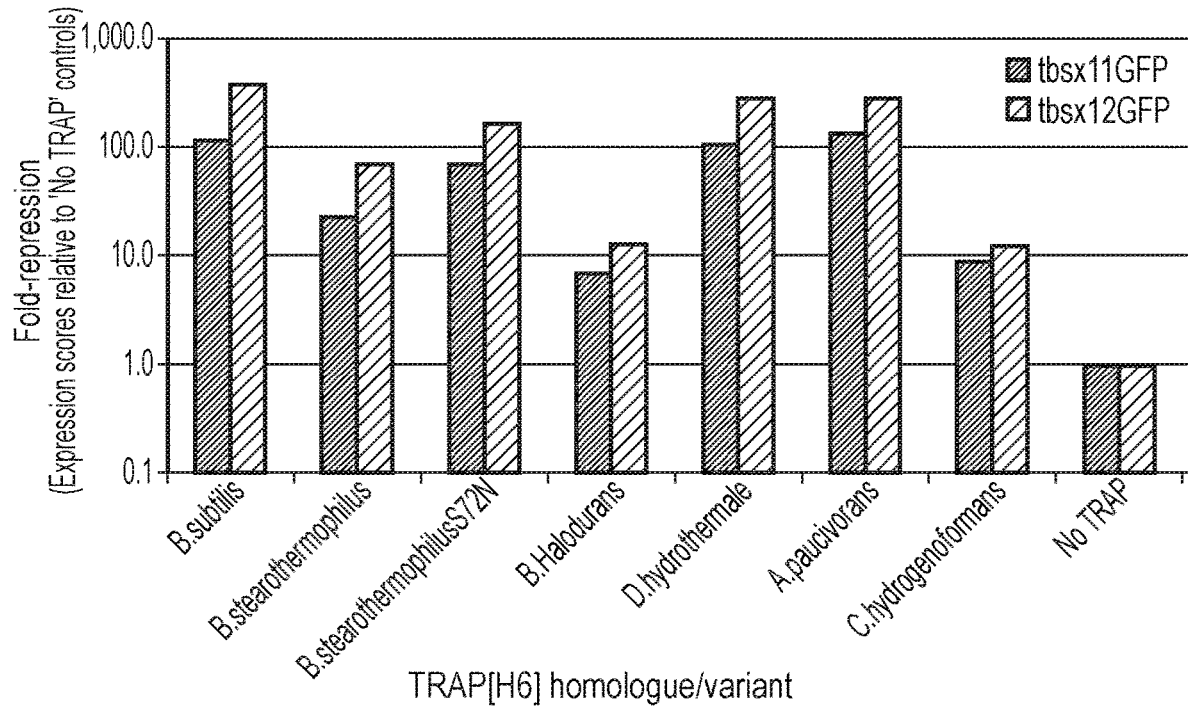

FIG. 21i. A list of tryptophan RNA-binding homologues from different bacterial species tested for TRAP-repression functionality in HEK293T cells. Name, lineage and NCBI reference number of TRAP homologues tested in the study. (Additional information relating to FIG. 11A).

FIG. 21ii. Testing of different TRAP homologues and S72N variant for repression function on x11- and x12-RAGNN repeat-containing tbs-GFP reporter cassettes. Six His-tagged TRAP homologues were cloned into the pEF1a-expression plasmid, and co-transfected into HEK293T cells with either pCMV-tbsx11-GFP or pCMV-tbsx12-GFP reporter plasmids at a ratio of 1:5 (pTRAP:pReporter). For 'No TRAP' controls, pBluescript was used to generate "on" levels of GFP expression to compare the TRAP variants. Cells were analysed by flow cytometry 2 days post-transfection, and GFP Expression scores generated in [A] (MFI×% GFP). [B] displays these data as fold-repression, relative to the "No TRAP" controls for each tbs-GFP reporter. (Additional information relating to FIG. 11A).

FIG. 21*iii*. Summary of functionalities of different TRAP homologues in the novel repression system. A summary of fold-repression of the different homologues and S72N variant using ×11- or ×12-RAGNN repeat tbs-GFP reporter cassettes in HEK293T cells. The homologues represent a diverse amino sequence variance (56-78%) compared to B. *Subtilis* TRAP (100%; alignments include His-tag). (Additional information relating to FIG. 11A).

Figure 22I:
Figure 22I:
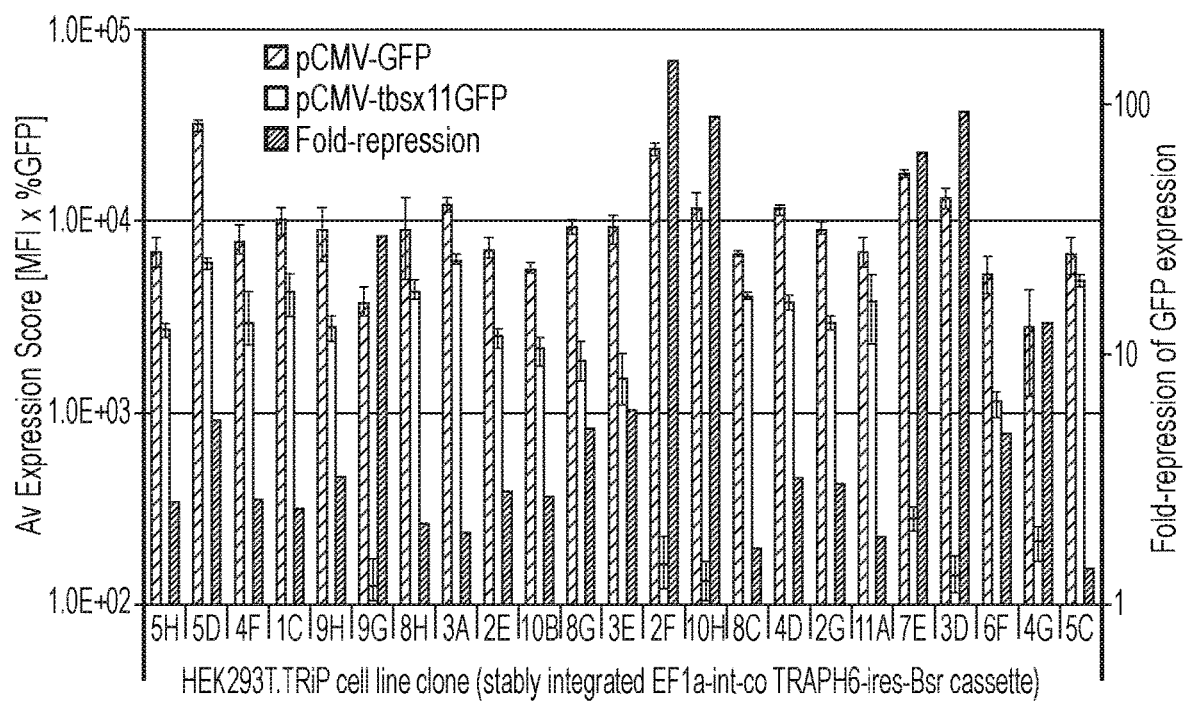
Figure 22I:
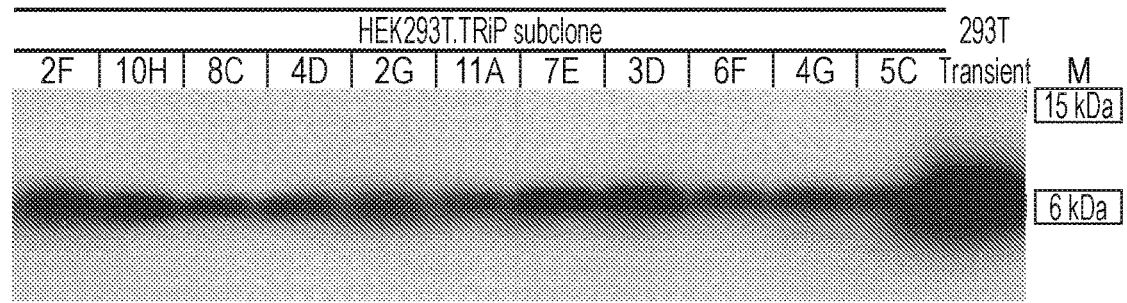
Figure 22I:
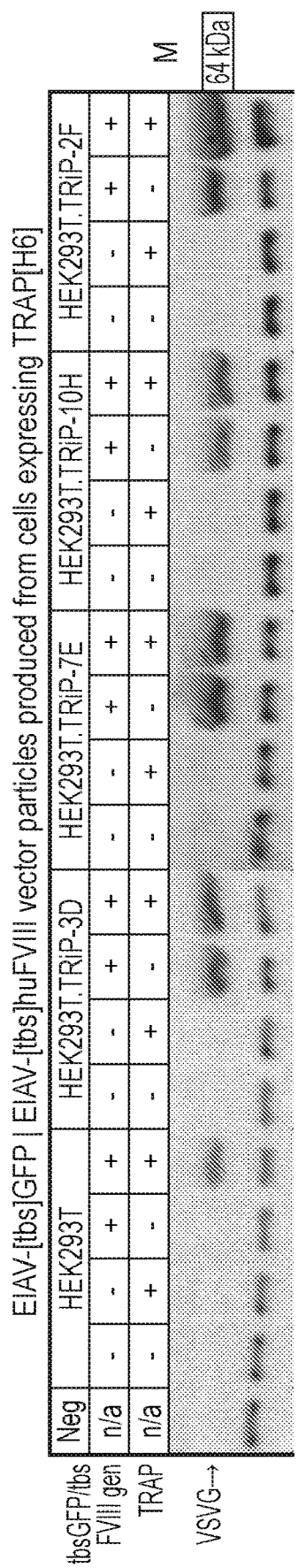

FIG. 22*i*. The TRAP expression cassette used to isolate stable cell lines. pEF1a-coTRAP[H6] was modified such that an IRES-Bsr sequence was inserted between TRAP[H6] and the polyadenylation signal. Bacterial sequences were removed from the DNA sequence during plasmid linearisation, and this cassette, encoding *B. subtilis* TRAP, was stably transfected into low passage HEK293T cells. (Additional information relating to FIG. 11B).

FIG. 22*ii*. Screening HEK293T.TRIP cell clones by transfection of GFP reporter plasmids.

A. Duplicate plates of subclone cells were transfected in triplicate with either pCMV-GFP or pCMV-tbsx111GFP, and FACS performed on cells 2 days later. Expression scores for each subclone were calculated (MFI×% GFP) and fold-repression calculated by dividing Expression scores for pCMV-GFP (i.e. no tbs) by the Expression scores for pCMV-tbsx1111GFP for each subclone ("Fold-repression"-labelled bars, right-hand axis). (Additional information relating to FIG. 11B).

B. Immunoblot of TRAP in clone cell lysates. Displaying results for eleven subclones expressing TRAP[H6]; monomeric TRAP detected by anti-HIS$_6$ antibody. HEK293T cells were transiently transfected with pEF1a-coTRAP[H6] and lysate used as a positive control for the immunoblot. (Additional information relating to FIG. 11B).

FIG. 22*iii*. Improved EIAV vector titre using production cells stably expressing TRAP; a case-study using 50:50 mix of EIAV-[tbs]GFP and EIAV-[tbs]huFVIII vector genomes during production.

A. GFP expression scores for vector production cells transfected with mixed vector genomes. Cells were transfected with EIAV-vector packaging components pGagPol, pVSVG, together with vector genome plasmids EIAV-[tbs]GFP and EIAV-[tbs]huFVIII at a 50:50 ratio. Thus, expression of huFVIII in production cells will negatively impact the titre of the mixed vector particles (EIAV-[tbs]huFVIII is the same as ReQuinate-tbs; see FIG. 17*i*). Genomes were either standard or contained the tbs upstream of the transgene. pEF1a-coTRAP[H6] (+TRAP TXN) or pBluescript (−) were also added where indicated. Production cells were either HEK293T cells or stable TRAP cell lines 2F, 10H, 7E and 3D. GFP expression scores were calculated (MFI×% GFP) on end-of-production cells.

B. Vector titration of mixed EIAV-[tbs]GFP/huFVIII crude vector harvest on HEK293T cells. Crude vector supernatants from vector production cells in [A] were titrated on HEK293T cells and titre measured by FACS. Expression of huFactorVIII is known to impact on EIAV vector virion activity (see FIG. 17*ii*); thus, only when transgene expression is repressed in production cells (measured by GFP in [A]) can vector titres be improved (measured by GFP in [B]).

FIG. 22*iv*. Improved incorporation of VSVG into mixed EIAV-[tbs]GFP|EIAV-[tbs]huFVIII vector particles produced in the stable or transient TRIP system. Vector supernatants from the production cells in the EIAV-[tbs]GFP|EIAV-[tbs]huFVIII vector genome mixing experiment were concentrated by centrifugation and analysed by immunoblot using an anti-VSVG antibody. Equal volumes of concentrated preps were loaded per well.

Figure 22V:
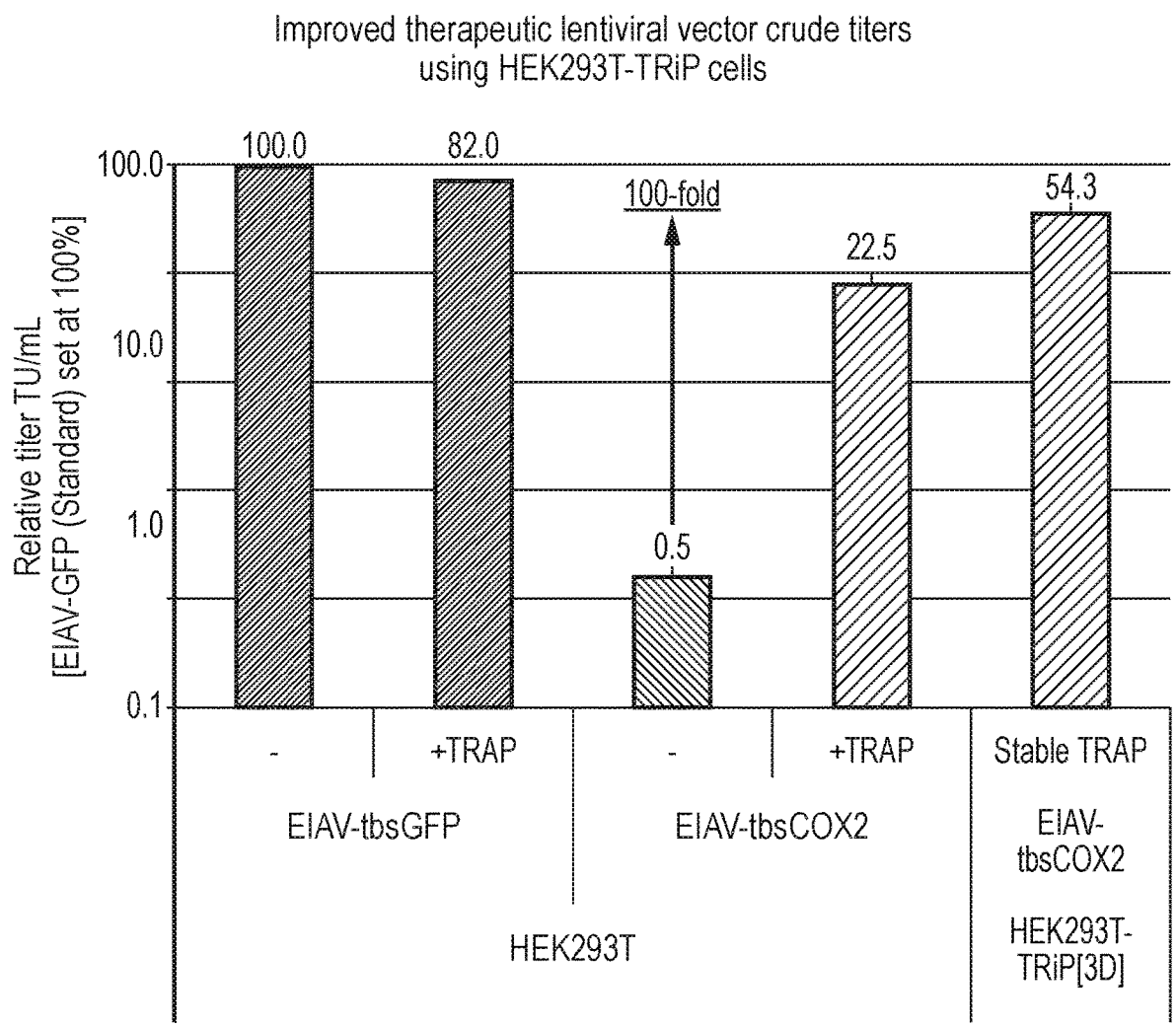

FIG. 22*v*. Improved production of a therapeutic transgene-encoding lentiviral vector using a HEK293T.TRIP stable cell line. The HEK293T.TRIP[3D] cell line (stably expressing *B. subtilis* TRAP[H6]) was used to produce EIAV-tbsCOX2 at Cell Factory™ scale, alongside standard (no TRAP) and transiently transfected TRAP in HEK293T cells. Vectors were titrated by DNA integration assay and TU/mL compared to EIAV-GFP vector titres (set as 100%). For EIAV-COX2 vectors, the use of HEK293T.TRIP[3D] cells enable further recovery of vector titre compared to transiently transfected TRAP in HEK293T cells.

Figure 23I:
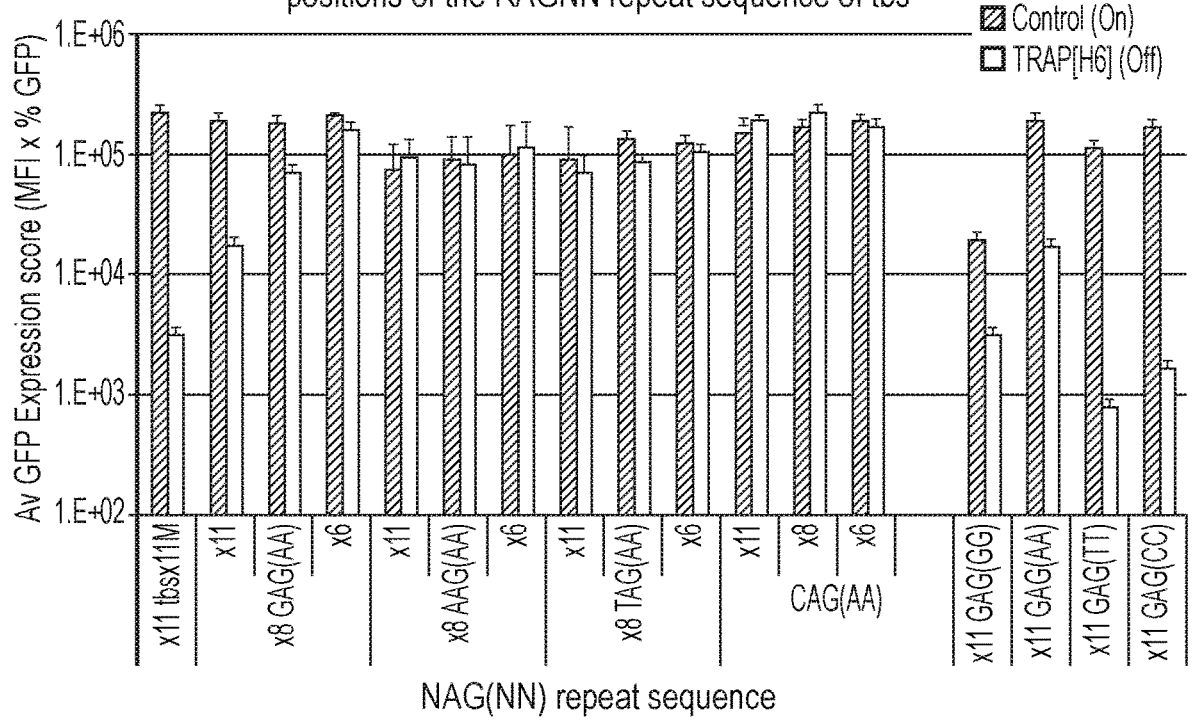
Figure 23I:
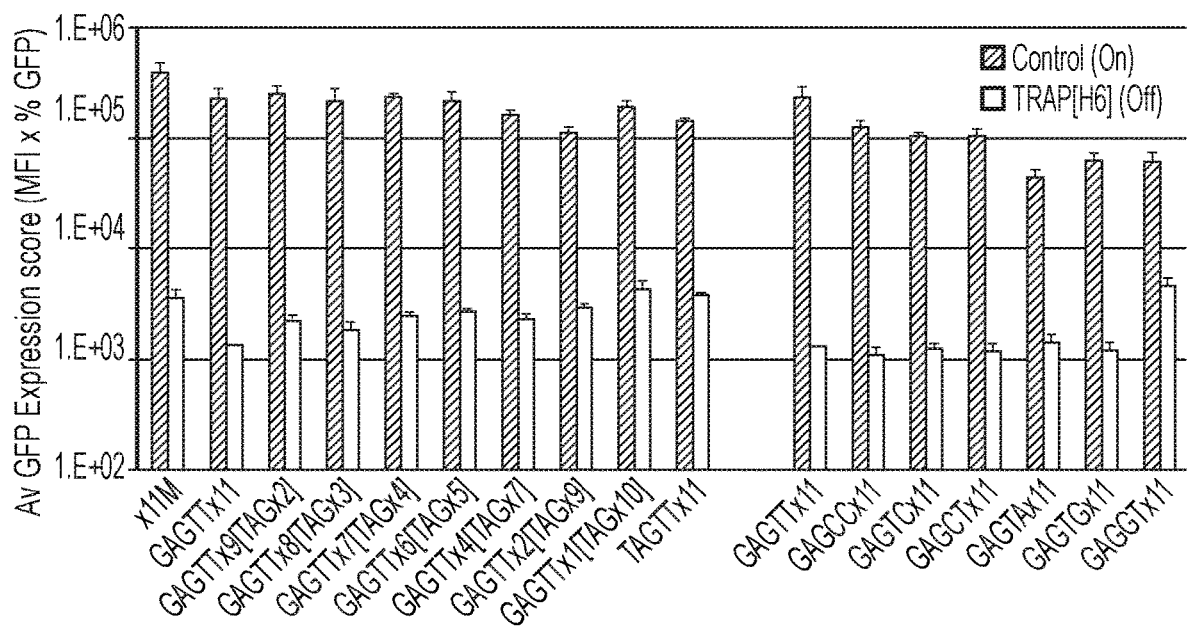

FIG. 23*i*. Testing the importance of nucleotide choice at the "R" and "NN" position of the RAGNN repeat in tbs sequences of varying length. Testing 11×RAGNN repeats wherein the NN sequence was either GG, AA, TT[UU] or CC, in the context of G at position R, revealed a preference for pyrimidines at the NN position. The general order of functionality was T[U]>C>G>A. In order to test the most functional nucleotide at the first (R) position, each nucleotide G, A, T[U] or C was inserted into xAGAA repeats within tbs' comprising ×11, ×8 or ×6 repeats.

FIG. 23*ii*. Testing GIT preference at the "R" position of the RAGTT repeat and testing nucleotide pairing with T within NN spacers. Within the context of a highly repressive tbs (11×GAGTT), TAGTT repeats were progressively swapped into this ×11 tbs sequence. Increasing TAGTT repeats (replacing GAGTT repeats) modestly reduced repression function of the tbs. Testing GAGNN repeats wherein at least one N=T, revealed that maximal repression is achieved when the first N (position 4 of RAGNN) is preferably a T[U] or pyrimidine. This revealed that the important features of the RAGNN are a pyrimidine at the first N spacer (position 4) and G>T at the R position. (GAGAT was not tested because tandem repeats of this RAGNN sequence results in multiple ATG codons upstream of the transgene ORF, which would likely attenuate expression of the transgene).

Figure 24I:
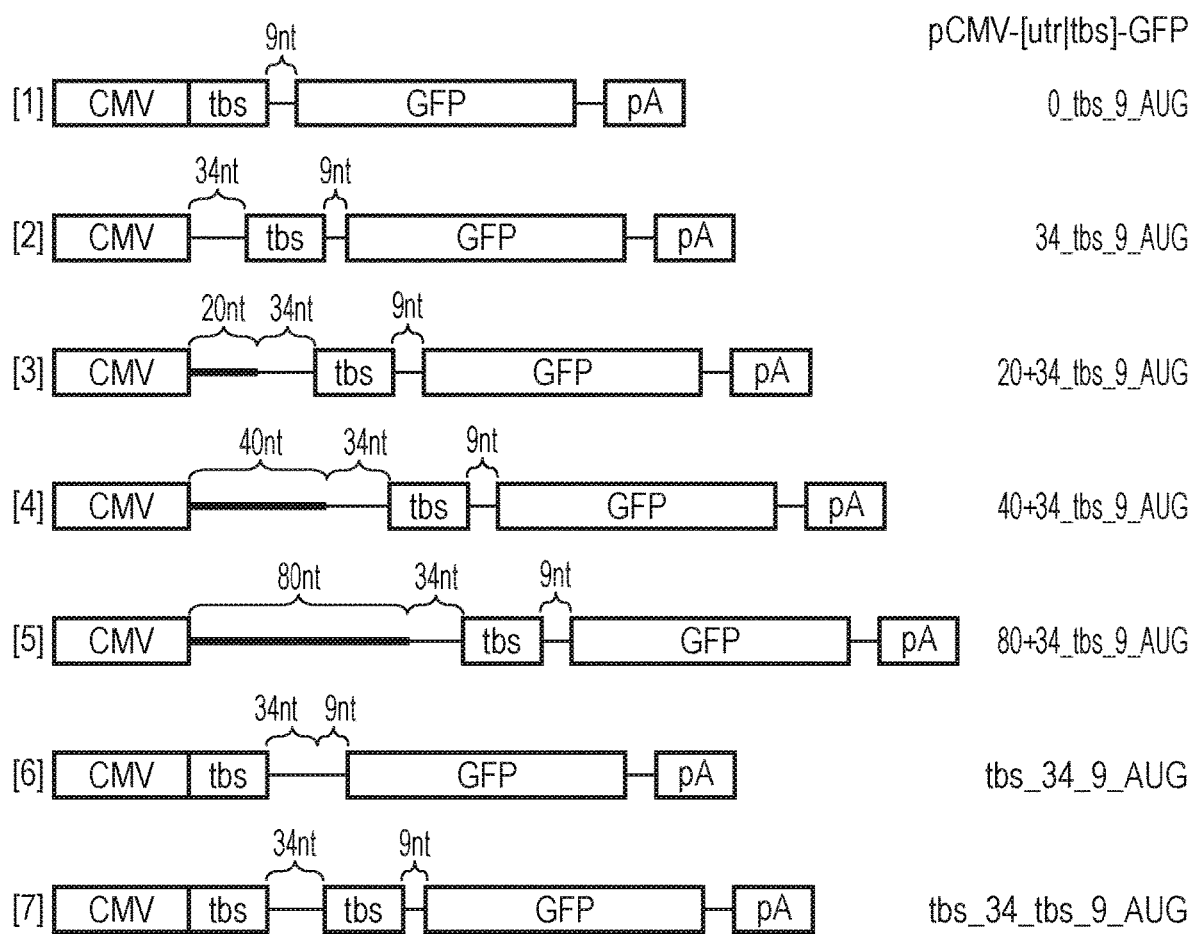

FIG. 24*i*. Varying the position and copy-number of the tbs within the 5'UTR of a GFP transgene to test repression activity by TRAP. The tbsx11M sequence was cloned into pCMV-GFP at different positions relative to the CAP site: 0 nt [1], 34 nt [2], 54 nt [3] 74 nt [4] or 114 nt [5]; additional sequences added onto the 34 nt leader comprising construct [2](effectively the standard tbsx11M reporter) were derived from the CMVp 5'UTR. The sequence between the tbs and the AUG was also increased to 43 nt in construct [6]. Finally, two copies of the tbs were positioned in the 5'UTR, with a 34 nt spacer between them [7].

FIG. 24*ii*. Testing variable positioning of the tbs within the 5'UTR of a GFP transgene on the effect of repression activity by TRAP. The seven tbs variant GFP reporter constructs in FIG. 24*i* were tested for their ability to be repressed by TRAP under three conditions: no TRAP (HEK293T), transiently co-transfected TRAP (HEK293T+TRAP) and under maximum TRAP repressive conditions (HEK293T.TRIP[Endogenous TRAP]+co-transfected TRAP). Cultures were analysed by flow cytometry to measure GFP expression 2 days post-transfection, and GFP Expression scores (MFI×% GFP) generated.

Figure 25I:
Figure 25I:
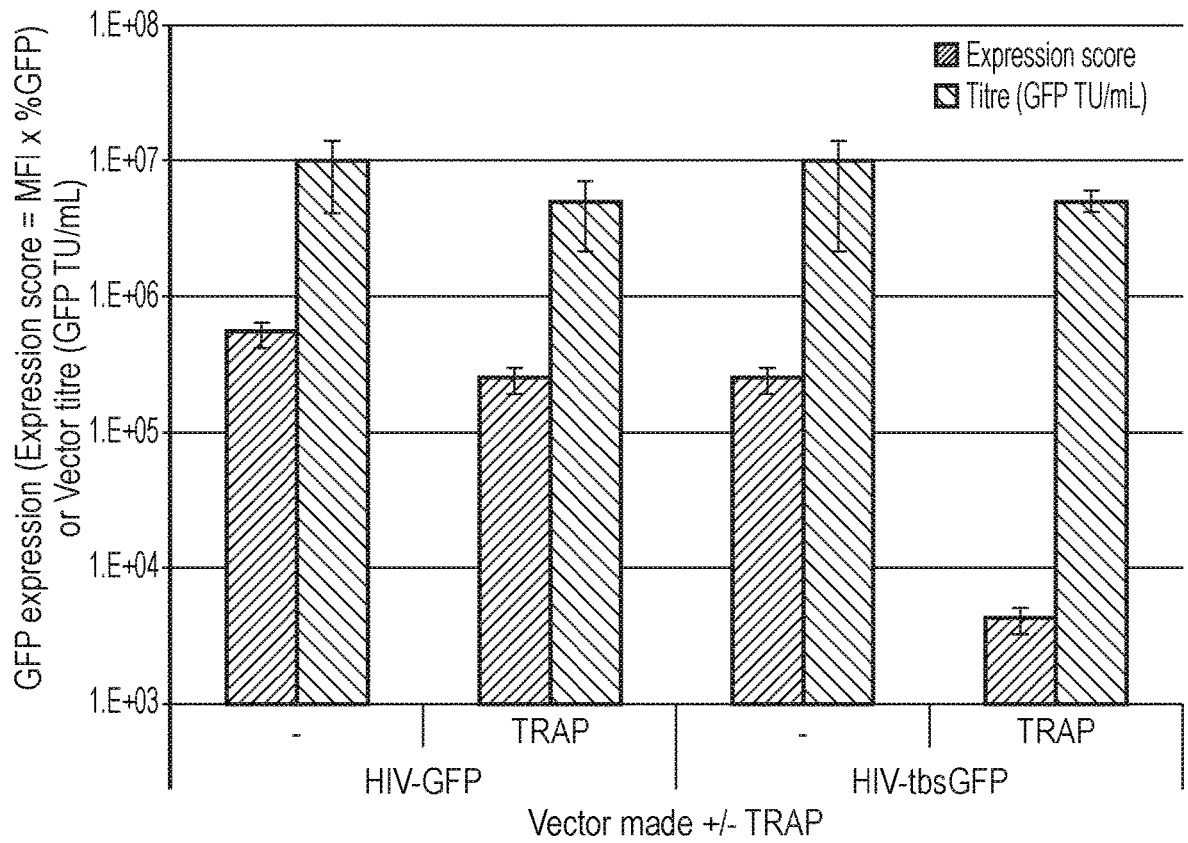
Figure 25I:
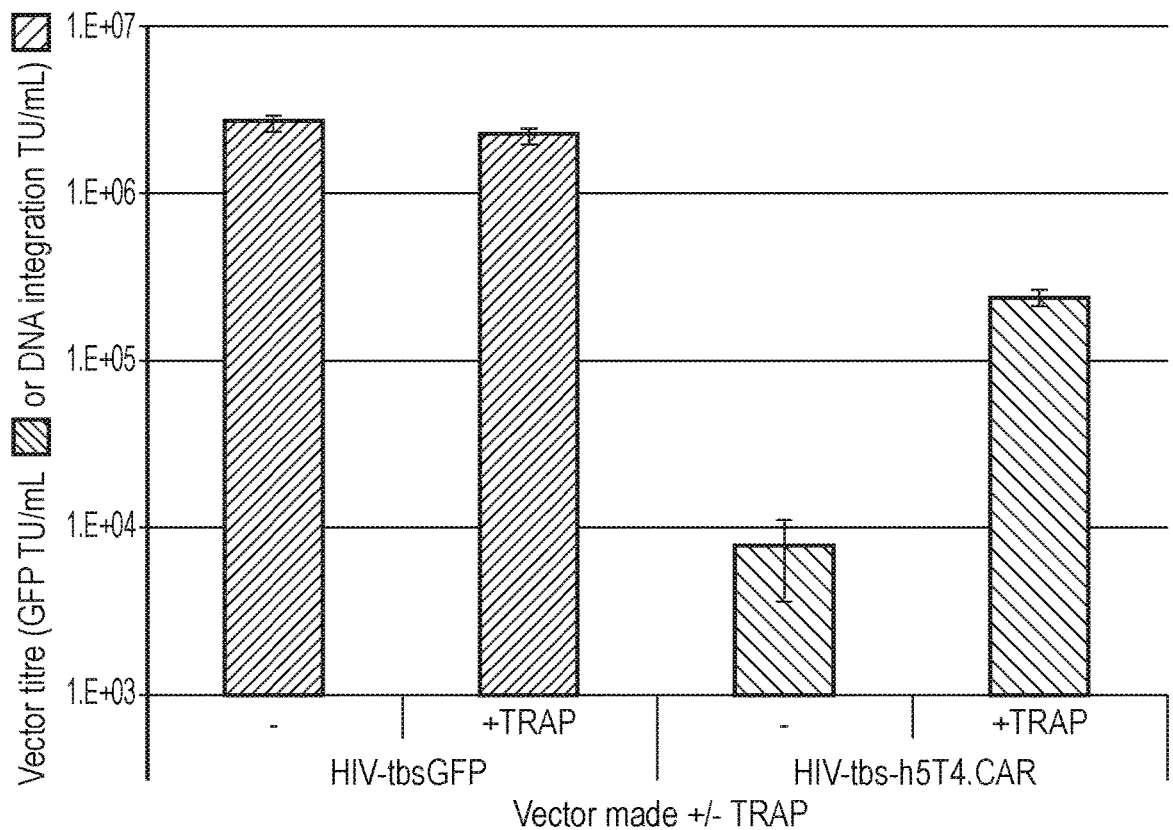

FIG. 25*i*. Application of the TRIP system to HIV-based GFP vector production. [A] The tbs (×11M variant) was inserted into an HIV-1-based lentiviral vector backbone encoding GFP and used to make crude vector preparations in HEK293T cells+/−pEF1a-coTRAP[H6]. [B] End-of-production cells were analysed by FACS to generate the GFP expression score (MFI×% GFP; "Expression score"-labelled bars). Crude vector supernatants were titrated by DNA integration assay on HEK293T cells ("Titre"-labelled bars). GFP expression was repressed by >100-fold vector in production cells shedding HIV-tbsGFP vector in the presence of TRAP but vector titres were not affected (as GFP protein is not detrimental to vector production). CMV—CMV promoter, ψ—packaging signal, RRE—rev responsive element, wPRE—woodchuck HBV post-transcriptional element, ppu—polypurine tract, SIN—self-inactivating U3/LTR.

FIG. 25ii. Application of TRIP system to HIV-based therapeutic vector production. [A] The tbs (×11M variant) was inserted into an HIV-1-based lentiviral vector backbone encoding 5T4-CAR and used to make crude vector preparations in HEK293T cells+/−pEF1a-coTRAP[H6]. [B] Crude vector supernatants were titrated by FACS (HIV-GFP; left-hand 2 bars) or DNA integration assay on HEK293T cells (HIV-5T4.CAR; right-hand 2 bars). The TRIP system enabled a 10-fold improvement of HIV-5T4.CAR vector titres compared to production without TRAP co-expression. CMV—CMV promoter, ψ—packaging signal, RRE—rev responsive element, wPRE—woodchuck HBV post-transcriptional element, ppu—polypurine tract, SIN—self-inactivating U3/LTR.

Figure 26:
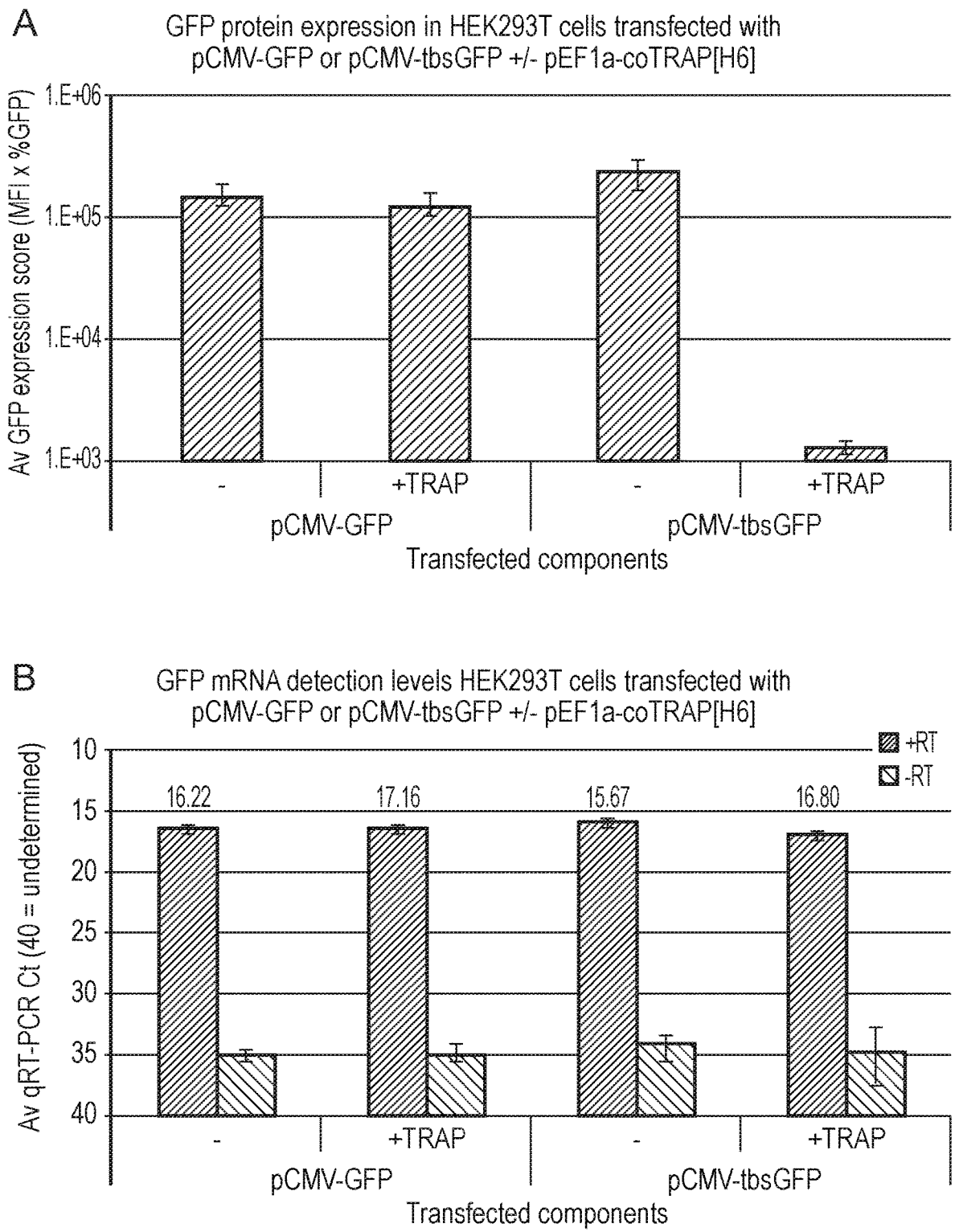

FIG. 26. Analysis of transgene mRNA levels within HEK293T cells transfected with standard or TRAP-tbs configuration components. HEK293T cells were transfected with either pCMV-GFP or pCMV-tbsGFP+/−pEF1a-coTRAP[H6] and cells analysed 48 hours later for GFP protein ([A]; FACS) and GFP mRNA levels in the cytoplasm ([B]; qRT-PCR of extracted, DNAse-treated cytoplasmic RNA using a GFP-specific primer/FAM-probe set). These data demonstrate that whilst >100-fold repression of GFP protein occurs in cells when using the TRAP-tbs configuration, GFP mRNA levels are not appreciably affected. [B] Ct reflects the PCR cycle at which signal was first detected; the lower the Ct the more abundant the target. Abundance therefore increases by ~1.5-fold for every cycle and 40 is undetectable signal. The −RT condition denotes minimal plasmid DNA contamination.

Figure 27I:
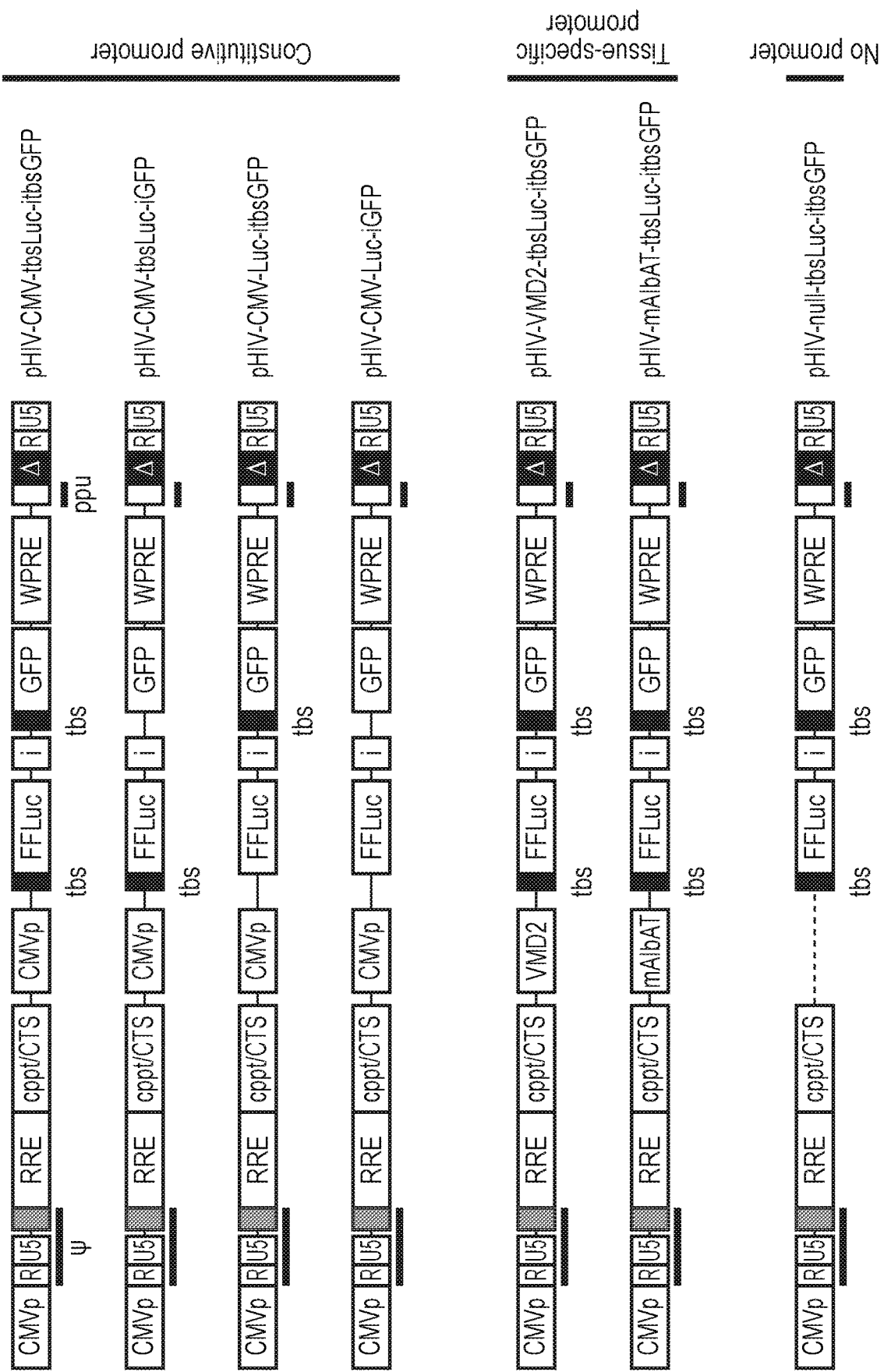
Figure 27I:
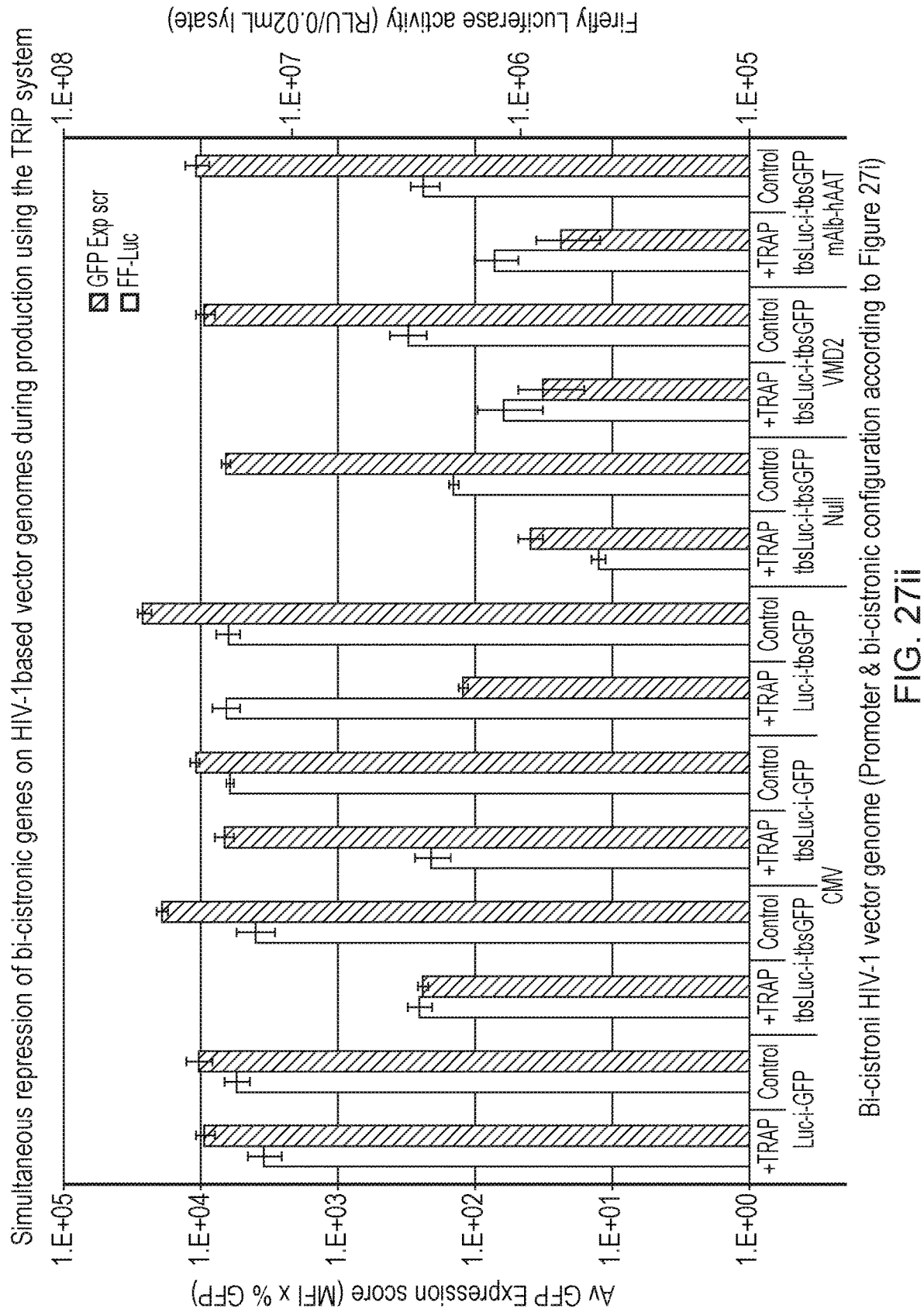

FIG. 27i. HIV-1 based vectors encoding a TRAP-tbs regulated, bi-cistronic transgene cassette driven by constitutive or tissue-specific promoters. Four constructs were generated wherein the bi-cistronic transgene cassette, encoding Firefly luciferase (1$^{st}$ position) and GFP (2$^{nd}$ position), is transcribed by the constitutive CMV promoter and differentially regulated at the translation level by TRAP-tbs. tbs sequences were inserted upstream of both transgene ORFs, or the 1$^{st}$ or the 2$^{nd}$ transgenes only, or without any tbs sequences. In addition, two constructs were made in which tissue specific promoters were utilised; either the VMD2 promoter that is restricted to photo-receptor cells or the mAlbAT promoter that is liver-specific. A control construct was made in which no internal promoter was present, so that any low-level expression from the full length vector RNA transcript could be measured.

FIG. 27ii. Evaluation of transgene expression from HIV-1 based vectors encoding a TRAP-tbs regulated, bi-cistronic transgene cassette driven by constitutive or tissue-specific promoters in HEK293T production cells. HEK293T cells were co-transfected with HIV-1 bi-cistronic vector genome (FIG. 27i), pGagPol, pRev and pVSVG, and with either pEF1a-coTRAP[H6] (+TRAP) or pBluescript (Control); the genome-to-TRAP plasmid ratio was 5-to-1. pGL3-control (Renilla luciferase expression plasmid) was present in all transfection mixes at a 1:40 ratio of total DNA mass. Transfections were carried out in triplicate on duplicate 96-well plates. One 96-well plate was used for end-of-production cell analysis by flow cytometry 2 days post-transfection, to generate GFP Expression scores (MFI×% GFP). The second plate was used to generate cell lysates 2 day post-transfection for dual luciferase assay (Promega).

FIG. 27iii. A schematic summarising the repression capabilities of the TRIP system when applied to production of retroviral (lentiviral) vectors encoding multi-cistronic transgenes. An example of a lentiviral vector production cell utilising the TRIP system to repress transgene expression from two open-reading frames (ORFs) utilising an internal ribosomal entry site [IRES]. The vector genome expression cassette is driven by a strong promoter [Ext Pro] to generate abundant quantities of vector genome RNA. The internal promoter [Int Pro] may be a strong/constitutive promoter, leading to abundant levels of transgene encoding/expressing mRNA, or a tissue-specific promoter that may or may not be leaky, leading to minimal/no transgene encoding/expressing mRNA levels. The TRAP-binding sequence [tbs] can be inserted upstream of one or both ORF positions; thus expression of TRAP within the production cell will repress protein production from either abundant or low levels of transgene mRNA. In addition, the vector genome RNA may express transgene protein in a Cap-dependent manner (typically low levels) or in a Cap-independent manner (from an IRES; typically at moderate to high levels). Thus, whether the internal promoter is active or not, transgene expression may be possible during vector production, and therefore the TRIP system is better able to repress this expression compared to use of tissue-specific promoters. Ext Pro—external promoter; ψ—packaging signal; RRE—rev-responsive element; cppt/CTS—central polypurine tract/central terminator sequence; Int Pro—internal promoter; tbs—TRAP binding sequence; ORF—open-reading frame; IRES—internal ribosomal entry site; WPRE—woodchuck Hepatitis post-transcriptional regulatory element; ppu—polypurine tract; Δ—partially deleted U3. (Note that vector packaging and TRAP expression cassettes are not displayed in the schematic but are assumed to be present within the TRIP system vector production cell in this example).

Figure 28I:
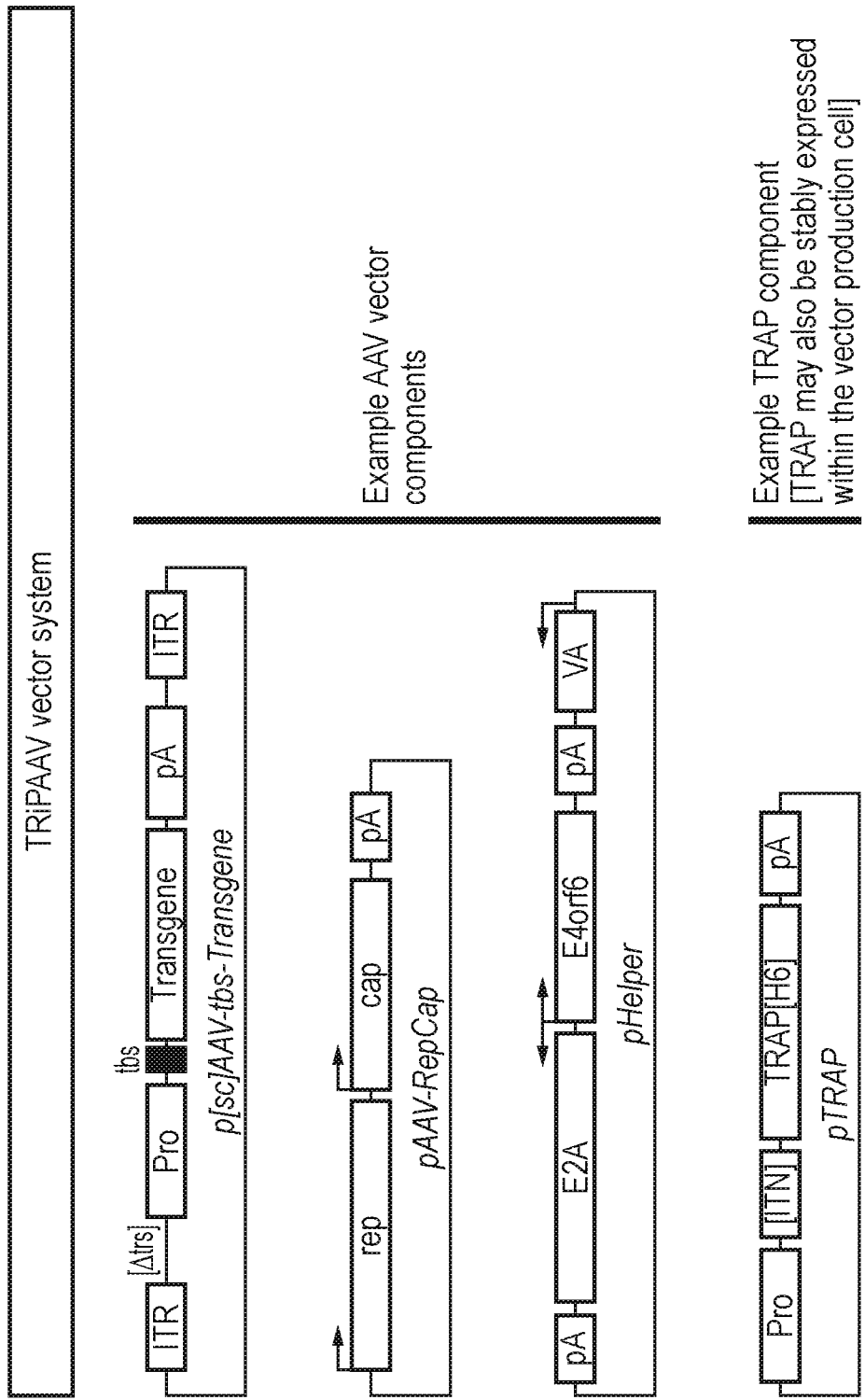
Figure 28I:
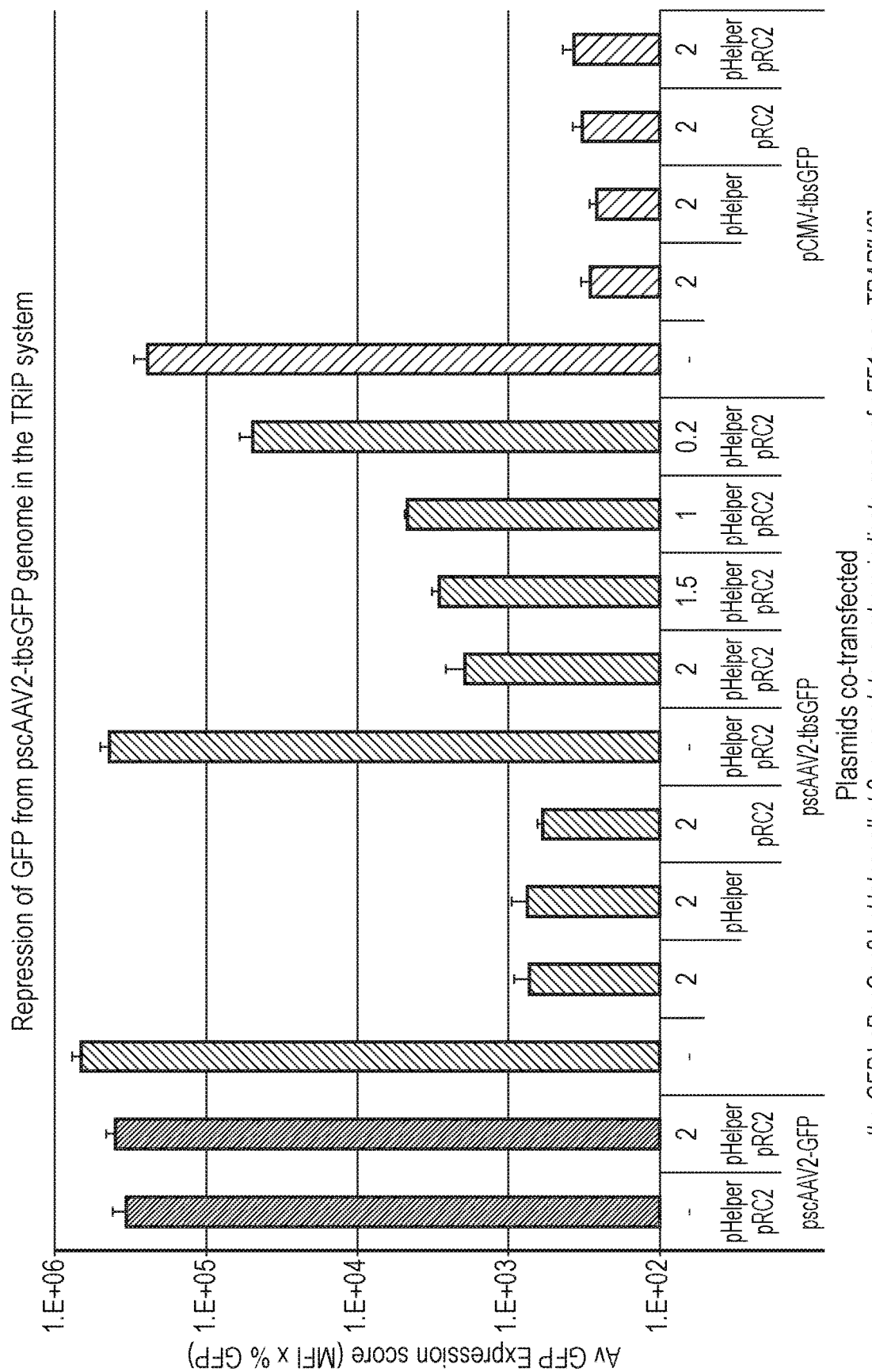
Figure 28I:
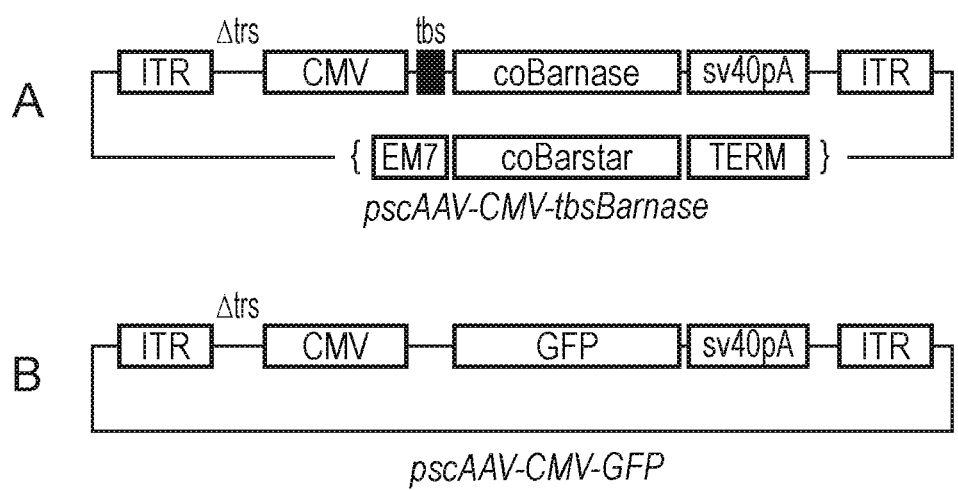

FIG. 28i. Development of the TRIPAAV system. Application of the TRAP-tbs configuration to production of AAV-based vectors. A standard AAV vector system utilises three DNA components for production of vectors in Adenovirus E1-expressing cells (e.g. HEK293-based cells): genome (optionally deleted in one trs [Δtrs] to generate a self-complementary [sc] AAV vector genome), RepCap and Helper functions (in this non-limiting example, Helper functions are provided by Adenovirus E2A, E4orf6 and VA). The TRIPAAV system utilises the TRAP-tbs configuration: the AAV vector genome is modified such that the tbs is inserted into the 5'UTR of the transgene cassette, and during vector production a TRAP expression cassette is co-introduced, either by co-transfection of TRAP-expressing plasmid and/or by use of a cell line stably expressing TRAP; TRAP may be optionally His$_6$-tagged. ITR—inverted terminal repeat; Pro—eukaryotic promoter element; tbs—TRAP-binding sequence; pA—polyadenylation signal; [ITN]—optional intron. Schematic not to scale.

FIG. 28ii. Repression of scAAV vector transgene expression in HEK293T cells using the TRIPAAV system. Plasmids encoding serotype 2 scAAV-GFP vector genomes (+/−the tbs) were co-transfected into HEK293T cells along with various components to measure their impact on TRAP-tbs mediated transgene repression. Mass ratios of pscAAV-[tbs]GFP|pRepCap2|pHelper|pEF1a-coTRAP[H6] or pBlueScript (−) were 2|2|2|2 µg per 10 cm TC plate, except where inputs of pEF1a-coTRAP[H6] varied as stated. The pCMV-tbsGFP control plasmid (lacking flanking AAV2 ITRs) was subjected to the same conditions to compare repression levels. GFP expression from the pscAAV2-[tbs] GFP plasmids was greater than pCMV-tbsGFP, possibly due to a more stable mRNA transcript (3'UTR sequences and polyA signal differed between constructs). TRAP was able to repress GFP expression from pscAAV2-tbsGFP by over 300-fold in the presence of pRepCap2 and pHelper i.e. during scAAV vector production. The equi-mass ratio of pEF1a-coTRAP[H6] to pscAAV2-tbsGFP allowed maximal repression under the transfection conditions employed; reducing pEF1a-coTRAP[H6] mass input by 10-fold still allowed for measurable GFP repression in the order of 1-Log. No repression was observed for pscAAV-GFP.

FIG. 28*iii*. Comparison of scAAV-[tbs]GFP vector production using the standard and TRIPAAV systems. scAAV-(CMV)-GFP or scAAV-(CMV)-tbsGFP vectors were produced by transient co-transfection of equal masses of genome, pRepCap2, pHelper and pEF1a-coTRAP[H6] or pBluescript in HEK293T cells. Approximately 53 hour post-transfection, cells were harvested and subjected to freeze-thaw cycles to release AAV virions. AAV virions were purified using a Virabind™ kit, resulting in 100 µL PBS containing vector from each 10 cm plate. Vector preps were titrated on HEK293T cells ("HEK293T"-labelled bars) or HEPG2 cells ("HEPG2"-labelled bars) by flow cytometry. The GFP expression scores for the respective vector production cells are co-plotted ("GFP Expr scr"-labelled bars). The data shows that whilst GFP expression in AAV vector production cells is repressed by >300-fold, and the TRAP-tbs configuration of the TRIPAAV system does not impact on the basic biology of AAV vector production, implying that problematic/cytotoxic transgenes can be shutdown during AAV vector production.

FIG. 28*iv*. Modelling production of AAV vectors encoding problematic/cytotoxic transgenes using Barnase.

A. The vector genome scAAV2-CMV-tbsBarnase encodes the bacteria RNAse Barnase, whose ORF is codon-optimised for expression in human cells. The tbs was inserted into the 5'UTR of the transgene cassette. Additionally, a bacterial expression cassette for Barstar (Barnase's natural inhibitor) is present in the plasmid backbone in order to aid plasmid propagation in bacteria, due to leaky expression of the CMV promoter in *E. coli*. The Barstar ORF is codon-optimised for expression in *E. coli*.

B. The pscAAV-CMV-GFP plasmid was used in genome mixing transfections to monitor the effect on Barnase on GFP expression.

Figure 28V:
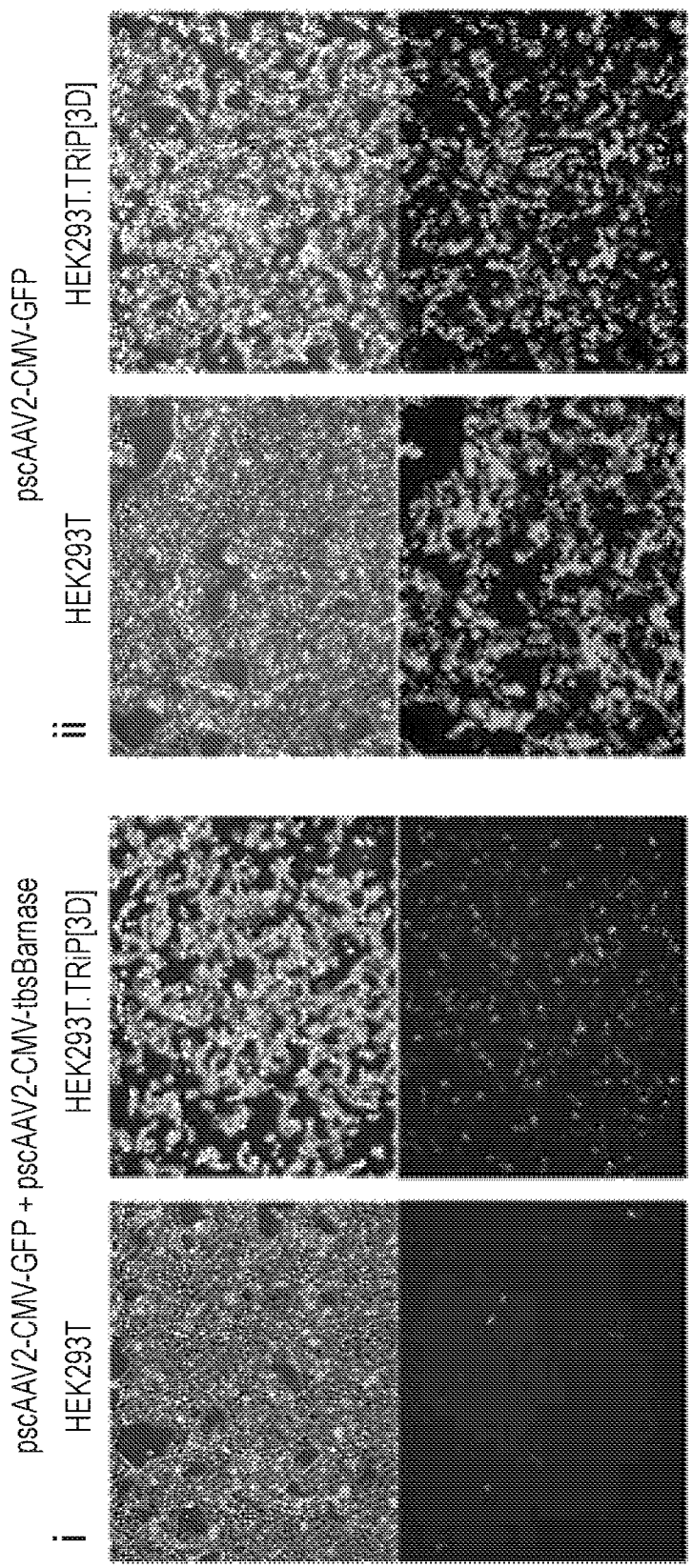

FIG. 28*v*. Genome mixing was performed by transfection of HEK293T or HEK293T.TRiP[3D] cells with a 50:50 mix of pscAAV-CMV-tbsBarnase and pscAAV-CMV-GFP vector genome plasmids, plus pRepCap2 and pHelper. Genome plasmids were each present at 1 µg/10 cm plate [i], or just pscAAV-CMV-GFP was present at 2 µg/10 cm plate [ii], with no additional TRAP-expression plasmid. Pictures were taken of GFP-expression in these cultures at 24 hours post-transfection.

Figure 29I:
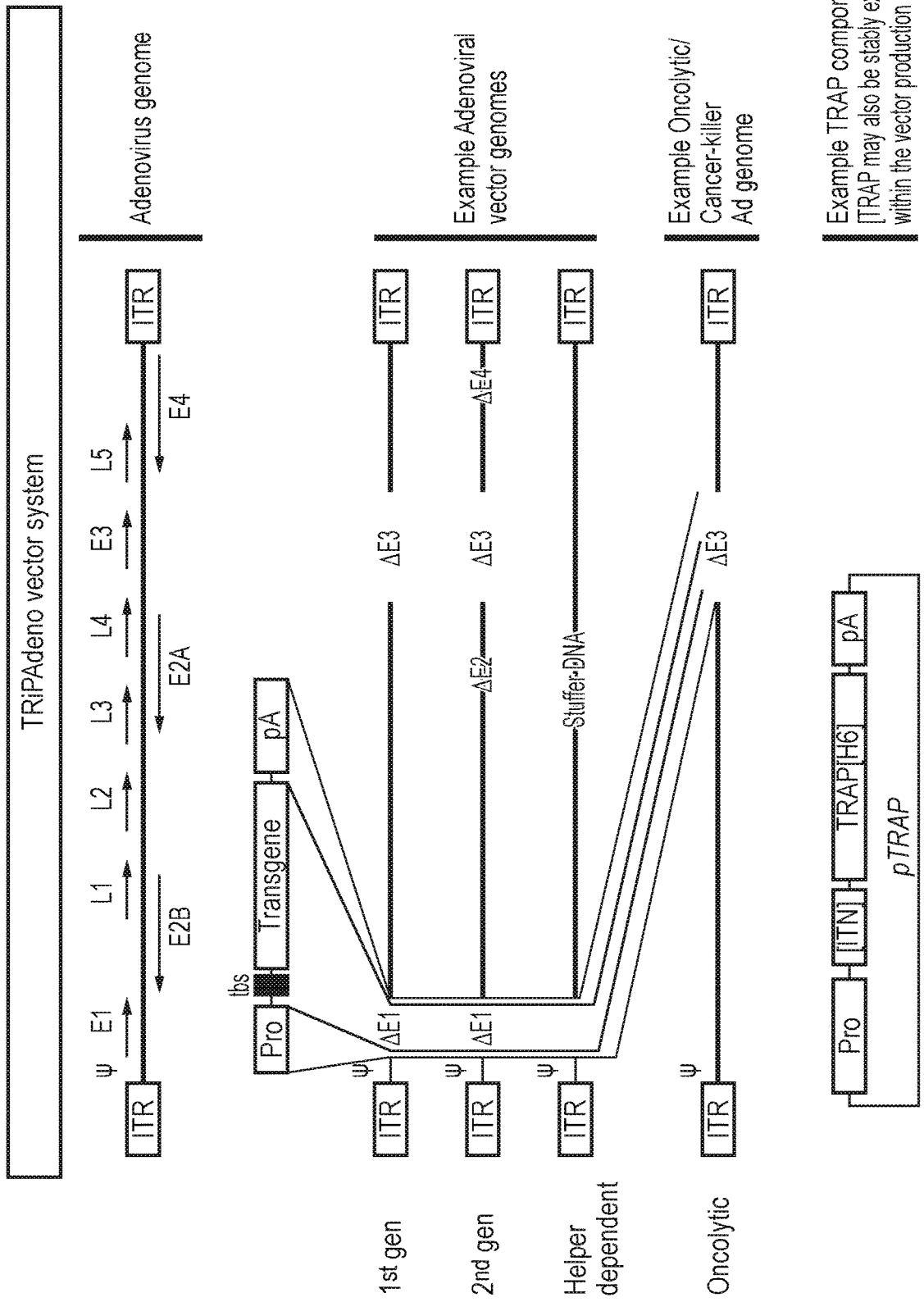
Figure 29I:
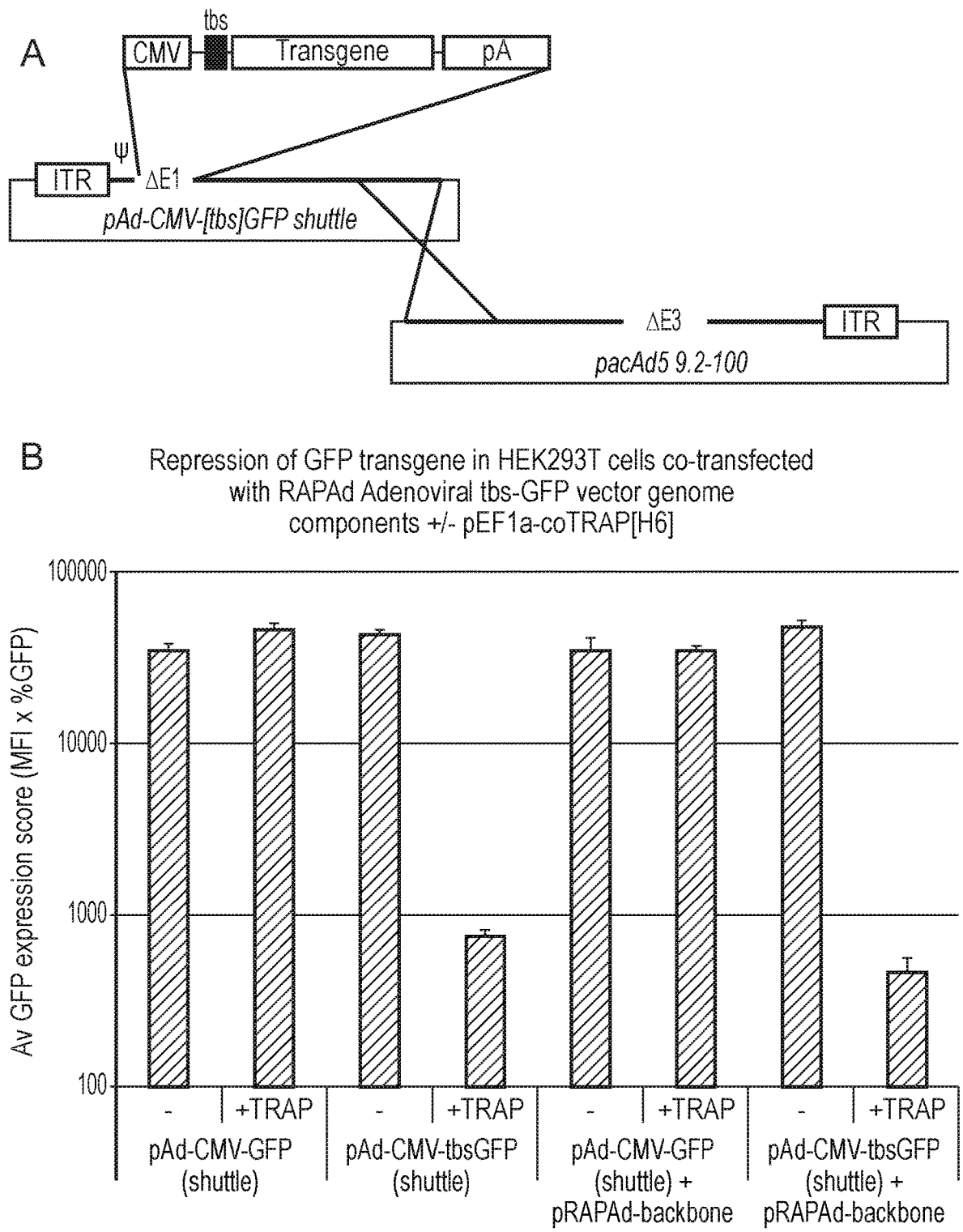

FIG. 29*i*. Development of the TRIPAdeno system. Application of the TRAP-tbs configuration to production of Adenovirus-based vectors. Standard Adenoviral vectors are categorised into 1$^{st}$ generation (deleted in E1/E3 regions), 2$^{nd}$ generation (deleted in E1/E2/E3/E4), and Helper-dependent, "gutted" vectors. In addition, E1-active oncolytic vectors may contain toxic transgenes encoded within the E3 region; for example, expression of the toxic gene may be governed by the adenovirus major late promoter or a heterologous promoter and adenovirus-encoded or a heterologous polyadenylation signal. TRIPAdeno system versions of these types of vector genomes harbor the tbs within the 5'UTR of the transgene encoding transcript. During vector production, a TRAP expression cassette is co-introduced, either by co-transfection of TRAP-expressing plasmid and/or by use of a cell line stably expressing TRAP; TRAP may be optionally His$_6$-tagged. ITR—inverted terminal repeat; ψ—packaging signal; Pro—eukaryotic promoter element; tbs—TRAP-binding sequence; pA—polyadenylation signal; [ITN]—optional intron. Schematic not to scale.

FIG. 29*ii*. Repression of GFP transgene from first generation Adenoviral vector genome components in HEK293T cells using the TRAP-tbs configuration. HEK293T cells were transfected with pAd-CMV-GFP or pAd-CMV-tbsGFP shuttle plasmids (containing the left-hand side of the Adenoviral vector genome) together with pEF1a-coTRAP[H6](+TRAP) or pBluescript (−) [A], and flow cytometry performed 48 hours later [B]. In addition, parallel transfections included the RAPAd®-backbone (pacAd5 9.2-100; containing the right hand side of the Adenoviral vector genome), simulating first generation Adenoviral vector production using the RAPAd® kit (wherein recombination of the vector genome occurs in HEK293T cells). GFP expression scores (MFI×% GFP) were generated under each condition. Over 100-fold repression of GFP was observed only when the tbs was present within the shuttle plasmid and when TRAP was expressed. ITR—inverted terminal repeat; CMV—CMV promoter; ψ—packaging signal; tbs—TRAP-binding sequence; pA—polyadenylation signal. Schematic not to scale.

FIG. 29*iii*. Repression of GFP transgene during Adeno-tbsGFP (E1/E3-deleted) vector amplification in HEK293T.TRIP cells. Stocks of Adeno-CMV-GFP and Adeno-CMV-tbsGFP vector generated by co-transfection of pAd-CMV-GFP or pAd-CMV-tbsGFP shuttles with the pRAPAd®-backbone and pEF1a-coTRAP[H6] (see FIG. 29*ii*), were used to transduce either HEK293T cells or HEK293T.TRIP[3D] cells (stably expressing TRAP[H6]) at an MOI of 0.01. [A] Replicate cultures were analysed by flow cytometry at different time points post-transduction in order to assess GFP expression during vector amplification. GFP expression scores (MFI×% GFP) were generated for each condition. [B] End-of-time course replicate cultures were freeze-thawed to release vector particles; cell debris was removed by centrifugation, and crude supernatants were titrated on HeLa cells.

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, molecular biology, microbiology and immunology, which are within the capabilities of a person of ordinary skill in the art. Such techniques are explained in the literature. See, for example, J. Sambrook, E. F. Fritsch, and T. Maniatis (1989) Molecular Cloning: A Laboratory Manual, Second Edition, Books 1-3, Cold Spring Harbor Laboratory Press; Ausubel, F. M. et al. (1995 and periodic supplements) Current Protocols in Molecular Biology, Ch. 9, 13, and 16, John Wiley & Sons, New York, NY; B. Roe, J. Crabtree, and A. Kahn (1996) DNA Isolation and Sequencing: Essential Techniques, John Wiley & Sons; J. M. Polak and James O'D. McGee (1990) In Situ Hybridization: Principles and Practice; Oxford University Press; M. J. Gait (ed.) (1984) Oligonucleotide Synthesis: A Practical Approach, IRL Press; and, D. M. J. Lilley and J. E. Dahlberg (1992) Methods of Enzymology: DNA Structure Part A: Synthesis and Physical Analysis of DNA Methods in Enzymology, Academic Press. Each of these general texts is herein incorporated by reference.

In one aspect, the present invention provides a nucleic acid sequence comprising a binding site operably linked to a nucleotide of interest, wherein the binding site is capable of interacting with an RNA-binding protein such that translation of the nucleotide of interest is repressed or prevented in a viral vector production cell.

The term "RNA-binding protein" is to be understood as a protein that is capable of binding to a nucleic acid sequence. In the context of the present invention, binding of the RNA-binding protein to its binding site sequence has the effect of repressing or preventing the translation of a nucleotide of interest to which the binding site is operably linked in a viral vector production cell.

In a preferred embodiment, the RNA-binding protein is tryptophan RNA-binding attenuation protein (TRAP), for example bacterial tryptophan RNA-binding attenuation protein.

In another embodiment the RNA-binding protein is a bacterial conserved carbon storage regulation system protein A (CsrA).

In another embodiment the RNA-binding protein is a Herpes simplex virus-1 RNA-binding protein US11.

Tryptophan RNA-Binding Attenuation Protein (TRAP)

Tryptophan RNA-binding attenuation protein (TRAP) is a bacterial protein that has been extensively characterised in *Bacillus subtilis*. It regulates tryptophan biosynthesis directed from the trpEDCFBA operon by participating in either transcription attenuation or translational control mechanisms (reviewed in Gollnick, B., Antson, and Yanofsky (2005) *Annual Review of Genetics* 39: 47-68).

In its natural context TRAP regulates tryptophan biosynthesis and transport by three distinct mechanisms:
1. Attenuation of transcription of the trpEDCFBA operon (Shimotsu H, K. M., Yanofsky C, Henner D J. (1986) *Journal of Bacteriology* 166: 461-471).
2. Promotion of formation of the trpE and trpD Shine-Dalgarno blocking hairpin (Yakhnin H, B. J., Yakhnin A V, Babitzke P. (2001) *Journal of Bacteriology* 183 (20): 5918-5926).
3. Blocking ribosome access to the trpG and yhaG ribosome binding sites (Yang M, d. S. A., van Loon APGM, Gollnick P. (1995) *Journal of Bacteriology* 177: 4272-4278).

In *Bacillus subtilis* TRAP is encoded by a single gene (mtrB) and the functional protein is composed of 11 identical subunits arranged as a toroid ring (Antson AA, D. E., Dodson G, Greaves R B, Chen X, Gollnick P. (1999) *Nature* 401(6750): 235-242). It is activated to interact with RNA by binding up to 11 molecules of tryptophan in pockets between neighbouring subunits. The target RNA is wound around the outside of this quaternary ring structure (Babitzke P, S. J., Shire S J, Yanofsky C. (1994) *Journal of Biological Chemistry* 269: 16597-16604).

Without wishing to be bound by theory, in the natural mechanism of sensing and controlling tryptophan synthesis, TRAP is understood to act at the level of transcription termination by binding to a binding site in the newly synthesised RNA leader. This destabilises an overlapping anti-terminator sequence such that a downstream rho-independent terminator is active, leading to the production of only short RNAs. When tryptophan is limiting within the bacterium, the TRAP ring can no longer bind to its RNA binding site. Accordingly, the anti-terminator is activated and transcription continues into the tryptophan synthesis gene operon. TRAP can also act at the translational level: tryptophan-dependent binding of TRAP to its binding site in the 5'-UTR of the RNA transcript liberates an anti-Shine-Dalgarno sequence, this forms a stable stem with the Shine-Dalgarno sequence so that ribosome initiation of translation is repressed. Finally, in other contexts when TRAP is bound to its nucleic acid binding site it is capable of repressing translation initiation by physically blocking the 40S scanning ribosome complex before it can reach the initiation codon, whereupon the more stable and higher-affinity translation machinery would otherwise form.

In one embodiment of the present invention, TRAP is derived from *Bacillus subtilis*. For example, TRAP may comprise the sequence:

(SEQ ID NO: 1)
MNQKHSSDFVVIKAVEDGVNVIGLTRGTDTKFHHSEKLDKGEVIIAQFTE

HTSAIKVRGEALIQTAYGEMKSEKK

In a preferred embodiment of the present invention SEQ ID NO: 1 is C-terminally tagged with six histidine amino acids (HIS×6 tag).

In an alternative embodiment TRAP is derived from *Aminomonas paucivorans*. For example, TRAP may comprise the sequence:

(SEQ ID NO: 2)
MKEGEEAKTSVLSDYVVVKALENGVTVIGLTRGQETKFAHTEKLDDGEVW

IAQFTEHTSAIKVRGASEIHTKHGMLFSGRGRNEKG

In an alternative embodiment TRAP is derived from *Desulfotomaculum hydrothermale*. For example, TRAP may comprise the sequence:

(SEQ ID NO: 3)
MNPMTDRSDITGDYVVVKALENGVTIIGLTRGGVTKFHHTEKLDKGEIMI

AQFTEHTSAIKIRGRAELLTKHGKIRTEVDS

In an alternative embodiment TRAP is derived from *B. stearothermophilus*. For example, TRAP may comprise the sequence:

(SEQ ID NO: 4)
MYTNSDFVVIKALEDGVNVIGLTRGADTRFHHSEKLDKGEVLIAQFTEHT

SAIKVRGKAYIQTRHGVIESEGKK

In an alternative embodiment TRAP is derived from *B. stearothermophilus* S72N. For example, TRAP may comprise the sequence:

(SEQ ID NO: 5)
MYTNSDFVVIKALEDGVNVIGLTRGADTRFHHSEKLDKGEVLIAQFTEHT

SAIKVRGKAYIQTRHGVIENEGKK

In an alternative embodiment TRAP is derived from *B. halodurans*. For example, TRAP may comprise the sequence:

```
                                                    (SEQ ID NO: 6)
MNVGDNSNFFVIKAKENGVNVFGMTRGTDTRFHHSEKLDKGEVMIAQFTE

HTSAVKIRGKAIIQTSYGTLDTEKDE
```

In an alternative embodiment TRAP is derived from *Carboxydothermus hydrogenoformans*. For example, TRAP may comprise the sequence:

```
                                                    (SEQ ID NO: 7)
MVCDNFAFSSAINAEYIVVKALENGVTIMGLTRGKDTKFHHTEKLDKGEV

MVAQFTEHTSAIKIRGKAEIYTKHGVIKNE
```

In one embodiment, TRAP is encoded by the tryptophan RNA-binding attenuation protein gene family mtrB (TrpBP superfamily e.g. with NCBI conserved domain database # cl03437).

In preferred embodiments, the TRAP is C-terminally tagged with six histidine amino acids (HIS×6 tag).

In a preferred embodiment, TRAP comprises an amino acid sequence that has 50%, 60%, 70%, 80%, 90%, 95%, 99% or 100% identity to any of SEQ ID NOs: 1 to 7 and is capable of interacting with an RNA-binding site such that expression of an operably linked NOI is modified, for example repressed or prevented, in a viral vector production cell.

In a preferred embodiment, TRAP comprises an amino acid sequence that has at least 50%, 55%, 60%, 65%, 70%, 75%, 80%, 85%, 90%, 95%, 97%, 99% or 100% identity to any of SEQ ID NOs: 1 to 7 and is capable of interacting with an RNA-binding site such that expression of an operably linked NOI is modified, for example repressed or prevented, in a viral vector production cell.

In another embodiment, the RNA-binding protein (e.g. TRAP) may be encoded by a polynucleotide comprising a nucleotide sequence which encodes a protein which is capable of interacting with an RNA-binding site such that expression of an operably linked NOI is modified, for example repressed or prevented, in a viral vector production cell. For example, TRAP may be encoded by a polynucleotide comprising a nucleotide sequence which encodes a protein of SEQ ID NOs: 1 to 7.

All variants, fragments or homologues of RNA-binding proteins such as TRAP for use in the invention will retain the ability to bind to the binding site of the invention such that translation of the NOI (which may be a marker gene) is repressed or prevented in a viral vector production cell.

Nucleic Acid Binding Site

The term "binding site" is to be understood as a nucleic acid sequence that is capable of interacting with a certain protein. The nucleic acid binding site of the present invention may be one that is capable of interacting with the RNA-binding protein of the invention, for example the tryptophan RNA-binding attenuation protein (TRAP).

In the case of the TRAP, a consensus nucleic acid binding site sequence that is capable of binding TRAP is [RAGNN] repeated multiple times (e.g. 6, 7, 8, 9, 10, 11, 12 or more times); such sequence is found in the native trp operon. In the native context, occasionally AAGNN is tolerated and occasionally additional "spacing" N nucleotides result in a functional sequence. In vitro experiments have demonstrated that at least 6 or more consensus repeats are required for TRAP-RNA binding (Babitzke P., Y. J., Campanelli D. (1996) *Journal of Bacteriology* 178(17): 5159-5163). Therefore, preferably in one embodiment there are 6 or more continuous [RAGN$_{≥2}$] sequences present within the tbs, wherein R may be T or G in DNA and U or G in RNA.

In one embodiment of the present invention, the TRAP binding site comprises the sequence RAGN$_{≥2}$ (e.g. RAGN$_{2-3}$). For the avoidance of doubt therefore, this nucleic acid binding site comprises, for example, any of the sequences UAGNN, GAGNN, TAGNN, UAGNNN, GAGNNN, or TAGNNN.

"N" is to be understood as specifying any nucleotide at that position in the sequence. For example, this could be G, A, T, C or U. The number of such nucleotides is preferably 2 but up to three, for example 1, 2 or 3, RAG repeats of an 11× repeat tbs may be separated by 3 spacing nucleotides and still retain some TRAP-binding activity that leads to translation repression. Preferably not more than one N$_3$ spacer will be used in an 11× repeat tbs in order to retain maximal TRAP-binding activity that leads to translation repression.

In another embodiment, the nucleic acid binding site comprises multiple repeats of RAGN$_{≥2}$ (e.g. multiple repeats of RAG N$_{2-3}$).

In another embodiment, the nucleic acid binding site comprises multiple repeats of the sequence RAGN$_2$.

In another embodiment, the nucleic acid binding site comprises at least 6 repeats of RAGN$_{≥2}$ (e.g. at least 6 repeats of RAG N$_{2-3}$).

In another embodiment, the nucleic acid binding site comprises at least 6 repeats of RAGN$_2$. For example, the nucleic acid binding site may comprise 6, 7, 8, 9, 10, 11, 12 or more repeats of RAGN$_2$.

In another embodiment, the nucleic acid binding site comprises at least 8 repeats of RAGN$_{≥2}$ (e.g. at least 8 repeats of RAG N$_{2-3}$).

Preferably, the number of RAGNNN repeats present in the nucleic acid binding site is 1 or less.

In another embodiment, the nucleic acid binding site comprises 11 repeats of RAGN$_{≥2}$ (e.g. 11 repeats of RAGN$_{2-3}$). Preferably, the number of RAGNNN repeats present in this nucleic acid binding site is 3 or less.

In another embodiment, the nucleic acid binding site comprises 12 repeats of RAGN$_{≥2}$ (e.g. 12 repeats of RAG N$_{2-3}$).

In a preferred embodiment, the nucleic acid binding site comprises 8-11 repeats of RAGN$_2$ (e.g. 8, 9, 10 or 11 repeats of RAGN$_2$).

For example, the TRAP binding site may comprise either of the following sequences:

```
                                                    (SEQ ID NO: 8)
GAGUUUAGCGGAGUGGAGAAGAGCGGAGCCGAGCCUAGCAGAGACGAGUG

GAGCU;
or (SEQ ID NO: 9)
GAGUUUAGCGGAGUGGAGAAGAGCGGAGCCGAGCCUAGCAGAGACGAGAA

GAGCU
```

By "repeats of RAGN$_{≥2}$" it is to be understood that the general RAGN$_{≥2}$ (e.g. RAGN$_{2-3}$) motif is repeated. Different RAGN$_{≥2}$ sequences satisfying the criteria of this motif may be joined to make up the nucleic acid binding site. It is not intended that the resulting nucleic acid binding site is limited to repeats of only one sequence that satisfies the requirements of this motif, although this possibility is included in the definition. For example, "6 repeats of RAGN$_{≥2}$" includes, but is not limited to, the sequences:

```
                                                        (SEQ ID NO: 10)
UAGUU-UAGUU-UAGUU-UAGUU-UAGUU-UAGUU;

(SEQ ID NO: 11)
UAGUU-UAGUU-GAGUU-UAGUU-GAGUU-UAGUU;

(SEQ ID NO: 12)
GAGUUU-GAGUU-GAGUU-GAGUUU-GAGUU-GAGUU
and:

(SEQ ID NO: 13)
UAGUUU-GAGUU-UAGUU-GAGUUU-UAGUU-GAGUU (the dashes are included here between the repeats
for clarity only).
```

An 8-repeat tbs containing one RAGNNN repeat and seven RAGNN repeats retains TRAP-mediated repression activity. Less than 8-repeat tbs sequences (e.g. 7- or 6-repeat tbs sequences) containing one or more RAGNNN repeats may have lower TRAP-mediated repression activity. Accordingly, when fewer than 8-repeats are present, it is preferred that the tbs comprises only RAGNN repeats.

Preferred nucleotides for use in the RAGNN repeat consensus are:
 a pyrimidine in at least one of the NN spacer positions;
 a pyrimidine at the first of the NN spacer positions;
 pyrimidines at both of the NN spacer positions;
 G at the R position.

It is also preferred that G is used at the R position when the NN spacer positions are AA (i.e. it is preferred that TAGAA is not used as a repeat in the consensus sequence).

By "capable of interacting" it is to be understood that the nucleic acid binding site is capable of binding to a protein, for example TRAP, under the conditions that are encountered in a cell, for example a eukaryotic viral vector production cell. Such an interaction with an RNA-binding protein such as TRAP results in the repression or prevention of translation of a NOI to which the nucleic acid binding site is operably linked.

By "operably linked" it is to be understood that the components described are in a relationship permitting them to function in their intended manner. Therefore an RNA-binding site of the invention operably linked to a NOI is positioned in such a way that translation of the NOI is modified when an RNA-binding protein such as TRAP binds to the RNA-binding site.

Placement of a nucleic acid binding site capable of interacting with an RNA-binding protein (e.g. a TRAP-binding sequence; tbs) upstream of a NOI translation initiation codon of a given open reading frame (ORF) allows specific translation repression of mRNA derived from that ORF. The number of nucleotides separating the TRAP-binding site and the translation initiation codon may be varied, for example from 0 to 12 nucleotides, without affecting the degree of repression. As a further example, 0 to 43 nucleotides may be used to separate the TRAP-binding site and the translation initiation codon.

Repression or prevention of the translation of the NOI is to be understood as alteration of the amount of the product (e.g. protein) of the NOI that is translated during viral vector production in comparison to the amount expressed in the absence of the nucleic acid binding site of the invention at the equivalent time point. Such alteration of translation results in a consequential repression or prevention of the expression of the protein encoded by the NOI.

In one embodiment of the present invention, the nucleic acid binding site is capable of interacting with an RNA-binding protein, such as tryptophan RNA-binding attenuation protein (TRAP), such that translation of the nucleotide of interest is repressed or prevented in a viral vector production cell.

The translation of the NOI at any given time during vector production may be reduced to 90%, 80%, 70%, 60%, 50%, 40%, 30%, 20%, 10%, 5%, 4%, 3%, 2%, 1%, 0.5% or 0.1% of the amount translated in the absence of the nucleic acid sequence of the invention at the same time-point in vector production.

The translation of the NOI at any given time during vector production may be reduced to less than 90%, 80%, 70%, 60%, 50%, 40%, 30%, 20%, 10%, 5%, 4%, 3%, 2%, 1%, 0.5% or 0.1% of the amount translated in the absence of the nucleic acid sequence of the invention at the same time-point in vector production.

Preventing the translation of the NOI is to be understood as reducing the amount of translation to substantially zero.

The expression of the protein from the NOI at any given time during vector production may be reduced to 90%, 80%, 70%, 60%, 50%, 40%, 30%, 20%, 10%, 5%, 4%, 3%, 2%, 1%, 0.5% or 0.1% of the amount expressed in the absence of the nucleic acid sequence of the invention at the same time-point in vector production.

The expression of the protein from the NOI at any given time during vector production may be reduced to less than 90%, 80%, 70%, 60%, 50%, 40%, 30%, 20%, 10%, 5%, 4%, 3%, 2%, 1%, 0.5% or 0.1% of the amount expressed in the absence of the nucleic acid sequence of the invention at the same time-point in vector production.

Preventing the expression of the protein from the NOI is to be understood as reducing the amount of the protein that is expressed to substantially zero.

Methods for the analysis and/or quantification of the translation of an NOI are well known in the art.

A protein product from lysed cells may be analysed using methods such as SDS-PAGE analysis with visualisation by Coomassie or silver staining. Alternatively a protein product may be analysed using Western blotting or enzyme-linked immunosorbent assays (ELISA) with antibody probes which bind the protein product. A protein product in intact cells may be analysed by immunofluorescence.

Nucleotide of Interest

In one embodiment of the invention, the nucleotide of interest is translated in a target cell which lacks the RNA-binding protein, for example tryptophan RNA-binding attenuation protein (TRAP).

"Target cell" is to be understood as a cell in which it is desired to express the NOI. The NOI may be introduced into the target cell using a viral vector of the present invention. Delivery to the target cell may be performed in vivo, ex vivo or in vitro.

In a preferred embodiment, the nucleotide of interest gives rise to a therapeutic effect.

The NOI may have a therapeutic or diagnostic application. Suitable NOIs include, but are not limited to sequences encoding enzymes, co-factors, cytokines, chemokines, hormones, antibodies, anti-oxidant molecules, engineered immunoglobulin-like molecules, single chain antibodies, fusion proteins, immune co-stimulatory molecules, immunomodulatory molecules, chimeric antigen receptors a transdomain negative mutant of a target protein, toxins, conditional toxins, antigens, tumour suppressor proteins, growth factors, membrane proteins, receptors, vasoactive proteins and peptides, anti-viral proteins and ribozymes, and derivatives thereof (such as derivatives with an associated reporter group). The NOIs may also encode micro-RNA.

Without wishing to be bound by theory it is believed that the processing of micro-RNA will be inhibited by TRAP.

In one embodiment, the NOI may be useful in the treatment of a neurodegenerative disorder.

In another embodiment, the NOI may be useful in the treatment of Parkinson's disease.

In another embodiment, the NOI may encode an enzyme or enzymes involved in dopamine synthesis. For example, the enzyme may be one or more of the following: tyrosine hydroxylase, GTP-cyclohydrolase I and/or aromatic amino acid dopa decarboxylase. The sequences of all three genes are available (GenBank® Accession Nos. X05290, U19523 and M76180, respectively).

In another embodiment, the NOI may encode the vesicular monoamine transporter 2 (VMAT2). In an alternative embodiment the viral genome may comprise a NOI encoding aromatic amino acid dopa decarboxylase and a NOI encoding VMAT2. Such a genome may be used in the treatment of Parkinson's disease, in particular in conjunction with peripheral administration of L-DOPA.

In another embodiment the NOI may encode a therapeutic protein or combination of therapeutic proteins.

In another embodiment, the NOI may encode a protein or proteins selected from the group consisting of glial cell derived neurotophic factor (GDNF), brain derived neurotrophic factor (BDNF), ciliary neurotrophic factor (CNTF), neurotrophin-3 (NT-3), acidic fibroblast growth factor (aFGF), basic fibroblast growth factor (bFGF), interleukin-1 beta (IL-13), tumor necrosis factor alpha (TNF-α), insulin growth factor-2, VEGF-A, VEGF-B, VEGF-C/VEGF-2, VEGF-D, VEGF-E, PDGF-A, PDGF-B, hetero- and homodimers of PDFG-A and PDFG-B.

In another embodiment, the NOI may encode an anti-angiogenic protein or anti-angiogenic proteins selected from the group consisting of angiostatin, endostatin, platelet factor 4, pigment epithelium derived factor (PEDF), restin, interferon-α, interferon-inducible protein, gro-beta and tubedown-1, interleukin(IL)-1, IL-12, retinoic acid, anti-VEGF antibodies or fragments/variants thereof, thrombospondin, VEGF receptor proteins such as those described in U.S. Pat. Nos. 5,952,199 and 6,100,071, and anti-VEGF receptor antibodies.

In another embodiment the NOI may encode cystic fibrosis transmembrane conductance regulator (CFTR).

In another embodiment the NOI may encode a protein normally expressed in an ocular cell.

In another embodiment, the NOI may encode a protein normally expressed in a photoreceptor cell and/or retinal pigment epithelium cell.

In another embodiment, the NOI may encode a protein selected from the group comprising RPE65, arylhydrocarbon-interacting receptor protein like 1 (AIPL1), CRB1, lecithin retinal acetyltransferace (LRAT), photoreceptor-specific homeo box (CRX), retinal guanylate cyclise (GUCY2D), RPGR interacting protein 1 (RPGRIP1), LCA2, LCA3, LCA5, dystrophin, PRPH2, CNTF, ABCR/ABCA4, EMP1, TIMP3, MERTK, ELOVL4, MYO7A, USH2A, VMD2, RLBP1, COX-2, FPR, harmonin, Rab escort protein 1, CNGB2, CNGA3, CEP 290, RPGR, RS1, RP1, PRELP, glutathione pathway enzymes and opticin.

In other embodiments, the NOI may encode human Factor VIII or Factor IX.

In other embodiments the NOI may encode a chimeric antigen receptor (CAR) or a T cell receptor (TCR).

In further embodiments the NOI may encode SGSH, SUMF1, GAA, the common gamma chain (CD132), adenosine deaminase, WAS protein, globins, alpha galactosidase A, δ-aminolevulinate (ALA) synthase, δ-aminolevulinate dehydratase (ALAD), Hydroxymethylbilane (HMB) synthase, Uroporphyrinogen (URO) synthase, Uroporphyrinogen (URO) decarboxylase, Coproporphyrinogen (CO-PRO) oxidase, Protoporphyrinogen (PROTO) oxidase, Ferrochelatase, α-L-iduronidase, Iduronate sulfatase, Heparan sulfamidase, N-acetylglucosaminidase, Heparan-α-glucosaminide N-acetyltransferase, 3 N-acetylglucosamine 6-sulfatase, Galactose-6-sulfate sulfatase, β-galactosidase, N-acetylgalactosamine-4-sulfatase, β-glucuronidase and Hyaluronidase.

In addition to the NOI the vector may also comprise or encode a siRNA, shRNA, or regulated shRNA. (Dickins et al. (2005) Nature Genetics 37: 1289-1295, Silva et al. (2005) Nature Genetics 37:1281-1288).

Indications

The vectors, including retroviral and AAV vectors, according to the present invention may be used to deliver one or more NOI(s) useful in the treatment of the disorders listed in WO 1998/05635, WO 1998/07859, WO 1998/09985. The nucleotide of interest may be DNA or RNA. Examples of such diseases are given below:

A disorder which responds to cytokine and cell proliferation/differentiation activity; immunosuppressant or immunostimulant activity (e.g. for treating immune deficiency, including infection with human immunodeficiency virus, regulation of lymphocyte growth; treating cancer and many autoimmune diseases, and to prevent transplant rejection or induce tumour immunity); regulation of haematopoiesis (e.g. treatment of myeloid or lymphoid diseases); promoting growth of bone, cartilage, tendon, ligament and nerve tissue (e.g. for healing wounds, treatment of burns, ulcers and periodontal disease and neurodegeneration); inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating, for example, septic shock or Crohn's disease); macrophage inhibitory and/or T cell inhibitory activity and thus, anti-inflammatory activity; anti-immune activity (i.e. inhibitory effects against a cellular and/or humoral immune response, including a response not associated with inflammation); inhibition of the ability of macrophages and T cells to adhere to extracellular matrix components and fibronectin, as well as up-regulated fas receptor expression in T cells.

Malignancy disorders, including cancer, leukaemia, benign and malignant tumour growth, invasion and spread, angiogenesis, metastases, ascites and malignant pleural effusion.

Autoimmune diseases including arthritis, including rheumatoid arthritis, hypersensitivity, allergic reactions, asthma, systemic lupus erythematosus, collagen diseases and other diseases.

Vascular diseases including arteriosclerosis, atherosclerotic heart disease, reperfusion injury, cardiac arrest, myocardial infarction, vascular inflammatory disorders, respiratory distress syndrome, cardiovascular effects, peripheral vascular disease, migraine and aspirin-dependent anti-thrombosis, stroke, cerebral ischaemia, ischaemic heart disease or other diseases.

Diseases of the gastrointestinal tract including peptic ulcer, ulcerative colitis, Crohn's disease and other diseases.

Hepatic diseases including hepatic fibrosis, liver cirrhosis or other diseases.

Renal and urologic diseases including thyroiditis or other glandular diseases, glomerulonephritis or other diseases.

Ear, nose and throat disorders including otitis or other oto-rhino-laryngological diseases, dermatitis or other dermal diseases.

Dental and oral disorders including periodontal diseases, periodontitis, gingivitis or other dental/oral diseases.

Testicular diseases including orchitis or epididimo-orchitis, infertility, orchidal trauma or other testicular diseases.

Gynaecological diseases including placental dysfunction, placental insufficiency, habitual abortion, eclampsia, pre-eclampsia, endometriosis and other gynaecological diseases.

Ophthalmologic disorders such as posterior uveitis, intermediate uveitis, anterior uveitis, conjunctivitis, chorioretinitis, uveoretinitis, optic neuritis, glaucoma, including open angle glaucoma and juvenile congenital glaucoma, intraocular inflammation, e.g. retinitis or cystoid macular oedema, sympathetic ophthalmia, scleritis, retinitis pigmentosa, macular degeneration including age related macular degeneration (AMD) and juvenile macular degeneration including Best Disease, Best vitelliform macular degeneration, Stargardt's Disease, Usher's syndrome, Doyne's honeycomb retinal dystrophy, Sorby's Macular Dystrophy, Juvenile retinoschisis, Cone-Rod Dystrophy, Corneal Dystrophy, Fuch's Dystrophy, Leber's congenital amaurosis, Leber's hereditary optic neuropathy (LHON), Adie syndrome, Oguchi disease, degenerative fondus disease, ocular trauma, ocular inflammation caused by infection, proliferative vitreo-retinopathies, acute ischaemic optic neuropathy, excessive scarring, e.g. following glaucoma filtration operation, reaction against ocular implants, corneal transplant graft rejection, and other ophthalmic diseases, such as diabetic macular oedema, retinal vein occlusion, RLBP1-associated retinal dystrophy, choroideremia and achromatopsia.

Neurological and neurodegenerative disorders including Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, strokes, post-polio syndrome, psychiatric disorders, myelitis, encephalitis, subacute sclerosing pan-encephalitis, encephalomyelitis, acute neuropathy, subacute neuropathy, chronic neuropathy, Pompe disease, Guillaim-Barre syndrome, Sydenham chorea, myasthenia gravis, pseudo-tumour cerebri, Down's Syndrome, Huntington's disease, CNS compression or CNS trauma or infections of the CNS, muscular atrophies and dystrophies, diseases, conditions or disorders of the central and peripheral nervous systems, motor neuron disease including amyotropic lateral sclerosis, spinal muscular atropy, spinal cord and avulsion injury.

Other diseases and conditions such as cystic fibrosis, mucopolysaccharidosis including Sanfilipo syndrome A, ADA-SCID, X-linked SCID, porphyria, haemophilia A, haemophilia B, post-traumatic inflammation, haemorrhage, coagulation and acute phase response, cachexia, anorexia, acute infection, septic shock, infectious diseases, complications or side effects of surgery, bone marrow transplantation or other transplantation complications and/or side effects, complications and side effects of gene therapy, e.g. due to infection with a viral carrier, or AIDS, to suppress or inhibit a humoral and/or cellular immune response, for the prevention and/or treatment of graft rejection in cases of transplantation of natural or artificial cells, tissue and organs such as cornea, bone marrow, organs, lenses, pacemakers, natural or artificial skin tissue.

siRNA, micro-RNA and shRNA

In certain other embodiments, the NOI comprises a micro-RNA. Micro-RNAs are a very large group of small RNAs produced naturally in organisms, at least some of which regulate the expression of target genes. Founding members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors which are processed to their mature forms by Dicer enzyme.

In addition to the NOI the vector may also comprise or encode a siRNA, shRNA, or regulated shRNA (Dickins et al. (2005) Nature Genetics 37: 1289-1295, Silva et al. (2005) Nature Genetics 37:1281-1288).

Post-transcriptional gene silencing (PTGS) mediated by double-stranded RNA (dsRNA) is a conserved cellular defence mechanism for controlling the expression of foreign genes. It is thought that the random integration of elements such as transposons or viruses causes the expression of dsRNA which activates sequence-specific degradation of homologous single-stranded mRNA or viral genomic RNA. The silencing effect is known as RNA interference (RNAi) (Ralph et al. (2005) Nature Medicine 11:429-433). The mechanism of RNAi involves the processing of long dsRNAs into duplexes of about 21-25 nucleotide (nt) RNAs. These products are called small interfering or silencing RNAs (siRNAs) which are the sequence-specific mediators of mRNA degradation. In differentiated mammalian cells, dsRNA >30 bp has been found to activate the interferon response leading to shut-down of protein synthesis and non-specific mRNA degradation (Stark et al., Annu Rev Biochem 67:227-64 (1998)). However this response can be bypassed by using 21 nt siRNA duplexes (Elbashir et al., EMBO J. December 3; 20(23):6877-88 (2001), Hutvagner et al., Science. August 3, 293(5531):834-8. Eupub July 12 (2001)) allowing gene function to be analysed in cultured mammalian cells.

Vectors

Another aspect of the invention relates to a viral vector comprising the nucleic acid sequence of the invention.

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous cDNA segment), to be transferred into a target cell. The vector may serve the purposes of maintaining the heterologous nucleic acid (DNA or RNA) within the cell, or facilitating the replication of the vector comprising a segment of DNA or RNA or the expression of the protein encoded by a segment of nucleic acid.

The vectors of the invention may be, for example, viral vectors provided with an origin of replication, optionally a promoter for the expression of the said polynucleotide and optionally a regulator of the promoter. The vectors may contain one or more selectable marker genes (e.g. a neomycin resistance gene) and/or traceable marker genes (e.g. a gene encoding GFP). Vectors may be used, for example, to infect and/or transduce a target cell.

The vector of the invention may be used to replicate the NOI in a compatible target cell in vitro. Thus, the invention provides a method of making proteins in vitro by introducing a vector of the invention into a compatible target cell in vitro and growing the target cell under conditions which result in expression of the NOI. Protein may be recovered from the target cell by methods well known in the art. Suitable target cells include mammalian cell lines and other eukaryotic cell lines.

The vector may be an expression vector. Expression vectors as described herein comprise regions of nucleic acid containing sequences capable of being transcribed. Thus, sequences encoding mRNA, tRNA and rRNA are included within this definition. Preferably, an expression vector comprises a polynucleotide of the invention operably linked to a control sequence that is capable of providing for the expression of the coding sequence by the target cell.

Viral Vectors

In one embodiment of the invention, the vector is a viral vector. A viral vector may also be called a vector, vector virion or vector particle.

In another embodiment, the viral vector is derived from a retrovirus, adenovirus, adeno-associated virus, herpes simplex virus, vaccinia virus or baculovirus.

It is anticipated that the repression system of the invention will be of benefit to any viral vector system. The system will find particular use where the nucleotide of interest causes adverse effects, for example on the viral vector production cell or during virion assembly.

In another embodiment, the retrovirus is derived from a foamy virus.

In another embodiment, the retroviral vector is derived from a lentivirus.

In another embodiment, the lentiviral vector is derived from HIV-1, HIV-2, SIV, FIV, BIV, EIAV, CAEV or visna lentivirus.

Vector Titre

The skilled person will understand that there are a number of different methods of determining the titre of viral vectors. Titre is often described as transducing units/mL (TU/mL). Titre may be increased by increasing the number of infectious particles and by increasing the specific activity of a vector preparation.

Retroviral and Lentiviral Vectors

The retroviral vector of the present invention may be derived from or may be derivable from any suitable retrovirus. A large number of different retroviruses have been identified. Examples include: murine leukemia virus (MLV), human T-cell leukemia virus (HTLV), mouse mammary tumour virus (MMTV), Rous sarcoma virus (RSV), Fujinami sarcoma virus (FuSV), Moloney murine leukemia virus (Mo MLV), FBR murine osteosarcoma virus (FBR MSV), Moloney murine sarcoma virus (Mo-MSV), Abelson murine leukemia virus (A-MLV), Avian myelocytomatosis virus-29 (MC29) and Avian erythroblastosis virus (AEV). A detailed list of retroviruses may be found in Coffin et al. (1997) "Retroviruses", Cold Spring Harbour Laboratory Press Eds: J M Coffin, S M Hughes, H E Varmus pp 758-763.

Retroviruses may be broadly divided into two categories, namely "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al (1997) ibid.

The basic structure of retrovirus and lentivirus genomes share many common features such as a 5' LTR and a 3' LTR, between or within which are located a packaging signal to enable the genome to be packaged, a primer binding site, integration sites to enable integration into a target cell genome and gag/pol and env genes encoding the packaging components—these are polypeptides required for the assembly of viral particles. Lentiviruses have additional features, such as the rev gene and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration, and transcription. LTRs also serve as enhancer-promoter sequences and can control the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a typical retroviral vector of the present invention, at least part of one or more protein coding regions essential for replication may be removed from the virus; for example, gag/pol and env may be absent or not functional. This makes the viral vector replication-defective.

Portions of the viral genome may also be replaced by a library encoding candidate nucleic acid binding sequences of the invention operably linked to a regulatory control region and a reporter gene in the vector genome in order to generate a vector comprising candidate nucleic acid binding sequences of the invention which is capable of transducing a target non-dividing cell and/or integrating its genome into a host genome.

Lentiviruses are part of a larger group of retroviruses. A detailed list of lentiviruses may be found in Coffin et al (1997) "Retroviruses" Cold Spring Harbour Laboratory Press Eds: J M Coffin, S M Hughes, H E Varmus pp 758-763). In brief, lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV), feline immunodeficiency virus (FIV) and bovine immunodeficiency virus (BIV).

The lentivirus family differs from retroviruses in that lentiviruses have the capability to infect both dividing and non-dividing cells (Lewis et al (1992) EMBO J 11(8):3053-3058 and Lewis and Emerman (1994) J Virol 68 (1):510-516). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be derived from either a primate lentivirus (e.g. HIV-1) or a non-primate lentivirus.

Examples of non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi visna virus (MW) or an equine infectious anaemia virus (EIAV).

Figure 1:
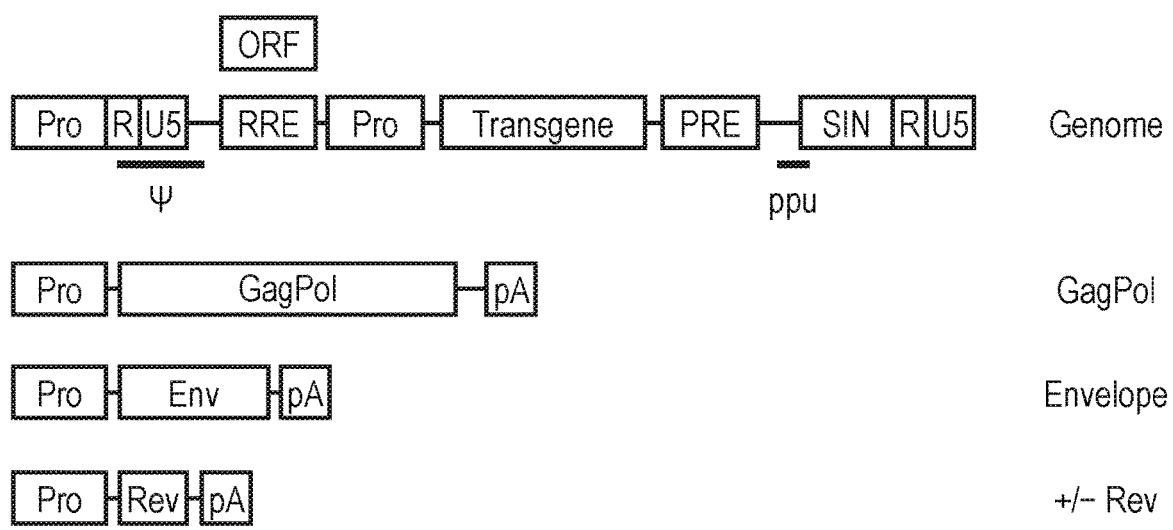
FIG. 1. A schematic displaying typical retroviral vector components. Therapeutic retroviral vector systems currently used have been highly engineered from the wild-type virus genomes from which they were derived. Gamma-retroviral vectors are typically produced using 3- or 4-component systems requiring vector genome, Gag/Pol and envelope expression constructs and, for HIV-based lentiviral vectors, the accessory gene Rev is also required. EIAV-based lentiviral vectors do not require Rev if an open-reading frame (ORF) replaces RRE. Vector genomes typically require a packaging signal (ψ), an NOI, (optionally) a post-transcriptional element (PRE), the 3'ppu and a self-inactivating (SIN) LTR. The R-U5 regions are required for correct polyadenylation of both vector genome RNA and transgene mRNA, as well as the process of reverse transcription. Usually both 'external' and 'internal' promoters (Pro) encoded within the genome cassette are strong eukaryotic or virus promoters, as are those driving the other vector system components.

In general terms, a typical retroviral vector production system involves the separation of the viral genome from the essential viral packaging functions. As illustrated in FIG. 1, these components are provided to the production cells on separate DNA expression cassettes (alternatively known as plasmids, expression plasmids, DNA constructs or expression constructs).

The vector genome comprises the NOI. Vector genomes typically require a packaging signal (ψ), the internal expression cassette harbouring the NOI, (optionally) a post-transcriptional element (PRE), the 3'-ppu and a self-inactivating (SIN) LTR. The R-U5 regions are required for correct polyadenylation of both the vector genome RNA and NOI mRNA, as well as the process of reverse transcription. The vector genome may optionally include an open reading frame, as described in WO 2003/064665.

The packaging functions include the gag/pol and env genes. These are required for the production of vector particles by the production cell. Providing these functions in trans to the genome facilitates the production of replication-defective virus.

Production systems for gamma-retroviral vectors are typically 3-component systems requiring genome, gag/pol and env expression constructs. Production systems for HIV-1-based lentiviral vectors additionally require the accessory gene rev to be provided in trans and for the vector genome to include the rev-responsive element (RRE). EIAV-based lentiviral vectors do not require rev if an open-reading frame (ORF) is present (see WO 2003/064665).

Usually both the "external" promoter (which drives the vector genome cassette) and "internal" promoter (which drives the NOI cassette) encoded within the vector genome cassette are strong eukaryotic or virus promoters, as are those driving the other vector system components. Examples of such promoters include CMV, EF1a, PGK, CAG, TK, SV40 and Ubiquitin promoters. Strong 'synthetic' promoters, such as those generated by DNA libraries (e.g. JeT promoter) may also be used to drive transcription. Alternatively, tissue-specific promoters such as rhodopsin (Rho), rhodopsin kinase (RhoK), cone-rod homeobox containing gene (CRX), neural retina-specific leucine zipper protein (NRL), Vitelliform Macular Dystrophy 2 (VMD2), Tyrosine hydroxylase, neuronal-specific neuronal-specific enolase (NSE) promoter, astrocyte-specific glial fibrillary acidic protein (GFAP) promoter, human al-antitrypsin (hAAT) promoter, phosphoenolpyruvate carboxykinase (PEPCK), liver fatty acid binding protein promoter, Fit-1 promoter, INF-β promoter, Mb promoter, SP-B promoter, SYN1 promoter, WASP promoter, SV40/hAlb promoter, SV40/CD43, SV40/CD45, NSE/RU5' promoter, ICAM-2 promoter, GPIIb promoter, GFAP promoter, Fibronectin promoter, Endoglin promoter, Elastase-1 promoter, Desmin promoter, CD68 promoter, CD14 promoter and B29 promoter may be used to drive transcription.

Production of retroviral vectors involves either the transient transfection of the production cells with these DNA components or use of stable producer cell lines (PCLs) wherein the components are integrated within the production cell genome (e.g. Stewart, H. J., M. A. Leroux-Carlucci, C. J. Sion, K. A. Mitrophanous and P. A. Radcliffe (2009) *Gene Ther.* 16(6): 805-814 Epub 29 Mar. 2005). An alternative approach is to use a stable packaging cell (into which the packaging components are stably integrated) and then transiently transfect in the vector genome plasmid as required. In order to generate the viral vectors of the present invention the production cells must be capable of expressing the RNA-binding protein (e.g. TRAP protein). Thus, in one embodiment of the invention the production cells will stably express the RNA-binding protein (e.g. TRAP) construct. In another embodiment of the invention the production cells will transiently express the RNA-binding protein (e.g. TRAP) construct. In another embodiment of the invention the production cells will stably express a RNA-binding protein (e.g. TRAP) construct and also transiently express a RNA-binding protein (e.g. TRAP) construct.

It should be noted that, although the TRIP system has been mainly described for producing retroviral vectors, analogous strategies can be applied to other viral vectors.

In one embodiment of the present invention, the viral vector is derived from EIAV. EIAV has the simplest genomic structure of the lentiviruses and is particularly preferred for use in the present invention. In addition to the gag/pol and env genes, EIAV encodes three other genes: tat, rev, and S2. Tat acts as a transcriptional activator of the viral LTR (Derse and Newbold (1993) Virology 194(2):530-536 and Maury et al (1994) Virology 200(2):632-642) and rev regulates and coordinates the expression of viral genes through rev-response elements (RRE) (Martarano et al. (1994) J Virol 68(5):3102-3111). The mechanisms of action of these two proteins are thought to be broadly similar to the analogous mechanisms in the primate viruses (Martarano et al. (1994) J Virol 68(5):3102-3111). The function of S2 is unknown. In addition, an EIAV protein, Ttm, has been identified that is encoded by the first exon of tat spliced to the env coding sequence at the start of the transmembrane protein. In an alternative embodiment of the present invention the viral vector is derived from HIV: HIV differs from EIAV in that it does not encode S2 but unlike EIAV it encodes vif, vpr, vpu and nef.

The term "recombinant retroviral or lentiviral vector" (RRV) refers to a vector with sufficient retroviral genetic information to allow packaging of an RNA genome, in the presence of packaging components, into a viral particle capable of infecting a target cell. Infection of the target cell may include reverse transcription and integration into the target cell genome. The RRV carries non-viral coding sequences which are to be delivered by the vector to the target cell. A RRV is incapable of independent replication to produce infectious retroviral particles within the target cell. Usually the RRV lacks a functional gag/pol and/or env gene, and/or other genes essential for replication.

Preferably the RRV vector of the present invention has a minimal viral genome.

As used herein, the term "minimal viral genome" means that the viral vector has been manipulated so as to remove the non-essential elements whilst retaining the elements essential to provide the required functionality to infect, transduce and deliver a nucleotide sequence of interest to a target cell. Further details of this strategy can be found in WO 1998/17815 and WO 99/32646. A minimal EIAV vector lacks tat, rev and S2 genes and neither are these genes provided in trans in the production system. A minimal HIV vector lacks vif, vpr, vpu, tat and nef.

However, the expression plasmid used to produce the vector genome within a production cell will include transcriptional regulatory control sequences operably linked to the retroviral genome to direct transcription of the genome in a production cell/packaging cell. These regulatory sequences may be the natural sequences associated with the transcribed retroviral sequence, i.e. the 5' U3 region, or they may be a heterologous promoter such as another viral promoter, for example the CMV promoter, as discussed below. Some lentiviral vector genomes require additional sequences for efficient virus production. For example, particularly in the case of HIV, RRE sequences may be included. However the requirement for RRE (and dependence on rev which is provided in trans) may be reduced or eliminated by codon optimisation. Further details of this strategy can be found in WO 2001/79518. Alternative sequences which perform the same function as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, it is also known that the Rex protein of HTLV-I can functionally replace the Rev protein of HIV-1. Rev and RRE may be absent or non-functional in the vector for use in the methods of the present invention; in the alternative rev and RRE, or functionally equivalent system, may be present.

SIN Vectors

The vectors for use in the methods of the present invention are preferably used in a self-inactivating (SIN) configuration in which the viral enhancer and promoter sequences have been deleted. SIN vectors can be generated and transduce non-dividing target cells in vivo, ex vivo or in vitro with an efficacy similar to that of wild-type vectors. The transcriptional inactivation of the long terminal repeat (LTR) in the SIN provirus should prevent mobilization by replication-competent virus. This should also enable the regulated expression of genes from internal promoters by eliminating any cis-acting effects of the LTR.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it is important to prevent the adventitious activation of any endogenous oncogene. Yu et al., (1986) PNAS 83: 3194-98; Marty et al., (1990) Biochimie 72: 885-7; Naviaux et al., (1996) J. Virol. 70: 5701-5; Iwakuma et al., (1999) Virol. 261: 120-32; Deglon et al., (2000) Human Gene Therapy 11: 179-90. SIN lentiviral vectors are described in U.S. Pat. Nos. 6,924,123 and 7,056,699.

Non-Replicating Lentiviral Vectors

In the genome of a replication-defective lentiviral vector the sequences of gag/pol and/or env may be mutated, absent and/or not functional.

In a typical lentiviral vector of the present invention, at least part of one or more coding regions for proteins essential for virus replication may be removed from the vector. This makes the viral vector replication-defective. Portions of the viral genome may also be replaced by a nucleotide of interest (NOI) in order to generate a vector comprising an NOI which is capable of transducing a non-dividing target cell and/or integrating its genome into the target cell genome.

In one embodiment the lentiviral vectors are non-integrating vectors as described in WO 2006/010834 and WO 2007/071994.

In a further embodiment the vectors have the ability to deliver a sequence which is devoid of or lacking viral RNA. In a further embodiment a heterologous binding domain (heterologous to gag) located on the RNA to be delivered and a cognate binding domain on Gag or GagPol can be used to ensure packaging of the RNA to be delivered. Both of these vectors are described in WO 2007/072056.

Adenoviral Vectors

In another embodiment of the present invention, the vector may be an adenovirus vector. The adenovirus is a double-stranded, linear DNA virus that does not replicate through an RNA intermediate. There are over 50 different human serotypes of adenovirus divided into 6 subgroups based on their genetic sequence.

Adenoviruses are double-stranded DNA non-enveloped viruses that are capable of in vivo, ex vivo and in vitro transduction of a broad range of cell types of human and non-human origin. These cells include respiratory airway epithelial cells, hepatocytes, muscle cells, cardiac myocytes, synoviocytes, primary mammary epithelial cells and post-mitotically terminally differentiated cells such as neurons.

Adenoviral vectors are also capable of transducing non-dividing cells. This is very important for diseases, such as cystic fibrosis, in which the affected cells in the lung epithelium have a slow turnover rate. In fact, several trials are underway utilising adenovirus-mediated transfer of cystic fibrosis transporter (CFTR) into the lungs of afflicted adult cystic fibrosis patients.

Adenoviruses have been used as vectors for gene therapy and for expression of heterologous genes. The large (36 kb) genome can accommodate up to 8 kb of foreign insert DNA and is able to replicate efficiently in complementing cell lines to produce very high titres of up to $10^{12}$ transducing units per ml. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, they function episomally (independently from the host genome) as a linear genome in the host nucleus.

Adeno-Associated Virus Vectors

Adeno-associated virus (AAV) is an attractive vector system for use in the present invention as it has a high frequency of integration and it can infect non-dividing cells. This makes it useful for delivery of genes into mammalian cells. AAV has a broad host range for infectivity. Details concerning the generation and use of rAAV vectors are described in U.S. Pat. Nos. 5,139,941 and 4,797,368, each incorporated herein by reference.

Recombinant AAV vectors have been used successfully for in vitro, ex vivo and in vivo transduction of marker genes and genes involved in human diseases.

Certain AAV vectors have been developed which can efficiently incorporate large payloads (up to 8-9 kb). One such vector has an AAV5 capsid and an AAV2 ITR (Allocca M, et al J. Clin Invest (2008) 118: 1955-1964).

Herpes Simplex Virus Vectors

Herpes simplex virus (HSV) is an enveloped double-stranded DNA virus that naturally infects neurons. It can accommodate large sections of foreign DNA, which makes it attractive as a vector system, and has been employed as a vector for gene delivery to neurons (Manservigiet et al Open Virol J. (2010) 4:123-156).

The use of HSV in therapeutic procedures requires the strains to be attenuated so that they cannot establish a lytic cycle. In particular, if HSV vectors are used for gene therapy in humans, the polynucleotide should preferably be inserted into an essential gene. This is because if a viral vector encounters a wild-type virus, transfer of a heterologous gene to the wild-type virus could occur by recombination. However, as long as the polynucleotide is inserted into an essential gene, this recombinational transfer would also delete the essential gene in the recipient virus and prevent "escape" of the heterologous gene into the replication competent wild-type virus population.

Vaccinia Virus Vectors

The vector of the present invention may be a vaccinia virus vector such as MVA or NYVAC. Alternatives to vaccinia vectors include avipox vectors such as fowlpox or canarypox known as ALVAC and strains derived therefrom which can infect and express recombinant proteins in human cells but are unable to replicate.

Baculovirus Vectors

The vector of the present invention may also be a baculovirus vector. The modification of baculovirus to enable the expression of encoded NOIs within mammalian cells is well known in the art. This can be achieved, for example, through the use of mammalian promoters upstream of the NOI.

Vectors Encoding Multiple NOIs

In one embodiment, the vector comprises more than one NOI wherein one or more NOI is operably linked to the nucleic acid binding site of the invention.

Internal Ribosome Entry Site (IRES)

As discussed above, the vectors of the invention may comprise more than one NOI. In order for these NOIs to be expressed, there may be two or more transcription units within the vector genome, one for each NOI. However, it is clear from the literature that retroviral vectors achieve the highest titres and most potent gene expression properties if they are kept genetically simple (WO 96/37623; Bowtell et al., 1988 J. Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197) and so it is preferable to use an internal ribosome entry site (IRES) to initiate translation of the second (and subsequent) coding sequence(s) in a polycistronic message (Adam et al 1991 J. Virol. 65, 4985).

Insertion of IRES elements into retroviral vectors is compatible with the retroviral replication cycle and allows expression of multiple coding regions from a single promoter (Adam et al (as above); Koo et al (1992) Virology 186:669-675; Chen et al 1993 J. Virol 67:2142-2148). IRES elements were first found in the non-translated 5' ends of picornaviruses where they promote cap-independent translation of viral proteins (Jang et al (1990) Enzyme 44: 292-309). When located between open reading frames in an RNA, IRES elements allow efficient translation of the downstream open reading frame by promoting entry of the ribosome at the IRES element followed by downstream initiation of translation.

A review on IRES is presented by Mountford and Smith (TIG May 1995 vol 11, No 5:179-184). A number of different IRES sequences are known including those from encephalomyocarditis virus (EMCV) (Ghattas, I. R., et al., Mol. Cell. Biol., 11:5848-5859 (1991); BiP protein [Macejak and Sarnow, Nature 353:91 (1991)]; the Antennapedia gene of Drosophila (exons d and e) [Oh, et al., Genes & Development, 6:1643-1653 (1992)] as well as those in polio virus (PV) [Pelletier and Sonenberg, Nature 334: 320-325 (1988); see also Mountford and Smith, TIG 11, 179-184 (1985)].

IRES elements from PV, EMCV and swine vesicular disease virus have previously been used in retroviral vectors (Coffin et al, as above).

The term "IRES" includes any sequence or combination of sequences which work as or improve the function of an IRES.

The IRES(s) may be of viral origin (such as EMCV IRES, PV IRES, or FMDV 2A-like sequences) or cellular origin (such as FGF2 IRES, NRF IRES, Notch 2 IRES or EIF4 IRES).

In order for the IRES to be capable of initiating translation of each polynucleotide it should be located between or prior to the polynucleotides in the vector genome.

Promoter

Expression of a NOI may be controlled using control sequences, which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters.

Suitable promoting sequences are strong promoters including those derived from the genomes of viruses, such as polyoma virus, adenovirus, fowlpox virus, bovine papilloma virus, avian sarcoma virus, cytomegalovirus (CMV), retrovirus and Simian Virus 40 (SV40), or from heterologous mammalian promoters, such as the actin promoter, EF1a, CAG, TK, SV40, ubiquitin, PGK or ribosomal protein promoter. Alternatively, tissue-specific promoters such as rhodopsin (Rho), rhodopsin kinase (RhoK), cone-rod homeobox containing gene (CRX), neural retina-specific leucine zipper protein (NRL), Vitelliform Macular Dystrophy 2 (VMD2), Tyrosine hydroxylase, neuronal-specific enolase (NSE) promoter, astrocyte-specific glial fibrillary acidic protein (GFAP) promoter, human al-antitrypsin (hAAT) promoter, phosphoenolpyruvate carboxykinase (PEPCK), liver fatty acid binding protein promoter, Flt-1 promoter, INF-β promoter, Mb promoter, SP-B promoter, SYN1 promoter, WASP promoter, SV40/hAlb promoter, SV40/CD43, SV40/CD45, NSE/RU5' promoter, ICAM-2 promoter, GPIIb promoter, GFAP promoter, Fibronectin promoter, Endoglin promoter, Elastase-1 promoter, Desmin promoter, CD68 promoter, CD14 promoter and B29 promoter may be used to drive transcription.

Transcription of a gene may be increased further by inserting an enhancer sequence into the vector. Enhancers are relatively orientation- and position-independent; however, one may employ an enhancer from a eukaryotic cell virus, such as the SV40 enhancer on the late side of the replication origin (bp 100-270) and the CMV early promoter enhancer. The enhancer may be spliced into the vector at a position 5' or 3' to the promoter, but is preferably located at a site 5' from the promoter.

The promoter can additionally include features to ensure or to increase expression in a suitable target cell. For example, the features can be conserved regions e.g. a Pribnow Box or a TATA box. The promoter may contain other sequences to affect (such as to maintain, enhance or decrease) the levels of expression of a nucleotide sequence. Suitable other sequences include the Sh1-intron or an ADH intron. Other sequences include inducible elements, such as temperature, chemical, light or stress inducible elements. Also, suitable elements to enhance transcription or translation may be present.

The RNA-binding protein-binding site (e.g. TRAP-tbs) interaction may be useful in forming the basis for a transgene protein repression system for the production of retroviral vectors, when a constitutive and/or strong promoter, including a tissue-specific promoter, driving the transgene is desirable and particularly when expression of the transgene protein in production cells leads to reduction in vector titres and/or elicits an immune response in vivo due to viral vector delivery of transgene-derived protein. FIG. 4 displays an example of how this may be applied in its preferred form.

Packaging Sequence

As utilized within the context of the present invention the term "packaging signal", which is referred to interchangeably as "packaging sequence" or "psi", is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon. In EIAV the packaging signal comprises the R region into the 5' coding region of Gag.

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles.

Feline immunodeficiency virus (FIV) RNA encapsidation determinants have been shown to be discrete and non-continuous, comprising one region at the 5' end of the genomic mRNA (R-U5) and another region that mapped within the proximal 311 nt of gag (Kaye et al., J Virol. October; 69(10):6588-92 (1995).

Viral Vector Production Systems and Cells

Another aspect of the invention relates to a viral vector production system comprising a set of nucleic acid sequences encoding the components required for production of the viral vector, wherein the vector genome sequence comprises the nucleic acid sequence of the invention.

"Viral vector production system" or "vector production system" or "production system" is to be understood as a system comprising the necessary components for viral vector production.

Accordingly, the vector production system comprises a set of nucleic acid sequences which encode the components necessary to generate viral vector particles. One such nucleic acid sequence may comprise the gene encoding a RNA-binding protein. In a preferred embodiment the RNA binding protein is the bacterial TRAP.

In one embodiment of the invention, the viral vector is a retroviral vector and the viral vector production system further comprises nucleic acid sequences encoding Gag and Gag/Pol proteins, and Env protein, or functional substitutes thereof and the vector genome sequence which comprises the binding site of the present invention. The production system may optionally comprise a nucleic acid sequence encoding the Rev protein.

In another embodiment of the viral vector production system of the invention, the viral vector is derived from a retrovirus, adenovirus or adeno-associated virus.

In another embodiment, the viral vector is derived from a lentivirus. In another embodiment, the viral vector is derived from HIV-1, HIV-2, SIV, FIV, BIV, EIAV, CAEV or visna lentivirus.

Another aspect of the invention relates to DNA constructs for use in the viral vector production system of the invention. Such DNA constructs (e.g. plasmids) may include the vector genome construct which comprises the nucleic acid sequence of the invention.

A further aspect of the invention relates to a DNA construct for use in the viral vector production system of the invention comprising a nucleic acid sequence encoding the RNA-binding protein of the invention, for example TRAP.

Another aspect of the invention relates to a set of DNA constructs for use in the viral vector production system of the invention comprising the DNA constructs of the invention and DNA constructs encoding Gag and Gag/Pol proteins and Env protein, or functional substitutes thereof.

In one embodiment of the invention, the set of DNA constructs additionally comprises a DNA construct encoding the RNA-binding protein, for example TRAP.

In one embodiment of the invention, the set of DNA constructs additionally comprises a DNA construct encoding Rev protein or a functional substitute thereof.

Another aspect of the invention relates to a viral vector production cell comprising the nucleic acid sequence, the viral vector production system, or some or all of the DNA constructs of the invention.

A "viral vector production cell" is to be understood as a cell that is capable of producing a viral vector or viral vector particle. Viral vector production cells may be "producer cells" or "packaging cells". One or more DNA constructs of the viral vector system may be stably integrated or episomally maintained within the viral vector production cell. Alternatively, all the DNA components of the viral vector system may be transiently transfected into the viral vector production cell. In yet another alternative, a production cell stably expressing some of the components may be transiently transfected with the remaining components.

The DNA expression cassette encoding the RNA binding protein (e.g. TRAP) may be stably integrated or episomally maintained within the viral vector production cell. Alternatively, the DNA expression cassette encoding the RNA binding protein (e.g. TRAP) may be transiently transfected into the viral vector production cell.

Thus, in one embodiment of the invention the production cells will stably express the RNA-binding protein (e.g. TRAP) construct. In another embodiment of the invention the production cells will transiently express the RNA-binding protein (e.g. TRAP) construct.

The level of repression required may vary in accordance with the NOI, thus the level of RNA-binding protein (e.g. TRAP) required in the production cell may also depend on the NOI. In some circumstances, a combination of stable and transient RNA-binding protein (e.g. TRAP) expression may therefore be desired. The stable expression may provide a continual level of RNA-binding protein expression in the production cell, while the transient expression may provide shorter term, increased levels of RNA-binding protein expression. For example, it is possible that repression of more problematic/toxic transgenes will benefit from both pre-existing (e.g. provided by stable expression) and high levels of RNA-binding protein during vector production.

Thus, in another embodiment of the invention the production cells will stably express a RNA-binding protein (e.g. TRAP) construct and also transiently express a RNA-binding protein (e.g. TRAP) construct. The transient expression may provide short term higher levels of RNA-binding protein expression than provided by the stable expression.

By "stable expression", it is to be understood that the expression of the RNA-binding protein from the construct providing the stable expression substantially does not vary over a prolonged period of time.

By "transient expression", it is to be understood that the expression of the RNA-binding protein from the construct providing the transient expression is not stable over a prolonged period of time. Preferably, the polynucleotide encoding the RNA-binding protein which provides for the transient expression does not integrate into the production cell genome and is not episomally maintained in the production cell.

As used herein, the term "packaging cell" refers to a cell which contains the elements necessary for production of infectious vector particles but which are lack the vector genome. Typically, such packaging cells contain one or more expression cassettes which are capable of expressing viral structural proteins (such as gag, gag/pol and env).

Producer cells/packaging cells can be of any suitable cell type. Producer cells are generally mammalian cells but can be, for example, insect cells.

As used herein, the term "producer/production cell" or "vector producing/production cell" refers to a cell which contains all the elements necessary for production of retroviral vector particles, and expression of the RNA-binding protein (e.g. TRAP).

The producer cell may be either a stable producer cell line or derived transiently.

In one embodiment of the invention the envelope and nucleocapsid, RNA-binding protein (e.g. TRAP) and, if present, rev nucleotide sequences are all stably integrated in the producer and/or packaging cell. However, any one or more of these sequences could also exist in episomal form and gene expression could occur from the episome, or could be transfected transiently into the production cell.

The vector production cells may be cells cultured in vitro such as a tissue culture cell line. Suitable cell lines include, but are not limited to, mammalian cells such as murine fibroblast derived cell lines or human cell lines. Preferably the vector production cells are derived from a human cell line.

In one embodiment the vectors of the present invention use as their production system, four transcription units expressing a vector genome comprising the binding site of the invention operably linked to the NOI, the gag-pol components, an envelope and the RNA-binding protein (e.g. TRAP). The envelope expression cassette may include one of a number of heterologous envelopes such as VSV-G. Optionally the rev component may also be included.

Viral Vector Production Processes

Another aspect of the invention relates to a process for producing viral vectors comprising introducing the nucleic acid sequence, the viral vector production system, or some or all of the DNA constructs of the invention into a viral vector production cell and culturing the production cell under conditions suitable for the production of the viral vectors.

Suitable "production cells" are those cells which are capable of producing viral vectors or viral vector particles when cultured under appropriate conditions. They are generally mammalian or human cells, for example HEK293T, HEK293, CAP, CAP-T or CHO cells, but can be, for example, insect cells such as SF9 cells.

The production cells may also be avian cells, for example EB66® (Sigma) cells. Avian cells may be particularly useful for the production of human and veterinary virus-based vaccines, for example influenza and Newcastle Disease virus vaccines.

Methods for introducing nucleic acids into production cells are well known in the art and have been described previously.

In one embodiment, the production cell comprises the RNA-binding protein (e.g. tryptophan RNA-binding attenuation protein, TRAP).

Another aspect of the invention relates to a viral vector produced by the viral vector production system of the invention, using the viral vector production cell of the invention or by the process of the invention.

In one embodiment, the viral vector particle comprises the nucleic acid binding site. The viral vector particle may be derived from a retrovirus, adenovirus or adeno-associated virus. The retroviral vector particle may be derived from a lentivirus. The lentiviral vector particle may be derived from HIV-1, HIV-2, SIV, FIV, BIV, EIAV, CAEV or visna lentivirus.

Methods for generating lentiviral vectors and in particular the processing of lentiviral vectors, are described in WO 2009/153563.

Another aspect of the invention relates to a cell transduced by the viral vector of the invention.

A "cell transduced by a viral vector particle" is to be understood as a cell, in particular a target cell, into which the nucleic acid carried by the viral vector particle has been transferred.

Pseudotyping

In one preferred aspect, the viral vector of the present invention has been pseudotyped. In this regard, pseudotyping can confer one or more advantages. For example, the env gene product of the HIV based vectors would restrict these vectors to infecting only cells that express a protein called CD4. But if the env gene in these vectors has been substituted with env sequences from other enveloped viruses, then they may have a broader infectious spectrum (Verma and Somia (1997) Nature 389(6648):239-242). By way of example, workers have pseudotyped an HIV based vector with the glycoprotein from VSV (Verma and Somia (1997) Nature 389(6648):239-242).

In another alternative, the Env protein may be a modified Env protein such as a mutant or engineered Env protein. Modifications may be made or selected to introduce targeting ability or to reduce toxicity or for another purpose (Valsesia-Wittman et al 1996 J Virol 70: 2056-64; Nilson et al (1996) Gene Ther 3(4):280-286; and Fielding et al (1998) Blood 91(5):1802-1809 and references cited therein).

The vector may be pseudotyped with any molecule of choice.

VSV-G

The envelope glycoprotein (G) of Vesicular stomatitis virus (VSV), a rhabdovirus, is an envelope protein that has been shown to be capable of pseudotyping certain enveloped viruses and viral vector virions.

Its ability to pseudotype MoMLV-based retroviral vectors in the absence of any retroviral envelope proteins was first shown by Emi et al. (1991) Journal of Virology 65:1202-1207). WO 1994/294440 teaches that retroviral vectors may be successfully pseudotyped with VSV-G. These pseudotyped VSV-G vectors may be used to transduce a wide range of mammalian cells. More recently, Abe et al. (1998) J Virol 72(8) 6356-6361 teach that non-infectious retroviral particles can be made infectious by the addition of VSV-G.

Burns et al. (1993) Proc. Natl. Acad. Sci. USA 90:8033-7) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al. (1993) ibid). They have also been shown to be more efficient than traditional amphotropic envelopes for a variety of cell lines (Yee et al., (1994) Proc. Natl. Acad. Sci. USA 91:9564-9568, Emi et al. (1991) Journal of Virology 65:1202-1207). VSV-G protein can be used to pseudotype certain retroviruses because its cytoplasmic tail is capable of interacting with the retroviral cores.

The provision of a non-retroviral pseudotyping envelope such as VSV-G protein gives the advantage that vector particles can be concentrated to a high titre without loss of infectivity (Akkina et al. (1996) J. Virol. 70:2581-5). Retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

WO 2000/52188 describes the generation of pseudotyped retroviral vectors, from stable producer cell lines, having vesicular stomatitis virus-G protein (VSV-G) as the membrane-associated viral envelope protein, and provides a gene sequence for the VSV-G protein.

Ross River Virus

The Ross River viral envelope has been used to pseudotype a non-primate lentiviral vector (FIV) and following systemic administration predominantly transduced the liver (Kang et al (2002) J Virol 76(18):9378-9388). Efficiency was reported to be 20-fold greater than obtained with VSV-G pseudotyped vector, and caused less cytotoxicity as measured by serum levels of liver enzymes suggestive of hepatotoxicity.

Baculovirus GP64

The baculovirus GP64 protein has been shown to be an alternative to VSV-G for viral vectors used in the large-scale production of high-titre virus required for clinical and commercial applications (Kumar M, Bradow B P, Zimmerberg J (2003) Hum Gene Ther. 14(1):67-77). Compared with VSV-G-pseudotyped vectors, GP64-pseudotyped vectors have a similar broad tropism and similar native titres. Because, GP64 expression does not kill cells, 293T-based cell lines constitutively expressing GP64 can be generated.

Alternative Envelopes

Other envelopes which give reasonable titre when used to pseudotype EIAV include Mokola, Rabies, Ebola and LCMV (lymphocytic choriomeningitis virus). Intravenous infusion into mice of lentivirus pseudotyped with 4070A led to maximal gene expression in the liver.

Polynucleotides

Polynucleotides of the invention may comprise DNA or RNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Proteins

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds.

Variants, Derivatives, Analogues, Homologues and Fragments

In addition to the specific proteins and nucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question retains at least one of its endogenous functions. A variant sequence can be obtained by addition, deletion, substitution, modification, replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins used in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non - polar | G A P |
| --- | --- | --- |
|  |  | I L V |
|  | Polar - uncharged | C S T M |
|  |  | N Q |
|  | Polar - charged | D E |
|  |  | K R H |
| AROMATIC |  | F W Y |

The term "homologue" means an entity having a certain homology with the wild type amino acid sequence and the wild type nucleotide sequence. The term "homology" can be equated with "identity".

In the present context, a homologous sequence is taken to include an amino acid sequence which may be at least 50%, 55%, 65%, 75%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 50%, 55%, 65%, 75%, 85% or 90% identical, preferably at least 95% or 97% or 99% identical to the subject sequence. Although homology can also be considered in terms of similarity, in the context of the present invention it is preferred to express homology in terms of sequence identity.

Homology comparisons can be conducted by eye, or more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Research 12:387). Examples of other software that can perform sequence comparisons include, but are not limited to, the BLAST package (see Ausubel et al. (1999) ibid—Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol Lett (1999) 174(2):247-50; FEMS Microbiol Lett (1999) 177(1):187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate percentage homology, preferably percentage sequence identity. The software typically does this as part of the sequence comparison and generates a numerical result.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

All variants, fragments or homologues of the RNA-binding protein of the invention will retain the ability to bind the cognate binding site of the invention such that translation of the NOI is repressed or prevented in a viral vector production cell.

All variants fragments or homologues of the binding site of the invention will retain the ability to bind the cognate RNA-binding protein, such that translation of the NOI is repressed or prevented in a viral vector production cell.

Codon Optimisation

The polynucleotides used in the present invention (including the NOI and/or components of the vector production system) may be codon-optimised. Codon optimisation has previously been described in WO 1999/41397 and WO 2001/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of a gene of interest, e.g. a NOI or packaging components in mammalian producer cells, can be achieved. Codon usage tables are known in the art for mammalian cells, as well as for a variety of other organisms.

Codon optimisation of viral vector components has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. In lentiviral vectors codon optimisation also overcomes the Rev/RRE requirement for export, rendering optimised sequences Rev-independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with some exceptions, for example the sequence encompassing the frameshift site of gag-pol (see below).

The gag-pol gene comprises two overlapping reading frames encoding the gag-pol proteins. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the Gag-Pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the Gag-Pol proteins.

In one embodiment, codon optimisation is based on lightly expressed mammalian genes. The third and sometimes the second and third base may be changed.

Due to the degenerate nature of the genetic code, it will be appreciated that numerous gag-pol sequences can be achieved by a skilled worker. Also there are many retroviral variants described which can be used as a starting point for generating a codon-optimised gag-pol sequence. Lentiviral genomes can be quite variable. For example there are many quasi-species of HIV-1 which are still functional. This is also the case for EIAV. These variants may be used to enhance particular parts of the transduction process. Examples of HIV-1 variants may be found at the HIV Databases operated by Los Alamos National Security, LLC at http://hiv-web.lanl.gov. Details of EIAV clones may be found at the National Center for Biotechnology Information (NCBI) database located at http://www.ncbi.nlm.nih.gov.

The strategy for codon-optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev-independent. In order to enable the use of anti-rev or RRE factors in the lentiviral vector, however, it would be necessary to render the viral vector generation system totally Rev/RRE-independent. Thus, the genome also needs to be modified. This is achieved by optimising vector genome components. Advantageously, these modifications also lead to the production of a safer system absent of all additional proteins both in the producer and in the transduced cell.

Use

Another aspect of the invention relates to the viral vector of the invention or a cell or tissue transduced with the viral vector of the invention for use in medicine.

Another aspect of the invention relates to the use of the viral vector of the invention or a cell or tissue transduced with the viral vector of the invention in medicine.

Another aspect of the invention relates to the use of the viral vector of the invention, a production cell of the invention or a cell or tissue transduced with the viral vector of the invention for the preparation of a medicament to deliver a nucleotide of interest to a target site in need of the same.

Such uses of the viral vector or transduced cell of the invention may be for therapeutic or diagnostic purposes, as described previously.

Therapeutic Vectors

Retroviral Therapeutic Vectors

In one embodiment, a retroviral vector of the invention may be used to introduce the three genes that encode three enzymes of the dopamine synthetic pathway to treat Parkinson's disease. The retroviral vector is a non-replicating, self-inactivating minimal lentiviral vector, derived from Human immunodeficiency virus (HIV) or Equine infectious anaemia virus (EIAV) which may be pseudotyped with VSV-G or an alternative viral envelope protein. The genes carried by the retroviral vector may comprise a truncated form of the human tyrosine hydroxylase (TH*) gene (which lacks the N-terminal 160 amino acids involved in feedback regulation of TH), the human aromatic L-amino-acid decarboxylase (AADC), and the human GTP-cyclohydrolase 1 (CH1) gene. The three enzymes may be encoded by the retroviral vector in three separate open reading frames. Alternatively, the retroviral vector may encode a fusion of the TH and CH1 enzymes in a first open reading frame and the AADC enzyme in a second open reading frame. Expression of the genes may be driven by a CMV promoter, and the expression cassette may include one or more IRES elements. The retroviral vector may be administered by direct injection into the striatum of the brain.

In another embodiment, a retroviral vector of the invention may be used as a gene therapy product designed to introduce the corrective MYO7A gene to photoreceptors and supporting retinal pigment epithelial (RPE) cells and thereby attenuate or reverse the deterioration in vision which is associated with Usher 1B Syndrome. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the MYO7A cDNA, which codes for the MYO7A protein (a large gene which is over 100 mb in length). Expression of the large MYO7A gene may be driven by a CMV promoter, a CMV/MYO7A chimeric promoter or an alternative promoter. The retroviral vector may be administered by direct subretinal injection following vitrectomy of the eye.

In another embodiment, a retroviral vector of the invention may be used to introduce the corrective ATP-binding cassette gene, ABCA4 (also known as ABCR), to photoreceptors and thereby attenuate or reverse the pathophysiology which leads to Stargardt disease. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the ABCA4 cDNA, which codes for ABCA4 protein. Expression of the ABCA4 gene may be driven by a CMV promoter, a photoreceptor-specific promoter, such as rhodopsin kinase or an alternative promoter. The retroviral vector may be administered by direct subretinal injection following vitrectomy of the eye.

In another embodiment, a retroviral vector of the invention may be used as a gene therapy product designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This retroviral vector delivers a gene or genes encoding an anti-angiogenic protein or proteins, such as angiostatin and/or endostatin. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. In one embodiment the retroviral vector expresses human endostatin and angiostatin genes in a bicistronic configuration utilising an internal ribosome entry site (IRES) for delivery to retinal pigment epithelial cells. Expression of the anti-angiogenic gene(s) may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used as a gene therapy product designed to prevent recurrence of aberrant blood vessel growth in oedema in the eyes of patients with wet-form age-related macular degeneration (AMD). This retroviral vector delivers a gene or genes encoding an anti-angiogenic protein or proteins, such as angiostatin and/or endostatin. The retroviral vector is a non-replicating, self-inactivating minimal lentiviral vector derived from Equine infectious anaemia virus (EIAV) which may be pseudotyped with VSV-G or an alternative viral envelope protein. In one embodiment the retroviral vector expresses human endostatin and angiostatin genes in a bicistronic configuration utilising an internal ribosome entry site (IRES) for delivery to retinal pigment epithelial cells. Expression of the anti-angiogenic gene(s) may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used as a gene therapy product designed to prevent corneal graft rejection as a result of neovascularization by delivery of anti-angiogenic gene(s) to the donor cornea prior to grafting. The retroviral vector is a non-replicating, self-inactivating minimal lentiviral vector derived from Human immunodeficiency virus (HIV) or Equine infectious anaemia virus (EIAV) which may be pseudotyped with VSV-G, Ebola or an alternative viral envelope protein. In one embodiment, the retroviral vector will express anti-angiogenic gene(s) such as human endostatin and angiostatin genes in a bicistronic configuration utilizing an internal ribosome entry site (IRES) for ex vivo delivery to corneal grafts. The retroviral vector may be applied to corneal graft tissue ex vivo, and the transduced donor tissue may also be stored prior to transplantation. Expression of the anti-angiogenic gene(s) may be driven by a constitutive promoter such as the CMV promoter; however it is also possible that alternative promoters may be used.

In another embodiment, a retroviral vector of the invention may be used as a gene therapy designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This retroviral vector delivers a gene encoding a soluble form of fms-like tyrosine kinase. (Soluble Fit-i) The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the soluble Fit-1 gene may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used as a gene therapy product designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This retroviral vector delivers a gene or genes encoding the pigment epithelium-derived factor protein (PEDF). The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the PEDF gene may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used as a gene therapy product designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This retroviral vector delivers a gene or genes encoding an inhibitor of vascular endothelial growth factor (VEGF), such as an anti-VEGF antibody or binding fragment thereof, a VEGF specific aptamer or a VEGF blocking peptide or polypeptide including, but not limited to, a soluble form of a VEGF receptor and/or an inhibitor of platelet-derived growth factor (PDGF), such as an anti-PDGF antibody or binding fragment thereof, a PDGF specific aptamer or a PDGF blocking peptide or polypeptide including, but not limited to, a soluble form of a PDGF receptor. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. In one embodiment the retroviral vector expresses an inhibitor of VEGF and an inhibitor of PDGF in a bicistronic configuration utilising an internal ribosome entry site (IRES) for delivery to retinal pigment epithelial cells. Expression of the gene(s) may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used to introduce the corrective gene vitelliform macular dystrophy 2 (VMD2) and a cassette encoding a micro-RNA (miRNA) specific for the disease-associated form of VMD2, or the corrective Peripherin 2 encoding RDS gene and a cassette encoding an miRNA specific for the disease-associated form of RDS to retinal pigment epithelial cells and thereby attenuate or reverse the pathophysiology which leads to Best disease or Best vitelliform macular degeneration (BVMD). The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the genes may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used to introduce the corrective retinaldehyde binding protein 1 gene, RLBP1, to retinal pigment epithelial cells and thereby attenuate or reverse the pathophysiology which leads to RLBP1-associated retinal dystrophy. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the RLBP1 cDNA, which codes for RLBP1 protein. Expression of the RLBP1 gene may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used as a gene therapy product designed to treat glaucoma. This retroviral vector delivers a gene or genes encoding COX-2 and/or Prostaglandin F2α receptor (FPR) which act to reduce intraocular pressure. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. In one embodiment the retroviral vector expresses COX-2 and Prostaglandin F2α receptor (FPR). genes in a bicistronic configuration utilizing an internal ribosome entry site (IRES) for delivery to the anterior chamber of the eye. Expression of the gene(s) may be driven by CMV or an alternative promoter. The retroviral vector may be administered by transcorneal injection.

In another embodiment, a retroviral vector of the invention may be used to introduce the corrective harmonin gene to attenuate or reverse the pathophysiology which leads to Usher Syndrome 1c. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the harmonin cDNA, which codes for the harmonin protein. Expression of the harmonin gene may be driven by a CMV promoter or an alternative promoter. The retroviral vector may be administered by direct subretinal injection following vitrectomy of the eye.

In another embodiment, a retroviral vector of the invention may be used to introduce the corrective Rab escort protein 1 (REP1) gene to attenuate or reverse the pathophysiology which leads to choroideremia. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the REP1 cDNA, which codes for the REP1 protein. Expression of the REP1 gene may be driven by a CMV promoter or an alternative promoter. The retroviral vector may be administered by direct subretinal injection following vitrectomy of the eye.

In another embodiment, a retroviral vector of the invention may be used to introduce the corrective Cyclic Nucleotide Gated Channel Beta 2 (CNGB2) and/or Cyclic Nucleotide Gated Channel Alpha 3 (CNGA3) genes(s) into the eye to attenuate or reverse the pathophysiology which leads to Achromatopsia. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene(s) carried by the retroviral vector are the CNGB2 and/or CNGA3 gene(s), that code for the CNGB2 and/or CNGA3 proteins. Expression of the gene(s) may be driven by a CMV promoter or an alternative promoter. The retroviral vector may be administered by direct subretinal injection following vitrectomy of the eye.

In another embodiment, a retroviral vector of the invention may be used to introduce the corrective CEP290 gene into the eye to attenuate or reverse the pathophysiology which leads to Leber Congenital Amaurosis (LCA). The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the CEP290 gene, that codes for the centrosomal protein of 290 kDa. Expression of the CEP290 gene may be driven by a CMV promoter or an alternative promoter. The retroviral vector may be administered by direct subretinal injection following vitrectomy of the eye.

In another embodiment, a retroviral vector of the invention may be used to introduce the corrective retinitis pigmentosa GTPase regulator (RPGR) gene into the eye to attenuate or reverse the pathophysiology which leads to x-linked retinitis pigmentosa. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the RPGR cDNA, which codes for the RPGR protein. Expression of the RPGR gene may be driven by a CMV promoter or an alternative promoter. The retroviral vector may be administered by direct subretinal injection following vitrectomy of the eye.

In another embodiment, a retroviral vector of the invention may be used to introduce the corrective retinoschisin 1 (RS1) gene into the eye to attenuate or reverse the pathophysiology which leads to x-linked retinochisis. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the RS1 cDNA, which codes for the RS1 protein. Expression of the RS1 gene may be driven by a CMV promoter or an alternative promoter. The retroviral vector may be administered by direct subretinal injection following vitrectomy of the eye.

In another embodiment, a retroviral vector of the invention may be used to introduce the corrective retinitis pigmentosa 1 (RP1) gene into the eye to attenuate or reverse the pathophysiology which leads to retinitis pigmentosa. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the RP1 cDNA, which codes for the RP1 protein. Expression of the RP1 gene may be driven by a CMV promoter, a photoreceptor-specific promoter, such as rhodopsin kinase or an alternative promoter. The retroviral vector may be administered by direct subretinal injection following vitrectomy of the eye.

In another embodiment, a retroviral vector of the invention may be used to introduce the corrective retinal pigment epithelium-specific 65 kDa protein (RPE65) gene to attenuate or reverse the pathophysiology which leads to Leber congenital amaurosis (LCA) type 2. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the RPE65 cDNA, which codes for the RPE65 protein. Expression of the RPE65 gene may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used to introduce the corrective human proline/arginine-rich end leucine-rich repeat protein (PRELP) gene to attenuate or reverse the pathophysiology which leads to wet-form age-related macular degeneration (AMD), dry-form AMD, diabetic macular oedema or retinal vein occlusion. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene carried by the retroviral vector is the PRELP cDNA, which codes for the PRELP protein. Expression of the PRELP gene may be driven by CMV, an RPE-specific promoter such as the vitelliform macular dystrophy 2 (VMD2) promoter (more recently known as the bestrophin promoter) or by an alternative promoter. The retroviral vector may be administered by direct subretinal injection following vitrectomy of the eye.

In another embodiment, a retroviral vector of the invention may be used to introduce a nucleic acid sequence encoding a synthetic myocilin-specific miRNA into the eye to attenuate or reverse the pathophysiology which leads to juvenile open angle glaucoma by knocking down the expression of myocilin. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the synthetic myocilin-specific miRNA may be driven by a CMV promoter or an alternative promoter. The retroviral vector may be administered by direct subretinal injection following vitrectomy of the eye.

In another embodiment, a retroviral vector of the invention may be used to introduce rate-limiting enzyme(s) from the glutathione biosynthesis pathway, glutamate-cysteine ligase (GCL) and/or glutathione synthetase (GSS), and/or a nucleic acid sequence encoding a synthetic gamma-glutamyltransferase (GGT) specific miRNA into the eye to attenuate or reverse the pathophysiology which leads to retinitis pigmentosa by gene augmentation and/or knock-down. The retroviral vector is a non-replicating, self-inactivating minimal lentiviral vector, for example derived from Human immunodeficiency virus (HIV) or Equine infectious anaemia virus (EIAV), which may be pseudotyped with VSV-G or an alternative viral envelope protein. Expression of the GCL and/or GSS gene(s) and/or the synthetic GGT specific miRNA may be driven by a CMV promoter or an alternative promoter. In one embodiment, the retroviral vector may express the gene(s) and/or the synthetic miRNA in a multicistronic configuration utilising one or more internal ribosome entry site (IRES). The retroviral vector may be administered by direct delivery to the anterior chamber of the eye.

In another embodiment, a retroviral vector of the invention may be used as a gene therapy product designed to treat neurodegenerative disorders such as frontotemporal lobe dementia, Alzheimer's disease, Parkinson's disease, Huntington's disease and motor neuron disorders such as Amyotrophic Lateral Sclerosis (ALS). This retroviral vector delivers a gene encoding a VEGF protein; which may be a VEGF-A isoform such as $VEGF_{145}$, $VEGF_{165}$, or $VEGF_{189}$; or may be VEGF-B, VEGF-C, or VEGF-D, such genes having a neuroprotective effect. The retroviral vector is a non-replicating, self-inactivating minimal lentiviral vector derived from Human immunodeficiency virus (HIV) or Equine infectious anaemia virus (EIAV) which may be pseudotyped with Rabies G or VSV-G or an alternative viral envelope protein. Expression of the gene may be driven by CMV or an alternative promoter. The retroviral vector may be administered by direct injection into large muscle groups or by direct injection into the cerebrospinal fluid via intrathecal or intraventricular injection.

In another embodiment, a retroviral vector of the invention may be used as a gene therapy product designed to treat cystic fibrosis. This retroviral vector delivers a gene encoding cystic fibrosis transmembrane conductance regulator (CFTR). The retroviral vector is a non-replicating, self-inactivating minimal lentiviral vector derived from Human immunodeficiency virus (HIV) or Equine infectious anaemia virus (EIAV) which may be pseudotyped with Flu-HA, Sendai virus envelope F or HN, Ebola, baculovirus GP64 or an alternative viral envelope protein. Expression of the gene may be driven by CMV or an alternative promoter. The retroviral vector may be administered intranasally, by use of a nebuliser, or by direct delivery via bronchial alveolar lavage into the lungs.

In another embodiment, a retroviral vector of the invention may be used to introduce the corrective N-Sulfoglucosamine Sulfohydrolase (SGSH) and/or Sulfatase Modifying Factor 1 (SUMF1) gene(s) into the brain to attenuate or reverse the pathophysiology which leads to Sanfilipo syndrome A. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. The gene(s) carried by the retroviral vector are the SGSH cDNA, which codes for the SGSH protein and/or the SUMF1 gene which codes for the SUMF1 protein. Expression of the gene(s) may be driven by a CMV promoter or an alternative promoter. In one embodiment, the retroviral vector may express the SGSH and SUMF1 genes in a bicistronic configuration utilising an internal ribosome entry site (IRES). The retroviral vector may be administered by direct intracerebral injection.

In another embodiment, a retroviral vector of the invention may be used to introduce the corrective acid-alpha glycosidase (GAA) gene into large muscle groups and/or the lungs to attenuate or reverse the pathophysiology which leads to Pompe Disease. This retroviral vector delivers a gene encoding a GAA protein. The retroviral vector is a non-replicating, self-inactivating minimal lentiviral vector derived from Human immunodeficiency virus (HIV) or Equine infectious anaemia virus (EIAV) which may be pseudotyped with Flu-HA, Sendai virus envelope F or HN, Ebola, baculovirus GP64, Rabies G, VSV-G or an alternative viral envelope protein. Expression of the gene may be driven by CMV or an alternative promoter. The retroviral vector may be administered by; (i) direct injection into large muscle groups and/or (ii) intranasally, by use of a nebuliser, or by direct delivery via bronchial alveolar lavage into the lungs.

In another embodiment, a retroviral vector of the invention may be used ex vivo to transduce autologous or allogeneic T cells with a nucleic acid sequence encoding a CD19-specific chimeric antigen receptor (CAR19). These transduced T cells are then infused into a subject to treat cancers and leukaemias expressing CD19. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the CAR encoding nucleic acid sequence may be driven by EF1a, CMV or an alternative promoter.

In another embodiment, a retroviral vector of the invention may be used ex vivo to transduce autologous or allogeneic T cells with a nucleic acid sequence encoding a 5T4-specific chimeric antigen receptor (CAR). These transduced T cells then are infused into a subject to treat cancers and leukaemias expressing 5T4. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the 5T4 CAR-encoding nucleic acid sequence may be driven by EF1α, CMV or an alternative promoter.

As will be known to those skilled in the art chimeric antigen receptors (CARs) can be produced that are specific for a range of cancer or leukaemia-associated polypeptides. A retroviral vector of the invention may be used ex vivo to transduce autologous or allogeneic T cells with a nucleic acid sequence encoding a chimeric antigen receptor (CAR) specific for any cancer or leukaemia-associated polypeptide. These transduced T cells then are infused into a subject to treat cancers and leukaemias expressing the cancer or leukaemia-associated polypeptide to which the CAR binds. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the CAR-encoding nucleic acid sequence may be driven by EF1α, CMV or an alternative promoter. Suitable cancer or leukaemia-associated polypeptides that may be targeted by said CARs include, but are not limited to, the following: mesothelin, folate receptor a, kappa light chain of immunoglobulin, CD30, Carcinoembryonic antigen (CEA), CD138, Ganglioside G2 (GD2), CD33, CD22, Epidermal growth factor receptors (EGFRs) such as EGFR VIII, IL-13Ra2, CD20, ErbBs such as Her2, prostate-specific membrane antigen (PSMA), Lewis Y antigen and fibroblast activation protein (FAB).

In another embodiment, a retroviral vector of the invention may be used ex vivo to transduce autologous or allogeneic T cells with a nucleic acid sequence encoding a T cell receptor (TCR) which is specific for a peptide-MHC expressed on diseased, leukemic or cancerous cells. These transfected T cells then are infused into a subject to treat the disease, cancer or leukaemia that is associated with the expression of the peptide-MHC to which the TCR binds. The retroviral vector is a non-replicating, self-inactivating minimal lentiviral vector derived from Human immunodeficiency virus (HIV) or Equine infectious anaemia virus (EIAV) which may be pseudotyped with VSV-G or an alternative viral envelope protein. Expression of the TCR-encoding nucleic acid sequence may be driven by EF1α, CMV or an alternative promoter. The TCRs that are encoded by the vectors of the invention may be single-chain TCRs (scTCRs) or dimeric TCRs (dTCRs). As will be known to those skilled in the art suitable dTCRs include those described in WO 2003/020763 and suitable scTCRs include those described in WO 1999/018129. In specific aspects of this embodiment the T cells transfected with TCRs may be used to treat AIDs, leukaemia, and cancers including myelomas and sarcomas.

In another embodiment, a retroviral vector of the invention may be used to introduce the gene that encodes the common gamma chain (CD132) to treat x-linked Severe combined immunodeficiency (SCID). The retroviral vector is a non-replicating, self-inactivating minimal lentiviral vector, derived from Equine infectious anaemia virus (EIAV) which may be pseudotyped with VSV-G or an alternative viral envelope protein. Expression of the gene may be driven by a CMV promoter or an alternative promoter. The retroviral vector of the invention may be used ex vivo to transduce bone marrow stem cells. These transduced bone marrow stem cells can then be infused into a subject to treat the disease.

In another embodiment, a retroviral vector of the invention may be used to introduce the gene that encodes adenosine deaminase to treat ADA Severe combined immunodeficiency (SCID). The retroviral vector is a non-replicating, self-inactivating minimal lentiviral vector, derived from derived from Human immunodeficiency virus (HIV) or Equine infectious anaemia virus (EIAV) which may be pseudotyped with VSV-G or an alternative viral envelope protein. Expression of the gene may be driven by a CMV promoter or an alternative promoter. The retroviral vector of the invention may be used ex vivo to transduce bone marrow stem cells. These transduced bone marrow stem cells can then be infused into a subject to treat the disease.

In another embodiment, a retroviral vector of the invention may be used to introduce the gene that encodes the WAS protein to treat Wiskott-Aldrich Syndrome (WAS). The retroviral vector is a non-replicating, self-inactivating minimal lentiviral vector, derived from derived from Human immunodeficiency virus (HIV) or Equine infectious anaemia virus (EIAV) which may be pseudotyped with VSV-G or an alternative viral envelope protein. Expression of the gene may be driven by a CMV promoter or an alternative promoter. The retroviral vector of the invention may be used ex vivo to transduce bone marrow stem cells. These transduced bone marrow stem cells can then be infused into a subject to treat the disease.

In another embodiment, a retroviral vector of the invention may be used to introduce a gene that encodes one of several globins, including wild-type β-globin, wild-type fetal globin, and mutated "anti-sickling" globins to treat Sickle Cell disease or thalassemia. As will be known to those skilled in the art examples of anti-sickling globins include, but are not limited to those described in WO 2014/043131 and WO 1996/009385. The retroviral vector is a non-replicating, self-inactivating minimal lentiviral vector, derived from Human immunodeficiency virus (HIV) or Equine infectious anaemia virus (EIAV) which may be pseudotyped with VSV-G or an alternative viral envelope protein. Expression of the gene may be driven by a CMV promoter or an alternative promoter. The retroviral vector of the invention may be used ex vivo to transduce bone marrow stem cells. These transduced bone marrow stem cells can then be infused into a subject to treat the disease.

In another embodiment, a retroviral vector of the invention may be used to introduce a corrective gene, Factor VIII, to liver, muscle or adipose cells to treat haemophilia A. The retroviral vector is a non-replicating, self-inactivating minimal lentiviral vector derived from the derived from Human immunodeficiency virus (HIV) or Equine infectious anaemia virus (EIAV) which may be pseudotyped with VSV-G or an alternative viral envelope protein. The gene carried by the retroviral vector is Factor VIII. Expression of the Factor VIII gene may be driven by a CMV promoter or an alternative promoter.

In another embodiment, a retroviral vector of the invention may be used to introduce a corrective gene, Factor IX, to liver, muscle or adipose cells to treat haemophilia B. The retroviral vector is a non-replicating, self-inactivating minimal lentiviral vector derived from the derived from Human immunodeficiency virus (HIV) or Equine infectious anaemia virus (EIAV) which may be pseudotyped with VSV-G or an alternative viral envelope protein. The gene carried by the retroviral vector is Factor IX. Expression of the Factor IX gene may be driven by a CMV promoter or an alternative promoter.

In another embodiment, a retroviral vector of the invention may be used to introduce the gene that encodes alpha galactosidase A (α-GAL A) to treat Fabry disease. The retroviral vector is a non-replicating, self-inactivating minimal lentiviral vector, derived from Human immunodeficiency virus (HIV) or Equine infectious anaemia virus (EIAV) which may be pseudotyped with VSV-G or an alternative viral envelope protein. The gene carried by the retroviral vector is the GLA cDNA, which codes for the α-GAL A protein Expression of the gene may be driven by a CMV promoter or an alternative promoter. The retroviral vector of the invention may be used ex vivo to transduce hematopoietic CD34$^+$ stem cells. These transduced hematopoietic CD34$^+$ stem cells can then be infused into a subject to treat the disease.

In another embodiment, a retroviral vector of the invention may be used to introduce the gene that encodes a deficient enzyme to treat a form of porphyria. The retroviral vector is a non-replicating, self-inactivating minimal lentiviral vector, derived from Human immunodeficiency virus (HIV) or Equine infectious anaemia virus (EIAV) which may be pseudotyped with VSV-G or an alternative viral envelope protein. The gene carried by the retroviral vector is that encoding the deficient enzyme associated with the type of porphyria to be treated selected from the table below. Expression of the gene may be driven by a CMV promoter or an alternative promoter.

| Porphyria type | Deficient enzyme |
| --- | --- |
| X-linked sideroblastic anemia (XLSA) | δ-aminolevulinate (ALA) synthase |
| Doss porphyria/ALA dehydratase deficiency | δ-aminolevulinate dehydratase (ALAD) |
| Acute intermittent porphyria (AIP) | Hydroxymethylbilane (HMB) synthase |
| Congenital erythropoietic porphyria (CEP) | Uroporphyrinogen (URO) synthase |
| Porphyria cutanea tarda (PCT) | Uroporphyrinogen (URO) decarboxylase |
| Hereditary coproporphyria (HCP) | Coproporphyrinogen (COPRO) oxidase |
| Variegate porphyria (VP) | Protoporphyrinogen (PROTO) oxidase |
| Erythropoietic protoporphyria (EPP) | Ferrochelatase |

In another embodiment, a retroviral vector of the invention may be used to introduce the gene that encodes a deficient enzyme to treat a form of mucopolysaccharidosis. The retroviral vector is a non-replicating, self-inactivating minimal lentiviral vector, derived from Human immunodeficiency virus (HIV) or Equine infectious anaemia virus (EIAV) which may be pseudotyped with VSV-G or an alternative viral envelope protein. The gene carried by the retroviral vector is that encoding the deficient enzyme associated with the type of musocpolysaccharidosis to be treated selected from the table below. Expression of the gene may be driven by a CMV promoter or an alternative promoter.

| Mucopolysaccharidosis type | Deficient enzyme |
| --- | --- |
| Hurler syndrome/Hurler-Scheie syndrome/Scheie syndrome | α-L-iduronidase |
| Hunter syndrome | Iduronate sulfatase |
| Sanfilippo syndrome A | Heparan sulfamidase |
| Sanfilippo syndrome B | N-acetylglucosaminidase |
| Sanfilippo syndrome C | Heparan-α-glucosaminide N-acetyltransferase |
| Sanfilippo syndrome D | 3 N-acetylglucosamine 6-sulfatase |
| Morquio syndrome A | Galactose-6-sulfate sulfatase |
| Morquio syndrome B | β-galactosidase |
| Maroteaux-Lamy syndrome | N-acetylgalactosamine-4-sulfatase |
| Sly syndrome | β-glucuronidase |
| Natowicz syndrome | Hyaluronidase |

Production of Retroviral Therapeutic Vectors

Retroviral vectors of the invention may be produced by the transient transfection of HEK293T cells with four plasmids:
(1) the recombinant retroviral vector genome plasmid encoding the required transgene(s) and a binding site that is capable of interacting with an RNA-binding protein,
(2) the synthetic retroviral gag/pol expression plasmid,
(3) the envelope (env) expression plasmid which may, for example, express VSV-G
(4) The RNA-binding protein expression plasmid.

Alternatively, retroviral vectors of the invention, such as HIV, may be produced by the transient transfection of HEK293T cells with five plasmids:
(1) the recombinant HIV vector genome plasmid encoding the required transgene(s), a binding site that is capable of interacting with an RNA-binding protein, and the RRE sequence,
(2) a synthetic gag/pol expression plasmid,
(3) the envelope (env) expression plasmid which may, for example, express VSV-G,
(4) The RNA-binding protein expression plasmid
(5) the REV expression plasmid.

Alternatively a transient transfection system may utilise a cell line which stably expresses the RNA-binding protein of the invention (for example, TRAP).

Alternatively, retroviral vectors of the invention may be produced by using packaging cells that stably express (1) gag/pol, (2) env and (3) the RNA-binding protein, and, for HIV vectors, Rev, and wherein a plasmid encoding the recombinant retroviral vector genome encoding the required transgene(s) and a binding site that is capable of interacting with the an RNA-binding protein, and for HIV vectors, includes the RRE sequence, is introduced into such cells by transient transfection.

Alternatively, retroviral vectors of the invention may be produced in producer cells that stably express (1) gag/pol, (2) env, (3) the RNA-binding protein, (4) the recombinant EIAV vector genome encoding the required transgene(s) and a binding site that is capable of interacting with an RNA-binding protein.

Alternatively, HIV vectors of the invention may be produced in producer cells that stably express (1) gag/pol, (2) env, (3) the RNA-binding protein, (4) the recombinant HIV vector genome encoding the required transgene(s), a binding site that is capable of interacting with an RNA-binding protein, and the RRE sequence, and (5) REV.

AAV Therapeutic Vectors

In another embodiment, an AAV vector of the invention may be used to introduce the three genes that encode three enzymes of the dopamine synthetic pathway to treat Parkinson's disease. The genes carried by the AAV vector may comprise a truncated form of the human tyrosine hydroxylase (TH*) gene (which lacks the N-terminal 160 amino acids involved in feedback regulation of TH), the human aromatic L-amino-acid decarboxylase (AADC), and the human GTP-cyclohydrolase 1 (CH1) gene. The three enzymes may be encoded by the AAV vector in three separate open reading frames. Alternatively, the AAV vector may encode a fusion of the TH and CH1 enzymes in a first open reading frame and the AADC enzyme in a second open reading frame. Expression of the genes may be driven by a CMV promoter, and the expression cassette may include one or more IRES elements. The AAV vector may be administered by direct injection into the striatum of the brain.

In another embodiment, an AAV vector of the invention may be used as a gene therapy product designed to introduce the corrective MYO7A gene to photoreceptors and supporting retinal pigment epithelial (RPE) cells and thereby attenuate or reverse the deterioration in vision which is associated with Usher 1B Syndrome. The gene carried by the AAV vector is the MYO7A cDNA, which codes for the MYO7A protein (a large gene which is over 100 mb in length). Expression of the large MYO7A gene may be driven by a CMV promoter, a CMV/MYO7A chimeric promoter or an alternative promoter. The AAV vector may be administered by direct subretinal injection following vitrectomy of the eye.

In another embodiment, an AAV vector of the invention may be used to introduce the corrective ATP-binding cassette gene, ABCA4 (also known as ABCR), to photoreceptors and thereby attenuate or reverse the pathophysiology which leads to Stargardt disease. The gene carried by the AAV vector is the ABCA4 cDNA, which codes for ABCA4 protein. Expression of the ABCA4 gene may be driven by a CMV promoter, a photoreceptor-specific promoter, such as rhodopsin kinase or an alternative promoter. The AAV vector may be administered by direct subretinal injection following vitrectomy of the eye.

In another embodiment, an AAV vector of the invention may be used as a gene therapy product designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This AAV vector delivers a gene or genes encoding an anti-angiogenic protein or proteins, such as angiostatin and/or endostatin. In one embodiment the AAV vector expresses human endostatin and angiostatin genes in a bicistronic configuration utilising an internal ribosome entry site (IRES) for delivery to retinal pigment epithelial cells. Expression of the anti-angiogenic gene(s) may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV vector of the invention may be used as a gene therapy product designed to prevent corneal graft rejection as a result of neovascularization by delivery of anti-angiogenic gene(s) to the donor cornea prior to grafting. In one embodiment, the AAV vector will express anti-angiogenic gene(s) such as human endostatin and angiostatin genes in a bicistronic configuration utilizing an internal ribosome entry site (IRES) for ex vivo delivery to corneal grafts. The AAV vector may be applied to corneal graft tissue ex vivo, and the transduced donor tissue may also be stored prior to transplantation. Expression of the anti-angiogenic gene(s) may be driven by a constitutive promoter such as the CMV promoter; however it is also possible that alternative promoters may be used.

In another embodiment, an AAV vector of the invention may be used as a gene therapy designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This AAV vector delivers a gene encoding a soluble form of fms-like tyrosine kinase. (Soluble Flt-1). Expression of the soluble Flt-1 gene may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, a AAV vector of the invention may be used as a gene therapy product designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This AAV vector delivers a gene or genes encoding the pigment epithelium-derived factor protein (PEDF). Expression of the PEDF gene may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV vector of the invention may be used as a gene therapy product designed to prevent recurrence of aberrant blood vessel growth and/or vascular leakage in the eyes of patients with wet-form age-related macular degeneration (AMD), diabetic macular oedema or retinal vein occlusion, and/or to prevent aberrant blood vessel growth in the eyes of patients with dry-form age-related macular degeneration (AMD). This AAV vector delivers a gene or genes encoding an inhibitor of vascular endothelial growth factor (VEGF), such as an anti-VEGF antibody or binding fragment thereof, a VEGF specific aptamer or a VEGF blocking peptide or polypeptide including, but not limited to, a soluble form of a VEGF receptor and/or an inhibitor of platelet-derived growth factor (PDGF), such as an anti-PDGF antibody or binding fragment thereof, a PDGF specific aptamer or a PDGF blocking peptide or polypeptide including, but not limited to, a soluble form of a PDGF receptor. In one embodiment the AAV vector expresses an inhibitor of VEGF and an inhibitor of PDGF in a bicistronic configuration utilising an internal ribosome entry site (IRES) for delivery to retinal pigment epithelial cells. Expression of the gene(s) may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV vector of the invention may be used to introduce the corrective gene vitelliform macular dystrophy 2 (VMD2) and a cassette encoding a micro-RNA (miRNA) specific for the disease-associated form of VMD2, or the corrective Peripherin 2 encoding RDS gene and a cassette encoding an miRNA specific for the disease-associated form of RDS to retinal pigment epithelial cells and thereby attenuate or reverse the pathophysiology which leads to Best disease or Best vitelliform macular degeneration (BVMD). Expression of the genes may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV vector of the invention may be used to introduce the corrective retinaldehyde binding protein 1 gene, RLBP1, to retinal pigment epithelial cells and thereby attenuate or reverse the pathophysiology which leads to RLBP1-associated retinal dystrophy. The gene carried by the AAV vector is the RLBP1 cDNA, which codes for RLBP1 protein. Expression of the RLBP1 gene may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV vector of the invention may be used as a gene therapy product designed to treat glaucoma. This AAV vector delivers a gene or genes encoding COX-2 and/or Prostaglandin F2α receptor (FPR). In one embodiment the AAV vector expresses COX-2 and Prostaglandin F2α receptor (FPR). genes in a bicistronic configuration utilizing an internal ribosome entry site (IRES) for delivery to the anterior chamber of the eye. Expression of the gene(s) may be driven by CMV or an alternative promoter. The AAV vector may be administered by transcorneal injection.

In another embodiment, an AAV vector of the invention may be used to introduce the corrective harmonin gene to attenuate or reverse the pathophysiology which leads to Usher Syndrome 1c. The gene carried by the AAV vector is the harmonin cDNA, which codes for the harmonin protein. Expression of the harmonin gene may be driven by a CMV promoter or an alternative promoter. The AAV vector may be administered by direct subretinal injection following vitrectomy of the eye.

In another embodiment, an AAV vector of the invention may be used to introduce the corrective Rab escort protein 1 (REP1) gene to attenuate or reverse the pathophysiology which leads to choroideremia. The gene carried by the AAV vector is the REP1 cDNA, which codes for the REP1 protein. Expression of the REP1 gene may be driven by a CMV promoter or an alternative promoter. The AAV vector may be administered by direct subretinal injection following vitrectomy of the eye.

In another embodiment, an AAV vector of the invention may be used to introduce the corrective Cyclic Nucleotide Gated Channel Beta 2 (CNGB2) and/or Cyclic Nucleotide Gated Channel Alpha 3 (CNGA3) genes(s) into the eye to attenuate or reverse the pathophysiology which leads to Achromatopsia. The gene(s) carried by the AAV vector are the CNGB2 and/or CNGA3 gene(s), that code for the CNGB2 and/or CNGA3 proteins. Expression of the gene(s) may be driven by a CMV promoter or an alternative promoter. The AAV vector may be administered by direct subretinal injection following vitrectomy of the eye.

In another embodiment, an AAV vector of the invention may be used to introduce the corrective CEP290 gene into the eye to attenuate or reverse the pathophysiology which leads to Leber Congenital Amaurosis (LCA). The gene carried by the AAV vector is the CEP290 gene, that codes for the centrosomal protein of 290 kDa. Expression of the CEP290 gene may be driven by a CMV promoter or an alternative promoter. The AAV vector may be administered by direct subretinal injection following vitrectomy of the eye.

In another embodiment, an AAV vector of the invention may be used to introduce the corrective retinitis pigmentosa GTPase regulator (RPGR) gene into the eye to attenuate or reverse the pathophysiology which leads to x-linked retinitis pigmentosa. The gene carried by the AAV vector is the RPGR cDNA, which codes for the RPGR protein. Expression of the RPGR gene may be driven by a CMV promoter or an alternative promoter. The AAV vector may be administered by direct subretinal injection following vitrectomy of the eye.

In another embodiment, an AAV vector of the invention may be used to introduce the corrective retinoschisin 1 (RS1) gene into the eye to attenuate or reverse the pathophysiology which leads to x-linked retinochisis. The gene carried by the AAV vector is the RS1 cDNA, which codes for the RS1 protein. Expression of the RS1 gene may be driven by a CMV promoter or an alternative promoter. The AAV vector may be administered by direct subretinal injection following vitrectomy of the eye.

In another embodiment, an AAV vector of the invention may be used to introduce the corrective retinitis pigmentosa 1 (RP1) gene into the eye to attenuate or reverse the pathophysiology which leads to retinitis pigmentosa. The gene carried by the AAV vector is the RP1 cDNA, which codes for the RP1 protein. Expression of the RP1 gene may be driven by a CMV promoter, a photoreceptor-specific promoter, such as rhodopsin kinase or an alternative promoter. The AAV vector may be administered by direct subretinal injection following vitrectomy of the eye.

In another embodiment, an AAV vector of the invention may be used to introduce the corrective retinal pigment epithelium-specific 65 kDa protein (RPE65) gene to attenuate or reverse the pathophysiology which leads to Leber congenital amaurosis (LCA) type 2. The gene carried by the AAV vector is the RPE65 cDNA, which codes for the RPE65 protein. Expression of the RPE65 gene may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV of the invention may be used to introduce the corrective human proline/arginine-rich end leucine-rich repeat protein (PRELP) gene to attenuate or reverse the pathophysiology which leads to wet-form age-related macular degeneration (AMD), dry-form AMD, diabetic macular oedema or retinal vein occlusion. The gene carried by the AAV vector is the PRELP cDNA, which codes for the PRELP protein. Expression of the PRELP gene may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV vector of the invention may be used to introduce a nucleic acid sequence encoding a synthetic myocilin-specific miRNA into the eye to attenuate or reverse the pathophysiology which leads to juvenile open angle glaucoma by knocking down the expression of myocilin. Expression of the synthetic myocilin-specific miRNA may be driven by a CMV promoter or an alternative promoter. The AAV vector may be administered by direct subretinal injection following vitrectomy of the eye.

In another embodiment, an AAV vector of the invention may be used to introduce rate-limiting enzyme(s) from the glutathione biosynthesis pathway, glutamate-cysteine ligase (GCL) and/or glutathione synthetase (GSS), and/or a nucleic acid sequence encoding a synthetic gamma-glutamyltransferase (GGT) specific miRNA into the eye to attenuate or reverse the pathophysiology which leads to retinitis pigmentosa by gene augmentation and/or knock-down. Expression of the GCL and/or GSS gene(s) and/or the synthetic GGT specific miRNA may be driven by a CMV promoter or an alternative promoter. In one embodiment, the AAV vector may express the gene(s) and/or the synthetic miRNA in a multicistronic configuration utilising one or more internal ribosome entry site (IRES). The AAV vector may be administered by direct delivery to the anterior chamber of the eye.

In another embodiment, an AAV vector of the invention may be used as a gene therapy product designed to treat neurodegenerative disorders such as frontotemporal lobe dementia, Alzheimer's disease, Parkinson's disease, Huntington's disease and motor neuron disorders such as Amyotrophic Lateral Sclerosis (ALS). This AAV vector delivers a gene encoding a VEGF protein; which may be a VEGF-A isoform such as $VEGF_{145}$, $VEGF_{165}$, or $VEGF_{189}$; or may be VEGF-B, VEGF-C, or VEGF-D, such genes having a neuroprotective effect. Expression of the gene may be driven by CMV or an alternative promoter. The AAV vector may be administered by direct injection into large muscle groups or by direct injection into the cerebrospinal fluid via intrathecal or intraventricular injection.

In another embodiment, an AAV vector of the invention may be used as a gene therapy product designed to treat cystic fibrosis. This AAV vector delivers a gene encoding cystic fibrosis transmembrane conductance regulator (CFTR). Expression of the gene may be driven by CMV or an alternative promoter. The AAV vector may be administered intranasally, by use of a nebuliser, or by direct delivery via bronchial alveolar lavage into the lungs.

In another embodiment, an AAV vector of the invention may be used to introduce the corrective N-Sulfoglucosamine Sulfohydrolase (SGSH) and/or Sulfatase Modifying Factor 1 (SUMF1) gene(s) into the brain to attenuate or reverse the pathophysiology which leads to Sanfilipo syndrome A. The gene(s) carried by the AAV vector are the SGSH cDNA, which codes for the SGSH protein and/or the SUMF1 gene which codes for the SUMF1 protein. Expression of the gene(s) may be driven by a CMV promoter or an alternative promoter. In one embodiment, the AAV vector may express the SGSH and SUMF1 genes in a bicistronic configuration utilising an internal ribosome entry site (IRES). The AAV vector may be administered by direct intracerebral injection.

In another embodiment, an AAV vector of the invention may be used to introduce the corrective acid-alpha glycosidase (GAA) gene into large muscle groups and/or the lungs to attenuate or reverse the pathophysiology which leads to Pompe Disease. This AAV vector delivers a gene encoding a GAA protein. Expression of the gene may be driven by CMV or an alternative promoter. The AAV vector may be administered by; (i) direct injection into large muscle groups and/or (ii) intranasally, by use of a nebuliser, or by direct delivery via bronchial alveolar lavage into the lungs.

In another embodiment, an AAV vector of the invention may be used to introduce a corrective gene, Factor VIII, to liver, muscle or adipose cells to treat haemophilia A. The gene carried by the AAV vector is Factor VIII. Expression of the Factor VIII gene may be driven by a CMV promoter or an alternative promoter.

In another embodiment, an AAV vector of the invention may be used to introduce a corrective gene, Factor IX, to liver, muscle or adipose cells to treat haemophilia B. The gene carried by the AAV vector is Factor IX. Expression of the Factor IX gene may be driven by a CMV promoter or an alternative promoter.

In another embodiment, an AAV vector of the invention may be used to introduce the gene that encodes a deficient enzyme to treat a form of porphyria. The gene carried by the AAV vector is that encoding the deficient enzyme associated with the type of porphyria to be treated selected from the table below. Expression of the gene may be driven by a CMV promoter or an alternative promoter.

| Porphyria type | Deficient enzyme |
| --- | --- |
| X-linked sideroblastic anemia (XLSA) | δ-aminolevulinate (ALA) synthase |
| Dose porphyria/ALA dehydratase deficiency | δ-aminolevulinate dehydratase (ALAD) |
| Acute intermittent porphyria (AIP) | Hydroxymethylbilane (HMB) synthase |
| Congenital erythropoietic porphyria (CEP) | Uroporphyrinogen (URO) synthase |
| Porphyria cutanea tarda (PCT) | Uroporphyrinogen (URO) decarboxylase |
| Hereditary coproporphyria (HCP) | Coproporphyrinogen (COPRO) oxidase |
| Variegate porphyria (VP) | Protoporphyrinogen (PROTO) oxidase |
| Erythropoietic protoporphyria (EPP) | Ferrochelatase |

In another embodiment, an AAV vector of the invention may be used to introduce the gene that encodes a deficient enzyme to treat a form of mucopolysaccharidosis. The gene carried by the AAV vector is that encoding the deficient enzyme associated with the type of musocpolysaccharidosis to be treated selected from the table below. Expression of the gene may be driven by a CMV promoter or an alternative promoter.

| Mucopolysaccharidosis type | Deficient enzyme |
| --- | --- |
| Hurler syndrome/Hurler-Scheie syndrome/Scheie syndrome | α-L-iduronidase |
| Hunter syndrome | Iduronate sulfatase |
| Sanfilippo syndrome A | Heparan sulfamidase |
| Sanfilippo syndrome B | N-acetylglucosaminidase |
| Sanfilippo syndrome C | Heparan-α-glucosaminide N-acetyltransferase |
| Sanfilippo syndrome D | 3 N-acetylglucosamine 6-sulfatase |
| Morquio syndrome A | Galactose-6-sulfate sulfatase |
| Morquio syndrome B | β-galactosidase |
| Maroteaux-Lamy syndrome | N-acetylgalactosamine-4-sulfatase |
| Sly syndrome | β-glucuronidase |
| Natowicz syndrome | Hyaluronidase |

In another embodiment, an AAV vector of the invention may be used as a gene therapy product designed to prevent recurrence of aberrant blood vessel growth in oedema in the eyes of patients with wet-form age-related macular degeneration (AMD). This AAV vector delivers a gene or genes encoding an anti-angiogenic protein or proteins, such as angiostatin and/or endostatin. In one embodiment the AAV vector expresses human endostatin and angiostatin genes in a bicistronic configuration utilising an internal ribosome entry site (IRES) for delivery to retinal pigment epithelial cells. Expression of the anti-angiogenic gene(s) may be driven by CMV, an RPE-specific promoter such as the vitelliform macular dystrophy 2 (VMD2) promoter (more recently known as the bestrophin promoter) or by an alternative promoter. The AAV vector may be administered by direct subretinal injection following vitrectomy of the eye.

In another embodiment, an AAV vector of the invention may be used as a gene therapy product designed to treat neurodegenerative disorders such as frontotemporal lobe dementia, Alzheimer's disease, Parkinson's disease, Huntington's disease and motor neuron disorders such as Amyotrophic Lateral Sclerosis (ALS). This AAV vector delivers a gene encoding a VEGF protein; which may be a VEGF-A isoform such as $VEGF_{145}$, $VEGF_{165}$, or $VEGF_{189}$; or may be VEGF-B, VEGF-C, or VEGF-D, such genes having a neuroprotective effect. Expression of the gene may be driven by CMV or an alternative promoter. The AAV vector may be administered by direct injection into the cerebrospinal fluid bathing the spinal cord via intraventricular or intrathecal injection.

Method of Treatment

Another aspect of the invention relates to a method of treatment comprising administering the viral vector of the invention or a cell transduced with the viral vector of the invention to a subject in need of the same.

It is to be appreciated that all references herein to treatment include curative, palliative and prophylactic treatment; although in the context of the present invention references to preventing are more commonly associated with prophylactic treatment. Treatment may also include prevention or slowing of disease progression. The treatment of mammals is particularly preferred. Both human and veterinary treatments are within the scope of the present invention.

In one embodiment, the viral vectors or viral vector particles of the invention may be for use as vaccines. The vaccines may be, for example, human or veterinary virus-based vaccines (e.g. influenza and Newcastle Disease virus vaccines).

The present invention may be of particular use where the vaccine is based on a modified competent virus that harbours a transgene.

As discussed above, avian production cells may be used in the production of viral vectors and viral vector particles for use as vaccines.

Pharmaceutical Compositions

Another aspect of the invention relates to a pharmaceutical composition comprising the viral vector of the invention or a cell or tissue transduced with the viral vector of the invention, in combination with a pharmaceutically acceptable carrier, diluent or excipient.

The present invention provides a pharmaceutical composition for treating an individual by gene therapy, wherein the composition comprises a therapeutically effective amount of a vector. The pharmaceutical composition may be for human or animal usage.

The composition may comprise a pharmaceutically acceptable carrier, diluent, excipient or adjuvant. The choice of pharmaceutical carrier, excipient or diluent can be made with regard to the intended route of administration and standard pharmaceutical practice. The pharmaceutical compositions may comprise, or in addition to, the carrier, excipient or diluent any suitable binder(s), lubricant(s), suspending agent(s), coating agent(s), solubilising agent(s) and other carrier agents that may aid or increase vector entry into the target site (such as for example a lipid delivery system).

Where appropriate, the composition can be administered by any one or more of inhalation; in the form of a suppository or pessary; topically in the form of a lotion, solution, cream, ointment or dusting powder; by use of a skin patch; orally in the form of tablets containing excipients such as starch or lactose, or in capsules or ovules either alone or in admixture with excipients, or in the form of elixirs, solutions or suspensions containing flavouring or colouring agents; or they can be injected parenterally, for example intracavernosally, intravenously, intramuscularly, intracranially, intraocularly or subcutaneously. For parenteral administration, the compositions may be best used in the form of a sterile aqueous solution which may contain other substances, for example enough salts or monosaccharides to make the solution isotonic with blood. For buccal or sublingual administration, the compositions may be administered in the form of tablets or lozenges which can be formulated in a conventional manner.

The vector of the invention may also be used to transduce target cells or target tissue ex vivo prior to transfer of said target cell or tissue into a patient in need of the same. An example of such cell may be autologous T cells and an example of such tissue may be a donor cornea.

Method of Screening

Another aspect of the invention relates to a method of identifying nucleic acid binding sites and/or cognate nucleic acid binding proteins which are capable of interacting such that the translation of a nucleotide of interest is repressed or prevented in a viral vector production cell when operably linked to the nucleic acid binding site, wherein the method comprises analysing the expression of a reporter gene in a cell comprising both the nucleic acid binding site operably linked to the reporter gene, and the nucleic acid binding protein.

The method may allow the identification of new RNA-binding proteins and their corresponding binding sites which are useful in the present invention. The method may also allow the identification of variants of known RNA-binding proteins or binding sites.

In one embodiment, the method allows the identification of binding sites which interact with TRAP.

In another embodiment, the method allows the identification of nucleic acid binding proteins which interact with a binding site that is capable of binding to TRAP.

In one embodiment, the reporter gene encodes a fluorescent protein.

In another embodiment, the reporter gene encodes a positive cell growth selection marker, for example the sh ble gene product enabling cell resistance to Zeocin™.

In another embodiment, the reporter gene encodes a negative cell growth selection marker, for example the HSV thymidine kinase gene product which causes cell death in the presence of Ganciclovir.

An example of screening TRAP-binding sites (tbs) for improved functionality may be as follows:

Synthesise a degenerate DNA library comprising 8 repeats of the sequence RAGNN or a total of 8 repeats of RAGNN and RAGNNN.

Clone the library within the 5' UTR of a reporter gene cassette such as GFP (preferably within 12 nucleotides of ORF). The library-linked reporter gene may be optionally cloned into a retroviral vector genome and a retroviral vector library produced.

Stably introduce the library-linked reporter gene cassette into a cell line (this can be achieved by transfection or retroviral vector delivery) and isolate single clones.

Screen clones by parallel transfection using control DNA (e.g. pBlueScript) or TRAP-expressing plasmid DNA. Measure reporter gene expression in both scenarios and identify clones with high, non-repressed reporter gene levels (control) and low, repressed reporter gene levels (TRAP).

Identify tbs sequences by PCR amplification and sequencing of the tbs sequence from target cell genomic DNA from candidate clones.

EXAMPLES

Description of Protocols, Data Analysis and Reporting
Transient Co-Transfection of (Tbs)GFP Reporter and TRAP-Expression Plasmids The testing of the TRAP-tbs configuration was carried out by transient co-transfection of HEK293T cells with pCMV- GFP or pCMV-tbsGFP (or variants thereof) together with TRAP-expressing plasmids using Lipofectamine 2000CD. Stuffer DNA (pBlueScript) was used to normalise DNA amount to 6.1 µg total DNA per 10 cm plate (pre-seeded with $3.5 \times 10^6$ cells 24 hours prior to transfection. These parameters were scaled down according to tissue culture vessel area when using multiwell plates. Transfections were carried out in triplicate. The molar ratio of GFP-reporter plasmid to TRAP-expressing plasmid is indicated in each experiment. Media was replaced ~18 hours post-transfection and GFP analysis was carried out on live cells 48 hours post-transfection.

Typical Retro(Lenti)-Viral Vector Production Protocol

Vector production by transient transfection of HEK293T cells using the 3 vector components occurred using Lipofectamine 2000CD; the ratio of pDNAs was 4 µg vector genome, 2 µg GagPol, 0.1 µg VSVG plasmid per 10 cm plate (plates pre-seeded with $3.5 \times 10^6$ cells 24 hours prior to transfection)—these parameters were scaled according to vessel area. Co-transfection of TRAP plasmid or stuffer plasmid (pBluescript) occurred at stated molar ratios with vector genome e.g. for a 10-to-1 molar ratio of vector genome plasmid to TRAP plasmid, the mass ratio was 4 µg vector genome to 0.28 µg TRAP plasmid. Sodium butyrate was added on day 2 post-transfection at 10 mM final concentration for 6 hours before replacement of fresh media; vector-containing harvest supernatant was taken 20-24 hours later. For production of GFP-encoding vectors, GFP analysis was carried out on live cells 48 hours post-transfection. End-of-vector-production cell samples for immunoblotting were typically made using fractionation buffer (130 mM NaCl, 20 mM Tris-HCl[pH7.4], 2 mM EDTA, 0.2% IEGPAL) and nuclei removed by centrifugation. Vector harvest supernatants were filtered through 0.45 µm filters and stored at −80° C. prior to vector titration assays. GFP-encoding vectors were titrated by transduction of target cells and analysis 3 days later by flow cytometry (see below). Therapeutic vectors were titrated by qPCR of host cell DNA 10 days post-transduction (DNA integration assay; see below) or by immunofluorescence against the transgene product 3 days post-transduction.

Assessment of Global GFP Protein within Transfected Cell Populations

The analysis of GFP-positive cells was carried out primarily with flow cytometry, which allowed sensitive quantification of both percentage GFP-positive cells in the population as well as the degree of GFP expression per cell, as measured by the median fluorescence intensity. It should be noted that the reporting of the magnitude of global GFP expression in the transfected population was carried out by multiplying the percentage GFP-positive cell number by the median fluorescence intensity (MFI; arbitrary units) to yield an 'Expression Score'. We believe that this measure is a better representation of the total level of GFP protein expression within the transfected cell population—it essentially assumes a normal distribution of GFP expression level within the transfected population and therefore approximates 'the area under the curve'. This was done because reporting of GFP expression based solely on either percentage-positive or MFI were limited in their 'description' of the population being analysed (see FIG. 5 for explanation). 'Fold-repression' was therefore a measure of the impact of TRAP on GFP translation, and was calculated by dividing the Expression Score of 'stuffer' controls by the Expression Score of the relevant TRAP-expression plasmid test sample.

SDS-PAGE and Immunoblotting

Standard SDS-PAGE and Immunoblotting protocols were carried out primarily on End-of-vector production cells, post vector harvest. For immunoblotting analysis of vector particles, ~2 mL of filtered vector supernatant was centrifuged at 21,000 rpm in a microfuge for 1-2 hours at 4° C., before the 'pellet' was resuspended in 20-30 µL PBS. These concentrated vector preparations were quantified by PERT assay (below) and $7 \times 10^4$ PERT-predicted TUs of vector loaded per well of a SDS-PAGE gel. Approximately $1 \times 10^6$ end-of-vector production cell were lysed in 200 µL fractionation buffer and the nuclei removed by centrifugation. Protein samples were quantified by BioRad assay and typically 5 µg of protein was loaded onto pre-formed, 12-15 well, 4-20% acrylamide gels. Proteins were transferred onto nitrocellulose at 45V for 3 hours on ice. Blots were blocked in 5% milk PBS/tween-20 overnight at 4° C. Blots were probed with primary antibodies and HRP-secondary antibodies at typically 1:100 dilution in blocking buffer. Immunoblots were analysed by ECL-detection followed by X-ray film exposure.

Retroviral Vector Titration

Integration assay

Harvested, filtered vector supernatants were diluted 1:5 in media before 0.5 mL volumes used to transduce $1 \times 10^5$ HEK293T cells at 12-well scale in the presence of 8 µg/mL polybrene. Cultures were passaged for 10 days (1:5 splits every 2-3 days) before host DNA was extracted from $1 \times 10^6$ cell pellets. Quantitative PCR was carried out using a FAM primer/probe set to the EIAV packaging signal (ψ), and vector titres (TU/mL) calculated using the following factors: transduction volume, vector dilution, ψ copies detected per cell, and the ψ copies detected per cell of a characterised 'single copy ψ' cell line control.

GFP-reporter assay

Harvested, filtered GFP-encoding vector supernatants were diluted in the range 1:10 to 1:160 in media before 0.25 mL volumes used to transduce $5 \times 10^4$ HEK293T cells or $3.74 \times 10^4$ D17 cells at 24-well scale in the presence of 8 µg/mL polybrene. Cultures were analysed by flow cytometry 3 days post transduction using a FACS Verse or FACS Calibur under manufacturer-suggested settings; 10,000 events were captured and dead cells out-gated using a DEAD/LIVE mix control based on SSC/FSC 2D plots and/or ToPro3 staining.

Immunofluorescence (IF) assay (Biological titration)

Harvested, filtered OXB-102-encoding vector supernatants were diluted 1:2 to 1:8 in media before 0.5 mL volumes used to transduce $1 \times 10^5$ HEK293T cells at 12-well scale in the presence of 8 µg/mL polybrene. Cultures were incubated for 3 days before IF on fixed and permeablised cells. A primary antibody to tyrosine hydroxylase (TH) and an Alexa-488 secondary antibody were both used at 1:500 dilutions in permeabilisation buffer.

LacZ-reporter assay

For LacZ-vector mixing experiments, harvested, filtered vector supernatants were 10-fold serially diluted to a factor of $10^{-5}$ before 0.5 mL volumes of $10^{-2}$, $10^{-3}$ $10^{-4}$ and $10^{-5}$ diluted vectors were used to transduce D17 cells on 12-well plates that had been pre-seeded with $7.5 \times 10^4$ cells 24 hours prior to transduction. Cultures were analysed 3 days post transduction by fixation and X-Gal addition, followed by blue colony counting to generate titres (LFU TU/mL).

PERT assay

The PERT assay has been described elsewhere (Arnold B A, et al., 1998, *Biotechniques* 25:98-106). PERT-predicted titre (PERT-TU/mL) is an arbitary physical particle titre based on the RT activity associated with the biological titre of a GFP-encoding EIAV vector prep used as the qRT-PCR standard curve in the PERT assay.

Assessment of the Impact on Retro/Lentiviral Vector Production by Expression of a Transgene Product in Production Cells by Vector Genome Mixing Experiments.

Figure 2:
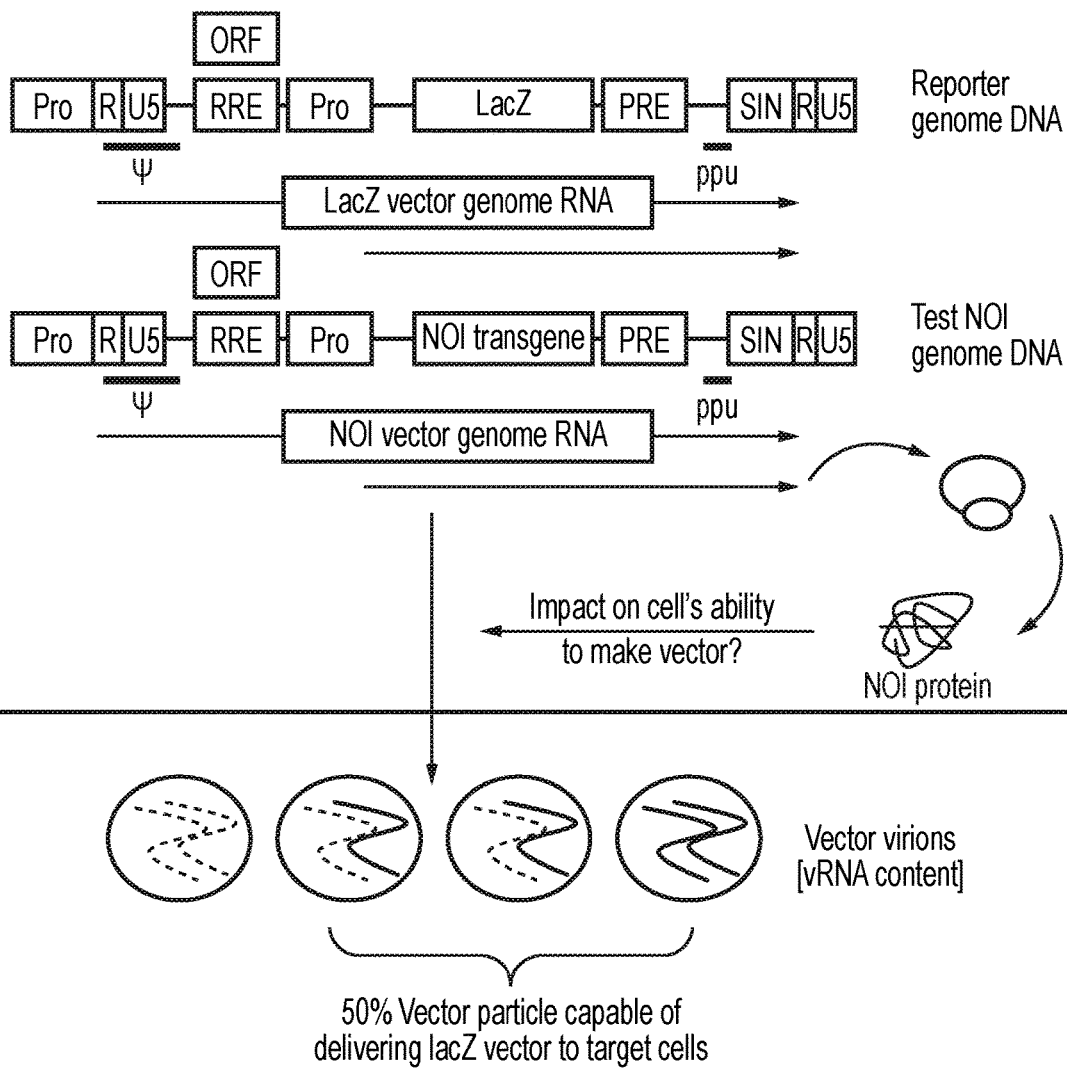
FIG. 2. A schematic describing a vector genome plasmid mixing experiment to determine the magnitude of negative impact of an NOI transgene product on the ability of production cells to produce vectors. In a vector genome mixing experiment, vector particles are produced by cotransfection of cells with vector packaging components and two types of vector genome plasmids: one reporter gene vector genome plasmid and a vector encoding an NOI transgene to test the impact of the transgene product on vector productivity of the cell. Since expression of lacZ or GFP reporter proteins does not impact on vector titres, these are used as control vectors. Introduction of the second vector genome plasmid encoding an NOI transgene that may negatively impact vector productivity of the cell will have a bystander effect on lacZ-vector production. Expression of the NOI transgene will occur mainly from the internal expression cassette, which is typically driven by a powerful, constitutive promoter. Due to the possible outcomes of packaging two copies of vector genome RNA molecules per virion and the fact that only one vector RNA becomes reverse transcribed and integrated into target cells, there will be a dilution effect of mixing-in the second genome with the lacZ-vector; this dilution effect becomes more apparent when proportionally more of the second genome plasmid is mixed with the lacZ-vector genome plasmid. Consequently, a 'dilution' control is required wherein the second vector genome plasmid is that of GFP; GFP is also known to have no negative impact on vector titres. Therefore, the impact of a given NOI transgene product on vector productivity can be measured against the LacZ:GFP vector genome mix control. Vectors produced from the mixing experiment are typically titrated by a read-out for the lacZ-vector e.g. X-gal staining of vector-transduced cells.

In order to assess the degree of negative impact of a NOI transgene product on retroviral vector production from a cell, a simple vector genome mixing experiment can be performed as outlined in FIG. 2. The 'retro(lenti)-viral vector production protocol' described above may be carried out using a mixture of reporter gene vector genome plasmid (e.g. lacZ or GFP transgene) and a vector genome plasmid expressing an NOI, together with the vector packaging components described in FIG. 1. The expression of the reporter proteins lacZ or GFP within a vector production cell, such as HEK293T, is generally accepted not to adversely impact the titre or specific activity of the vector particles produced; therefore vectors encoding these reporters can be made at high titres. Thus, the mixing of plasmids encoding a vector genome with such a reporter gene and that of a vector genome encoding a transgene that does impact vector titres, allows a degree of measure of that impact by titration of vector using the reporter gene activity as a read-out in target cells. This is because there will be a 'bystander' effect on reporter gene vector titre from the impact of the 'problematic' transgene protein, since all vector particles will be made in the same cell, utilising the same cellular machinery/pathways for virion assembly. The ratio of the reporter-to-NOI vector genome plasmids used at transfection is typically between 1:1 and 1:5. Note that since retroviral vector particles package two copies of genome RNA per virion, there will be a 'dilution' effect on reporter-specific vector titre even when two non-problematic proteins (e.g. Lac Z and GFP) are expressed from two different vector genome plasmids within the production cell. For example, when using a 1:1 ratio of lacZ and GFP vector genome plasmids, the laws of probability dictate that 25% of the virions will contain two copies of lacZ vector RNA, 25% will contain two copies of GFP vector RNA and the remaining 50% of virions will contain one of each vector RNA. In the latter scenario, only one of the two genomic RNA molecules will be reverse transcribed into DNA, so there is a 50:50 chance of either reporter vector genome being integrated into the target cells, resulting in expression of said reporter. Taken together, this means that when two plasmids of vector genomes are mixed at the 1:1 ratio, the specific reporter vector titre will be reduced by 2-fold compared to production single vector genome preparations. When using a greater mix ratio (e.g. 1:5), then the diluting effect will be greater. For this reason, the mixing of two reporter vector genome plasmids is used as a 'mixing' control for the dilution effect, alongside any mixing of the reporter vector genome plasmid with the vector genome plasmid expressing the NOI transgene under assessment.

By way of example, FIGS. 3*i* and 3*ii* display the data from various vector genome plasmid mixing experiments using a lacZ reporter vector genome plasmid, with vector titre read-out based on X-gal staining in target cells. The majority of vector genome plasmids tested including those of RetinoStat®, StarGen™, UshStat® and ReQuinate®, as well as vectors expressing COX-2 and/or FPR, impact vector titres by 7-to-100 fold, depending on the ratio of lacZ vector plasmid-to-test vector plasmid employed. These data clearly show that transgene protein expression within vector production cells contributes significantly for the low vector titres observed with clinically relevant vectors compared to reporter gene vectors.

Description of the Invention in Relation to Retroviral Vector Production; Translation Repression In Vector Production Cell [TRIP] System FIG. 4 displays a simplified schematic of the Translation Repression In vector Production cell [TRIP] system as applied to retro/lentiviral vector production. TRIP systems describing components necessary to repress transgene translation in other viral vector systems (e.g Adenoviral and AAV vector based vectors) can be described to include virus-specific packaging components. All such TRIP systems must contain the two following components in addition to the necessary vector components: a TRAP expression cassette and the TRAP-binding site (tbs) inserted within the 5'UTR of the NOI transgene such that production of the POI is repressed in the presence of TRAP. Multiple NOI ORFs within a vector genome molecule may be regulated by TRAP i.e. the vector genome may be multicistronic (e.g. containing IRES element) and more than one ORF may have a TRAP-binding site inserted upstream of its translation initiation codon (e.g. between the IRES and downstream ORF).

DESCRIPTION OF KEY EXPERIMENTS

Initial Testing of TRAP/Tbs Configuration by Use of GFP Plasmids and GFP-Expressing Lentiviral Vector Genome Plasmids Example 1. Testing GFP Expression Regulation in Transient Co-Transfection with TRAP-Expression Plasmids The GFP reporter construct pCMV-tbsGFP was constructed as described in FIG. 6. A TRAP binding sequence (tbs) was inserted into the construct such that the 5'UTR encoded (from 5' to 3') a 41 nt leader, the 55 nt tbs and a 9 nt region encoding the kozak consensus sequence immediately upstream of the GFP ATG codon. These GFP reporter constructs were derived from the experimental EIAV vector genome pONY8.4RC-GFP by deletion of the region between the two CMV promoters (see FIG. 6).

In more detail, regarding the details of the fluorescent gene expression reporters, the GFP reporter gene was chosen for the initial evaluation experiments so that relatively quick assessment of gene regulation could be carried out by flow cytometry. GFP is not known to be toxic or detrimental to vector production but was used as a sensitive model for gene expression regulation by TRAP/tbs. Moreover, the existing vector genome pONY8.4RC-GFP was available for manipulation; this vector utilises a wild type EIAV U3 within the 3'LTR and a DsRED-express ORF upstream of the internal transgene cassette as depicted in FIG. 6. Therefore, this vector genome plasmid is capable of both GFP and DsRed-express expression within vector production cells.

All these reporter constructs contained the wild type EIAV LTR that allowed polyadenylation of mRNA derived from transcription from the strong CMV promoter. Thus, the expression of GFP from both pCMV-tbsGFP and the control plasmid pCMV-GFP in HEK293T cells was robust (see FIGS. 8 and 9).

The TRAP expression constructs were created using a codon/sequence-optimised TRAP ORF from *Bacillus subtilis* for high expression in human cells. In more detail, FIG. 7 displays the type of TRAP expression plasmids initially evaluated in transient transfection experiments. Since the TRAP protein is of bacterial origin, the publically available nucleotide sequence is of the bacterial sequence encoded within the mtrB/TrpBP 'Transcription attenuation protein gene family' operon. However, in order to potentially increase expression in mammalian cells, and to eliminate any sub-optimal sequences such as splice-donor/acceptor sites, the TRAP nucleotide sequence was codon/sequence optimised for expression in *Homo sapiens*. The synthetic sequence was designed for cloning into pCI-NEO to yield pCI-coTRAP. SapI sites were positioned such that digestion and re-circularisation allowed fusion of a $HIS_6$-tag to the C-terminus of the TRAP protein. This ultimately yielded pCI-coTRAP[H6]. Previous reports using non-codon optimised TRAP expression plasmids have also used C-terminally $HIS_6$-tagged TRAP without detriment to TRAP function. Since there is currently no commercially available TRAP antibody, $HIS_6$-tagged TRAP was used to determine the level of expression of TRAP during experiments.

The first set of experiments utilised both untagged TRAP and C-terminally $HIS_6$-tagged TRAP. Co-transfection experiments with the TRAP+/–$His_6$-tag plasmids and the tbs-GFP reporter constructs demonstrated that both versions of TRAP were capable of repressing GFP expression from pCMV-tbsGFP in HEK293T cells (FIGS. 8 and 9). TRAP and TRAP[H6] repressed GFP expression by 3-fold and 27-fold respectively, when TRAP plasmid and reporter were cotransfected at a 1:1 ratio (FIG. 9B). Some minimal repression was observed even when the TRAP plasmids were co-transfected at a $10^{th}$ of this dose i.e. 10:1 molecular ratio (reporter:TRAP). Neither version of TRAP impacted on GFP expression of pCMV-GFP, demonstrating that the tbs was essential for TRAP-mediated repression.

Example 2. Optimisation of TRAP-Expression Plasmid Expression

Expression from pCI-Neo based plasmids can be subject to or direct competition with other CMV-driven DNA cassettes. For this reason it was hypothesised that pCI-coTRAP[H6]cotransfected with pCMV-tbsGFP at the $\frac{1}{10}^{th}$ dose might have been subject to this type of competition, since also pCI-Neo was used as stuffer DNA to normalise DNA load (after this experiment pBlueScript was then used as the standard stuffer DNA for all other experiments). Therefore, the EF1α-driven construct pEF1a-coTRAP[H6] was made as described above and tested in cotransfections with pCMV-tbsGFP at different ratios. FIG. 9D summarises the repression of GFP in cells cotransfected with either pCI-coTRAP[H6] or pEF1a-coTRAP[H6] together with the GFP reporter constructs. These data demonstrate that pEF1a-coTRAP[H6] can be cotransfected with tbs-GFP reporter DNA at the $\frac{1}{10}^{th}$ dose and maintain the level of GFP repression observed at the 1:1 ratio (in this case, MFI data was compared), in contrast to pCI-coTRAP[H6]. Therefore, the EF1a-promoter may be more preferable in driving TRAP expression.

Due to the method of cloning pCI-coTRAP and pCI-coTRAP[H6], the 3'UTRs of these constructs were not identical (FIG. 7), and so the potential reason for the observed difference in functionality between the two constructs (FIG. 9) may have been due to TRAP mRNA/protein levels, rather than because of any amino acid difference. To assess whether the C-terminal $HIS_6$ tag on TRAP is important for functionality, pEF1a-coTRAP was constructed by removing the sequence from pEF1a-coTRAP[H6] (FIG. 7); these constructs are identical except for the $HIS_6$-tag sequence. pEF1a-coTRAP[H6] and pEF1a-coTRAP were compared directly by cotransfection of HEK293T cells with tbs-GFP reporter plasmids at different ratios (FIG. 10).

These data demonstrate that both $HIS_6$-tagged and untagged TRAP proteins are capable of repressing GFP expression to almost undetectable levels when supplied at 1:1 or 1:0.1 molar ratio with tbs-containing GFP reporter plasmid. The untagged TRAP version was 2-fold less effective in repression than TRAP[H6] in all measures of expression. Therefore, the $HIS_6$ tag may afford some minimal advantage over untagged TRAP; this may be due to enhanced protein stability, and/or solubility/folding and/or functionality (e.g RNA binding).

Example 3. Evaluation of Different TRAP Homologues

In addition to TRAP of *Bacillus subtilis*, two other TRAP homologues were shown to mediate repression of GFP expression from cells co-transfected with pCMV-tbsGFP and TRAP-expression plasmid (FIG. 11A). The TRAP genes from *Desulfotomaculum hydrothermale* and *Aminomonas paucivorans* were codon/sequence-optimised and cloned into the pEF1a-based expression plasmid; both of these variants included C-terminal $HIS_6$ tags. These TRAP variants shared 75% and 55% amino acid homology with that of *Bacillus subtilis* TRAP, respectively. All three variants were capable of GFP expression repression in HEK293T cells in the order of 2 Logs, demonstrating that TRAP homologues with only 55% sequence homology are capable of function in the TRIP system. All three homologues were conserved in sequences involved in RNA and tryptophan binding sites (data not shown).

Example 3b. Evaluation of Different TRAP Homologues and Variants

In order to test if homologues of TRAP from bacterial strains in addition to *Bacillus Subtilis* could function in the repression system, five TRAP variants of varying sequence identity to *Bacillus Subtilis* TRAP were identified from the NCBI database (FIG. 21*i*). The variants represented a wide range of different TRAP variants from across the Bacterial lineage. Gene sequences for these TRAP variants were codon-optimised for high expression in human cells and included a C-terminal $HIS_6$ (akin to *Bacillus Subtilis* TRAP [H6] previously shown to enhance TRAP-mediated repression; FIG. 10), and cloned into the pEF1a-promoter plasmid (FIG. 7). The *B. halodurans* TRAP variant forms a natural 12-mer (Bayfield, O. W. et al. (2012) *PLoS ONE* 7: e44309. doi:10.1371/journal.pone.0044309), indicating that potentially, 12 RAGNN repeats within a tbs may be bound by this TRAP. It has also been shown that artificial 12-mer versions of natural 11-mer TRAP variants can be engineered through modifications in the C-terminus of the protein. A S72N modification of *Bacillus Stearothermophilus* TRAP has been shown to result in 12-mer proteins as judged by X-ray crystallography (Bayfield, O. W et al. (2012) *PLoS ONE* 7: e44309. doi:10.1371/journal.pone.044309), although it is not known whether 11-mers or 12-mers of these variants are formed in the cellular environment. The *Bacillus Stearothermophilus* TRAP-S72N variant was also constructed and tested alongside the other TRAP homologues for potential function in the TRAP-repression system. Two GFP reporter plasmids containing either an 11×RAGNN or 12×RAGNN repeat tbs were used; it was hypothesised that the 12-mer TRAPs might repress transgene expression from the pCMV-tbsx12GFP reporter to a greater extent than the 11-mers on the pCMV-tbsx11GFP reporter.

Data from the comparison of the different TRAP homologues and *B. stearothermophilus* TRAP-S72N variant are displayed in FIG. 21iiA-B. All of the homologues and the *B. stearothermophilus* TRAP-S72N variant were capable of at least 10-fold repression of GFP. Given the relatively low amino acid sequence homology between these TRAP homologues (56-78% compared to *B. subtilis* TRAP; see FIG. 21iii), this suggests that TRAP proteins from diverse bacterial species form the similar quaternary structure required for interaction with tbs RNA sequences in mammalian cells. All homologues contained the amino acid residues known to be important for contact with RNA and L-tryptophan-binding; however, it is expected that L-tryptophan-binding mutants, which constitutively bind tbs-RNA (even in absence of L-tryptophan) such as *B. subtilis* TRAP T30V (Yakhnin et al. (2000) *J. Biol. Chem.* 275: 4519-4524), will also function in the TRAP-mediated repression configuration.

Example 4. Evaluation of Transgene Repression in Stable HEK293T-TRAP Cell Lines In order to evaluate TRAP-mediated repression of transgene expression in the context of a stable TRAP-expressing cell line, the construct pEF1a-coTRAP[H6]-iBsr was made and used to stably transfect HEK293T cells by blasticidin selection (FIG. 11B). From ~100 stable clones, four subcloned HEK293T-TRAP[H6] cell lines 2F, 10H, 7E and 3D were isolated and tested for their ability to repress GFP expression from transfected pCMV-tbsGFP. Cultures were co-transfected with either stuffer plasmid or pEF1a-coTRAP[H6] plasmid to assess whether the endogenous levels of TRAP[H6] were capable of achieving the same level of GFP repression as observed with transiently transfected TRAP-expression plasmid. These data demonstrate that stable TRAP-expressing cell lines are capable of a similar level of transgene repression (in order of 2 Logs) from endogenous TRAP compared to HEK293T cells transiently transfected with TRAP-expression plasmid. However, even greater levels of transgene repression were observed in the HEK293T-TRAP[H6] clones when additional TRAP-expressing plasmid was transfected transiently (in order of 4 Logs). The reason for this effect is likely due to the pre-existing TRAP pool in HEK293T-TRAP[H6] clone cells. To explain further, in the transiently transfected scenario there will be an early time point post-co-transfection of pCMV-tbsGFP and pEF1a-coTRAP[H6] where insufficient TRAP[H6] protein has accumulated resulting in a small but measurable amount of GFP expression before TRAP-mediated repression of pCMV-tbsGFP-derived mRNA can occur. This small amount of GFP expression is not observed in HEK293T-TRAP[H6] cells because the pre-existing pool of TRAP[H6] can act immediately on de novo tbsGFP mRNA. This effect, in partnership with additional TRAP-expressing plasmid, allows for a much greater 'fold-repression' in GFP expression in the stable TRAP cell lines. This suggests that the maximum amount of TRAP[H6] expression in stable cell lines is not as high as that observed in transient transfection of HEK293T cells (this has been confirmed by immunoblot to TRAP[H6], data not shown). However, it is likely that the ability of the stable TRAP[H6] cell lines to repress transgene expression by over 2 Logs will be sufficient to improve vector titres.

Example 4b. Development of HEK293T Cell Lines Stably Expressing TRAP[H6] and their Use in Production of Vectors This example builds on that presented in example 4, and provides more information on how the stable TRAP[H6] cell lines were developed. HEK293T cells were stably transfected with the EF1α-coTRAP[H6]-iBsr expression cassette (FIG. 22i) and clones isolated by blasticidin selection. These stably expressing TRAP[H6] (*B. subtilis*) clones were subcloned twice and then screened for repression functionality by transfection with pCMV-GFP (no repression) or pCMV-tbsGFP. The total GFP expression in cell populations was estimated by generating the Expression score (FIG. 22iiA; MFI×% GFP). Four clones (2F, 10H, 7E, and 3D) were identified as having up to 2-Log repression activity as well as low, absolute GFP expression scores under repressive conditions (i.e. in presence of TRAP). Repression levels of GFP transgene within stable clones correlated reasonably well with the level of TRAP[H6] detected within cells (FIG. 22iiB). These data indicate that TRAP expression is not toxic to HEK293T cells and that 'HEK293T.TRIP' cells (stably expressing TRAP; also known as 'HEK293T.TRAP') are capable of repressing transgene expression in a similar manner to that previously observed in transient transfections of TRAP plasmids.

We show in another example that the TRIP system can improve the vector titres of ReQuinate—an EIAV vector expressing huFactor VIII—over the standard vector production system (FIG. 17). HuFactor VIII impedes incorporation of VSVG into EIAV vector virions. It is theorised that a stable TRIP system (i.e. integrated TRAP cassette) may offer improvements in the timing of transgene repression compared to the transient TRIP system (i.e. co-transfection of 'pTRAP' plasmid with vector components). This is because pre-existing pools of TRAP protein in stable cells will be immediately available to repress the transgene, whereas in the transient system 'pTRAP' requires to be expressed until sufficient levels of the TRAP protein are present to repress the transgene mRNA; at this early time therefore, some 'leaky' expression of the transgene may occur and possibly have a negative impact on active vector production. To test this, a vector mixing experiment was performed wherein EIAV-[tbs]GFP and EIAV-[tbs]FVIII (also known as ReQuinate-tbs) genomes were mixed 50:50 during transfection of cells with vector components+/−pEF1a-coTRAP[H6].

Therefore any negative impact of huFVIII expression on general EIAV vector virion activity would be measurable on EIAV-GFP vector titres. HEK293T cells and the stable HEK293T.TRIP cell lines 2F, 10H, 7E and 3D were tested. End-of-production cells were analysed form GFP expression by flow cytometry (FIG. 22iiiA) and crude vector produced was titrated on fresh HEK293T cells and also analysed by flow cytometry (FIG. 22iiiB).

The data in FIG. 22iiiA demonstrate that stable cells expressing TRAP are capable of greater transgene repression compared to the transient TRIP system; GFP expression was reduced by 1000-fold in HEK293T.TRIP-10H (FIG. 22iiiA; comparing EIAV-GFP and EIAV-tbsGFP genomes). The degree of GFP (and by extension, huFVIII) repression in production cells correlated with the titre of vectors produced (see FIG. 22iiiB). Overall, the stable HEK293T.TRIP cell lines produced ~3-fold greater titre than the transient TRIP system. Although additional TRAP expression in the stable HEK293T.TRIP cell lines (+TRAP TXN) allowed further repression of transgene expression, this did not translate to a further improvement in titre of this specific transgene-encoding vector. Therefore, it is likely that the pre-existing pool of TRAP, not maximal TRAP protein per se, is responsible for the improvement in vector titres over the transient system in this example (i.e. vectors expressing huFVIII). It is possible that repression of more problematic/toxic transgenes will benefit from both pre-existing and high levels of TRAP during vector production.

The vector particle-containing supernatants harvested from the EIAV-[tbs]GFP|EIAV-[tbs]huFVIII producing cells were analysed for VSVG content by immunoblotting (FIG. 22iv). These data reveal that only when the tbs is utilised on the vector genome and TRAP is supplied during vector production (either in trans—HEK293T+pEF1a-coTRAP [H6] or by stable TRAP expression) can VSVG become incorporated into vector particles.

Example 5. Testing the TRIP System on Production of GFP-Encoding Lentiviral Vectors The aim of the experiment was to evaluate the potential impact of the presence of the tbs within a vector genome. To expand, since TRAP is capable of binding to the tbs within the vector genome RNA molecule (as well as on the transgene mRNA) and therefore be packaged into de novo vector virions, the process of reverse transcription was reasonably expected to be adversely affected. The TRAP-tbs interaction is particularly high affinity (nM range) and it was not known whether reverse transcriptase was capable of disrupting this interaction during the RT step. In order to apply the TRAP/tbs configuration to repression of a vector transgene in production cells, the EIAV vector genome pONY8.4RC-tbsGFP was constructed from pCMV-tbsGFP (See FIG. 6). Vector was produced in HEK293T cells using the genomes pONY8.4RC-tbsGFP or pONY8.4RC-GFP, packaging components (GagPol and VSVG) and co-transfected with or without pCI-coTRAP[H6] (this experiment was performed before construction of pEF1a-coTRAP[H6]). End-of-production cells were analysed by flow cytometry for GFP expression (FIGS. 12A and B) and vector supernatants were used to transduce D17 cells (FIG. 12C).

The TRAP/tbs configuration was capable of repressing GFP from the internal transgene cassette of the tbs-containing vector genome to a similar level to that of pCMV-tbsGFP, in contrast to the vector genome without tbs (FIG. 12A). DsRed-X expression was not affected by TRAP, indicating that full length vector genome RNA was made and was translatable (data not shown). The fold-repression of GFP from the vector genome plasmid by TRAP was 50-to-100-fold (FIG. 12B). Whilst the fold-repression was lower than that observed for pCMV-tbsGFP, this was likely due to the lower un-repressed levels of GFP observed from the vector genome, which was probably a result of competition with the external CMVp driving vector genome RNA. These data also indicate that Sodium butyrate addition during vector production—a known activator of the CMV promoter—did not seem to impact the TRIP system (Sodium butyrate was also added to pCMV-tbsGFP transfections in this experiment).

FIG. 12C demonstrates that tbs-containing GFP vectors could be produced at very similar titres to standard GFP vectors; pONY8.4RC-tbsGFP produced in the presence of TRAP protein gave $1.4\times10^6$ TU/ml compared to the $1.8\times10^6$ TU/ml of pONY8.4RC-GFP produced in the absence of TRAP protein. These data demonstrate for the first time that the TRIP system can be utilised in generating a retroviral vector wherein the transgene is translationally silenced.

Fundamental Characterisation of Tbs Sequence Requirements for TRAP-Mediated Repression Example 6. Testing the Short Spacing Requirements Between the Tbs and Translation Initiation Codon The first experiment in characterising sequences important in the TRAP-binding site (tbs) asked the question of whether the short spacing distance between the tbs and the AUG translation initiation codon is important for translation repression. The configuration of tbs within pCMV-tbsGFP and pONY8.4RC-tbsGFP is such that the tbs is separated from the GFP AUG translation initiation codon by 9 nucleotides. In other artificial gene regulation systems, such as Tet-ON/OFF, spacing parameters have been shown to contribute to functionality. To assess the importance of short-range spacing, a series of variants were constructed in which 1 to 9 of these spacer nucleotides were progressively deleted. In addition, the spacing was increased to 10 and 11 nucleotides in two other variants. Finally, the standard tbs-9 nt-AUG configuration was appended with a 5' proximal stem loop (SL) sequence taken from the *Bacillus subtilis* trpEDCFBA operon, which has been shown to be important for TRAP-tbs binding for the transcription attenuation mechanism in vivo (McGraw A P, M. A., Major F, Bevilacqua P C, Babitzke P. (2009) *RNA* 15(1): 55-66). The SL mutant was included to test if TRAP-mediated repression could be enhanced. These variants were cloned into the vector genome pONY8.4RC-tbsGFP and co-transfected with limiting quantities of pEF1a-coTRAP[H6] (ratio of 1:0.05) in order that subtle differences in translation repression might be more easily quantified.

The results of this experiment are depicted in FIG. 13B. None of the spacer deletion variants or increased spacer variants showed any altered TRAP-mediated repression compared to the 9 nt spacer. The '0' variant, showed approximately 2-fold reduction in GFP expression compared to the other variants +11 to +1, but this occurred in the presence or absence of TRAP, indicating that general ability of GFP to be translated from this variant mRNA was less efficient (likely due to deletion of optimal kozak consensus sequence). Interestingly, the presence of the 5' stem loop from the natural trp operon completely ablated functionality of tbs to repress translation in concert with TRAP. This unexpected result suggests that whatever the other features of the SL-tbs configuration that allow functionality in vivo, they are either lacking from this artificial configuration or not in the correct sequence spacing/context or that TRAP binding to SL-tbs in *Bacillus subtilis* follows a different mechanism in transcription attenuation compared to translation attenuation, the latter being independent of the SL. All these data suggest that the translation repression directed by TRAP binding to the tbs in this artificial system is not altered by the short distance between tbs and the translation initiation codon.

Figure 24I:
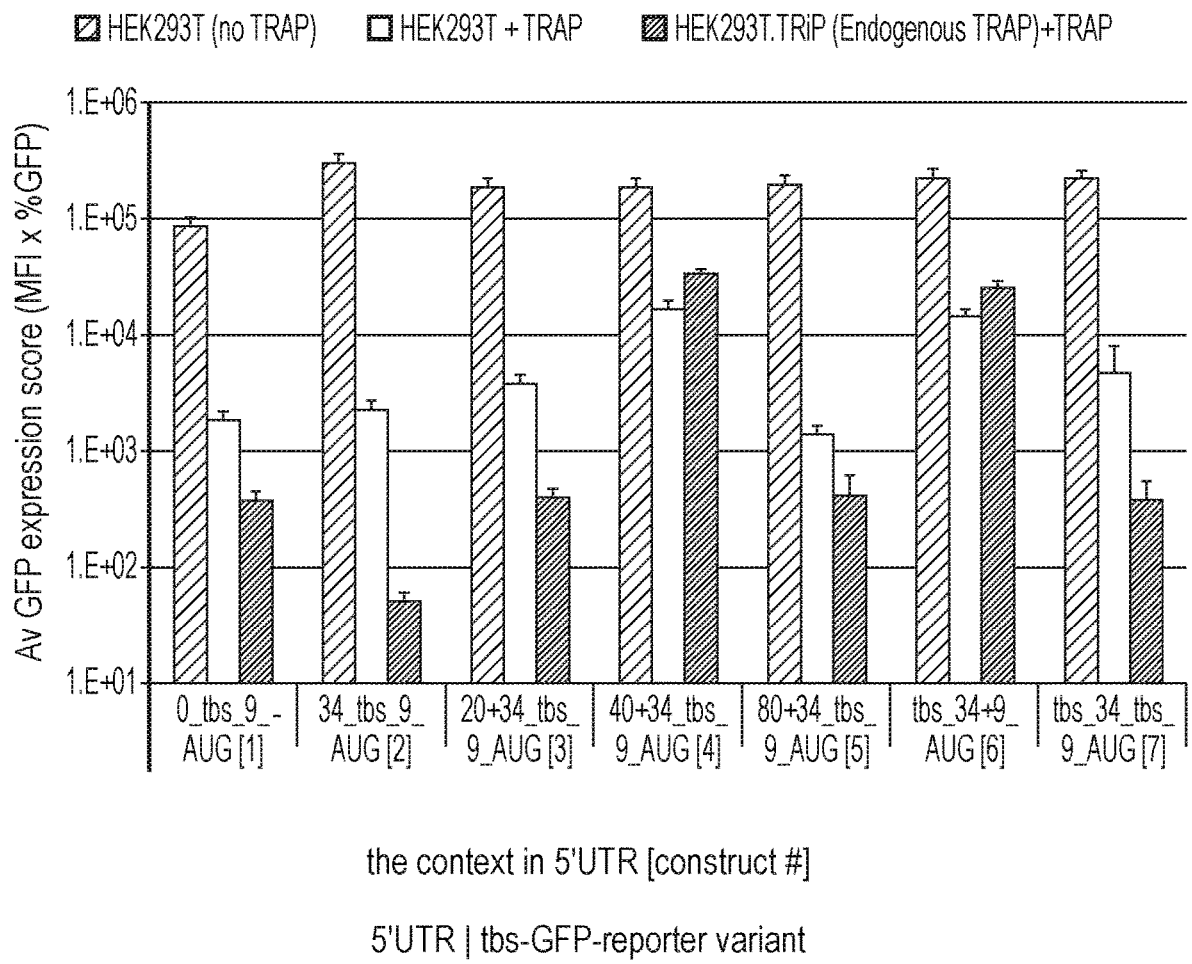

Example 6b. Testing the Impact of Position of the Tbs within the 5'UTR of a Transgene Cassette on TRAP-Mediated Repression To further characterise the importance of tbs position within the 5'UTR of the transgene in regard to TRAP-mediated repression activity, a series of 5'UTR variants of pCMV-tbsGFP were constructed wherein the relative distance of the tbs from the Cap site and AUG initiation codon was varied (FIG. 24$i$). In addition, another construct was made in which two copies of the tbs were inserted within the 5'UTR with a 34 nt intervening sequence between the two tbs sequences. This was constructed to test whether TRAP-tbs mediated repression could be enhanced over the single copy tbs configuration.

The seven tbs variant GFP reporter constructs in FIG. 24$i$ were tested for their ability to be repressed by TRAP under three conditions: no TRAP (HEK293T), transiently co-transfected with pEF1a-coTRAP[H6] (HEK293T+TRAP) and under maximum TRAP repressive conditions (HEK293T.TRIP[Endogenous TRAP]+co-transfected TRAP). All the 5'UTR tbs variants were capable of being repressed by TRAP[H6] by 10-to-100-fold. Reducing upstream UTR length to zero (i.e. the whole of the UTR was comprised of just a single tbs) did not appear to affect TRAP-mediated repression; construct #[1] was capable of ~2-Log repression of GFP by TRAP, although unrepressed levels of GFP were lower than the other constructs.

Increasing the spacing between the tbs and the AUG initiation codon from 9 to 43 nt still allowed 10-fold TRAP-mediated repression via the tbs. The double tbs-encoding 5'UTR variant (FIG. 24$ii$, construct #[7]) did not improve TRAP-mediated repression compared to single tbs-containing variants.

These data show that: [1] a single tbs may be inserted anywhere within the 5'UTR allowing some degree of TRAP-mediated repression of a transgene, [2] it is preferable to insert the tbs close to the AUG initiation codon to facilitate maximal TRAP-mediated repression, and [3] 5'UTR sequence length upstream of the tbs can be reduced to zero without affecting the magnitude of repression.

Example 7. Identification of the Minimum Number of [RAGNN] Repeats within the Tbs Required for TRAP-Mediated Repression of Translation The next experiment was performed in order to identify the minimum number of [RAGNN] repeats required to allow TRAP-mediated repression. One report in the literature used in vitro binding to indicate that that as few as 5 repeats might be sufficient to allow TRAP binding (Babitzke P, Y. J., Campanelli D. (1996) *Journal of Bacteriology* 178(17): 5159-5163). A series of tbs deletion variants were generated wherein 1 to 7 repeats were progressively deleted (FIG. 14$i$A). The optimal Kozak sequence was maintained in all variants. In addition, a TG>AA change was made in the tbs between the 10$^{th}$ and 11$^{th}$ repeats; this was done after other work suggested that this region might contain a non-canonical splice donor site (this later proved to be incorrect)—data not shown. The variant tbs GFP reporter constructs were co-transfected into HEK293T cells with pEF1a-coTRAP [H6] (the former at 10:1 molar excess over the latter) or pBlueScript, and GFP expression measured by flow cytometry (FIG. 14$i$B). The TG>AA modification to tbs had no detectable effect in TRAP-mediated repression, as the tbsx11M variant allowed 1000-fold repression of GFP expression. Variants tbsx10M, tbsx9 and tbsx8 also allowed 1000-fold repression in GFP expression, whilst tbsx7 allowed 500-fold repression (FIGS. 14$i$ C and D). Deletion of a further RAGNN repeat yielding tbsx6 resulted in a further reduction in functionality as this variant was able to repress GFP expression by 30-fold. Variants tbsx5 and tbsx4 showed neglible repression compared to no tbs sequence.

These data clearly demonstrate that the most potent levels of repression by the TRAP/tbs configuration requires at least 7× (preferably at least 8) RAGNN repeats, whilst 6 repeats may allow some useful knock-down in transgene expression.

Figure 18I:
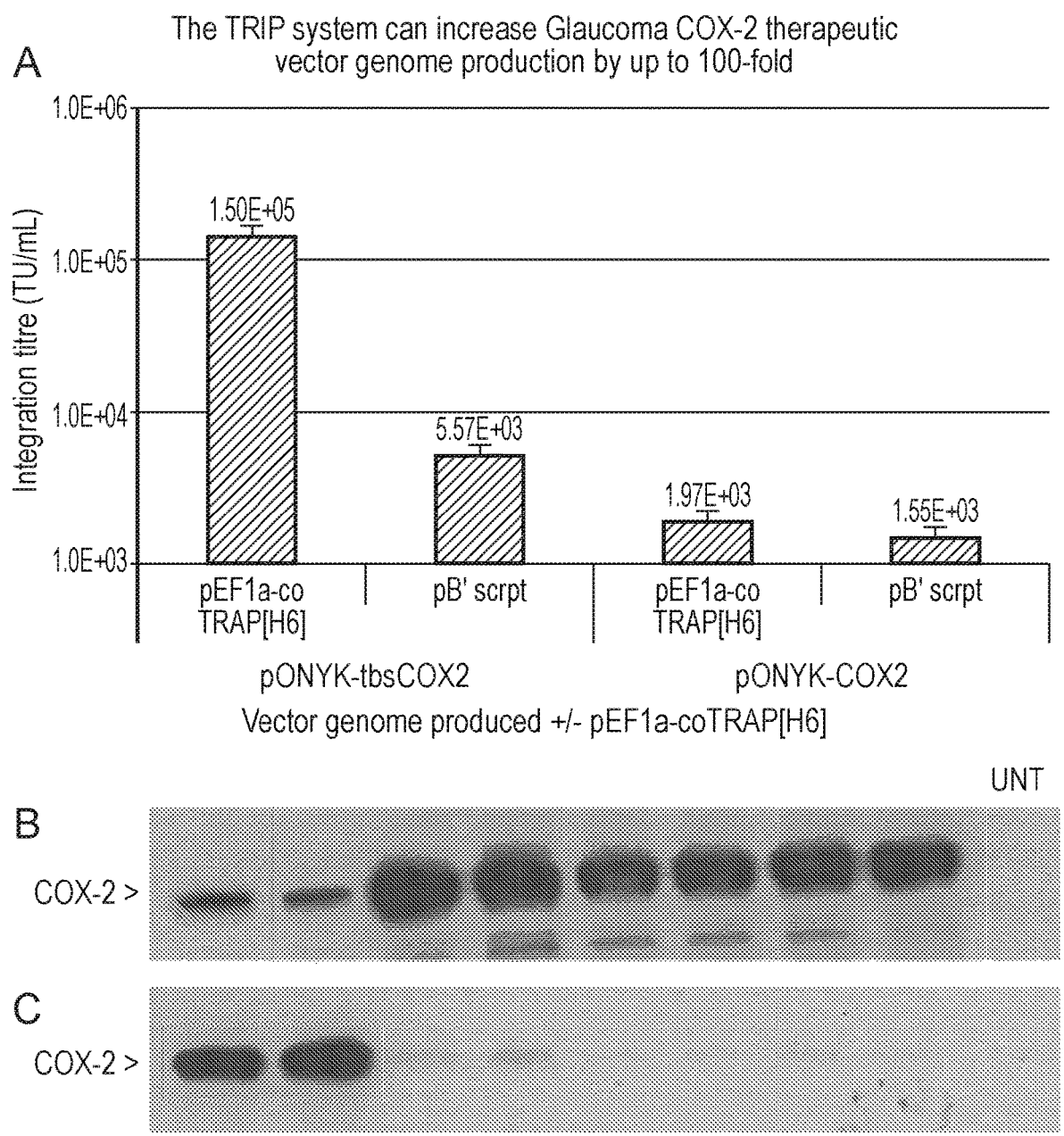

Example 8. Identification of the Number of [RAGNNN] Repeats Tolerated within the Tbs Whilst the general consensus is TRAP binding to a tbs containing $N_2$ spacers between RAG repeats is optimal, in vitro tbs-TRAP binding studies have also suggested that nucleotide spacers of three nucleotides between the RAG repeats of the tbs might be tolerated (Babitzke P, Y. J., Campanelli D. (1996) *Journal of Bacteriology* 178(17): 5159-5163). Indeed, natural tbs sequences found in vivo have occasional spacers longer than two nucleotides, although it is likely that this is because the TRAP/tbs interaction in vivo has evolved under specific cellular conditions where other protein interactions and/or selective pressures may be in play. It is possible that the natural TRAP/tbs interaction does not need to be at maximal efficiency in order to comply with biological functionality. However, in the artificial TRIP system it is desirable for the TRAP/tbs interaction to be maximally efficient. In order to test how tolerant the functionality of the 11×RAGNN tbs sequence is to serial replacement with RAGNNN repeats, a series of variant tbs sequences were designed (FIG. 14$ii$A) and cloned into an EIAV vector genome expressing the COX2 transgene (see FIG. 18$i$). These were based on the tbsx11M sequence first tested in FIG. 14$i$A. RAGNNN repeats replaced RAGNN repeats within tbsx11M from the centre position outwards yielding tbs sequences with 1×, 3×, 5× 7× and finally 11×RAGNNN repeats (note that for the $N_3$×11M tbs sequence, only 10 NNN spacers are effectively present, since the most 3' distal repeat spacer does not count as a spacer). These vector genome plasmids were transiently co-transfected into HEK293T cells with EIAV vector packaging components +/pEF1a-coTRAP[H6] and vector supernatants harvested (vector titres of these COX2 vectors are described below). End-of-production cell lysates were analysed by immunoblot to COX2 to measure transgene repression in the cell compared to stuffer plasmid (un-repressed) (FIG. 14$ii$B).

The data indicate that up to three RAGNNN repeats within the 11× repeat tbs allows some detectable repression of transgene expression within vector production cells; this may be sufficient to improve vector titres in some cases, depending on the magnitude of impact of the transgene protein on vector titres without the TRIP system. A single RAGNNN repeat within the tbs appears to be as functional as the $N_2$×11 repeat tbs.

Example 8b. Identification of the Number of [RAGNNN] Repeats Tolerated within the Tbs Further work was carried out regarding the number of Ns comprising the spacer between RAG repeats in the consensus repeat $RAGN_{23}$ that allow TRAP-mediated repression. FIG. 14$i$B presents COX2 expression analysis in end-of-production cells, approximately 2 days post-transfection. To test if transgene (COX2) expression in the contexts of the $N_3N_2$ tbs variants differed at early times post-transfection (compared to later times), production cell lysates at 8 hours post-transfection were analysed by immunoblotting to COX2 (FIG. 14$iii$). These data indicate that a similar pattern of COX2 expression occurs from the $N_3N_2$ tbs variants at both early and late time during vector production i.e. the magnitude of TRAP-tbs mediated repression for a given tbs variant appears to be similar during the course of vector production.

To measure the impact of the different levels of COX2 repression of the $N_3N_2$ tbs variant-containing vector genomes on vector titre, the crude supernatant harvests were subjected to DNA integration assay. FIG. 14iv displays these data and shows that vector titres were increased for the $N_3N_2$ tbs variants in which there was clear COX2 repression in production cells; namely '$N_3N_2$×11 [3]', '$N_3N_2$ ×11 [1]' and '$N_2$ ×11 [0]'. This confirms that up to three repeats within an ×11 tbs composed of RAGNN can be replaced with RAGNNN repeats and retain some TRAP-mediated repression activity resulting in improved vector titres. However, it should be noted that the RAGNN ×8-11 tbs configuration remains the preference for reasons other than increased vector production i.e. massively reduced transgene protein associated with the vector product that might otherwise lead to an immune response to the transgene during vector administration.

Previously it was shown that RAGNN ×7-8 tbs variants retain near maximal TRAP-mediated repression activity (FIG. 14i). To test the impact of a single RAGNN repeat replacement by RAGNNN within these shorter tbs variants, a second series of $N_3N_2$ tbs variants were constructed and inserted into the COX2 vector genome (FIG. 14vA). These vector genome plasmids were transiently co-transfected into HEK293T cells with EIAV vector packaging components+/pEF1a-coTRAP[H6] and at 8 hours post-transfection, cell lysates analysed by immunoblot to COX2 to measure transgene repression in the cell compared to stuffer plasmid (un-repressed) (FIG. 14vB). These data show that an 8-repeat tbs containing one RAGNNN repeat and seven RAGNN repeats retains TRAP-mediated repression activity. Less than 8-repeat tbs sequences containing one or more RAGNNN repeats may have lower TRAP-mediated repression activity.

Example 8c. Characterisation of Preferred Nucleotides at the Five Positions of the RAGNN Repeat Consensus To further characterise the RAGNN consensus repeat of the tbs, the NN spacer was tested with each nucleotide (G|A|T[U]|C) in the context of an ×11 repeat tbs comprised of all GAGxx repeats. These tbs variants were cloned into pCMV-[tbs]GFP, replacing the ×11M tbs, and tested by transient co-transfection of HEK293T cells+/−pEF1a-coTRAP[H6]. After 48 hours, cells were analysed by flow cytometry and GFP Expression scores calculated (FIG. 23i). This revealed a preference for pyrimidines at the NN position. The general order of functionality was T[U]>C>G/A. In order to test the most functional nucleotide at the first (R) position, each nucleotide G, A, T[U] or C was inserted into xAGAA repeats within tbs' comprising ×11, ×8 or ×6 repeats. This revealed that in the context of the weakest spacer repeat (NN=AA), G was most functional at the first position. T[U] at the first position in [TAGAA]×11 was only minimally functional, and A and C were not functional in any of these xAGAA repeats. Therefore in the context of tandem xAGAA repeat-containing tbs', x must be G and not T.

Next, the relative preference of G or T in the $1^{st}$ of the RAGNN repeat consensus was tested. Within the context of a highly functional tbs (11×GAGTT), GAGTT repeats were progressively replaced with TAGTT repeats. Increasing TAGTT repeats (replacing GAGTT repeats) only modestly reduced repression function of the tbs. Given the results of FIG. 23i, this suggests that in the RAGNN repeat consensus, of the variable nucleotides the most important positions for functionality are the NN spacers, followed by R. The data indicated that pyrimidines in the NN positions are most preferred.

To further characterize this feature of the RAGNN repeat consensus, another series of tbs variants were constructed wherein at least one N=T, in the context of GAGxx (FIG. 23ii). This revealed that maximal repression is achieved when the first N (position 4 of RAGNN) is preferably a pyrimidine, and even more preferably a T[U]. Note that GAGAT was not tested because tandem repeats of this RAGNN sequence results in multiple ATG codons upstream of the transgene ORF, which would likely attenuate expression of the downstream transgene.

Many of these findings are in agreement with published reports on TRAP-tbs interactions tested in vitro or in vivo [Bacteria] (Babitzke P, Y. J., Campanelli D. (1996) *Journal of Bacteriology* 178(17): 5159-5163), although some differences were observed. For example, in the present study the RAGCC repeat proved to be a highly effective mediator of TRAP repression, whereas others have suggested that this spacer has reduced activity due to secondary structure (Xirasagar et al., J. Biol. Chem., Vol 273(42):27146-27153, October 1998). This indicates that a specific tbs sequence comprising RAGNN repeats is required to be tested empirically within the TRAP-tbs repression system in cells intended for vector production (typically, but not limited to, HEK293-based cells), in order to test for the magnitude of repression possible by the specific tbs in the presence of TRAP. Altogether, the data in this study has revealed that the preferable nucleotides of the RAGNN repeat consensus are:
 a pyrimidine in at least one of the NN spacer positions;
 a pyrimidine at the first of the NN spacer positions;
 pyrimidines at both of the NN spacer positions;
 preferably G at the R position.

Example 9. Testing the TRAP/Tbs Configuration in Transgene Cassettes where Translation is Dependent on an IRES Multi-cistronic vectors are useful tools in delivering more than one gene to target cells in patients. Therefore it would be advantageous to be able to repress multiple transgenes within a vector genome using the TRIP system, including those dependent on IRES elements. To test if the TRIP system can be applied to transgene expression cassettes wherein the distal ORF is dependent on an internal ribosomal entry site (IRES), bicistronic vectors described in FIG. 15A were constructed. Briefly, a sequence encoding the Vascular Endothelial Growth Factor (VEGF) and the EMCV IRES element was inserted into pCMV-tbsGFP giving rise to the bicistronic gene cassette VEGF-IRES-tbsGFP encoded within pCMV-Vi-tbsx11GFP. Two further control constructs were made that contained either only 4 [RAGNN] repeats or no repeats; these were not predicted to be repressible by TRAP. The constructs were co-transfected in HEK293T cells with either stuffer plasmid or pEF1a-coTRAP[H6], and GFP expression assessed by flow cytometry. These data are displayed in FIG. 15B. The level of GFP expression from the distal position in the bicistronic cassette was approximately 7-fold lower than that of the single cistron construct, which is not atypical for bistronic gene configurations. The level of GFP expression in pCMV-Vi-tbsx11GFP-transfected cells was a further 2-fold lower, indicating that the placement of the tbs sequence had a small reduction on IRES-dependent translation efficiency. The level of GFP expression in pCMV-Vitbsx11G+pEF1a-coTRAP[H6]-transfected cells was 17-fold lower than with stuffer plasmid, demonstrating that the TRAP/tbs configuration can function in the context of internal ribosome entry. Moreover, this functionality was dependent on the presence of the tbs, as well as the presence of TRAP protein, since the control and 4× repeat constructs did not respond significantly to TRAP. These data demonstrate for the first time the novel use of TRAP/tbs in regulating gene expression by control of IRES-dependent translation. (The data in FIGS. 19i and 19ii further demonstrate that multiple ORFs within multicistronic mRNAs can be repressed simultaneously using the TRIP system).

Repression of GFP Transgene in Production Cells from WPRE-Containing, SIN Vector by TRAP/Tbs Configuration Example 10. Production of SIN-Lentiviral Vectors Containing the WPRE Using the TRIP System The TRIP system was applied to production of a SIN-vector that also contained the Woodchuck post-transcriptional element (WPRE). The initial vector genome (pONY8.4RC-tbsGFP) used to exemplify transgene translation repression using the TRAP/tbs configuration was not a SIN vector and did not contain a post-transcriptional regulatory element (PRE)—a feature of typical of contemporary retroviral vectors and other viral vector systems. The WPRE has been shown to function by decreasing read-through at polyadenylation sites (Higashimoto T, U. F., Perumbeti A, Jiang G, Zarzuela A, Chang L J, Kohn D B, Malik P. (2007) *Gene Therapy* 14(17): 1298-1304). However, earlier reports suggested that the WPRE might act at RNA level in other ways. To test if the TRAP/tbs configuration could be used to repress transgene expression from a SIN-vector genome containing the WPRE, the vector genome pONY8.9RCTG(+WPRE) was constructed and tested in repressing GFP expression in HEK293T cells. FIG. 16 demonstrated that the inclusion of WPRE on a SIN-vector genome has no adverse effect on the TRIP system: GFP repression from pONY8.4RC-tbsGFP and pONY8.9RCTG(+WPRE) was equivalent.

Use of TRIP System to Increase Production Titres of Vectors Expressing Therapeutic Transgenes Example 11. Production of a huFactor VIII-Expressing Vector Using the TRIP System ReQuinate®, developed for treatment of haemophilia A, is difficult to produce in HEK293T cells because the transgene huFactor VIII has been shown to severely inhibit VSVG envelope incorporation into vector virions. ReQuinate® vector titres are low (see FIG. 3i for mixing experiment data) unless a tissue-specific promoter that is not active in HEK293T cells is used to drive huFactor VIII expression (Radcliffe PA, S. C., Wilkes F J, Custard E J, Beard G L, Kingsman S M, Mitrophanous K A (2008) *Gene Therapy* 15(4): 289-297). The TRIP system was applied to ReQuinate® to test if vector titres could be enhanced by repressing huFactor VIII expression in HEK293T production cells. Vector genomes ReQuniate-tbs and ReQuniate-con were constructed (FIG. 17i), wherein the 5'UTR within the original ReQuinate® genome was replaced with the same 5'UTR from the tbs-GFP reporter vectors (depicted in FIG. 6). The ReQuinate-con vector genome contained the same 5'UTR as ReQuinate-tbs except that the tbs was scrambled; this was done so that translation of huFactor VIII from tbs-negative mRNA was in the context of a similar 5'UTR in terms of sequence length and nucleotide content compared to tbs-containing mRNA. These vectors were made in HEK293T cells using vector genome plasmid DNA at a 5-fold molar excess over pEF1a-coTRAP[H6]. Filtered vector supernatants were subject to DNA integration assay to determine titres. Vector supernatants were also concentrated ~100-fold, subject to PERT assay to quantify particle numbers, and equal numbers of vector particle analysed for VSVG content by immunblotting. Data from these analyses are displayed in FIG. 17ii. The TRIP system improved the DNA integration titre of huFactor VIII-expressing vector genome by 30-fold, comparing ReQuinate-tbs produced in the presence of TRAP[H6] and ReQuinate®. The degree of VSVG incorporation into vector particles was massively increased using the TRAP/tbs configuration, and this correlated closely with vector titre. Interestingly, the VSVG incorporation into vector particles made with ReQuniate-con were also slightly increased and a small concomitant increase in vector titre was observed +/−pEF1a-coTRAP[H6]; this may have been due to sub-optimal expression of huFactorVIII from this construct.

Example 12. Production of COX2 and/or FRP-Expressing Vectors Using the TRIP System In connection with the development of retroviral vectors to treat glaucoma, a number of transgenes being evaluated to reduce intra-ocular pressure, including Prostaglandin F receptor (FPR), which is a receptor for prostaglandin $F_{20}$ that is encoded by the PTGFR gene, and Cyclooxygenase-2 (COX-2), the rate limiting enzyme in prostaglandin biosynthesis. The delivery of both of these genes simultaneously (either by separate single gene vectors or by a bicistronic gene vector) is hoped to be of benefit to glaucoma patients. However, it has been found that titres of vectors encoding these transgenes are markedly reduced compared to marker gene vector titres. At least part of this effect has been demonstrated to be due to the transgene products because mixing of these vector genomes with a lacZ-vector genome during vector production results in reduction of the lacZ-vector titre (see FIG. 3ii).

In order to test whether the TRIP system could increase glaucoma vector titres the tbsx11m variant sequence (see FIG. 14iA) was cloned into the single transgene vector genomes depicted in FIG. 18i. Viral vector preps were produced in HEK293 Ts whilst also co-transfecting pEF1a-coTRAP[H6] or stuffer plasmid at a molar ratio of 1:0.2 vector genome:TRAP plasmid. Vector preps were titrated by standard DNA integration assay (FIG. 18iiA) and cell lysates taken from both COX-2 vector production cells and COX-2 vector-transduced cells in order to assess the expression of COX-2 from the tbs-containing transcription unit in target cells. Data from these analyses are shown in FIGS. 18iiB and 18iiC respectively. The titres of the tbs-COX-2 vector were 100-fold higher than that of the unmodified COX-2 vector (FIG. 18iiA), and the level of COX-2 within production cells was inversely correlated with titre (FIG. 18iiB). COX-2 expression could be robustly detected only within target cells that had been transduced with vector produced using the TRIP system, demonstrating that the tbs sequence did not affect expression of the transgene in target cells (FIG. 18iiC). The titre of FPR-vector produced using the TRIP system was increased by 24-fold compared to standard vectors (FIG. 18iii); again, this was dependent on both TRAP and tbs in the system.

To test a mulitcistronic vector expressing both COX-2 and FPR, the tbsx11M sequence was cloned into vector genome plasmids depicted in FIG. 19*i*; bicistronic vector genome plasmids encoding COX-2 and FRP at either position+/−tbs were created. Viral vector preps were produced in HEK293 Ts under standard conditions whilst also co-transfecting pEF1a-coTRAP[H6] or stuffer plasmid at a molar ratio of 1:0.2 vector genome:TRAP plasmid. Vector preps were titrated by standard DNA integration assay and cell lysates taken from vector production cells (FIG. 19*ii*). Immunoblotting of cell lysates was carried out using antibody to COX-2 only as there is no commercially available antibody to FPR. These data show that multicistronic mRNA can be simultaneously repressed at more than one ORF position using the TRIP system. The result of this repression allowed a 100-fold increase in vector titre (compare pKCMV-COX2-i-FPR [+stuffer] with pKCMV-tbsCOX2-i-tbsFPR [+pEF1a-coTRAP[H6]]).

Example 13. Production of OXB-102 Vectors Using the TRIP System

OXB-102 is an EIAV vector being developed for the treatment of Parkinson's disease and which express 3 proteins involved in dopamine biosynthesis: tyrosine hydroxylase, GTP-cyclohydrolase and aromatic L-amino acid decarboxylase (described in WO 2013/061076). Whilst it is known that these enzymes do not adversely impact vector titres, as mentioned previously, it may be beneficial to repress transgene expression within vector production cells from the perspective of vector processing/concentration, as well as delivering a less immunogenic vector preparation to the patient. Therefore, the tbsx111M sequence was cloned into the 5' proximal ORF of the multicistronic OXB-102 vector genome plasmid as depicted in FIG. 20*i*. In the resulting vector, translation of the fusion gene Tyrosine hydroxylase:GTP-cyclohydrolase 1 (TH-CH1) would be predicted to be repressed by TRAP only in vector production cells. Viral vector preps were produced in HEK293 Ts whilst also co-transfecting pEF1a-coTRAP[H6] or stuffer plasmid at a molar ratio of 1:0.2 vector genome:TRAP plasmid. Vector preparations were titrated by standard DNA integration assay and cell lysates taken from vector production cells. FIGS. 20*ii*A and 20*ii*B indeed show that the TH-CH1 fusion protein is repressed in vector production cells as judged by immunoblot using antibodies to both TH and CH1 (FIG. 20*ii*B) but is readily detected in transduced cells as judged by immunostaining using anti-TH antibodies.

Example 14. Production of HIV-1-Based Lentiviral Vectors Using the TRIP System

We sought to demonstrate utility of the TRIP system in producing HIV-1 based lentiviral vectors. The tbsx11M sequence was cloned into a standard HIV-1 vector genome encoding GFP under the control of the CMV promoter (FIG. 25*i*A). GFP-encoding vectors were produced by transient co-transfection of HEK293T cells with packaging component plasmids in the following mass ratio; 4.5 µg vector genome, 1.5 µg gagpol, 1.1 µg rev, 0.7 µg vsvg with either 0.56 µg of pEF1a-coTRAP[H6] (+TRAP) or 0.56 µg pBlueScript (~), using 25 µL Lipofectamine 2000CD per 10 cm plate (seeded at 3.5×10$^6$ cell/plate 24 hours pre-transfection). Cultures were incubated overnight before sodium butyrate was added to a final concentration of 10 mM for 5 hours. Media was then replaced and cultures incubated until 2 days post-transfection, when crude vector supernatants were harvested, filtered (0.2 µm) and stored at −80° C. End-of-production cells were analysed by flow cytometry and GFP Expression score calculated. Vector supernatants were titrated by transduction of HEK293T cells followed by analysis by flow cytometry. FIG. 25*ii*B displays both the GFP Expression scores (MFI×% GFP) for end-of-production cells and vector titres produced. GFP expression was repressed by 2-Logs only when the HIV-1 vector genome contained the tbs sequence as described and when TRAP was co-introduced. However, vector titres were not affected by these modifications. These data demonstrate that in principle, any transgene may be repressed in HIV-1 based vector production cells using the TRIPLenti system.

To assess if the titre of an HIV-1 based vector encoding a therapeutic gene could be improved using the TRIPLenti system, the tbsx11M tbs was inserted into the 5'UTR of the transgene cassette of an HIV-1 vector genome encoding 5T4-CAR (FIG. 25*ii*A); this therapeutic vector is for the genetic modification of T-cells enabling them to target and kill tumour cells expressing the antigen 5T4. The resulting vector HIV-tbs-h5T4.CAR was produced under the same conditions described above (for GFP vector) i.e. co-transfection of HEK293T cells with vector components+/−pEF1a-coTRAP[H6]. Vector supernatants were titrated by DNA integration assay in HEK293T cells. FIG. 25*ii*B displays the results of this experiment; the titre of HIV-tbs-h5T4.CAR were 30-fold greater when TRAP[H6] was co-expressed in production cells compared to the control (pBlueScript). These data demonstrate that 5T4.CAR expression within production cells is detrimental to active vector production, and that the TRIP system overcomes this problem through repression of transgene expression.

Example 15. The TRAP-Tbs Configuration does not Affect Transgene mRNA Levels in the Cytoplasm The TRAP-tbs configuration is capable of extremely potent transgene repression and thought to act solely at the translation level. To test if the steady-state pool of tbs-encoding mRNA is affected in the presence of TRAP (e.g. a possible destabilising effect), which might also contribute to repression in transgene expression, the relative levels of transgene cytoplasmic RNA was measured in HEK293T cells transfected with pCMV-[tbs]GFP+/−pEF1a-coTRAP [H6]. Cells were transfected and GFP expression measured by flow cytometry at 2 days post-transfection (FIG. 26A). Replicate cultures were fractionated, nuclei removed and total cytoplasmic RNA purified using a QIAGEN RNAeasy kit. RNA was DNAse-treated before qRT-PCR performed using a FAM-probe/primer set to a GFP target sequence (FIG. 26B). In agreement with previous data, the TRAP-tbs configuration was capable of repressing GFP expression in HEK293T cells by 2-Logs. However, the detection level of GFP mRNA within the cytoplasm varied by no more than ~2-fold across all conditions (all Ct values varied less than 1.5 cycles). These data confirm that the most likely mechanism of TRAP-mediated transgene repression is at translation.

Example 16. Comparison of TRAP/Tbs-Mediated Bi-Cistronic Transgene Repression in Vector Production Cells from HIV-1-Based Vectors Encoding Constitutive Versus Tissue-Specific Promoters To test TRAP-mediated repression (at translation level) in comparison to transgene repression at the transcription level, HIV-1-based vector genomes were constructed in which transgene transcription was driven by either tissue specific promoters (VMD2; photo-receptor cell expression (Esumi, N. et al. (2004) *J. Biol. Chem.* 279: 19064-73), mAlbAT; liver hepatocyte cells expression (Kramer, M. G. et al. (2003) *Mol. Ther.* 7: 375-385)) or the constitutive CMV promoter. The transgene cassette was bi-cistronic, encoding Firefly (*Photinus pyralis*) luciferase at the $1^{st}$ ORF and GFP at the $2^{nd}$ ORF, with the EMCV IRES element inserted between the two ORFs. Single tbs (×11M) sequences were inserted upstream of both reporter genes. Alternative CMV-promoter constructs were made in which only the $1^{st}$ or $2^{nd}$ ORF were regulated by TRAP-tbs, and controls without any tbs sequences or no promoter (FIG. 27*i*).

The seven vector genomes were used to make vector particles in HEK293T cells. Cells were co-transfected with vector genome plasmid plus packaging components and either pEF1a-coTRAP[H6] or pBluescript (control). In addition, pGL3-control (SV40-promoter-driven *Renilla reniformis*, luciferase) was added (1:40 ratio to total DNA) to provide a transfection efficiency control. Ratios of plasmids were: genome (4.5)|GagPol (1.5)|Rev (1.1)|VSVG (0.7) |TRAP/Bluescript (0.56)|pGL3 control (0.23). Transfections occurred at 96-well scale in duplicate plates, with each condition in triplicate. One day post-transfection, cultures were induced with 10 mM sodium butyrate for 5-6 hours (a typical vector production method), before replacing the media with fresh media. End-of-production cells were either analysed by flow cytometry to generate GFP Expression scores (MFI×% GFP) to measure expression at the $2^{nd}$ position or lysed in passive lysis buffer according to the Dual Luciferase® reporter assay protocol (Promega) to measure expression at the $1^{st}$ position. Lysates were analysed for Firefly luciferase expression using a Dynex MLX plate reader according to the above protocol using the manufacturer's method.

The expression data for the bi-cistronic cassettes in the vector production cells is presented in FIG. 27*ii*. As expected, no repression of either Luciferase or GFP was observed from pHIV-CMV-Luc-iGFP when TRAP was supplied, due to absence of tbs'. Repression of luciferase expression was observed from pHIV-CMV-tbsLuc-itbsGFP and pHIV-CMV-tbsLuc-iGFP but not pHIV-CMV-Luc-itbsGFP. Repression of GFP expression was observed from pHIV-CMV-tbsLuc-itbsGFP and pHIV-CMV-Luc-itbsGFP but not pHIV-CMV-tbsLuc-iGFP.

Interestingly, whilst the promoter-less vector genome pHIV-Null-tbsLuc-itbsGFP expressed Luciferase at 100-fold lower levels than the CMVp variants, this level of expression could be repressed by TRAP. It is likely that this lower level expression of luciferase (in the absence of TRAP) is derived from the full length vector genome RNA in a CAP-dependent manner i.e. ribosome scanning from 5' end of full length vector RNA. Thus, TRAP can bind the tbs on the full length vector genome RNA, and block transgene expression from this longer RNA, as well as the internal transcript. This is further evidenced by the fact that high levels of GFP were expressed by pHIV-Null-tbsLuc-itbsGFP, presumably due to the IRES element driving just GFP translation. TRAP was capable of repressing this expression of GFP from the full length vector genome RNA derived from pHIV-Null-tbsLuc-itbsGFP. This is supported by the fact that the tissue-specific constructs pHIV-VMD2-tbsLuc-itbsGFP and pHIV-mAlb-hAAT-tbsLuc-itbsGFP, produced similar levels of GFP compared to pHIV-Null-tbsLuc-itbsGFP (in the absence of TRAP), despite Luciferase expression being low (compared to CMVp constructs), demonstrating that most of the GFP expression was not coming from the internal promoter-driven cassette. This level of GFP expression (from full length vector genome RNA) could also be efficiently repressed by TRAP. Finally, the levels of Luciferase expression from pHIV-VMD2-tbsLuc-itbsGFP and pHIV-mAlb-hAAT-tbsLuc-itbsGFP were ~2-fold above that of pHIV-Null-tbsLuc-itbsGFP, indicating that these tissue-specific promoters are slightly leaky in HEK293T cells. Even this low level of Luciferase expression was repressed by TRAP.

These observations are summarised in the schematic presented in FIG. 27*iii*. These data show that the TRIP system is capable of simultaneous repression of multi-cistronic transgenes, and has advantages over using tissue specific promoters. For retroviral vector production, large quantities of full length, vector genome RNA must be transcribed within a cell, but here we demonstrate that translation of transgene protein is possible from this full length molecule, particularly if an IRES element is employed. Since the TRIP system mediates repression at the translation level, it is capable of repressing transgene expression from the full length vector genome RNA, as well as the internally derived transgene cassette mRNA.

Example 17. Demonstration of the Utility of TRAP/Tbs-Mediated Transgene Repression in Production of a DNA-Based Viral Vector; Case Study 1—AAV-Based Vectors The following work describes the TRiPAAV vector production system, which employs the TRAP-tbs configuration in a similar manner as described for RNA-based viral vector systems such as retro/lentivirus. FIG. 28*i* displays a non-limiting example of the TRiPAAV system, which comprises production cells (e.g. Adenovirus E1-expressing cells; HEK293-based cells, PER.C6-based cells) containing the following expression cassettes: [1] an AAV vector genome modified such that a tbs is inserted within the 5'UTR of the transgene (and/or between an IRES and downstream transgene), [2] a repcap expression plasmid, [3] helper functions (e.g. Adenovirus E2A, E4orf6, VA genes), and [4] a TRAP expression cassette (transiently transfected or stable TRAP cell line).

To test if transgene expression can be repressed in AAV vector production cells, the TRiPAAV system was applied to production of a self-complementary (sc)AAV-(CMV)-tbsGFP vector (serotype 2) in HEK293T cells. First, the impact of co-expression of repcap and Adenovirus helper functions on TRAP-mediated repression was tested, and compared to the pCMV-tbsGFP reporter plasmid (FIG. 28*ii*). HEK293T cells were transfected in triplicate with either pscAAV-GFP or pscAAV-tbsGFP or pCMV-tbsGFP, in different combinations of pEF1a-coTRAP[H6], pRepCap2 and pHelper (all at equi-mass ratio of 2 μg per 10 cm plate unless otherwise stated for pEF1a-coTRAP[H6]—see FIG. 28*ii*). As expected, expression of TRAP had no impact on GFP expression by pscAAV-GFP, which lacked a tbs. GFP expression from pscAAV-tbsGFP was repressed by almost 3-Logs in the presence of TRAP (TRAP and scAAV vector genome plasmids at 1:1 ratio). The co-expression of pHelper or pRepCap2 did not affect this level of TRAP-mediated repression. When pscAAV-tbsGFP, pRepCap2, pHelper and pEF1a-coTRAP[H6] were all transfected together (i.e. under conditions were scAAV-tbsGFP vector particles would be produced) the level of GFP repression by TRAP was over 300-fold. The 10-fold titration of pEF1a-coTRAP[H6] (ratio with genome from 1:1 [2 μg] to 10:1 [0.2 μg]) under conditions of scAAV-tbsGFP production indicates that 3-Log repression might be possible with greater inputs of TRAP plasmid. These data demonstrate that expression of a transgene cassette within an AAV vector genome can be repressed by at least 300-fold using the TRiPAAV system, and that the packaging/helper functions per se do not inhibit TRAP-mediated repression.

To demonstrate that functional AAV vector particles can be produced using the TRiPAAV system, scAAV2-[tbs]GFP vector particles were produced at 10 cm plate scale, by transfecting cells with pscAAV2-GFP genomes (+/−tbs), pRepCap2, pHelper and either pEF1a-coTRAP[H6] (TRAP) or pBluescript (−) (2 µg of all DNAs). After ~53 hours, cells were freeze-thawed, and vector particles were purified using a Virabind™ kit, concentrated to a final volume of 100 µL PBS, and then titrated by transduction of HEK293T and HEPG2 cells (FIG. 28*iii*). These data show that AAV-GFP vectors can be produced to equivalent titres under the TRiPAAV system as under the standard method, indicating that the tbs modification and co-expression of TRAP does not intrinsically impede AAV vector biology. Therefore, this work shows that potent repression of transgene expression in AAV vector production cells using the TRiPAAV system is possible, and that if the transgene product's activity is detrimental to AAV vector particle titre or potency, this activity will be greatly diminished.

To demonstrate that the TRiPAAV vector system is capable of repressing a highly toxic/problematic transgene encoded by an AAV vector genome in production cells, scAAV2-tbsBarnase was constructed (FIG. 28*iv*A). Barnase is a potent bacterial RNAse that is toxic to eukaryotic cells when expressed, and has been shown to compromise AAV vector production unless silenced (Chen H., Mol Ther Nuc Acids., 1, e57; doi:10.1038/mtna.2012.48, November 2012). HEK293T and HEK293T.TRiP[3D] cell cultures were transfected with the pRepCap2 and pHelper packaging components (without pEF1a-coTRAP[H6]), except either equal masses of pscAAV2-GFP (FIG. 28*iv*B) and pscAAV2-tbsBarnase genome plasmids were mixed, to observe the effect of Barnase on GFP expression, or only pscAAV-(CMV)-GFP was transfected. Pictures of these cultures were taken 24 hours post-transfection, which are displayed in FIG. 28*v*: i-ii. The HEK293T and HEK293T.TRiP[3D] cultures transfected with pscAAV-(CMV)-GFP alone produced high levels of GFP expression (FIG. 28*v*: ii). However, HEK293T cultures co-transfected with pscAAV-(CMV)-GFP genome and pscAAV-(CMV)-tbsBarnase expressed negligible levels of GFP (FIG. 28*v*: i), demonstrating that Barnase expression had resulted in a global effect of reduced protein expression, presumably due to degradation of transgene mRNA and ribosomal RNA. In contrast, HEK293T.TRiP cultures transfected with the same DNA mix, allowed some substantial GFP expression, indicating that the endogenous levels of TRAP[H6] in these cells had inhibited Barnase expression. It is likely to be possible to improve Barnase repression by isolating stable cell lines with even greater levels of endogenous TRAP. The modelling of Barnase as a toxic transgene protein expressed during viral vector production represents a worst-case scenario, wherein de novo protein synthesis (including viral vector components) is effectively shutdown. Given the observed moderate recovery of GFP expression in HEK293T.TRiP cells, this suggests that expression of AAV vector component proteins also occurred, and that production of Barnase-encoding AAV vector particles is possible in stable TRAP cell lines.

Example 18. Demonstration of the Utility of TRAP/Tbs-Mediated Transgene Repression in Production of a DNA-Based Viral Vector; Case Study 2—Adenovirus-Based Vectors The following work describes the TRIPAdeno vector production system, which employs the TRAP-tbs configuration in a similar way as described for RNA-based viral vector systems such as retro/lentivirus, and for DNA-based AAV vectors (Example 17). FIG. 29*i* displays a non-limiting example of the TRIPAdeno system, which comprises production cells (e.g. Adenovirus E1-expressing cells; HEK293-based cells, PER.C6-based cells) containing the following expression cassettes: [1] an Adenovirus-based vector genome modified such that a tbs is inserted within the 5'UTR of the transgene (and/or between an IRES and downstream transgene), and [2] a TRAP expression cassette (transiently transfected or stable TRAP cell line). Optionally an E1-deleted helper virus may be co-introduced for Helper-dependent vector production.

To demonstrate that transgene expression can be repressed in the TRIPAdeno system during vector DNA recombination in mammalian cells, thus generating full length Adeno-tbsTransgene vector genomes, pAdeno-CMV-GFP and pAdeno-tbsGFP shuttle plasmids (RAPAd® kit, Cell BioLabs) were constructed (FIG. 29*ii*A). These contained the left-hand side of the Adenovirus genome (E1-deleted) encoding the transgene cassette. These shuttle plasmids were co-transfected into HEK293T cells with pEF1a-coTRAP[H6] (TRAP) or pBlueScript (−), and in parallel transfections with pacAd5 9.2-100 (RAPAd® kit, Cell Bio-Labs), which contains overlapping homology with Ad5 sequences in the shuttles, and the remainder of the Ad5 genome (E3-deleted) to the right-hand ITR (FIG. 29*ii*B). The mass ratio of shuttle plasmid to TRAP plasmid was 5:1. Replicate cultures were incubated for either 48 hours and then analysed for GFP expression by flow cytometry (GFP Expression scores were generated; MFI×% GFP), or incubated until cytopathic effect was observed (~14 days). Crude Adeno-CMV-GFP and Adeno CMV-tbsGFP vector stocks were made by freeze-thawing cells and removal of cell debris, followed by titration on HeLa cells.

The data in FIG. 29*ii*B display global GFP expression within cultures after 48 hours post-transfection, and show that transgene expression can be repressed from the Ad shuttle plasmids by 2-Logs only when the tbs is present within the transgene 5'UTR and in the present of TRAP. Co-transfection with pacAd5 9.2-100 did not affect repression levels, thus demonstrating that it is possible to repress transgene expression during vector DNA recombination in mammalian cells. This represents a major step forward in Adenoviral vector generation in mammalian cells, as toxic transgene expression might others negate the ability to recover vector recombinants.

To test if the TRIPAdeno system could repress transgene expression during Ad vector amplification, HEK293T cells or HEK293T.TRIP[3D] cells (stably expressing TRAP[H6]) were transduced with Adeno-CMV-GFP and Adeno-CMV-tbsGFP at an MOI of 0.01. Replicate cultures were analysed for GFP expression during vector amplification at different time-points post-inoculation, and GFP Expression scores generated (MFI×% GFP). The results of this experiment are displayed in FIG. 29*iii*, and show that GFP expression is repressed by >400-fold during Adeno-CMV-tbsGFP amplification only in the HEK293T.TRIP[3D] cell line (FIG.

29iiiA). GFP expression during Adeno-CMV-GFP amplification was similar (i.e. not repressed) in either of the cell lines, as expected.

Vector stocks of Adeno-CMV-GFP and Adeno-CMV-tbsGFP that were produced in the presence of TRAP, were harvested from cells at 48 hours post-inoculation; debris removed and titrated on HeLa cells (FIG. 29iiiB). The titres of vector produced either in HEK293T or HEK293T.TRIP [3D] cells were equivalent, indicating that the tbs modification and co-expression of TRAP does not intrinsically impede Adenovirus vector biology. Therefore, this work shows that potent repression of transgene expression in Adenovirus vector production cells using the TRIPAdeno system is possible, and that if the transgene product's activity is detrimental to Adenovirus vector particle titre or potency, this activity will be greatly diminished.

All publications mentioned in the above specification are herein incorporated by reference. Various modifications and variations of the described aspects of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A nucleic acid sequence comprising an RNA-binding protein (RBP) binding site operably linked to a nucleotide of interest (NOI), wherein the RBP binding site is capable of interacting with an RBP such that translation of the NOI is repressed in a viral vector production cell, wherein the RBP is heterologous to the NOI, and wherein the RBP is tryptophan RNA-binding attenuation protein (TRAP).

2. The nucleic acid sequence of claim 1, wherein the TRAP binding site comprises multiple repeats of the sequence $RAGN_{2-3}$.

3. The nucleic acid sequence of claim 2, wherein the number of RAGNNN repeats is 1 or less.

4. The nucleic acid sequence of claim 2, wherein the TRAP binding site comprises at least 8-11 repeats of the sequence $RAGN_2$.

5. The nucleic acid sequence of claim 2, wherein the TRAP binding site comprises 11 repeats of the sequence $RAGN_{2-3}$, wherein the number of RAGNNN repeats is 3 or less.

6. The nucleic acid sequence of claim 1, wherein the NOI encodes a therapeutic protein.

7. A viral vector comprising the nucleic acid sequence of claim 1.

8. The viral vector of claim 7, comprising a second NOI.

9. The viral vector of claim 7, which is a retroviral vector, an adenoviral vector, an adeno-associated viral vector, a herpes simplex viral vector, a vaccinia viral vector, or a baculoviral vector.

10. The viral vector of claim 7, which is a lentiviral vector.

11. A cell transduced by the viral vector of claim 7.

12. A method of identifying a nucleic acid binding site and/or a nucleic acid binding protein, the method comprising analysing expression of the NOI in a cell comprising the nucleic acid sequence of claim 1 and a nucleic acid sequence encoding the RBP, wherein the NOI is a reporter gene.

13. A method of repressing translation of a nucleotide of interest (NOI) in a viral vector production cell, the method comprising introducing into the viral vector production cell the nucleic acid sequence of claim 1 and a nucleic acid sequence encoding an RNA binding protein (RBP), wherein the RBP binds to the RBP binding site, thereby repressing translation of the NOI.

* * * * *

```
                         SEQUENCE LISTING

<160> NUMBER OF SEQ ID NOS: 43

<210> SEQ ID NO 1
   <211> LENGTH: 75
   <212> TYPE: PRT
   <213> ORGANISM: Bacillus subtilis

<400> SEQUENCE: 1

Met Asn Gln Lys His Ser Ser Asp Phe Val Val Ile Lys Ala Val Glu
   1               5                   10                  15

Asp Gly Val Asn Val Ile Gly Leu Thr Arg Gly Thr Asp Thr Lys Phe
                   20                  25                  30

His His Ser Glu Lys Leu Asp Lys Gly Glu Val Ile Ile Ala Gln Phe
               35                  40                  45

Thr Glu His Thr Ser Ala Ile Lys Val Arg Gly Glu Ala Leu Ile Gln
       50                  55                  60

Thr Ala Tyr Gly Glu Met Lys Ser Glu Lys Lys
   65                  70                  75

<210> SEQ ID NO 2
   <211> LENGTH: 86
   <212> TYPE: PRT
   <213> ORGANISM: Aminomonas paucivorans

<400> SEQUENCE: 2

Met Lys Glu Gly Glu Ala Lys Thr Ser Val Leu Ser Asp Tyr Val
   1               5                   10                  15

Val Val Lys Ala Leu Glu Asn Gly Val Thr Val Ile Gly Leu Thr Arg
                   20                  25                  30

Gly Gln Glu Thr Lys Phe Ala His Thr Glu Lys Leu Asp Asp Gly Glu
               35                  40                  45

Val Trp Ile Ala Gln Phe Thr Glu His Thr Ser Ala Ile Lys Val Arg
       50                  55                  60

Gly Ala Ser Glu Ile His Thr Lys His Gly Met Leu Phe Ser Gly Arg
   65                  70                  75                  80

Gly Arg Asn Glu Lys Gly
                   85

<210> SEQ ID NO 3
   <211> LENGTH: 81
   <212> TYPE: PRT
   <213> ORGANISM: Desulfotomaculum hydrothermale

<400> SEQUENCE: 3

Met Asn Pro Met Thr Asp Arg Ser Asp Ile Thr Gly Asp Tyr Val Val
```

```
                1               5                   10                  15
            Val Lys Ala Leu Glu Asn Gly Val Thr Ile Ile Gly Leu Thr Arg Gly
                            20                  25                  30
            Gly Val Thr Lys Phe His His Thr Glu Lys Leu Asp Lys Gly Glu Ile
                        35                  40                  45
            Met Ile Ala Gln Phe Thr Glu His Thr Ser Ala Ile Lys Ile Arg Gly
                    50                  55                  60
            Arg Ala Glu Leu Leu Thr Lys His Gly Lys Ile Arg Thr Glu Val Asp
            65                  70                  75                  80

Ser

<210> SEQ ID NO 4
<211> LENGTH: 74
<212> TYPE: PRT
<213> ORGANISM: Bacillus stearothermophilus

<400> SEQUENCE: 4

Met Tyr Thr Asn Ser Asp Phe Val Val Ile Lys Ala Leu Glu Asp Gly
            1               5                   10                  15

Val Asn Val Ile Gly Leu Thr Arg Gly Ala Asp Thr Arg Phe His His
                            20                  25                  30

Ser Glu Lys Leu Asp Lys Gly Glu Val Leu Ile Ala Gln Phe Thr Glu
                        35                  40                  45

His Thr Ser Ala Ile Lys Val Arg Gly Lys Ala Tyr Ile Gln Thr Arg
                    50                  55                  60

His Gly Val Ile Glu Ser Glu Gly Lys Lys
            65                  70

<210> SEQ ID NO 5
<211> LENGTH: 74
<212> TYPE: PRT
<213> ORGANISM: Bacillus stearothermophilus

<400> SEQUENCE: 5

Met Tyr Thr Asn Ser Asp Phe Val Val Ile Lys Ala Leu Glu Asp Gly
            1               5                   10                  15

Val Asn Val Ile Gly Leu Thr Arg Gly Ala Asp Thr Arg Phe His His
                            20                  25                  30

Ser Glu Lys Leu Asp Lys Gly Glu Val Leu Ile Ala Gln Phe Thr Glu
                        35                  40                  45

His Thr Ser Ala Ile Lys Val Arg Gly Lys Ala Tyr Ile Gln Thr Arg
                    50                  55                  60

His Gly Val Ile Glu Asn Glu Gly Lys Lys
            65                  70

<210> SEQ ID NO 6
<211> LENGTH: 76
<212> TYPE: PRT
<213> ORGANISM: Bacillus halodurans

<400> SEQUENCE: 6

Met Asn Val Gly Asp Asn Ser Asn Phe Phe Val Ile Lys Ala Lys Glu
            1               5                   10                  15

Asn Gly Val Asn Val Phe Gly Met Thr Arg Gly Thr Asp Thr Arg Phe
                            20                  25                  30

His His Ser Glu Lys Leu Asp Lys Gly Glu Val Met Ile Ala Gln Phe
                        35                  40                  45
```

```
Thr Glu His Thr Ser Ala Val Lys Ile Arg Gly Lys Ala Ile Ile Gln
 50                  55                  60

Thr Ser Tyr Gly Thr Leu Asp Thr Glu Lys Asp Glu
 65                  70                  75

<210> SEQ ID NO 7
<211> LENGTH: 80
<212> TYPE: PRT
<213> ORGANISM: Carboxydothermus hydrogenoformans

<400> SEQUENCE: 7

Met Val Cys Asp Asn Phe Ala Phe Ser Ser Ala Ile Asn Ala Glu Tyr
 1               5                  10                  15

Ile Val Val Lys Ala Leu Glu Asn Gly Val Thr Ile Met Gly Leu Thr
                20                  25                  30

Arg Gly Lys Asp Thr Lys Phe His His Thr Glu Lys Leu Asp Lys Gly
            35                  40                  45

Glu Val Met Val Ala Gln Phe Thr Glu His Thr Ser Ala Ile Lys Ile
     50                  55                  60

Arg Gly Lys Ala Glu Ile Tyr Thr Lys His Gly Val Ile Lys Asn Glu
 65                  70                  75                  80

<210> SEQ ID NO 8
<211> LENGTH: 55
<212> TYPE: DNA
<213> ORGANISM: Artificial Sequence
<220> FEATURE:
<223> OTHER INFORMATION: TRAP binding site

<400> SEQUENCE: 8
gaguuuagcg gaguggagaa gagcggagcc gagccuagca gagacgagug gagcu        55

<210> SEQ ID NO 9
<211> LENGTH: 55
<212> TYPE: DNA
<213> ORGANISM: Artificial Sequence
<220> FEATURE:
<223> OTHER INFORMATION: TRAP binding site

<400> SEQUENCE: 9
gaguuuagcg gaguggagaa gagcggagcc gagccuagca gagacgagaa gagcu        55

<210> SEQ ID NO 10
<211> LENGTH: 30
<212> TYPE: DNA
<213> ORGANISM: Artificial Sequence
<220> FEATURE:
<223> OTHER INFORMATION: 6 repeats of RAGN>2

<400> SEQUENCE: 10
uaguuuaguu uaguuuaguu uaguuuaguu                                   30

<210> SEQ ID NO 11
<211> LENGTH: 30
<212> TYPE: DNA
<213> ORGANISM: Artificial Sequence
<220> FEATURE:
<223> OTHER INFORMATION: 6 repeats of RAGN>2

<400> SEQUENCE: 11
uaguuuaguu gaguuuaguu gaguuuaguu                                   30

<210> SEQ ID NO 12
```

```
<211> LENGTH: 32
<212> TYPE: DNA
<213> ORGANISM: Artificial Sequence
<220> FEATURE:
<223> OTHER INFORMATION: 6 repeats of RAGN>2

<400> SEQUENCE: 12
gaguuugagu ugaguugagu uugaguugag uu                                     32

<210> SEQ ID NO 13
<211> LENGTH: 32
<212> TYPE: DNA
<213> ORGANISM: Artificial Sequence
<220> FEATURE:
<223> OTHER INFORMATION: 6 repeats of RAGN>2

<400> SEQUENCE: 13
uaguuugagu uuaguugagu uuuaguugag uu                                     32

<210> SEQ ID NO 14
<211> LENGTH: 68
<212> TYPE: DNA
<213> ORGANISM: Artificial Sequence
<220> FEATURE:
<223> OTHER INFORMATION: tbs and kozak sequences

<400> SEQUENCE: 14
gagtttagcg gagtggagaa gagcggagcc gagcctagca gagacgagtg gagtcacagc       60
caccatgg                                                                68

<210> SEQ ID NO 15
<211> LENGTH: 13
<212> TYPE: DNA
<213> ORGANISM: Artificial Sequence
<220> FEATURE:
<223> OTHER INFORMATION: Spacer variant sequence

<400> SEQUENCE: 15
acagccacca tgg                                                          13

<210> SEQ ID NO 16
<211> LENGTH: 12
<212> TYPE: DNA
<213> ORGANISM: Artificial Sequence
<220> FEATURE:
<223> OTHER INFORMATION: Spacer variant sequence

<400> SEQUENCE: 16
cagccaccat gg                                                           12

<210> SEQ ID NO 17
<211> LENGTH: 11
<212> TYPE: DNA
<213> ORGANISM: Artificial Sequence
<220> FEATURE:
<223> OTHER INFORMATION: Spacer variant sequence

<400> SEQUENCE: 17
agccaccatg g                                                            11

<210> SEQ ID NO 18
<211> LENGTH: 10
<212> TYPE: DNA
<213> ORGANISM: Artificial Sequence
<220> FEATURE:
<223> OTHER INFORMATION: Spacer variant sequence
```

<400> SEQUENCE: 18
gccaccatgg                                                                10

<210> SEQ ID NO 19
<211> LENGTH: 14
<212> TYPE: DNA
<213> ORGANISM: Artificial Sequence
<220> FEATURE:
<223> OTHER INFORMATION: Spacer variant sequence

<400> SEQUENCE: 19
acacgccacc atgg                                                           14

<210> SEQ ID NO 20
<211> LENGTH: 15
<212> TYPE: DNA
<213> ORGANISM: Artificial Sequence
<220> FEATURE:
<223> OTHER INFORMATION: Spacer variant sequence

<400> SEQUENCE: 20
acacagccac catgg                                                          15

<210> SEQ ID NO 21
<211> LENGTH: 13
<212> TYPE: DNA
<213> ORGANISM: Artificial Sequence
<220> FEATURE:
<223> OTHER INFORMATION: Spacer variant sequence

<400> SEQUENCE: 21
acagccacca tgg                                                            13

<210> SEQ ID NO 22
<211> LENGTH: 13
<212> TYPE: DNA
<213> ORGANISM: Artificial Sequence
<220> FEATURE:
<223> OTHER INFORMATION: Spacer variant sequence

<400> SEQUENCE: 22
acagccacct agg                                                            13

<210> SEQ ID NO 23
<211> LENGTH: 68
<212> TYPE: DNA
<213> ORGANISM: Artificial Sequence
<220> FEATURE:
<223> OTHER INFORMATION: tbs sequence

<400> SEQUENCE: 23
gagtttagcg gagtggagaa gagcggagcc gagcctagca gagacgagtg gagctacagc         60
caccatgg                                                                  68

<210> SEQ ID NO 24
<211> LENGTH: 68
<212> TYPE: DNA
<213> ORGANISM: Artificial Sequence
<220> FEATURE:
<223> OTHER INFORMATION: tbs-x11M

<400> SEQUENCE: 24
gagtttagcg gagtggagaa gagcggagcc gagcctagca gagacgagaa gagctacagc         60
caccatgg                                                                      68

<210> SEQ ID NO 25
<211> LENGTH: 63
<212> TYPE: DNA
<213> ORGANISM: Artificial Sequence
<220> FEATURE:
<223> OTHER INFORMATION: tbs-x10M

<400> SEQUENCE: 25
gagtttagcg gagtggagaa gagcggagcc gagcctagca gagacgagaa acagccacca    60
tgg                                                                  63

<210> SEQ ID NO 26
<211> LENGTH: 58
<212> TYPE: DNA
<213> ORGANISM: Artificial Sequence
<220> FEATURE:
<223> OTHER INFORMATION: tbs-x9

<400> SEQUENCE: 26
gagtttagcg gagtggagaa gagcggagcc gagcctagca gagacacagc caccatgg     58

<210> SEQ ID NO 27
<211> LENGTH: 53
<212> TYPE: DNA
<213> ORGANISM: Artificial Sequence
<220> FEATURE:
<223> OTHER INFORMATION: tbs-x8

<400> SEQUENCE: 27
gagtttagcg gagtggagaa gagcggagcc gagcctagca acagccacca tgg          53

<210> SEQ ID NO 28
<211> LENGTH: 48
<212> TYPE: DNA
<213> ORGANISM: Artificial Sequence
<220> FEATURE:
<223> OTHER INFORMATION: tbs-x7

<400> SEQUENCE: 28
gagtttagcg gagtggagaa gagcggagcc gagccacagc caccatgg                48

<210> SEQ ID NO 29
<211> LENGTH: 43
<212> TYPE: DNA
<213> ORGANISM: Artificial Sequence
<220> FEATURE:
<223> OTHER INFORMATION: tbs-x6

<400> SEQUENCE: 29
gagtttagcg gagtggagaa gagcggagcc acagccacca tgg                     43

<210> SEQ ID NO 30
<211> LENGTH: 38
<212> TYPE: DNA
<213> ORGANISM: Artificial Sequence
<220> FEATURE:
<223> OTHER INFORMATION: tbs-x5

<400> SEQUENCE: 30
gagtttagcg gagtggagaa gagcgacagc caccatgg                           38

<210> SEQ ID NO 31
<211> LENGTH: 33

```
<212> TYPE: DNA
<213> ORGANISM: Artificial Sequence
<220> FEATURE:
<223> OTHER INFORMATION: tbs-x4

<400> SEQUENCE: 31
gagtttagcg gagtggagaa acagccacca tgg                              33

<210> SEQ ID NO 32
<211> LENGTH: 65
<212> TYPE: DNA
<213> ORGANISM: Artificial Sequence
<220> FEATURE:
<223> OTHER INFORMATION: H3x11 (10) tbs variant

<400> SEQUENCE: 32
gagatttaga cggagttgga gaaagagacg gagaccgaga cctagacaga gaacgagaaa      60
gagct                                                                 65

<210> SEQ ID NO 33
<211> LENGTH: 62
<212> TYPE: DNA
<213> ORGANISM: Artificial Sequence
<220> FEATURE:
<223> OTHER INFORMATION: N3N2x11 (7) tbs variant

<400> SEQUENCE: 33
gagtttagac ggagttggag aaagagacgg agccgagacc tagacagaga acgagaagag      60
ct                                                                    62

<210> SEQ ID NO 34
<211> LENGTH: 60
<212> TYPE: DNA
<213> ORGANISM: Artificial Sequence
<220> FEATURE:
<223> OTHER INFORMATION: N3N2x11 (5) tbs variant

<400> SEQUENCE: 34
gagtttagac ggagtggaga aagagacgga gccgagacct agcagagaac gagaagagct      60

<210> SEQ ID NO 35
<211> LENGTH: 58
<212> TYPE: DNA
<213> ORGANISM: Artificial Sequence
<220> FEATURE:
<223> OTHER INFORMATION: N3N2x11 (3) tbs variant

<400> SEQUENCE: 35
gagtttagcg gagtggagaa agagacggag ccgagaccta gcagagacga gaagagct        58

<210> SEQ ID NO 36
<211> LENGTH: 56
<212> TYPE: DNA
<213> ORGANISM: Artificial Sequence
<220> FEATURE:
<223> OTHER INFORMATION: N3N2x11 (1) tbs variant

<400> SEQUENCE: 36
gagtttagcg gagtggagaa gagacggagc cgagcctagc agagacgaga agagct          56

<210> SEQ ID NO 37
<211> LENGTH: 55
<212> TYPE: DNA
<213> ORGANISM: Artificial Sequence
<220> FEATURE:
```

<223> OTHER INFORMATION: N2x11 (0) tbs variant

<400> SEQUENCE: 37
gagtttagcg gagtggagaa gagcggagcc gagcctagca gagacgagaa gagct    55

<210> SEQ ID NO 38
<211> LENGTH: 55
<212> TYPE: DNA
<213> ORGANISM: Artificial Sequence
<220> FEATURE:
<223> OTHER INFORMATION: N2x11 (0) tbs variant

<400> SEQUENCE: 38
gagtttagcg gagtggagaa gagcggagcc gagcctagca gagacgagaa gagct    55

<210> SEQ ID NO 39
<211> LENGTH: 41
<212> TYPE: DNA
<213> ORGANISM: Artificial Sequence
<220> FEATURE:
<223> OTHER INFORMATION: N3N2x8 (1) tbs variant

<400> SEQUENCE: 39
gagtttagcg gagtggagaa agagcggagc cgagcctagc a    41

<210> SEQ ID NO 40
<211> LENGTH: 36
<212> TYPE: DNA
<213> ORGANISM: Artificial Sequence
<220> FEATURE:
<223> OTHER INFORMATION: N3N2x7 (1) tbs variant

<400> SEQUENCE: 40
gagtttagcg gagtggagaa agagcggagc cgagcc    36

<210> SEQ ID NO 41
<211> LENGTH: 35
<212> TYPE: DNA
<213> ORGANISM: Artificial Sequence
<220> FEATURE:
<223> OTHER INFORMATION: N2x7 (0) tbs variant

<400> SEQUENCE: 41
gagtttagcg gagtggagaa gagcggagcc gagcc    35

<210> SEQ ID NO 42
<211> LENGTH: 30
<212> TYPE: DNA
<213> ORGANISM: Artificial Sequence
<220> FEATURE:
<223> OTHER INFORMATION: N2x6 (0) tbs variant

<400> SEQUENCE: 42
gagtttagcg gagtggagaa gagcggagcc    30

<210> SEQ ID NO 43
<211> LENGTH: 25
<212> TYPE: DNA
<213> ORGANISM: Artificial Sequence
<220> FEATURE:
<223> OTHER INFORMATION: N2x5 (0) tbs variant

<400> SEQUENCE: 43
gagtttagcg gagtggagaa gagcg    25